United States Patent
Patel et al.

(10) Patent No.: US 6,797,820 B2
(45) Date of Patent: Sep. 28, 2004

(54) SUCCINATE COMPOUNDS, COMPOSITIONS AND METHODS OF USE AND PREPARATION

(75) Inventors: Dinesh Patel, Fremont, CA (US); Jeffrey W. Jacobs, San Mateo, CA (US); Rakesh Jain, Fremont, CA (US); Zhi-Jie Ni, Fremont, CA (US); Zhengyu Yuan, Fremont, CA (US)

(73) Assignee: Vicuron Pharmaceuticals Inc., Fremont, CA (US)

( * ) Notice: Subject to any disclaimer, the term of this patent is extended or adjusted under 35 U.S.C. 154(b) by 47 days.

(21) Appl. No.: 09/738,859

(22) Filed: Dec. 13, 2000

(65) Prior Publication Data

US 2002/0115863 A1 Aug. 22, 2002

Related U.S. Application Data

(60) Provisional application No. 60/266,329, filed on Dec. 17, 1999.

(51) Int. Cl.$^7$ ............... A61K 31/5377; A61K 31/4025; C07D 207/09; C07D 413/04
(52) U.S. Cl. .................... 544/111; 514/231.5; 514/343; 514/423; 546/279.1; 548/517; 548/579
(58) Field of Search ....................... 546/279.1; 514/343, 514/423; 548/517, 579

(56) References Cited

U.S. PATENT DOCUMENTS

| | | |
|---|---|---|
| 3,166,587 A | 1/1965 | Bernstein et al. |
| 3,335,145 A | 8/1967 | Cislak et al. |
| 4,052,511 A | 10/1977 | Cushman |
| 4,303,662 A | 12/1981 | Sprague |
| 4,311,705 A | 1/1982 | Ondetti et al. |
| 4,321,383 A | 3/1982 | Sprague |
| 4,599,361 A | 7/1986 | Dickens et al. |
| 4,618,708 A | 10/1986 | Roques et al. |
| 4,738,803 A | 4/1988 | Roques et al. |
| 4,801,721 A | 1/1989 | Ryan et al. |
| 4,804,676 A | 2/1989 | Inaoka et al. |
| 4,971,978 A | 11/1990 | Nadzan et al. |
| 4,996,358 A | 2/1991 | Handa et al. |
| 5,095,126 A | 3/1992 | Witiak et al. |
| 5,128,346 A | 7/1992 | Nadzan et al. |
| 5,214,197 A | 5/1993 | Hayashi et al. |
| 5,232,929 A | 8/1993 | Desai et al. |
| 5,256,657 A | 10/1993 | Singh et al. |
| 5,268,384 A | 12/1993 | Galardy |
| 5,318,964 A | 6/1994 | Broadhurst et al. |
| 5,332,817 A | 7/1994 | Desai et al. |
| 5,387,610 A | 2/1995 | Gray et al. |
| 5,447,929 A | 9/1995 | Broadhurst et al. |
| 5,453,423 A | 9/1995 | Long et al. |
| 5,453,438 A | 9/1995 | Campion et al. |
| 5,514,677 A | 5/1996 | Davidson et al. |
| 5,521,199 A | 5/1996 | Jacobs et al. |
| 5,532,265 A | 7/1996 | Gijbels et al. |
| 5,536,727 A | 7/1996 | Witzel et al. |
| 5,550,147 A | 8/1996 | Matsuo et al. |
| 5,552,419 A | 9/1996 | MacPherson et al. |
| 5,563,151 A | 10/1996 | Bowles et al. |
| 5,594,106 A | 1/1997 | Black et al. |
| 5,610,162 A | 3/1997 | Witzel et al. |
| 5,614,625 A | 3/1997 | Broadhurst et al. |
| 5,616,605 A | 4/1997 | Gray et al. |
| 5,629,285 A | 5/1997 | Black et al. |
| 5,643,908 A | 7/1997 | Sugimura et al. |
| 5,643,964 A | 7/1997 | Dickens et al. |
| 5,652,262 A | 7/1997 | Crimmin et al. |
| 5,670,136 A | 9/1997 | Bacon et al. |
| 5,670,533 A | 9/1997 | Matsuo et al. |
| 5,691,382 A | 11/1997 | Crimmin et al. |
| 5,696,082 A | 12/1997 | Crimmin et al. |
| 5,700,838 A | 12/1997 | Dickens et al. |
| 5,712,300 A | 1/1998 | Jacobsen |
| 5,741,771 A | 4/1998 | Dawson et al. |
| 5,741,794 A | 4/1998 | Bowles et al. |
| 5,747,514 A | 5/1998 | Beckett et al. |
| 5,753,671 A | 5/1998 | Miller et al. |
| 5,763,621 A | 6/1998 | Beckett et al. |
| 5,821,262 A | 10/1998 | Crimmin et al. |
| 5,834,243 A | 11/1998 | Bogosian |
| 5,840,939 A | 11/1998 | Beckett et al. |
| 5,849,951 A | 12/1998 | Floyd et al. |
| 5,859,253 A | 1/1999 | Beckett et al. |
| 5,861,436 A | 1/1999 | Beckett et al. |
| 5,866,588 A | 2/1999 | Ayscough et al. |
| 5,866,717 A | 2/1999 | Beckett et al. |
| 5,869,518 A | 2/1999 | Bedoya Zurita et al. |
| 5,872,152 A | 2/1999 | Brown et al. |
| 5,879,905 A | 3/1999 | RajBhandary |
| 5,902,791 A | 5/1999 | Beckett et al. |
| 5,908,851 A | 6/1999 | Beckett et al. |
| 5,910,609 A | 6/1999 | Campion et al. |

(List continued on next page.)

FOREIGN PATENT DOCUMENTS

| | | |
|---|---|---|
| AU | 31199/89 | 8/1992 |
| DE | 3320175 | 12/1984 |
| EP | 0 082 088 | 6/1983 |

(List continued on next page.)

OTHER PUBLICATIONS

Bord, et al. *Bone* 23(1): 7–12 (1998).
Chang, et al. *J. Bacteriol.* 171: 4071–4072 (1989).
Cushman, et al. "Specific Inhibitors of Zinc Metallopeptidases." Ch. 5 in *Topics in Molecular Pharmacology* (Burgen & Roberts, eds.), 1981.

(List continued on next page.)

*Primary Examiner*—Taofiq A. Solola
(74) *Attorney, Agent, or Firm*—Morrison & Foerster LLP

(57) ABSTRACT

Novel hydroxamic acid compounds are disclosed. These hydroxamates inhibit peptidyl deformylase (PDF), an enzyme present in prokaryotes. The hydroxymates are useful as antimicrobials and antibiotics. The compounds of the invention display selective inhibition of peptidyl deformylase versus other metalloproteinases such as matrix metalloproteinases (MMPs). Methods of synthesis and of use of the compounds are also disclosed.

48 Claims, No Drawings

U.S. PATENT DOCUMENTS

| | | |
|---|---|---|
| 5,912,360 A | 6/1999 | Dickens |
| 5,917,090 A | 6/1999 | Huxley et al. |
| 5,919,940 A | 7/1999 | Martin |
| 5,932,695 A | 8/1999 | Floyd et al. |
| 5,936,116 A | 8/1999 | Martin et al. |
| 5,962,529 A | 10/1999 | Miller et al. |
| 5,972,980 A | 10/1999 | Cornicelli et al. |
| 5,986,132 A | 11/1999 | Reeve et al. |
| 6,037,472 A | 3/2000 | Castelhano et al. |

FOREIGN PATENT DOCUMENTS

| | | |
|---|---|---|
| EP | 0 214 639 | 9/1987 |
| EP | 0 236 872 | 9/1987 |
| EP | 0 274 453 | 7/1988 |
| EP | 0 334 244 | 9/1989 |
| EP | 0 342 325 | 11/1989 |
| EP | 0 423 943 | 4/1991 |
| EP | 0 489 577 | 6/1992 |
| EP | 0 489 579 | 6/1992 |
| EP | 0 497 192 | 8/1992 |
| EP | 0 177 366 | 12/1992 |
| EP | 0 574 758 | 12/1993 |
| EP | 0 863 152 | 9/1998 |
| EP | 0 863 205 | 9/1998 |
| EP | 0 879 879 | 11/1998 |
| EP | 0 911 409 | 4/1999 |
| EP | 0 949 238 | 10/1999 |
| GB | 1028921 | 5/1966 |
| JP | 56-97266 | 8/1981 |
| JP | 3-53891 | 3/1991 |
| JP | 3-157372 | 7/1991 |
| JP | 5-92948 | 4/1993 |
| JP | 9-003094 | 1/1997 |
| WO | WO 89/10752 | 11/1989 |
| WO | WO 90/05716 | 5/1990 |
| WO | WO 90/05719 | 5/1990 |
| WO | WO 91/02716 | 3/1991 |
| WO | WO 92/13831 | 8/1992 |
| WO | WO 92/22523 | 12/1992 |
| WO | WO 93/09090 | 5/1993 |
| WO | WO 93/09097 | 5/1993 |
| WO | WO 93/20047 | 10/1993 |
| WO | WO 93/24449 | 12/1993 |
| WO | WO 93/24475 | 12/1993 |
| WO | WO 93/25574 | 12/1993 |
| WO | WO 94/02446 | 2/1994 |
| WO | WO 94/02447 | 2/1994 |
| WO | WO 94/07527 | 4/1994 |
| WO | WO 94/10990 | 5/1994 |
| WO | WO 94/21612 | 9/1994 |
| WO | WO 94/25434 | 11/1994 |
| WO | WO 94/25435 | 11/1994 |
| WO | WO 95/06031 | 3/1995 |
| WO | WO 95/29892 | 11/1995 |
| WO | WO 95/32944 | 12/1995 |
| WO | WO 95/33731 | 12/1995 |
| WO | WO 96/16027 | 5/1996 |
| WO | WO 96/25156 | 8/1996 |
| WO | WO 96/26918 | 9/1996 |
| WO | WO 96/33165 | 10/1996 |
| WO | WO 96/33166 | 10/1996 |
| WO | WO 97/30707 | 8/1997 |
| WO | WO 97/32846 | 9/1997 |
| WO | WO 97/38705 | 10/1997 |
| WO | WO 97/49674 | 12/1997 |
| WO | WO 98/03664 | 1/1998 |
| WO | WO 98/17655 | 4/1998 |
| WO | WO 98/18754 | 5/1998 |
| WO | WO 98/33788 | 8/1998 |
| WO | WO 98/24474 | 9/1998 |
| WO | WO 98/38179 | 9/1998 |
| WO | WO 98/46563 | 10/1998 |
| WO | WO 98/52910 | 11/1998 |
| WO | WO 98/55449 | 12/1998 |
| WO | WO 99 02510 | 1/1999 |
| WO | WO 99/39704 | 8/1999 |
| WO | WO 99/59568 | 11/1999 |
| WO | WO 00/04892 | 2/2000 |
| WO | WO 01/10834 | 2/2001 |
| WO | WO 01/44178 | 6/2001 |
| WO | WO 01/44179 | 6/2001 |

OTHER PUBLICATIONS

Durand, et al. *Arch. Biochem. Biophys.* 367(2): 297–302 (1999).

Gearing, et al. *Nature* 370: 555–557 (1994).

Ghose, A.K., et al. "Determination of Pharmacophoric Geometry for Collagenase Inhibitors Using a Novel Computational Method and Its Verification Using Molecular Dynamics, NMR, and X–Ray Crystal." *J. Am Chem. Soc.* 117(16): 4671–4682 (1995).

Hao, et al. *Biochemistry.* 38: 4712–4719 (1999).

Hu, et al. *Bioorg. Med. Chem. Lett.* 8: 2479–2482 (1998).

Inaoka, Y., et al. "Propioxatins A and B, New Enkephalinase B Inhibitors. IV. Characterization of the Active Site of the Enzyme Using Synthetic Propioxatin Analogues." *J. Biochem.* 104(5): 706–711 (1988).

Izquierdo–Martin, et al. *J. Am Chem. Soc.* 114: 325–331 (1992).

Lelievre, Y., et al. "Low molecular weight, sequence based, collagenase inhibitors selectively block the interaction between collagenase and TIMP (tissue inhibitor of metalloproteinases." Chem. Abstracts, vol. 114, No. 11, Mar. 18, 1991.

Liu, et al. *Endocrinology* 140(11): 5330–5338 (1999).

Mazel, D., et al. *Embo J.* 13(4): 914–923 (1994).

McGeehan, et al. *Nature* 370: 558–561 (1994).

Meinnel T., et al. *J. Bacteriol.* 176(23): 7387–7390 (1994).

Meinnel, et al. *J. Mol. Biol.* 262: 375–386 (1996).

Meinnel, et al. *J. Mol. Biol.* 267: 749–791 (1997).

Meinnel, et al. *Biochemistry.* 38(14): 4288–4295 (1999).

Mohler, et al. *Nature.* 370: 218–220 (1994).

Murao, S., et al. "Propioxatin A as Serratia protease inhibitors for treatment of corneal infection." Chem. Abstracts vol. 126, No. 13, Mar. 25, 1997.

Rajagopalan, et al. *J. Am. Chem. Soc.* 119: 12418–12419 (1997).

O'Connell, et al. *J. Biomol. NMR* 13(4): 311–324 (1999).

Tamaki, K., et al. "Synthesis and structure–actve relationships of gelatinase inhibitors derived from matlystatins." *Chemical and Pharmaceutical Bulletin.* 43(11): 1883–1893 (1995).

Vencill, C.F., et al. "Clostridium histolyticum collagenase: development of new thio ester, fluorogenic, and new depsipeptide substrates and new inhibitors." *Biochemistry.* 24(13): 3149–3157 (1985).

Yamagiwa, et al. *Bone* 25(2): 197–203 (1999).

(1989) *Chemical Abstracts* vol. 111, p. 668.

Beckett, R. Paul et al., (Feb. 1993) "A Short Diastereoselective Synthesis of 2,3–Disubstituted Succinates" SYNLETT, pp. 137–138.

Broadhurst, M.J. et al., (1997) Design and Sythesis of the Cartilage Protective Agent (CPA, Ro32–3555) *Bioorganic & Medicinal Chemistry Letters* 7(17): 2299–2302.

Chan, Michael K. et al., (1997) "Crystal Structure of the *Escherichia coli* Peptide Deformylase" *Biochemistry* 36:13904–13909.

Cotter, Cheryl S. et al., (Oct. 1996) "Inhibition of proteases in Psudomonas otitis media in chinchillas" *Otolaryngology–Head and Neck Surgery*, 115(4): 342–351.

Cushman, David W. and Ondetti, Miguel A. (1980) "Chapter 2: Inhibitiors of Angiotensin–Converting Enzyme" in *Progress in Medicinal Chemistry vol. 17*, G. P. Ellis and G.B. West (ed), Elsevier/North–Holland Biomedical Press, pp. 41–104.

Cushman, D. W. et al., (1977) "Design of Potent Competitive Inhibitors of Angiotensin–Converting Enzyme. Carboxyalkanoyl and Mercaptoalkanoyl Amino Acids" *Biochemistry* 16:5484–5491.

Czapski, G. and Goldstein, S. (1990) "Superoxide Scavengers and Sod or Sod Mimics," *Adv. Exper. Med. & Biol.* 264:45–50.

Dardel, Frederic et al. (1998) "Solution Structure of Nickel–Peptide Deformylase" *J. Mol. Biol.* 280:501–513.

Decicco, Carl P. et al., (Jun 1995) "An Improved Asymmetric Synthesis of Piperazic Acids: Retro–Reaction in the Chiral Oxazolidinone Controlled Di–Azo Addition Reaction in a Dopolar Aprotic Medium" *SYNLETT*, pp. 615–616.

Dugger, Robert W. et al., (1992) "A Novel Synthesis of nor–C–Statine" *Tetrahedron Letters* 33(45):6763–6733.

Dupont Merck Pharm. Co. (1996) "Patent Evaluation: Pulmontary–Allergy, Dermatological, Gastrointestinal & Arthrtis: Matrix Metalloproteinase Inhibitors" for WO 95/29892 *Exp. Opin. Ther. Patents* 6(5):499–501.

Foye, W. O. (1981) "Chapter 37: Radioprotective Drugs," *Burgers Med. Chem.* 4th Edition, 3:11, 22, 29–35, 39, 44.

Fujii, Hideji et al., (1996) "Inhibition of Tumor Cell Invasion and Matrix Degradation by Aminopeptidase Inhibitors" *Biol: Pharm. Bull.* 19(1):6–10.

Galardy, Richard E., (1993) "Galardin™; Antiinflammatory Protease Inhibitor" *Drugs of The Future* 18(12):1109–1111.

Giglione, Carmela et al., (2000) "Peptide Deformylase as a Target for New Generation, Broad Spectrum Antimicrobial Agents" *Molecular Microbiology* 36(6):1197–1205.

Gordon, James J. et al., (1975) "Studies concerning the Antibiotic Actinonin. Part I. The Constitution of Actinonin. A Natural Hydroxamic Acid with Antibiotic Activity" *J.C.S. Perkin I*, pp. 819–860.

Haruyama, Hideyuki et al., (Dec. 1994) "Matlystatins, New Inhibitors of Type IV Collagenases from *Actinomadura atramentaria*" *The Journal of Antibiotics* 47(12);1473–1480.

Hu, Yun–Jin et al., (1999) "Determination of Substrate Specificity for Peptide Deformylase through the Screening of a Combinatorial Peptide Library" *Biochemistry* 38:643–650.

Jacobson, Irina C. et al., (1998) "Structure–Based Design and Synthesis of a Series of Hydroxamic Acids with a Quaternary–Hydroxy Group in P1 as Inhibitors of Matrix Metalloproteinases" *Bioorganic & Medicinal Chemistry Letters* 8:837–842.

Jacobson, Irina C. et al., (1996) "Asymmetric Reactions of Chiral Imide Enolates with α–Keto Esters" *Tetrahedron Letters*, 37(46):8263–8266.

Levy, Daniel E. et al., (1998) "Matrix Metalloproteinase Inhibitors: A Structure–Activity Study" *J. Med. Chem.* 41:199–223.

Linderman, Russell, J. et al., (1992) "A Direct Conversion of (α–Hydroxyalkl)silanes to Carboxylic Acids" *Tetrahedron Letters*, 33(45): 6767–6770.

Matsushita, T. and Shorno, T. (1981) "Reactions of Maganses (III) Schiff Base Complexes With Superoxide Ion in Dimethyl Sulfoxide," *Bull. Chem. Soc. Jpn.* 54:3743–3748.

Matsushita, T. et al., (1981) "The Preparation and Characterization of Dichloromanganese (IV) Schiff Base Complexes," *Bull. Chem. Soc. Jpn.* 54(9):2646–2651.

McClure, Kim F. et al., (1998) "Alkylation of Succinates: of RO 32–3555," *Bioorganic & Medicinal Chemistry Letters* 8:143–146.

Meinnel, T. (2000) "Peptide Deformylase of Eukaryotic Protists: A Target for new Antiparasitic Agents?" *Parasitology Today* 16(4):165–168.

Nugiel, David A. et al., (1995) "Probing the P3' Pocket of Stromelysin with Piperazic Acid Analogs" *Bioorganic & Medicinal Chemistry Letters* 5(24): 3053–3056.

Ogita, Takeshi, et al., (1992) "Matlystatins, New Inhibitors of Type IV Collagenases from Actinomadura Atramentaria" *The Journal of Antibiotics* 45(11):1723–1732.

Ragusa, Stephane et al., (1999) "Substrate Recognition and Selectivity of Peptide Deformylase, Similarities and Differences with Metzincins and Thermolsin" *J. Mol. Biol.* 289:1445–1457.

Steinman, Douglas et al., (1998) "The Design, Synthesis, and Structure–Activity Relationships of a Series of Macrocyclic MMP Inhibitors" *Bioorganic & Medicinal Chemistry Letters* 8:2087–2092.

Tamaki, Kazuhiko et al., (Jan. 1995) "Total Synthesis and Inhibitory Activity Relationships of a Gelatinase B of YL–01869P" *The Journal of Antibiotics* 48(1):87–88.

Tamaki, Kazuhiko et al., (Dec. 1994) "Matlystatins, New Inhibitors of Type IV Collagenases from *Actinomadura artamentaria*" *The Journal of Anitbiotics* 47(12):1481–1492.

Tamaki, Kazuhiko et al., (1993) "Synthesis and Determination of the Absolute Configuration of Matlystatin B" *Tetrahedron Letters* 34(4):683–686.

Tamaki, Kazuhiko et al., (1993) "Total Synthesis of Matlystatin A" *Tetrahedron Letters* 34(52):8477–8480.

Tanzawa, Kazuhiko et al., (Nov. 1992) "Matlystatins, New Inhibitors of Type IV Collagenases from *Actinomadura atramentaria*" *The Journal of Antibiotics* 45(11):1733–1737.

SUCCINATE COMPOUNDS, COMPOSITIONS AND METHODS OF USE AND PREPARATION

CROSS-REFERENCE TO RELATED APPLICATIONS

The application claims priority under 35 U.S.C. 119(e) to U.S. Provisional Application Serial No. 60/266,324, which was converted pursuant to 37 C.F.R. § 1.53(b)(2)(ii) from U.S. patent application Ser. No. 09/466,402, filed on Dec. 17, 1999, the disclosure of which is incorporated herein in its entirety.

BACKGROUND OF THE INVENTION

1. Field of the Invention

This invention is directed to novel succinate compounds. This invention is also directed to uses of these compounds in various medicinal applications, including treating disorders amenable to treatment by peptidyl deformylase inhibitors. This invention is still further directed to pharmaceutical compounds comprising these compounds and methods of synthesis thereof.

2. State of the Art

Treatment of microbial infection in host organisms requires an effective means to kill the microbe while doing as little harm to the host as possible. Accordingly, agents which target characteristics unique to a pathology-causing microorganism are desirable for treatment. Penicillin is an extremely well known example of such an agent. Penicillin acts by inhibiting biosynthesis of bacterial cell walls. Since mammalian cells do not require cell walls for survival, administration of penicillin to a human infected with bacteria can kill the bacteria without killing human cells.

However, the use of antibiotics and antimicrobials has also resulted in increased resistance to these agents. As bacteria become resistant to older, more widely used antimicrobial agents, new antimicrobials must be developed in order to provide effective treatments for human and non-human animals suffering from microbial infection.

Peptide deformylase is a metallopeptidase found in prokaryotic organisms such as bacteria. Protein synthesis in prokaryotic organisms begins with N-formyl methionine (fMet). After initiation of protein synthesis, the formyl group is removed by the enzyme peptide deformylase (PDF); this activity is essential for maturation of proteins. It has been shown that PDF is required for bacterial growth (Chang et al. *J. Bacteriol.* 171:4071–4072 (1989); Meinnel T, Blanquet S, *J. Bacteriol.* 176(23):7387–90 (1994); Mazel D et al., *EMBO J.* 13(4):914–23 (1994)). Since protein synthesis in eukaryotic organisms does not depend on fMet for initiation, agents that will inhibit PDF are attractive candidates for development of new antimicrobial and antibacterial drugs. Prokaryotic organisms, including disease-causing prokaryotes, are described in Balows, A., H. G. Truper, M. Dworkin, W. Harder, and K. -H. Schleifer (eds.), *The Prokaryotes,* 2nd ed., New York: Springer-Verlag, 1992; and Holt, J. G. (editor-in-chief). *Bergey's Manual of Systematic Bacteriology,* Vols. 1–4, Baltimore: Williams & Wilkins, 1982, 1986, 1989.

PDF is part of the metalloproteinase superfamily. While PDF clearly shares many of the features which characterize metalloproteinases, it differs from other members of the superfamily in several important respects. First, the metal ion in the active enzyme appears to be Fe (II), or possibly another divalent cationic metal, instead of the zinc ion more commonly encountered. Rajagopalan et al., *J. Am. Chem. Soc.,* 119:12418–19 (1997). Second, the divalent ion appears to play an important role, not only in catalysis, but also in the structural integrity of the protein. Third, the third ligand of the divalent ion is a cysteine, rather than a histidine or a glutamate, as in other metalloproteinases and is not located at the C-terminal side of the HEXXH motif but far away along the amino acid sequence and N-terminal to the motif. Finally, the solution structure shows significant differences in the secondary and tertiary structure of PDF compared to other prototypical metalloproteinases see Meinnel et al. *J. Mol. Biol.* 262:375–386 (1996). PDF from *E. coli, Bacillus stearothermophilus,* and *Thermus thermophilus* have been characterized see Meinnel et al., *J. Mol. Biol.* 267:749–761 (1997). The enzyme studied by Meinnel et al. contained a zinc ion as the divalent ion and the structural features summarized above were obtained from zinc-containing proteins. The structure of the protein has also been determined by NMR (see O'Connell et al., *J. Biomol. NMR* 13(4): 311–24 (1999)).

Metalloproteinases are critical to many aspects of normal metabolism. The class known as matrix metalloproteinases (MMPs) are involved in tissue remodeling, such as degradation of the extracellular matrix. These enzymes are believed to play a role in normal or beneficial biological events such as the formation of the corpus luteum during pregnancy (see Liu et al., *Endocrinology* 140(11):5330–8 (1999)), wound healing (Yamagiwa et al., *Bone* 25(2):197–203 (1999)), and bone growth in healthy children (Bord et al., *Bone* 23(1):7–12 (1998)). Disorders involving metalloproteinases have been implicated in several diseases such as cancer, arthritis, and autoimmune diseases.

Because of the importance of MMPs in normal physiological processes, it would be preferable to develop agents that inhibit PDF, a metalloproteinase present only in prokaryotes, while avoiding significant inhibition of MMPs. Alternatively, PDF inhibitors which also inhibit MMPs can be of use where the therapeutic benefits of inhibiting PDF outweigh the risk of side effects from MMP inhibition.

A wide variety of compounds have been developed as candidate inhibitors of MMPs and other metalloproteinases, and much effort has also been directed at synthetic methods for these compounds and related compounds. See Izquierdo-Martin et al. (1992) *J. Sm. Chem. Soc.* 114:325–331; Cushman et al. (1981) Chapter 5 "*Specific Inhibitors of Zinc Metallopeptidases*" in *Topics in Molecular Pharmacology* (Burgen & Roberts, eds.); Mohler et al. *Nature* 370:218–220 (1994); Gearing et al., *Nature* 370:555–557 (1994); McGeehan et al., *Nature* 370:558–561 (1994); U.S. Pat. Nos. 4,052,511, 4,303,662, 4,311,705, 4,321,383, 4,599,361, 4,804,676, 5,128,346, 5,256,657, 5,268,384, 5,447,929, 5,453,423, 5,552,419, 5,614,625, 5,643,908, 5,712,300, and 5,869,518; European patent publications EP 236872, EP 274453, EP 334244, EP 423943, EP 489577, EP 489579, EP 497192, EP 574758; and International PCT Patent Applications Publication Nos. WO 90/05716, WO 90/05719, WO 91/02716, WO 92/13831, WO 92/22523, WO 93/09090, WO 93/09097, WO 93/20047, WO 93/24449, WO 93/24475, WO 94/02446, WO 94/02447, WO 94/21612, WO 94/25434, WO 94/25435, WO 95/33731, WO 96/25156, WO 96/26918 WO 97/30707, WO 97/49674, WO 98/55449, and WO 99/02510.

Research on inhibitors of PDF is much less extensive than that for inhibitors of MMPs. N-formyl hydroxylamine derivatives are described in International Patent Application WO 99/39704. Peptide aldehyde inhibitors of PDFs are described in Durand et al., *Arch. Biochem. Biophys.*, 367(2): 297–302 (1999). The PDF inhibitor (S)-2-O-(H-phosphonoxy)-L-caproyl-L-leucyl-p-nitroanilide is described in Hao et al., *Biochemistry* 38:4712–4719 (1999), and peptidyl H-phosphonate inhibitors of PDF are discussed in Hu et al., *Bioorg. Med. Chem. Lett.* 8:2479–2482 (1998). Formylated peptides and pseudopeptides are described in Meinnel et al., *Biochemistry* 38(14):4288–4295 (1999) as inhibitors of PDF.

In view of the importance of identifying new antibiotics to treat bacteria resistant to existing antibiotics, and the relatively small amount of work that has been carried out on PDF inhibitors, it is desirable to develop novel inhibitors of PDF for evaluation and use as antibacterial and antimicrobial agents. The present invention fulfills this need.

SUMMARY OF THE INVENTION

In one aspect, this invention is directed to a compound of Formula (I):

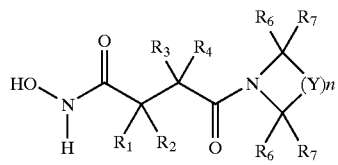

wherein:

$R_1$ is hydrogen, halo, —OH, —$R_8OR_9$, —$R_9$, —$OR_9$, —SH, —$SR_9$, —$NH_2$, —$NHR_9$, —$NR_9R_{10}$, —NHC(=O)H, —$NR_9C$(=O)H, —NHC(=O)$R_9$, —$NR_9C$(=O)$R_{10}$, —NHC(=O)$NH_2$, —$NR_9C$(=O)$NH_2$, —NHC(=O)$NHR_9$, —NHC(=O)$NR_9R_{10}$, —$NR_9C$(=O)$NR_{9a}R_{10}$, —NHC(=O)$OR_9$, —$NR_9C$(=O)$OR_{10}$, —NHS(=O)$_2R_9$, —$NR_9S$(=O)$_2R_{10}$, —NHS(=O)$_2OR_9$, or —$NR_9S$(=O)$_2OR_{10}$ where $R_8$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n1}$—($C_3$–$C_{12}$ arylene or heteroarylene)($C_1$–$C_8$ alkyl or substituted alkyl)$_{n2}$ where n1 and n2 are independently 0 or 1; and $R_9$, $R_{9a}$ and $R_{10}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n3}$—($C_3$–$C_{12}$ arylene or heteroarylene)—($C_1$–$C_8$ alkyl or substituted alkyl)$_{n4}$ where n3 and n4 are independently 0 or 1;

$R_2$ is independently hydrogen or —$R_9$ wherein $R_9$ is as defined above;

$R_3$ is hydrogen, halo, —$R_{11}$, —OH, —$OR_{11}$, —$R_{12}OR_{11}$, —SH, —$SR_{11}$, —$NH_2$, —$NHR_{11}$, —$NR_{11}R_{13}$, —NHC(=O)H, —$NR_{11}C$(=O)H, —NHC(=O)$R_{11}$, —$NR_{11}C$(=O)$R_{13}$, —NHC(=O)$NH_2$, —$NR_{11}C$(=O)$NH_2$, —NHC(=O)$NHR_{11}$, —NHC(=O)$NR_{11}R_{13}$, —$NR_{11}C$(=O)$NR_{11a}R_{13}$, —NHC(=O)$OR_{11}$, —$NR_{11}C$(=O)$OR_{13}$, —NHS(=O)$_2R_{13}$, —$NR_{11}S$(=O)$_2R_{13}$, —NHS(=O)$_2OR_{11}$, or —$NR_{11}S$(=O)$_2OR_{13}$, where $R_{12}$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n5}$—($C_3$–$C_{12}$ arylene or heteroarylene)—($C_1$–$C_8$ alkyl or substituted alkyl)$_{n6}$ where n5 and n6 are independently 0 or 1; and $R_{11}$, $R_{11a}$ and $R_{13}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1;

$R_4$ is hydrogen or —$R_{11}$ where —$R_{11}$ is as defined above;

n is an integer from 1 to 5;

zero or one Y is selected from the group consisting of —O—, —$NR_{11}$— where $R_{11}$ is as defined above, and —S—, and all remaining Y are —$CR_6R_7$— where $R_6$ and $R_7$ are each independently selected from the group consisting of hydrogen, —$R_{14}$, —OH, —$OR_{14}$, —SH, —$SR_{14}$, —$NH_2$, —$NHR_{14}$, —$NR_{14}R_{15}$, —C(=O)H, —C(=O)$R_{14}$, —C(=O)$NH_2$, —C(=O)$NHR_{14}$, —C(=O)$NR_{14}R_{15}$, —C(=O)OH, —C(=O)$OR_{14}$, —C(=O)SH, —C(=O)$SR_{14}$, —C(=O)$CH_3$, —C(=O)$CH_2R_{14}$, —C(=O)$CHR_{14}R_{15}$, —(=O)$CR_{14}R_{15}R_{16}$, —(=O)$OCH_3$, —(=O)$OCH_2R_{14}$, —(=O)$OCHR_{14}R_{15}$, —(=O)$OCR_{14}R_{15}R_{16}$, —S(=O)$_2NH_2$, —S(=O)$_2NHR_{14}$, —S(=O)$_2NR_{14}R_{15}$, —NHC(=O)H, —N($R_{14}$)C(=O)H, —NHC(=O)$R_{15}$, —N($R_{14}$)C(=O)$R_{15}$, —NHC(=O)$OR_{14}$, —NHS(=O)$_2H$, —N($R_{14}$)S(=O)$_2H$, —NHS(=O)$_2OR_{15}$, —N($R_{14}$)S(=O)$_2OR_5$, —N(H)S(=O)$_2R_{15}$, —N($R_{14}$)S(=O)$_2R_{15}$ and where two vicinal $R_6$ or $R_7$ groups combine to form a substituted or unsubstituted —$C_4$–$C_{10}$ cyclic alkyl, cyclic heteroalkyl, aryl or heteroaryl group where $R_{14}$, $R_{15}$ and $R_{16}$ are each independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or when $R_{14}$ and $R_{15}$ are attached to a nitrogen atom they can combine to form a substituted or unsubstituted —$C_4$–$C_{10}$ cyclic alkyl, cyclic heteroalkyl, aryl or heteroaryl group; or a pharmaceutically acceptable salt thereof.

Preferably the compound of Formula (I) inhibits peptidyl deformylase at an $IC_{50}$ of less than or equal to about 100 nm, preferably of less than or equal to 10 nm, more preferably of less than or equal to 1 nm.

Preferably the compound of Formula (I) displays a selectivity for peptidyl deformylase over at least one metalloproteinase selected from the group consisting of ACE and Matrilysin of greater than or equal to about 10 times, more preferably of greater than or equal to about 100 times, still more preferably of greater than or equal to about 1000 times.

In a second aspect, this invention is directed to pharmaceutical compositions comprising a therapeutically effective amount of a compound of Formula (I) or a pharmaceutically acceptable salt thereof and a pharmaceutically acceptable excipient.

In a third aspect, this invention is directed to a method of treatment of a disease in a mammal treatable by administration of a peptidyl deformylase inhibitor which method comprises administration of a therapeutically effective amount of a pharmaceutical composition comprising a therapeutically effective amount of a compound of Formula (I) or a pharmaceutically acceptable salt thereof and a pharmaceutically acceptable excipient either alone or in combination with other pharmacologically active agents. In particular, the compounds of this invention are useful in treating microbial diseases. The microbial infection can be due to bacteria, other prokaryotes, or other organisms, including parasites, dependent on peptide deformylase for growth or survival.

In a fourth aspect, this invention is directed to the use of a compound of Formula (I) or a pharmaceutically acceptable salts thereof in the preparation of a medicament for use in the treatment of diseases mediated by peptidyl deformylase enzyme.

In a fifth aspect, this invention is directed to a method for identifying compounds useful in treating microbial infections, comprising performing an assay to identify compounds which meet the criterion of either i) an $IC_{50}$ for peptide deformylase of less than or equal to about 1 $\mu$M, or ii) an MIC for a disease-causing pathogen of less than or equal to about 32 $\mu$g/ml; performing an assay to identify compounds which meet the criterion of iii) displaying a selectivity for peptide deformylase over at least one metalloproteinase selected from the group consisting of Angiotensin Converting Enzyme (ACE) and Matrilysin of greater than or equal to about 10 times; and selecting compounds which meet either both criteria i) and iii), or both criteria ii) and iii). More preferably, the compounds so identified meet the criterion of either i) an $IC_{50}$ for peptide deformylase of less than or equal to about 100 nM, or ii) an MIC for a disease-causing pathogen of less than or equal to about 10 $\mu$g/ml.

DETAILED DESCRIPTION OF THE INVENTION

Unless otherwise stated, the following terms as used in the specification have the following meaning.

The term "alkyl" refers to saturated aliphatic groups including straight-chain, branched-chain, cyclic groups, and combinations thereof, having the number of carbon atoms specified, or if no number is specified, having 1 to 12 carbon atoms. Examples of alkyl groups include, but are not limited to, groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, cyclobutylmethyl, cyclobutylethyl, cyclopentylmethyl, cyclopentylethyl, and adamantyl. Cyclic alkyl groups can consist of one ring, including, but not limited to, groups such as cycloheptyl, or multiple fused rings, including, but not limited to, groups such as adamantyl or norbomyl.

The term "alkylene" means a saturated divalent aliphatic groups including straight-chain, branched-chain, cyclic groups, and combinations thereof, having the number of carbon atoms specified, or if no number is specified, having 1 to 12 carbon atoms, e.g., methylene, ethylene, 2,2-dimethylethylene, propylene, 2-methyl-propylene, butylene, pentylene, cyclopentylmethylene, and the like.

The term "substituted alkyl" means an alkyl group as defined above that is substituted with one or more substituents, preferably one to three substituents selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to, —$CF_3$, —$CF_2$—$CF_3$, hydroxymethyl, 1- or 2-hydroxyethyl, methoxymethyl, 1- or 2-ethoxyethyl, carboxymethyl, 1- or 2-carboxyethyl, methoxycarbonylmethyl, 1- or 2-methoxycarbonyl ethyl, benzyl, and the like.

The term "substituted alkylene" means an alkylene group as defined above that is substituted with one or more substituents, preferably one to three substituents, selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents selected from the group consisting of halogen (fluoro, chloro, bromo, and iodo, preferably fluoro, chloro, or bromo), alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to, —$CF_2$—, —$CF_2$—$CF_2$—, hydroxymethylene, 1- or 2-hydroxyethylene, methoxymethylene, 1- or 2-ethoxyethylene, carboxymethylene, 1- or 2-carboxyethylene, and the like.

The term "alkenyl" refers to unsaturated aliphatic groups including straight-chain, branched-chain, cyclic groups, and combinations thereof, having the number of carbon atoms specified, or if no number is specified, having 1 to 12 carbon atoms, which contain at least one double bond (—C=C—). Examples of alkenyl groups include, but are not limited to, allyl vinyl, —$CH_2$—CH=CH—$CH_3$, —$CH_2$—$CH_2$-cyclopentenyl and —$CH_2$—$CH_2$-cyclohexenyl where the ethyl group can be attached to the cyclopentenyl, cyclohexenyl moiety at any available carbon valence.

The term "alkenylene" refers to unsaturated divalent aliphatic groups including straight-chain, branched-chain, cyclic groups, and combinations thereof, having the number of carbon atoms specified, or if no number is specified, having 1 to 12 carbon atoms, which contain at least one double bond (—C=C—). Examples of alkenylene groups include, but are not limited to, —CH=CH—, —$CH_2$—CH=CH—$CH_2$—, —$CH_2$—CH(cyclopentenyl)— and the like.

The term "alkynyl" refers to unsaturated aliphatic groups including straight-chain, branched-chain, cyclic groups, and combinations thereof, having the number of carbon atoms specified, or if no number is specified, having 1 to 12 carbon atoms, which contain at least one triple bond (—C≡C—). Examples of alkynyl groups include, but are not limited to, acetylene, 2-butynyl, and the like.

The term "alkynylene" refers to unsaturated divalent aliphatic groups including straight-chain, branched-chain, cyclic groups, and combinations thereof, having the number of carbon atoms specified, or if no number is specified, having 1 to 12 carbon atoms, which contain at least one triple bond (—C≡C—). Examples of alkynylene groups include, but are not limited to, —C≡C—, —C≡C—$CH_2$—, and the like.

The term "substituted alkenyl" or "substituted alkynyl," refers to the alkenyl and alkynyl groups as defined above that are substituted with one or more substituents, selected from the group consisting of halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkenyl and alkynyl groups include, but are not limited to, —CH=CF$_2$, hydroxyethenyl, methoxypropenyl, hydroxypropynyl, and the like.

The term "substituted alkenylene" or "substituted alkynylene," refers to the alkenylene and alkynylene groups as defined above that are substituted with one or more substituents, selected from the group consisting of halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

The term "aryl" or "Ar" refers to an aromatic carbocyclic group of 6 to 14 carbon atoms having a single ring (including, but not limited to, groups such as phenyl) or multiple condensed rings (including, but not limited to, groups such as naphthyl or anthryl), and includes both unsubstituted and substituted aryl groups. Substituted aryl is an aryl group that is substituted with one or more substituents, preferably one to three substituents, selected from the group consisting of alkyl, alkenyl, alkynyl, halogen, alkoxy, acyloxy, amino, mono or dialkylamino, hydroxyl, mercapto, carboxy, benzyloxy, phenyl, aryloxy, benzyl, cyano, nitro, thioalkoxy, carboxaldehyde, carboalkoxy and carboxamide, or a functionality that can be suitably blocked, if necessary for purposes of the invention, with a protecting group.

Representative examples include, but are not limited to, naphthyl, phenyl, chlorophenyl, iodophenyl, methoxyphenyl, carboxyphenyl, and the like.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "thioalkoxy" means a radical —SR where R is an alkyl as defined above e.g., methylthio, ethylthio, propylthio, butylthio, and the like.

The term "mono and "dialkylamino" means a radical —NHR and —NRR' respectively where R and R' independently represent an alkyl group as defined herein. Representative examples include, but are not limited to dimethylamino, methylethylamino, di(1-methylethyl)amino, (cyclohexyl)(methyl)amino, (cyclohexyl)(ethyl)amino, (cyclohexyl)(propyl)amino, (cyclohexylmethyl)(methyl)-amino, (cyclohexylmethyl)(ethyl)amino, and the like.

The term "acyloxy" means a radical —OC(O)R, where R is hydrogen, alkyl, aryl, heteroaryl or substituted alkyl wherein alkyl, aryl, heteroaryl, and substituted alkyl are as defined herein. Representative examples include, but are not limited to formyl, acetyloxy, cylcohexylcarbonyloxy, cyclohexylmethylcarbonyloxy, benzoyloxy, benzylcarbonyloxy, and the like.

The term "heteroalkyl," "heteroalkenyl," and "heteroalkynyl" refers to alkyl, alkenyl, and alkynyl groups respectively as defined above, that contain the number of carbon atoms specified (or if no number is specified, having 1 to 12 carbon atoms) which contain one or more heteroatoms, preferably one to three heteroatoms, as part of the main, branched, or cyclic chains in the group. Heteroatoms are independently selected from the group consisting of —NR—, —NRR, (where each R is hydrogen or alkyl), —S—, —O—, —SR (R is hydrogen or alkyl), —OR (R is hydrogen or alkyl), and P; preferably —NR where R is hydrogen or alkyl and/or O. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$, —CH$_2$—CH$_2$—NH—CH$_2$—CH$_3$, 1-ethyl-6-propylpiperidino, 2-ethylthiophenyl, piperazino, pyrrolidino, piperidino, morpholino, and the like. Examples of heteroalkenyl groups include, but are not limited to, groups such as —CH=CH—NH—CH(CH$_3$)—CH$_3$, and the like.

The term "carboxaldehyde" means —CHO.

The term "carboalkoxy" means —C(O)OR where R is alkyl as defined above and include groups such as methoxycarbonyl, ethoxycarbonyl, and the like.

The term "carboxamide" means —C(O)NHR or C(O)NRR' where R and R' are independently hydrogen or alkyl as defined above. Representative examples include groups such as aminocarbonyl, methylaminocarbonyl, dimethylaminocarbonyl, and the like.

The term "heteroaryl" or "HetAr" refers to an aromatic carbocyclic group of 3 to 9 ring atoms forming a single ring and having at least one hetero atom, preferably one to three heteroatoms including, but not limited to, heteroatoms such as N, O, P, or S, within the ring. Representative examples include, but are not limited to single ring such as imidazolyl, pyrazolyl, pyrazinyl, pyridazinyl, pyrimidinyl, pyrrolyl, pyridyl, thiophene, and the like, or multiple condensed rings such as indolyl, quinoline, quinazoline, benzimidazolyl, indolizinyl, benzothienyl, and the like.

The heteroalkyl, heteroalkenyl, heteroalkynyl and heteroaryl groups can be unsubstituted or substituted with one or more substituents, preferably one to three substituents, selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, pyrrolidine, morpholine, or piperidine, substituted at a nitrogen or carbon by a phenyl or benzyl group, and attached to the remainder of the molecule by any available valence on a carbon or nitrogen, —NH—SO$_2$-phenyl, —NH—(C=O)O-alkyl, —NH—(C=O)O-alkyl-aryl, and the like. The heteroatom(s) as well as the carbon atoms of the group can be substituted. The heteroatom(s) can also be in oxidized form.

The term "heteroarylene" refers to the diradical group derived from heteroaryl (including substituted heteroaryl), as defined above, and is exemplified by the groups 2,6-pyridylene, 2,4-pyridinylene, 1,2-quinolinylene, 1,8-quinolinylene, 1,4-benzofuranylene, 2,5-pyridnylene, 2,5-indolenyl, and the like.

The term "heteroalkylene", "heteroalkenylene", and "heteroalkynylene" refers to the diradical group derived from heteroalkyl, heteroalkenyl, and heteroalkynyl (including substituted heteroalkyl, heteroalkenyl, and heteroalkynyl), as defined above.

The term "alkylaryl" refers to an alkyl group having the number of carbon atoms designated, appended to one, two, or three aryl groups.

The term "alkoxy" as used herein refers to an alkyl, alkenyl, or alkynyl linked to an oxygen atom and having the number of carbon atoms specified, or if no number is specified, having 1 to 12 carbon atoms. Examples of alkoxy groups include, but are not limited to, groups such as methoxy, ethoxy, tert-butoxy, and allyloxy.

The term "aryloxy" as used herein refers to an aryl group linked to an oxygen atom at one of the ring carbons. Examples of alkoxy groups include, but are not limited to, groups such as phenoxy, 2-, 3-, or 4-methylphenoxy, and the like.

The term "halogen" as used herein refer to Cl, Br, F or I substituents, preferably fluoro or chloro.

The term "—$(C_1-C_{12})$ alkyl, substituted alkyl, or heteroalkyl" means an alkyl, substituted alkyl or heteroalkyl group respectively as defined above and having 1 to 12 carbon atoms. For example, when $R_1$ is —$(C_1-C_{12})$ alkyl, substituted alkyl, or heteroalkyl it means that $R_1$ can be —$(C_1-C_{12})$ alkyl or —$(C_1-C_{12})$substituted alkyl, or —$(C_1-C_{12})$heteroalkyl.

The term "—$(C_1-C_{12})$ alkenyl, substituted alkenyl, or heteroalkenyl" means an alkenyl, substituted alkenyl, or heteroalkenyl group as defined above and having 1 to 12 carbon atoms.

The "—$(C_1-C_{12})$ alkynyl, substituted alkynyl, or heteroalkynyl" means an alkynyl, substituted alkynyl, or heteroalkynyl group as defined above and having 1 to 12 carbon atoms.

The term "—$(C_1-C_{12})$ alkylene, substituted alkylene, or heteroalkylene" means an alkylene, substituted alkylene, or heteroalkylene group as defined above and having1 to 12 carbon atoms.

The term "—$(C_1-C_{12})$ alkenylene, substituted alkenylene, or heteroalkenylene" means that the alkenylene, substituted alkenylene, or heteroalkenylene group as defined above and having 1 to 12 carbon atoms.

The term "—$(C_1-C_{12})$ alkynylene, substituted alkynylene, or heteroalkynylene" means an alkynylene, substituted alkynylene, or heteroalkynylene group as defined above and having 1 to 12 carbon atoms.

The term "and —$(C_1-C_8$ alkylene or substituted alkylene)$_{n5}$—$(C_3-C_{12}$ arylene or heteroarylene)—$(C_1-C_8$ alkyl or substituted alkyl)$_{n6}$ where n5 and n6 are independently 0 or 1" means that "when n5 and/or n6 are 0 then —$(C_1-C_8$ alkylene or substituted alkylene)$_{n5}$ and/or —$(C_1-C_8$ alkylene or substituted alkylene)$_{n6}$" are a covalent bond or when n5 and/or n6 are 1, then the alkylene or substituted alkylene group is present and can have 1 to 8 carbon atoms. The term —$(C_3-C_{12}$ arylene or heteroarylene)—means that the arylene has 6 to 12 carbon atoms (e.g., phenylene, naphtylene, and the like) and heteroarylene groups have 3 to 12 carbons atoms and additionally contain one to three heteroatoms including, but not limited to, heteroatoms such as N, O, P, or S, within the ring (e.g., 2,6-pyridylene, 2,4-pyridinylene, 1,2-quinolinylene, 1,8-quinolinylene, 1,4-benzofuranylene, 2,5-pyridylene, 2,5-indolenyl, and the like) in accordance with the definition of the heteroarylene above. Additionally, it will be recognized by a person skilled in the art that when "—$(C_1-C_8$ alkylene or substituted alkylene)—" and "—$(C_1-C_8$ alkyl or substituted alkyl)—" are a covalent bond then —$(C_3-C_{12}$ arylene or heteroarylene)— is an aryl or heteroaryl group as defined above.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis*, 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDIMS), 9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include Fmoc, TBDIMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy-methyloxycarbonyl).

"Inhibitor" refers to a compound that interferes with the interaction between a target and its respective substrate(s) or endogenous ligand(s). Target molecules include, but are not limited to, enzymes and receptors. Enzyme inhibitors have been extensively studied from kinetic and mechanistic standpoints; see, e.g., Fersht, A., *Enzyme Structure and Mechanism*, 2nd Ed., New York, W. H. Freeman, 1985. A useful measure of the effectiveness of a compound at inhibiting enzyme catalysis is the $IC_{50}$ of that compound. The $IC_{50}$ of a compound can determined by the equation $$y=y_o/(1+[In]/IC_{50})$$

where y is the measured reaction velocity, $y_o$ is the reaction velocity in the absence of inhibitor, and [In] is the inhibitor concentration. Solving this equation at the inhibitor concentration [In] when $y=y_o/2$ yields $IC_{50}$ of the inhibitor for the enzyme under study. Useful inhibitors have an $IC_{50}$ equal to or less than about 10 TM, preferably equal to or less than about 1 TM. More preferably, the inhibitor has an $IC_{50}$ equal to or less than about 100 nM, still more preferably equal to or less than about 10 nM, even more preferably equal to or less than about 1 nM. Most preferably, inhibitors have an $IC_{50}$ equal to or less than about 100 pM, or equal to or less than about 10 pM.

A selective inhibitor refers to an inhibitor that will inhibit the activity of one macromolecule, typically an enzyme, while exhibiting little or no inhibitory effect on another macromolecule, typically another enzyme. The compounds of the invention are particularly useful in that they display selective inhibition of peptidyl deformylase while exhibiting much lower inhibitory activity towards metalloproteinases such as matrilysin. The selectivity of an enzyme inhibitor can be indicated by dividing the $IC_{50}$ of the compound for the enzyme which is not intended to be inhibited, by the $IC_{50}$ of the compound for the enzyme which is intended to be inhibited. Thus, if a compound has an $IC_{50}$ for matrilysin of 1 µM, and an $IC_{50}$ for peptidyl deformylase of 0.01 µM, the compound displays a 100-fold (or 100 times) selectivity for peptidyl deformylase over matrilysin, or alternatively is said to be 100 times more selective for peptidyl deformylase compared to matrilysin. Useful compounds display a selectivity of greater than or equal to about 10 times, preferably greater than or equal to about 100 times, more preferably greater than or equal to about 1000 times, still more preferably greater than or equal to about 10,000, for peptidyl deformylase over one or more other metalloproteinases, for example for peptidyl deformylase over matrilysin.

The compounds of the invention are intended for use in eukaryotic animals. Preferably, the animal is a vertebrate; more preferably, the animal is a mammal; most preferably, the animal is a human.

By "hydroxamic acid derivative," "hydroxamic acid derivative compound," "hydroxamic acid compound," "hydroxamate derivative," "hydroxamate derivative compound," or "hydroxamate compound" is meant any compound containing the functional group HN(OH)—C(=O)—.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. For example, if the $R_6$ substituent in a compound of Formula (I) is 2-hydroxyethyl, then the carbon to which the hydroxy group is attached is an asymmetric center and therefore the compound of Formula (I) can exist as an (R)- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A compound of Formula (I) may act as a pro-drug. Prodrug means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

PREFERRED EMBODIMENTS

While the broadest definition of this invention is set forth in the Summary of the Invention, certain compounds of Formula (I) are preferred. For example, (A) (i) A preferred group of compounds is that wherein $R_1$ is hydrogen or hydroxy, preferably hydroxy. The stereochemistry at the carbon carrying the $R_1$ group is (R) or (S).

(ii) Another preferred group of compounds is that wherein $R_1$ is halo; preferably chloro or fluoro; more preferably fluoro. The stereochemistry at the carbon carrying the $R_1$ group is (R) or (S), preferably (S) when $R_1$ is fluoro. Within the above preferred groups, a more preferred group of compounds is that wherein $R_2$ and $R_4$ are hydrogen.

(iii) Yet another preferred group of compounds is that wherein $R_3$ is hydrogen or $R_{11}$ where $R_{11}$ is —$C_1$–$C_{12}$ alkyl or —$(C_1$–$C_8$ alkylene$)_{n7}$—$(C_3$–$C_{12}$ aryl or heteroaryl), preferably methyl, ethyl, n-propyl, iso-propyl, n-butyl, iso-butyl, tert-butyl, n-pentyl, iso-pentyl, neo-pentyl, n-hexyl, 2-, 3-, 4-, or 5-methylpentyl, 4,4-dimethylbutyl, benzyl, 3-phenylpropyl, 2-phenylethyl, or 4-phenylbutyl, more preferably n-butyl. The stereochemistry at the carbon carrying the $R_3$ group is (R) or (S), preferably (R).

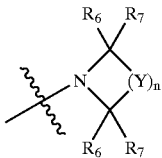

(iv) Yet another preferred group of compounds is that wherein the group is a group of formula:

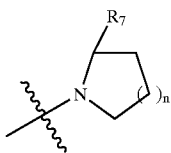

wherein:
n is 1 or 2, preferably 1; and
$R_7$ is:

(a) —C(=O)NR$_{14}$R$_{15}$ where $R_{14}$ and $R_{15}$ are independently selected from the group consisting of hydrogen, —$(C_1$–$C_{12})$ alkyl, substituted alkyl, or heteroalkyl, —$(C_1$–$C_{12})$ alkenyl, substituted alkenyl, or heteroalkenyl, —$(C_1$–$C_{12})$ alkynyl, substituted alkynyl, or heteroalkynyl, alkoxy, and —$(C_1$–$C_8$ alkyl or substituted alkyl$)_{n9}$—$(C_3$–$C_{12}$ arylene or heteroarylene)—$(C_1$–$C_8$ alkyl or substituted alkyl$)_{n10}$ where n9 and n10 are independently 0 or 1; or $R_{14}$ and $R_{15}$ combine to form a substituted or unsubstituted —$(C_4$–$C_{10})$cyclic alkyl, cyclic heteroalkyl, aryl or heteroaryl group.

Preferably, $R_7$ is —C(=O)NR$_{14}$R$_{15}$ where $R_{14}$ and $R_{15}$ are each independently hydrogen or —$(C_1$–$C_{12})$ alkyl, alkoxy, aryl, heteroaryl or $R_{14}$ and $R_{15}$, when attached to the same carbon, combine to form a cyclic heteroalkyl, aryl or heteroaryl group.

More preferably, $R_7$ is —C(=O)NHR$_{15}$ where $R_{15}$ is H Or —$(C_1$–$C_{12})$ alkyl, aryl, or heteroaryl or —C(=O) NR$_{14}$R$_{15}$ and $R_{14}$ where $R_{15}$ form a substituted or unsubstituted —$(C_4$–$C_{10})$cyclic heteroalkyl.

Even more preferably $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenyl-aminocarbonyl, cyclopropylmethyl-aminocarbonyl, pyridin-2-ylaminocarbonyl, pyridin-3-ylaminocarbonyl, pyridin-4-ylmethylaminocarbonyl, morpholin-4-ylcarbonyl, 3,4-methylenedioxy-phenylaminocarbonyl, quinolin-3-ylaminocarbonyl, methylaminocarbonyl, 4-biphenylaminocarbonyl, 3-phenoxyphenylamino-carbonyl, 3,4-dichlorophenyl-aminocarbonyl, 4-tert-butylphenylaminocarbonyl, 4-tert-butylaminocarbonyl, indan-2-ylaminocarbonyl, 2,2-dimethylpropyl-aminocarbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenyl-aminocarbonyl, 2,5-dimethylphenylaminocarbonyl, 2,5-dimethoxyphenyl-aminocarbonyl, 3,4-dichlorophenyl- aminocarbonyl, benzthiazol-2-ylaminocarbonyl, 3-phenoxyphenylamino-carbonyl, 2-hydroxybutylamino- carbonyl, 4-hydroxybutyl-aminocarbonyl, 1,4-benzodioxan-6-ylaminocarbonyl, isoquinolin-6-ylaminocarbonyl, methylaminocarbonyl, thiazol-2-yl-aminocarbonyl, 4-methylthiazol-2-yl-aminocarbonyl, 3-methylbutyl-aminocarbonyl, n-pentylaminocarbonyl, cyclohexylaminocarbonyl, 5-methyltbiazol-2-ylaminocarbonyl, 4-methylthiazol-2-yl-aminocarbonyl, 2,4-dimethoxyphenyl-aminocarbonyl, 3,4-methylene- dioxyphen-5-ylmethylaminocarbonyl, allylaminocarbonyl, 2-methylallylaminocarbonyl, pyrrolidin-1-ylcarbonyl, ethylaminocarbonyl, phenylaminocarbonyl, indan-1-ylaminocarbonyl, 2-methoxyethylaminocarbonyl, indan-5-yl-aminocarbonyl, 3,4-difluorophenyl-aminocarbonyl, 5-methylisoxazol-5-ylaminocarbonyl, 3-fluorophenyl- aminocarbonyl, 4-fluorophenylaminocarbonyl, N-methyl-N-phenylaminocarbonyl, 2-propylaminocarbonyl, 2-phenylpropylaminocarbonyl, n-propylaminocarbonyl, N-ethyl-N-(n-butyl)aminocarbonyl, benzylaminocarbonyl, thiazolidin-1-ylcarbonyl, piperazin-1-yl-carbonyl, piperidin-1-ylcarbonyl, azetidin-1-ylcarbonyl, homopiperdin-1-ylcarbonyl, pyrimidin-2-ylaminocarbonyl, 4-methylpiperazin-1-ylcarbonyl, 4-methylpyrimidin-2-ylaminocarbonyl, pyrimidin-4-ylaminocarbonyl, pyrazin-2-ylaminocarbonyl, imidazol-2-ylaminocarbonyl.

In particular, $R_7$ is piperidin-1-ylcarbonyl, azetidin-1-ylcarbonyl, ethylaminocarbonyl, phenylaminocarbonyl, pyrimidin-2-ylaminocarbonyl, or thiazol-2-ylaminocarbonyl.

More particularly, $R_7$ is piperidin-1-ylcarbonyl, azetidin-1-ylcarbonyl, ethylaminocarbonyl or thiazol-2-ylaminocarbonyl. The stereochemistry at the C2 carbon atom of the pyrrolidine ring, i.e., carbon carrying the $R_7$ group is either (R) or (S), preferably (S); or (b) $R_7$ is —NHC(=O)OR$_{14}$ where $R_{14}$ is hydrogen, —$(C_1$–$C_{12})$ alkyl, substituted alkyl, or heteroalkyl, —$(C_1$–$C_{12})$ alkenyl, substituted alkenyl, or heteroalkenyl, —$(C_1$–$C_{12})$ alkynyl, substituted alkynyl, or heteroalkynyl, alkoxy, or —$(C_1$–$C_8$ alkyl or substituted alkyl$)_{n9}$—$(C_3$–$C_{12}$ arylene or heteroarylene)—$(C_1$–$C_8$ alkyl or substituted alkyl$)_{n10}$ where n9 and n10 are independently 0 or 1.

Preferably, $R_7$ is —NHC(=O)OR$_{14}$ where $R_{14}$ is hydrogen or —$(C_1$–$C_{12})$ alkyl, alkoxy, aryl, heteroaryl; or (c) $R_7$ is —C(=O)OR$_{14}$ where $R_{14}$ is hydrogen, —$(C_1$–$C_{12})$ alkyl, substituted alkyl, or heteroalkyl, —$(C_1$–$C_{12})$ alkenyl, substituted alkenyl, or heteroalkenyl, —$(C_1$–$C_{12})$ alkynyl, substituted alkynyl, or heteroalkynyl, alkoxy, or —$(C_1$–$C_8$ alkyl or substituted alkyl$)_{n9}$—$(C_3$–$C_{12}$ arylene or heteroarylene)—$(C_1$–$C_8$ alkyl or substituted alkyl$)_{n10}$ where n9 and n 10 are independently 0 or 1.

Preferably, $R_7$ is —C(=O)OR$_{17}$ where $R_{14}$ is hydrogen or —$(C_1$–$C_{12})$ alkyl, alkoxy, aryl, or heteroaryl.

More preferably, —C(=O)OR$_{14}$ where $R_{14}$ is alkyl, even more preferably $R_7$ is tert-butoxycarbonyl. The stereochemistry at the $C_2$ carbon atom of the pyrrolidine ring, i.e., carbon carrying the $R_7$ group is either (R) or (S), preferably (S).

The above defined embodiments of (i)–(iv) are employed either singularly or in any combination.

(B) Another preferred group of compounds is represented as Formula (IIa):

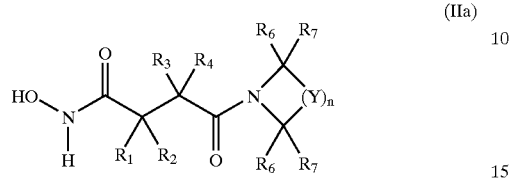

(IIa)

wherein:

$R_1$ is —OH, —$OR_9$, —$R_8OR_9$, —SH, —$SR_9$, —$NH_2$, —$NHR_9$ —$NR_9R_{10}$, —NHC(=O)H, —$NR_9$C(=O)H, —NHC(=O)$R_9$, —$NR_9$C(=O)$R_{10}$, —NHC(=O) $NH_2$, —$NR_9$C(=O)$NH_2$, —NHC(=O)$NHR_9$, —NHC (=O)$NR_9R_{10}$, $NR_9$C(=O)$NR_{9a}R_{10}$, —NHC(=O) $OR_9$, —$NR_9$C(=O)$OR_{10}$, —NHS(=O)$_2R_9$, —$NR_9$S (=O)$_2R_{10}$, —NHS(=O)$_2OR_9$, or —$NR_9$S(=O)$_2OR_{10}$ where $R_9$ is selected from the group consisting of —$C_1$–$C_{12}$ alkylene, —$C_1$–$C_{12}$ alkenylene, and —$C_1$–$C_{12}$ alkynylene and $R_9$, $R_{9a}$ and $R_{10}$ are independently selected from the group consisting of —$C_1$–$C_{12}$ alkyl, —$C_1$–$C_{12}$ alkenyl, and —$C_1$–$C_{12}$ alkynyl;

$R_2$ is hydrogen or —$R_9$ where $R_9$ is as defined above;

$R_3$ is —$R_{11}$, —OH, —$OR_{11}$, —$R_{12}OR_{11}$, —SH, —$SR_{11}$, —$NH_2$, —$NHR_{11}$ —$NR_{11}R_{13}$, —NHC(=O)H, —$NR_{11}$C(=O)H, —NHC(=O)$R_{11}$, —$NR_{11}$C(=O) $R_{13}$, —NHC(=O)$NH_2$, —$NR_{11}$C(=O)$NH_2$, —NHC (=O)$NHR_{11}$, —NHC(=O)$NR_{11}R_{13}$, —$NR_{11}$C(=O) $NR_{11a}R_{13}$, —NHC(=O)$OR_{11}$, —$NR_{11}$C(=O)$OR_{13}$, —NHS(=O)$_2R_{11}$, —$NR_{11}$S(=O)$_2R_{13}$, —NHS(=O)$_2$ $OR_{11}$, or —$NR_{11}$S(=O)$_2OR_{13}$, where $R_{12}$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n5}$—($C_3$–$C_{12}$ arylene or heteroarylene)—($C_1$–$C_8$ alkyl or substituted alkyl)$_{n6}$ where n5 and n6 are independently 0 or 1; and $R_{11}$, $R_{11a}$, and $R_{13}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1;

$R_4$ is hydrogen or $R_{11}$ where $R_{11}$ is as defined above;

n is an integer from 1 to 5;

zero or one Y is selected from the group consisting of —O—, —$NR_{11}$— where $R_{11}$ is as defined above, and —S—, and all remaining Y are —$CR_6R_7$— where $R_6$ and $R_7$ are each independently selected from the group consisting of hydrogen, —$R_{14}$, —OH, —$OR_{14}$, —SH, —$SR_{14}$, —$NH_2$, —$NHR_{14}$, —$NR_{14}R_{15}$, —(=O)H, —(=O)$R_{14}$, —(=O)$NH_2$, —(=O)$NHR_{14}$, —C(=O)$NR_{14}R_{15}$, —C(=O)OH, —C(=O)$OR_{14}$, —C(=O)SH, —C(=O)$SR_{14}$, —C(=O)$CH_3$, —C(=O)$CH_2R_{14}$, —C(=O)$CHR_{14}R_{15}$, —C(=O) $CR_{14}R_{15}R_{16}$, —C(=O)$OCH_3$, —C(=O)$OCH_2R_{14}$, —C(=O)$OCHR_{14}R_{15}$, —C(=O)$OCR_{14}R_{15}R_{16}$, —S(=O)$_2NH_2$, —S(=O)$_2NHR_{14}$, —S(=O)$_2$ $NR_{14}R_5$, —NHC(=O)H, —N($R_{14}$)C(=O)H, —NHC (=O)$R_{15}$, —N($R_{14}$)C(=O)$R_{15}$, —NHS(=O)$_2$H, —N($R_{14}$)S(=O)$_2$H, —NHS(=O)$_2OR_{15}$, —N($R_{14}$)S (=O)$_2OR_{15}$, —N(H)S(=O)$_2R_{15}$, —N($R_{14}$)S(=O)$_2$ $R_{15}$ and where two vicinal $R_6$ or $R_7$ groups combine to form a substituted or unsubstituted $C_4$–$C_{10}$ cyclic alkyl, cyclic heteroalkyl, aryl or heteroaryl group; where $R_{14}$, $R_{15}$ and $R_{16}$ are each independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or a pharmaceutically acceptable salt thereof.

Within this group of compounds (IIa), a preferred group of compounds is that wherein the embodiments of (i)–(iv) defined below are employed either singularly or in any combination:

(i) A preferred group of compounds is that wherein $R_1$ is hydrogen or hydroxy and the stereochemistry at the carbon carrying the $R_1$ group is (R) or (S), preferably (S).

(ii) Another preferred group of compounds is that wherein $R_2$ and $R_4$ are hydrogen.

(iii) Another preferred group of compounds is that wherein $R_3$ is hydrogen or $R_9$ where $R_9$ is —$C_1$–$C_{12}$ alkyl or —($C_1$–$C_8$ alkylene)$_{n7}$—($C_3$–$C_{12}$ aryl or heteroaryl) where n7, preferably methyl, ethyl, n-propyl, iso-propyl, n-butyl, iso-butyl, tert-butyl, n-pentyl, iso-pentyl, neo-pentyl, n-hexyl, 2-, 3-, 4-, or 5-methylpentyl, 4,4-dimethylbutyl, benzyl, 3-phenylpropyl, 2-phenylethyl, or 4-phenylbutyl, more preferably n-butyl. The stereochemistry at the carbon carrying the $R_3$ group is (R) or (S), preferably (R).

(iv) Another preferred group of compounds is that wherein the

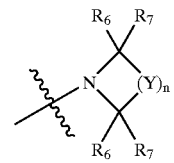

group is a group of formula:

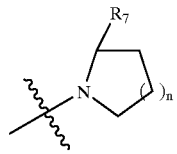

wherein:

n is 1 or 2, preferably 1; and $R_7$ is:

(a) —C(=O)$NR_{14}R_{15}$ where $R_{14}$ and $R_{15}$ are independently selected from the group consisting of hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1.

Preferably, $R_7$ is —C(=O)$NR_{14}R_{15}$ where $R_{14}$ and $R_{15}$ are each independently hydrogen or —($C_1$–$C_{12}$) alkyl, alkoxy, aryl, heteroaryl. More preferably, $R_7$ is —C(=O)$NHR_{15}$ where $R_{15}$ is H or —($C_1$–$C_{12}$) alkyl, aryl, or heteroaryl.

Even more preferably $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenyl-aminocarbonyl, cyclopropylmethylaminocarbonyl, pyridin-2-ylaminocarbonyl, pyridin-3-ylaminocarbonyl, pyridin-4-ylmethylaminocarbonyl, 3,4-methylenedioxyphenyl-aminocarbonyl, quinolin-3-ylaminocarbonyl, methylaminocarbonyl, 4-biphenylaminocarbonyl, 3-phenoxyphenylaminocarbonyl, 3,4-dichlorophenyl-aminocarbonyl, 4-tert-butylphenylaminocarbonyl, 4-tert-butylaminocarbonyl, indan-2-ylaminocarbonyl, 2,2-dimethylpropylaminocarbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenylaminocarbonyl, 2,5-dimethylphenylaminocarbonyl, 2,5-dimethoxyphenyl-amino-arbonyl, 3,4-dichlorophenylaminocarbonyl, benzthiazol-2-ylaminocarbonyl, 3-phenoxyphenylamino-carbonyl, 2-hydroxybutylaminocarbonyl, 4-hydroxybutylaminocarbonyl, 1,4-benzodioxan-6-ylaminocarbonyl, isoquinolin-6-ylaminocarbonyl, methylaminocarbonyl, thiazol-2-ylaminocarbonyl, 4-methylthiazol-2-yl-aminocarbonyl, 3-methylbutylamino-carbonyl, n-pentylaminocarbonyl, cyclohexylamino-carbonyl, 5-methylthiazol-2-ylaminocarbonyl, 4-methylthiazol-2-ylaminocarbonyl, 2,4-dimethoxyphenylaminocarbonyl, 3,4-methylenedioxyphen-5-ylmethylaminocarbonyl, allylaminocarbonyl, 2-methylallylaminocarbonyl, ethylaminocarbonyl, phenylaminocarbonyl, indan-1-ylaminocarbonyl, 2-methoxyethylaminocarbonyl, indan-5-ylaminocarbonyl, 3,4-difluorophenylaminocarbonyl, 5-methylisoxazol-5-ylaminocarbonyl, 3-fluorophenylaminocarbonyl, 4-fluorophenylaminocarbonyl, N-methyl-N-phenylaminocarbonyl, 2-propylaminocarbonyl, 2-phenylpropylaminocarbonyl, n-propylaminocarbonyl, N-ethyl-N-(n-butyl)aminocarbonyl, benzylaminocarbonyl, thiazolidin-1-ylcarbonyl, pyrimidin-2-ylaminocarbonyl, 4-methylpyrimidin-2-ylaminocarbonyl, pyrimidin-4-ylaminocarbonyl, pyrazin-2-ylaminocarbonyl, imidazol-2-ylaminocarbonyl.

In particular, $R_7$ is ethylaminocarbonyl, phenylaminocarbonyl, pyrimidin-2-ylaminocarbonyl, or thiazol-2-ylaminocarbonyl. More particularly, $R_7$ is phenylaminocarbonyl or pyrimidin-2-ylaminocarbonyl. The stereochemistry at the C2 carbon atom of the pyrrolidine ring, i.e., carbon carrying the $R_7$ group is either (R) or (S), preferably (S); or (b) —NHC(=O)$OR_{14}$ where $R_{14}$ is hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1. Preferably, $R_7$ is —NHC(=O)$OR_{14}$ where $R_{14}$ is hydrogen or —($C_1$–$C_{12}$) alkyl, alkoxy, aryl, heteroaryl; or (c) —C(=O)$OR_{14}$ where $R_{14}$ is hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1. Preferably, $R_7$ is —C(=O)$OR_{14}$ where $R_{14}$ is hydrogen or —($C_1$–$C_{12}$) alkyl, alkoxy, aryl, or heteroaryl. More preferably, —C(=O)$OR_{14}$ where $R_{14}$ is alkyl, even more preferably $R_7$ is tert-butoxycarbonyl. The stereochemistry at the C2 carbon atom of the pyrrolidine ring, i.e., carbon carrying the $R_7$ group is either (R) or (S), preferably (S).

(C) Another preferred group of compounds is represented by Formula (IIb):

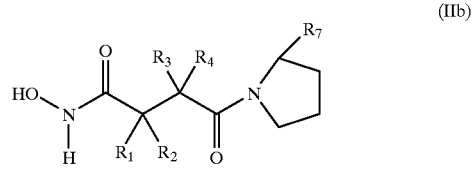

(IIb)

wherein:

$R_1$ is —$R_9$, —OH, —$OR_9$, —$R_8OR_9$, —SH, —$SR_9$, —$NH_2$, —$NHR_9$, —$NR_9R_{10}$, —NHC(=O)H, —$NR_9$C(=O)H, —NHC(=O)$R_9$, —$NR_9$C(=O)$R_{10}$, —NHC(=O)$NH_2$, —$NR_9$C(=O)$NH_2$, —NHC(=O)$NHR_9$, —NHC(=O)$NR_9R_{10}$, —$NR_9$C(=O)$NR_{9a}R_{10}$, —NHC(=O)$OR_9$, —$NR_9$C(=O)$OR_{10}$, —NHS(=O)$_2R_9$, —$NR_9$S(=O)$_2R_{10}$, —NHS(=O)$_2OR_9$, or —$NR_9$S(=O)$_2OR_{10}$ where $R_8$ is selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n1}$—($C_3$–$C_{12}$ arylene or heteroarylene)—($C_1$–$C_8$ alkyl or substituted alkyl)$_{n2}$ where n1 and n2 are independently 0 or 1; and $R_9$, $R_{9a}$, and $R_{10}$ are each independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n3}$—($C_3$–$C_{12}$ arylene or heteroarylene)—($C_1$–$C_8$ alkyl or substituted alkyl)$_{n4}$ where n3 and n4 are independently 0 or 1;

$R_2$ is —H or —$R_9$ where $R_9$ is as defined above;

$R_3$ is —$R_{11}$, —OH, —$OR_{11}$, —$R_{12}OR_{11}$, —SH, —$SR_{11}$, —$NH_2$, —$NHR_{11}$, —$NR_aR_b$, —NHC(=O)H, —$NR_{11}$C(=O)H, —NHC(=O)$R_{11}$, —$NR_{11}$C(=O)$R_{13}$, —NHC(=O)$NH_2$, —$NR_{11}$C(=O)$NH_2$, —NHC(=O)$NHR_{11}$, —NHC(=O)$NR_{11}R_{13}$, —$NR_{11}$C(=O)$NR_{11a}R_{13}$, —NHC(=O)$OR_{11}$, —$NR_{11}$C(=O)$OR_{13}$, —NHS(=O)$_2R_{11}$, —$NR_{11}$S(=O)$_2R_{13}$, —NHS(=O)$_2OR_{11}$, or —$NR_{11}$S(=O)$_2OR_{13}$ where $R_{12}$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n5}$—($C_3$–$C_{12}$ arylene or heteroarylene)—($C_1$–$C_8$ alkyl or substituted alkyl)$_{n6}$ where n5 and n6 are independently 0 or 1; and $R_{11}$, $R_{11a}$, and $R_{13}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1;

$R_4$ is hydrogen or —$R_{11}$ where $R_{11}$ is as defined above; $R_7$ is —C(=O)H, —C(=O)$R_{14}$, —C(=O)$NH_2$, —C(=O)$NHR_{14}$, —(=O)$NR_{14}R_{15}$, —C(=O)SH, or —C(=O)$SR_{14}$ where where $R_{14}$ and $R_{15}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; and where $R_7$ is —C(=O)$NR_{14}R_{15}$, then the $R_{14}$ and $R_{15}$ groups additionally can combine to form a substituted or unsubstituted $C_4$–$C_{10}$ cyclic alkyl, cyclic heteroalkyl, aryl or heteroaryl group; or a pharmaceutically acceptable salt thereof.

Within this group of compounds, a preferred group of compounds is that wherein the embodiments of (i)–(iv) defined below are employed either singularly or in any combination:

(i) A preferred group of compounds is that wherein $R_1$ is hydroxy and the stereochemistry at the carbon carrying the $R_1$ group is (R) or (S), preferably (S).

(ii) Another preferred group of compounds is that wherein $R_2$ is hydrogen.

(iii) Another preferred group of compounds is that wherein $R_3$ is hydrogen or $R_9$ where $R_9$ is —$C_1$–$C_{12}$ alkyl or —($C_1$–$C_8$ alkylene)$_{n5}$—($C_3$–$C_{12}$ aryl or heteroaryl) where n5 is 0 or 1, preferably methyl, ethyl, n-propyl, iso-propyl, n-butyl, iso-butyl, tert-butyl, n-pentyl, iso-pentyl, neo-pentyl, n-hexyl, 2-, 3-, 4-, or 5-methylpentyl, 4-dimethylbutyl, benzyl, 3-phenylpropyl, 2-phenylethyl, or 4-phenylbutyl, more preferably n-butyl. The stereochemistry at the carbon carrying the $R_3$ group is (R) or (S), preferably (R).

(iv) Yet another preferred group of compounds is that wherein $R_7$ is:

(a) —C(=O)$NHR_{14}$ where $R_{14}$ is selected from the group consisting of —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1. Preferably, $R_7$ is —C(=O)$NHR_{14}$ where $R_{14}$ is —($C_1$–$C_{12}$) alkyl, alkoxy, aryl, or heteroaryl. More preferably, $R_7$ is —C(=O)$NHR_{14}$ where $R_{14}$ is —($C_1$–$C_{12}$) alkyl, aryl, or heteroaryl. Even more preferably $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenylaminocarbonyl, cyclopropylmethylaminocarbonyl, pyridin-2-ylaminocarbonyl, pyridin-3-ylaminocarbonyl, pyridin-4-ylmethylaminocarbonyl, morpholin-4-ylcarbonyl, 3,4-methylenedioxyphenylaminocarbonyl, quinolin-3-ylaminocarbonyl, methylaminocarbonyl, 4-biphenylaminocarbonyl, 3-phenoxyphenylaminocarbonyl, 3,4-dichlorophenylaminocarbonyl, 4-tert-butylphenylaminocarbonyl, 4-tert-butylaminocarbonyl, indan-2-ylaminocarbonyl, 2,2-dimethylpropylaminocarbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenyl-aminocarbonyl, 2,5-dimethylphenylaminocarbonyl, 2,5-dimethoxyphenylaminocarbonyl, 3,4-dichlorophenylaminocarbonyl, benzthiazol-2-ylaminocarbonyl, 3-phenoxyphenylaminocarbonyl, 2-hydroxybutylaminocarbonyl, 4-hydroxybutylaminocarbonyl, 1,4-benzodioxan-6-ylaminocarbonyl, isoquinolin-6-ylaminocarbonyl, methylaminocarbonyl, thiazol-2-ylaminocarbonyl, 4-methylthiazol-2-ylaminocarbonyl, 3-methylbutyl-aminocarbonyl, n-pentylaminocarbonyl, cyclohexylaminocarbonyl, 5-methylthiazol-2-ylaminocarbonyl, 4-methylthiazol-2-ylaminocarbonyl, 2,4-dimethoxyphenyl-aminocarbonyl, 3,4-methylenedioxyphen-5-ylmethylaminocarbonyl, allylaminocarbonyl, 2-methylallylaminocarbonyl, pyrrolidin-1-ylcarbonyl, ethylaminocarbonyl, phenylaminocarbonyl, indan-1-ylaminocarbonyl, 2-methoxyethylaminocarbonyl, indan-5-ylaminocarbonyl, 3,4-difluorophenylaminocarbonyl, 5-methylisoxazol-5-ylaminocarbonyl, 3-fluorophenylaminocarbonyl, 4-fluorophenylaminocarbonyl, N-methyl-N-phenylaminocarbonyl, 2-propylaminocarbonyl, 2-phenylpropylaminocarbonyl, n-propylaminocarbonyl, N-ethyl-N-(n-butyl) aminocarbonyl, benzylaminocarbonyl, thiazolidin-1-ylcarbonyl, piperazin-1-ylcarbonyl, piperidin-1-ylcarbonyl, azetidin-1-ylcarbonyl, homopiperdin-1-ylcarbonyl, pyrimidin-2-ylaminocarbonyl, 4-methylpiperazin-1-ylcarbonyl, 4-methylpyrimidin-2-ylaminocarbonyl, pyrimidin-4-ylaminocarbonyl, pyrazin-2-ylaminocarbonyl, imidazol-2-ylaminocarbonyl. In particular, $R_7$ is piperidin-1-ylcarbonyl, azetidin-1-ylcarbonyl, ethylaminocarbonyl, phenylaminocarbonyl, pyrimidin-2-ylaminocarbonyl, or thiazol-2-ylaminocarbonyl.

More particularly, $R_7$ is phenylaminocarbonyl or pyrimidin-2-ylaminocarbonyl. The stereochemistry at the C2 carbon atom of the pyrrolidine ring, i.e., carbon carrying the $R_7$ group is either (R) or (S), preferably (S); or (b) $R_7$ is —C(=O)$OR_{14}$ where $R_{14}$ is selected from the group consisting of hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1.

Preferably, $R_7$ is —C(=O)$OR_{14}$ where $R_{17}$ is hydrogen, —($C_1$–$C_{12}$) alkyl, alkoxy, aryl, or heteroaryl. More preferably, —C(=O)$OR_{14}$ where $R_{14}$ is alkyl, even more preferably $R_7$ is tert-butoxycarbonyl. The stereochemistry at the C2 carbon atom of the pyrrolidine ring, i.e., carbon carrying the $R_7$ group is either (R) or (S), preferably (S).

(D) Another preferred group of compounds if represented by Formula (IIc):

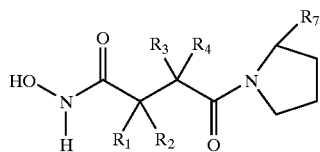

(IIc)

wherein:

$R_1$ is —OH, —$OR_9$, —SH or —$SR_9$ wherein $R_9$ is selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n1}$—($C_3$–$C_{12}$ arylene or heteroarylene)—($C_1$–$C_8$ alkyl or substituted alkyl)$_{n2}$ where n1 and n2 are independently 0 or 1;

$R_2$ is hydrogen;

$R_3$ is —$R_{11}$, —OH, —$OR_{11}$, —$R_{12}OR_{11}$, —SH, —$SR_{11}$, —$NH_2$, —$NHR_{11}$, —$NR_{11}R_{13}$, —NHC(=O)H, —$NR_{11}$C(=O)H, —NHC(=O)$R_{11}$, —$NR_{11}$C(=O)$R_{13}$, —NHC(=O)$NH_2$, —$NR_{11}$C(=O)$NH_2$, —NHC(=O)$NHR_{11}$, —NHC(=O)$NR_{11}R_{13}$, —$NR_{11}$C(=O)$NR_{11a}R_{13}$, —NHC(=O)$OR_{11}$, —$NR_{11}$C(=O)$OR_{13}$, —NHS(=O)$_2R_{11}$, —$NR_{11}$S(=O)$_2R_{13}$, —NHS(=O)$_2$$OR_{11}$, or —$NR_{11}$S(=O)$_2OR_{13}$ where $R_{12}$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n5}$—($C_3$–$C_{12}$ arylene or heteroarylene)—($C_1$–$C_8$ alkyl or substituted alkyl) n6 where n5 and n6 are independently 0 or 1; and $R_{11}$ and $R_{13}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1;

$R_4$ is hydrogen or —$R_{11}$ wherein $R_{11}$ is as defined above; and $R_7$ is —C(=O)$OR_{14}$, where $R_{14}$ is selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or a pharmaceutically acceptable salt thereof.

In another embodiment of this series of compounds, $R_1$ is —OH or —$OR_9$. In another embodiment of this series of compounds, $R_3$ is —$C_1$–$C_{12}$ alkyl, such as $C_4$ alkyl and $R_4$ is H. In another embodiment of this series of compounds, $R_{14}$ is —C(=O)O—$C_1$–$C_{12}$ alkyl, such as —C(=O)O—$C_1$–$C_4$ alkyl, for example —C(=O)O-t-butyl.

(E) Another preferred group of compounds if represented by Formula (IId):

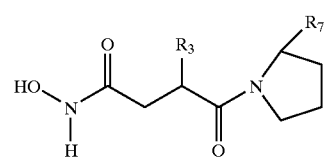

(IId)

wherein:

$R_3$ is —$R_{11}$ where $R_{11}$ is selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1; and $R_7$ is —C(=O)$OR_{14}$ where $R_{14}$ is selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or a pharmaceutically acceptable salt thereof.

In one embodiment, $R_3$ is —($C_1$–$C_{12}$)alkyl, preferably n-butyl. In another embodiment of this series of compounds, $R_7$ is —C(O)O—$C_1$–$C_{12}$ alkyl, such as —C(O)O—$C_1$–$C_4$ alkyl, for example —C(O)O-tert-butyl.

(F) Another preferred group of compounds if represented by Formula (IIe):

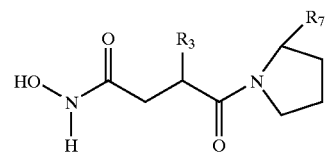

(IIe)

wherein:

$R_3$ is —$R_{11}$ where —$R_{11}$ is selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1;

$R_7$ is —$NH_2$, —$NHR_{13}$, or —$NHR_{14}R_{15}$ where $R_{13}$, $R_{14}$ and $R_{15}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or where $R_{14}$ and $R_{15}$ combine to form a substituted or unsubstituted $C_4$–$C_{10}$ cyclic alkyl, cyclic heteroalkyl, aryl or heteroaryl group; or a pharmaceutically acceptable salt thereof.

In one embodiment of this series of compounds, R$_3$ is C$_1$–C$_{12}$ alkyl, preferably n-butyl. In another embodiment of this series of compounds, R$_7$ is —NHR$_{13}$ where R$_{13}$ is as defined above.

(G) Another preferred group of compounds if represented by Formula (IIf):

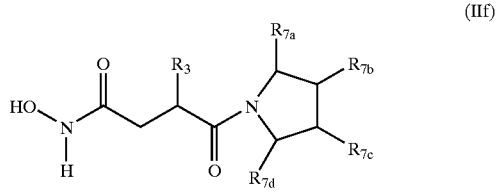

(IIf)

wherein:
R$_3$ is —R$_{11}$ wherein R$_{11}$ is selected from the group consisting of hydrogen, —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n7}$—(C$_3$–C$_{12}$ arylene or heteroarylene)—(C$_1$–C$_8$ alkyl or substituted alkyl)$_{n8}$ where n7 and n8 are independently 0 or 1;

R$_{7a}$, R$_{7b}$, R$_{7c}$ and R$_7$d are independently selected from the group consisting of hydrogen, —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n9}$—(C$_3$–C$_{12}$ arylene or heteroarylene)—(C$_1$–C$_8$ alkyl or substituted alkyl)$_{n10}$ where n9 and n10 are independently 0 or 1; or two vicinal R$_7$ groups can combine to form a substituted or unsubstituted C$_4$–C$_{10}$ cyclic alkyl, cyclic heteroalkyl, aryl or heteroaryl group; or a pharmaceutically acceptable salt thereof.

In one embodiment of this series of compounds, R$_3$ is n-butyl. In another embodiment of this series of compounds, at least one R$_7$ is selected from the group consisting of —C(=O)OR$_{14}$, —OH, —OR$_{14}$, —R$_{14}$, —NH(C=O)OR$_{14}$, or —NH(C=O)R$_{15}$, where R$_{14}$ and R$_{15}$ are independently selected from the group consisting of —C$_1$–C$_{12}$ alkyl, substituted alkyl, or heteroalkyl, —C$_1$–C$_{12}$ alkenyl, substituted alkenyl, or heteroalkenyl, C$_1$–C$_{12}$ alkynyl, substituted alkynyl, or heteroalkynyl, and (C$_1$–C$_8$ alkyl or substituted alkyl)$_{n9}$—(C$_3$–C$_{12}$ arylene or heteroarylene)—(C$_1$–C$_8$ alkyl or substituted alkyl)$_{n10}$ where n9 and n10 are independently 0 or 1.

(H) Another preferred group of compounds if represented by Formula (IIg):

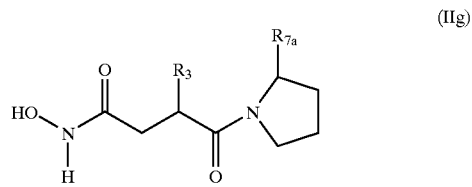

(IIg)

wherein:
R$_3$ is —R$_{11}$ where R$_{11}$ is selected from the group consisting of hydrogen, —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n7}$—(C$_3$–C$_{12}$ arylene or heteroarylene)—(C$_1$–C$_8$ alkyl or substituted alkyl)$_{n8}$ where n7 and n8 are independently 0 or 1; and R$_{7a}$ is selected from the group consisting of hydrogen, —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n9}$—(C$_3$–C$_{12}$ arylene or heteroarylene)—(C$_1$–C$_8$ alkyl or substituted alkyl)$_{n10}$ where n9 and n10 are independently 0 or 1; or a pharmaceutically acceptable salt thereof.

In another embodiment of this series of compounds, R$_{7a}$ is —CH$_2$—R$_d$ where R$_d$ is selected from the group consisting of H, —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n9}$—(C$_3$–C$_{12}$ arylene or heteroarylene)—(C$_1$–C$_8$ alkyl or substituted alkyl)$_{n10}$ where n9 and n10 are independently 0 or 1. In another embodiment of this series of compounds, R$_d$ is selected from the group consisting of —O—CH$_3$, —OH, —NH—(C=O)—CH$_3$, and

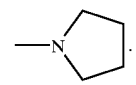

(I) Another preferred group of compounds if represented by Formula (IIh):

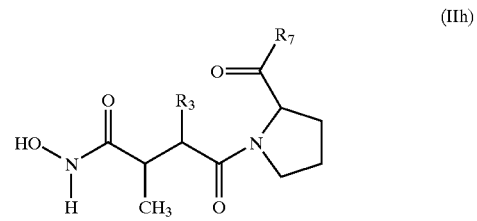

(IIh)

wherein:
R$_3$ is —R$_{11}$ where R$_{11}$ is selected from the group consisting of hydrogen, —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n7}$—(C$_3$–C$_{12}$ arylene or heteroarylene)—(C$_1$–C$_8$ alkyl or substituted alkyl)$_{n8}$ where n7 and n8 are independently 0 or 1; and R$_7$ is selected from the group consisting of —R$_{14}$ or —OR$_{14}$ where R$_{14}$ is selected from the group consisting of —C$_1$–C$_{12}$ alkyl, substituted alkyl, or heteroalkyl, —C$_1$–C$_{12}$ alkenyl, substituted alkenyl, or heteroalkenyl, —C$_1$–C$_{12}$ alkynyl, substituted alkynyl, or heteroalkynyl, and —(C$_1$–C$_8$ alkyl or substituted alkyl)$_{n9}$—(C$_3$–C$_{12}$ arylene or heteroarylene)—(C$_1$–C$_8$ alkyl or substituted alkyl)$_{n10}$ where n9 and n10 are independently 0 or 1; or a pharmaceutically acceptable salt thereof.

In one embodiment of this series of compounds, R$_3$ is n-butyl. In another embodiment of this series of compounds, R$_7$ is —OCH$_3$ or —O-tert-butyl.

(J) Another preferred group of compounds if represented by Formula (IIi):

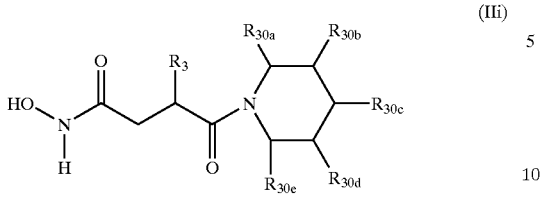

wherein:

$R_3$ is —$R_{11}$ where $R_{11}$ is hydrogen, —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, or —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1; and $R_{30a}$, $R_{30b}$, $R_{30c}$, $R_{30d}$, and $R_{30e}$ are independently selected from the group consisting of hydrogen, —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or where two vicinal $R_{30}$ groups can combine to form a substituted or unsubstituted $C_4$–$C_{10}$ cyclic alkyl, cyclic heteroalkyl, aryl or heteroaryl group; and all salts and stereoisomers thereof.

In one embodiment of this series of compounds, at least one $R_{30}$ is selected from the group consisting of —(=O)O$R_{15}$ and —(=O)$R_{15}$, where $R_{15}$ is independently selected from the group consisting of $C_1$–$C_{12}$ alkyl, substituted alkyl, or heteroalkyl, $C_1$–$C_{12}$ alkenyl, substituted alkenyl, or heteroalkenyl, $C_1$–$C_{12}$ alkynyl, substituted alkynyl, or heteroalkynyl, and ($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1.

(K) Another preferred group of compounds if represented by Formula (IIj):

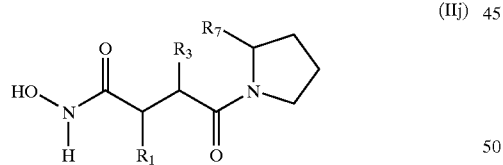

where:

$R_1$ is halo;

$R_3$ is hydrogen, $R_{11}$, —OH, —O$R_{11}$, —$R_{12}$O$R_{11}$, —SH, —S$R_{11}$, —NH$_2$, —NH$R_{11}$, —N$R_{11}R_{13}$, —NHC(=O)H, —N$R_{11}$C(=O)H, —NHC(=O)$R_{11}$, —N$R_{11}$C(=O)$R_{13}$, —NHC(=O)NH$_2$, —N$R_{11}$C(=O)NH$_2$, —NHC(=O)NH$R_{11}$, —NHC(=O)N$R_{11}R_{13}$, —N$R_{11}$C(=O)N$R_{11a}R_{13}$, —NHC(=O)O$R_{11}$, —N$R_{11}$C(=O)O$R_{13}$, —NHS(=O)$_2R_{13}$, —N$R_{11}$S(=O)$_2R_{13}$, —NHS(=O)$_2$O$R_{11}$, or —N$R_{11}$S(=O)$_2$O$R_{13}$, where $R_{12}$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n5}$—($C_3$–$C_{12}$ arylene or heteroarylene)—($C_1$–$C_8$ alkyl or substituted alkyl)$_{n6}$ where n5 and n6 are independently 0 or 1; and $R_{11}$, $R_{11a}$ and $R_{13}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroarylene)—($C_1$–$C_8$ alkyl or substituted alkyl)$_{n8}$ where n7 and n8 are independently 0 or 1;

$R_7$ is hydrogen, $R_{14}$, —OH, —O$R_{14}$, —SH, —S$R_{14}$, —NH$_2$, —NH$R_{14}$, —N$R_{14}R_{15}$, —(=O)H, —(=O)$R_{14}$, —(=O)NH$_2$, —(=O)NH$R_{14}$, —(=O)N$R_{14}R_{15}$, —(=O)OH, —(=O)O$R_{14}$, —(=O) SH, —(=O) S$R_{14}$, —(=O)CH$_3$, —(=O)CH$_2R_{14}$, —(=O)CHR$_{14}R_{15}$, —(=O)C$R_{14}R_{15}R_{16}$, —(=O)OCH$_3$, —(=O)OCH$_2R_{14}$, —(=O)OCHR$_{14}R_{15}$, —(=O)OC$R_{14}R_{15}R_{16}$, —S(=O)$_2$NH$_2$, —S(=O)$_2$NH$R_{14}$, —S(=O)$_2$N$R_{14}R_{15}$, —NHC(=O)H, —N($R_{14}$)C(=O)H, —NHC(=O)$R_{15}$, —N($R_{14}$)C(=O)$R_{15}$, —NHC(=O)O$R_{14}$, —NHS(=O)$_2$H, —N($R_{14}$)S(=O)$_2$H, —NHS(=O)$_2$O$R_{15}$, —N($R_{14}$)S(=O)$_2$O$R_{15}$, —N(H)S(=O)$_2R_{15}$, or —N($R_{14}$)S(=O)$_2R_{15}$, or where two vicinal $R_6$ or $R_7$ groups combine to form a substituted or unsubstituted —$C_4$–$C_{10}$ cyclic alkyl, cyclic heteroalkyl, aryl or heteroaryl group where $R_{14}$, $R_{15}$ and $R_{16}$ are each independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n9}$—($C_3$–$C_{12}$ arylene or heteroarylene)—($C_1$–$C_8$ alkyl or substituted alkyl)$_{n10}$ where n9 and n10 are independently 0 or 1; or when $R_{14}$ and $R_{15}$ are attached to a nitrogen atom they can combine to form a substituted or unsubstituted $C_4$–$C_{10}$ cyclic alkyl, cyclic heteroalkyl, aryl or heteroaryl group; or a pharmaceutically acceptable salt thereof.

Within this group of compounds, a preferred group of compounds is that wherein the embodiments of (i)–(iii) defined below are employed either singularly or in any combination:

(i) A preferred group of compounds is that wherein $R_1$ is fluoro. The stereochemistry at the carbon carrying the $R_1$ group is (R) or (S), preferably (S).

(ii) Another preferred group of compounds is that wherein $R_3$ is hydrogen or $R_9$ where $R_9$ is —$C_1$–$C_{12}$ alkyl or —($C_1$–$C_8$ alkylene)$_{n5}$—($C_3$–$C_{12}$ aryl or heteroaryl) where n5 is 0 or 1, preferably methyl, ethyl, n-propyl, iso-propyl, n-butyl, iso-butyl, tert-butyl, n-pentyl, iso-pentyl, neo-pentyl, n-hexyl, 2-, 3-, 4-, or 5-methylpentyl, 4,4-dimethylbutyl, benzyl, 3-phenylpropyl, 2-phenylethyl, or 4-phenylbutyl, more preferably n-butyl. The stereochemistry at the carbon carrying the $R_3$ group is (R) or (S), preferably (R); and (iii) $R_7$ is:

(a)—(=O)N$R_{14}R_{15}$, where $R_{14}$ and $R_{15}$ are independently hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_1$–$C_8$ alkyl or substituted alkyl)$_{n9}$—($C_3$–$C_{12}$ arylene or heteroarylene)-($C_1$–$C_8$ alkyl or substituted alkyl)$_{n10}$ where n9 and n10 are independently 0 or 1; or $R_{14}$ and $R_{15}$ combine to form a substituted or unsubstituted —($C_4$–$C_{10}$)cyclic alkyl, cyclic heteroalkyl, aryl or heteroaryl group.

Preferably, $R_7$ is —(=O)$NR_{14}R_{15}$ where $R_{14}$ and $R_{15}$ are each independently hydrogen or —($C_1$–$C_{12}$) alkyl, alkoxy, aryl, heteroaryl or $R_{14}$ and $R_{15}$, when attached to the same carbon, combine to form a cyclic heteroalkyl, aryl or heteroaryl group. More preferably, $R_7$ is —(=O)$NHR_{15}$ where $R_{15}$ is H or —($C_1$–$C_{12}$) alkyl, aryl, or heteroaryl or —(=O)$NR_{14}R_{15}$ where $R_{14}$ and $R_{15}$ form a substituted or unsubstituted —($C_4$–$C_{10}$)cyclic heteroalkyl.

Even more preferably $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenyl-aminocarbonyl, cyclopropylmethylaminocarbonyl, pyridin-2-ylaminocarbonyl, pyridin-3-ylaminocarbonyl, pyridin-4-ylmethylaminocarbonyl, morpholin-4-ylcarbonyl, 3,4-methylenedioxyphenylaminocarbonyl, quinolin-3-ylaminocarbonyl, methylaminocarbonyl, 4-biphenylaminocarbonyl, 3-phenoxyphenyl-aminocarbonyl, 3,4-dichlorophenylaminocarbonyl, 4-tert-butylphenylaminocarbonyl, 4-tert-butylaminocarbonyl, indan-2-ylaminocarbonyl, 2,2-dimethylpropylamino-carbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenylaminocarbonyl, 2,5-dimethylphenylaminocarbonyl, 2,5-dimethoxyphenyl-aminocarbonyl, 3,4-dichlorophenylaminocarbonyl, benzthiazol-2-ylaminocarbonyl, 3-phenoxyphenyl-aminocarbonyl, 2-hydroxybutylaminocarbonyl, 4-hydroxybutylaminocarbonyl, 1,4-benzodioxan-6-ylaminocarbonyl, isoquinolin-6-ylaminocarbonyl, methylaminocarbonyl, thiazol-2-ylaminocarbonyl, 4-methylthiazol-2-yl-aminocarbonyl, 3-methylbutyl-aminocarbonyl, n-pentylaminocarbonyl, cyclohexylaminocarbonyl, 5-methylthiazol-2-ylaminocarbonyl, 4-methylthiazol-2-yl-aminocarbonyl, 2,4-dimethoxyphenyl-aminocarbonyl, 3,4-methylene-dioxyphen-5-ylmethylaminocarbonyl, allylaminocarbonyl, 2-methylallylaminocarbonyl, pyrrolidin-1-ylcarbonyl, ethylaminocarbonyl, phenylaminocarbonyl, indan-1-ylaminocarbonyl, 2-methoxyethylaminocarbonyl, indan-5-ylaminocarbonyl, 3,4-difluorophenyl-aminocarbonyl, 5-methylisoxazol-5-ylaminocarbonyl, 3-fluorophenyl-aminocarbonyl, 4-fluorophenylaminocarbonyl, N-methyl-N-phenylaminocarbonyl, 2-propylaminocarbonyl, 2-phenylpropylaminocarbonyl, n-propylaminocarbonyl, N-ethyl-N-(n-butyl)aminocarbonyl, benzylaminocarbonyl, thiazolidin-1-ylcarbonyl, piperazin-1-yl-carbonyl, piperidin-1-ylcarbonyl, azetidin-1-ylcarbonyl, homopiperdin-1-ylcarbonyl, pyrimidin-2-ylaminocarbonyl, 4-methylpiperazin-1-ylcarbonyl, 4-methylpyrimidin-2-ylaminocarbonyl, pyrimidin-4-ylaminocarbonyl, pyrazin-2-ylaminocarbonyl, imidazol-2-ylaminocarbonyl.

In particular, $R_7$ is piperidin-1-ylcarbonyl, azetidin-1-ylcarbonyl, ethylaminocarbonyl, phenylaminocarbonyl, pyrimidin-2-ylaminocarbonyl, or thiazol-2-ylaminocarbonyl.

More particularly, $R_7$ is piperidin-1-ylcarbonyl, azetidin-1-ylcarbonyl, ethylaminocarbonyl or thiazol-2-ylaminocarbonyl. The stereochemistry at the C2 carbon atom of the pyrrolidine ring, i.e., carbon carrying the $R_7$ group is either (R) or (S), preferably (S); or (b) $R_7$ is —NHC(=O)$OR_{14}$ where $R_{14}$ is hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_1$–$C_8$ alkyl or substituted alkyl)$_{n9}$—($C_3$–$C_{12}$ arylene or heteroarylene)-($C_1$–$C_8$ alkyl or substituted alkyl)$_{n10}$ where n9 and n10 are independently 0 or 1. Preferably, $R_7$ is —NHC(=O)$OR_{14}$ where $R_{14}$ is hydrogen or —($C_1$–$C_{12}$) alkyl, alkoxy, aryl, heteroaryl; or (c) $R_7$ is —(=O)$OR_{14}$ where $R_{14}$ is hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, or —($C_1$–$C_8$ alkyl or substituted alkyl)$_{n9}$—($C_3$–$C_{12}$ arylene or heteroarylene)-($C_1$–$C_8$ alkyl or substituted alkyl)$_{n10}$ where n9 and n10 are independently 0 or 1. Preferably, $R_7$ is —(=O)$OR_{17}$ where $R_{14}$ is hydrogen or —($C_1$–$C_{12}$) alkyl, alkoxy, aryl, or heteroaryl. More preferably, —C(=O)$OR_{14}$ where $R_{14}$ is alkyl, even more preferably $R_7$ is tert-butoxycarbonyl. The stereochemistry at the C2 carbon atom of the pyrrolidine ring, i.e., carbon carrying the $R_7$ group is either (R) or (S), preferably (S).

Preferred Compounds of the Invention are

N-hydroxy-3-[(S)-(n-butyl)-3-(2-(S)-1,1-dimethyl-ethyloxycarbonyl)-pyrrolidin-1-carbonyl)]-2-(S)-fluoropropionamide;

N-hydroxy-3-[(S)-(n-butyl)-3-(2-(S)-pyridin-1-ylcarbonyl)pyrrolidin-1-carbonyl)]-2-(S)-fluoropropionamide;

N-hydroxy-3-[(S)-(n-butyl)-3-(2-(S)-azetidin-1-ylcarbonyl)-pyrrolidin-1-carbonyl)]-2-(S)-fluoropropionamide;

N-hydroxy-3-[(S)-(n-butyl)-3-(2-(S)-ethylaminocarbonyl)pyrrolidin-1-carbonyl)]-2-(S)-fluoropropionamide;

N-hydroxy-3-[(S)-(n-butyl)-3-(2-(S)-phenylamino-carbonyl)-pyrrolidin-1-carbonyl)]-2-(S)-hydroxypropionamide;

N-hydroxy-3-[(S)-(n-butyl)-3-(2-(S)-pyrimidin-2-ylaminocarbonyl)pyrrolidin-1-carbonyl)]-2-(S)-hydroxypropionamide; and N-hydroxy-3-[(S)-(n -butyl)-3-(2-(S)-thiazol-2-ylaminocarbonyl)-pyrrolidin-1-carbonyl)]-2-(S)-fluoropropionamide.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emka-Chemie, or Sigma (St. Louis, Miss., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of Compounds of Formula (I)

Compounds of Formula (I) can be prepared by methods well known in the art of organic chemistry. Representative synthetic procedures for preparing compounds of the present invention are illusted and described in detail below. For example, compounds of Formula (I) can be prepared as described in Schemes A–D below.

A compound of Formula (I) where $R_1$, $R_2$, and $R_4$ are hydrogen, and $R_3$, $R_6$, $R_7$, Y, and n are as defined in the Summary of the Invention can be prepared as described in Scheme A below.

methyl-2-(R)-butylsuccinate as described in detail in Example 16 below.

Amines of formula 2 are commercially available or they can be prepared by methods well known in the art. For example, N,N-dialkylamines such as pyrrolidine, piperidine, piperazine, morpholine, thiomorpholine, homopiperidine, homopiperazine, proline tert-butyl ester, L-proline-2-methylamide, (S)-(+)-2-(methoxymethyl)-pyrrolidine, L-proline-N-methoxy-N-methylamide, (S)-2-(pyrrolidinylmethyl)-pyrrolidine, L-proline-N-morpholineamide, L-proline-N,N-dimethylamide, homoproline methyl ester, L-homoproline tert-butylester, 3-(R)-tert-butoxy-L-proline-O-t-butyl ester, pipecolinic acid, 1,2,3,4-tetrahydroquinoline, 1-hydroxyethyl-piperazine, 2-hydroxyethylpiperidine, 3-hydroxypiperidine, 4-hydroxypiperidine, 4-hydroxyproline, L-tetrahydroisoquinoline tert-butyl ester, 3-(N-Boc-amino) pyrrolidine, and N-Boc-L-prolinol are commerically available. Other N,N-dialkylamines 2 such as 2-acetylaminomethylpyrrolidine can be prepared from N-Boc-L-prolinol as described in Example 16 below. trans-

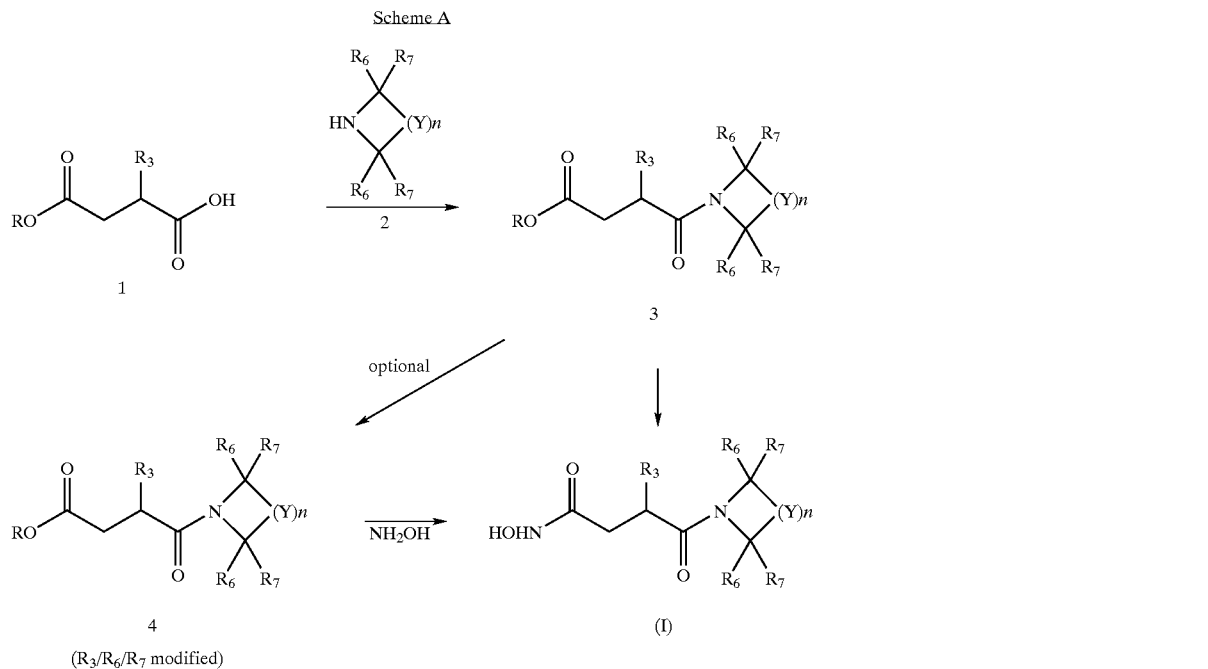

Scheme A

Treatment of a solution of a mono-protected succinate of formula 1 where R is an alkyl group such as methyl, ethyl, and the like, and $R_3$ is as defined in the Summary of the Invention, with an N,N-dialkylamine of formula 2, where $R_6$ and $R_7$ are as defined in the Summary of the Invention, provides a 3-aminocarbonyl-propionate derivative of formula 3. The reaction is typically carried out in the presence of an inert, polar aprotic solvent (e.g. DMF, dioxane, etc.) in the presence of a non-nucleophilic base (e.g. triethylamine, diisopropylethylamine, etc.) and a coupling reagent (e.g. EDCI, PyBOP, DIC, etc.). The reaction is initially started at low temperature, such as 0° C., and then allowed to warm to room temperature, and then stirred for several hours. Some compounds of formula 1 are commercially available. Others can be prepared by methods well known in the art. For example mono-methyl succinate, mono-4-methyl-2-(R)-methylsuccinate is available commercially, while mono-4-

3-Acetoxy-L-proline O-tert-butyl ester can be prepared from Cbz protected trans-3-hydroxy-L-proline as described in Example 17 below which can then be converted to trans 3-hydroxy-L-proline O-tert-butyl ester, if desired, by hydrolysis of the acetoxy group in trans-3-acetoxy-L-proline O-tert-butyl ester as described in Example 17 below.

Also, it will be recognized by a person skilled in the art that if compound 1 and/or 2 have additional reactive groups, then they must be suitably protected prior to carrying out the coupling reaction. Examples of suitable protecting groups and their introduction and removal are described in T. W. Greene and G. M. Wuts, "*Protecting Groups in Organic Synthesis*" Third Ed., Wiley, New York, 1999 and references cited therein. For example, if $R_6$ or $R_7$ is a carboxyl group or a hydroxy group then it can be protected as a t-butyl ester or benzyl ester or other suitable protecting group prior to the coupling reaction.

Compound 3 can optionally be converted to a compound of formula 4 where prior to converting it to a compound of Formula (I). This would be desirable if certain group(s) in compound 3, e.g., $R_3$, $R_6$, and/or $R_7$ had to transformed to other group(s) within the scope of the invention prior to introducing the hydroxamate group in the molecule. For example, a compound of formula 3 where $R_6$ or $R_7$ is a tert-butoxyamino group, can be converted to a corresponding compound of formula 4 where $R_6$ or $R_7$ is an acetylamino group by first treating 3 with an acid such as diluted hydrochloric acid at ambient temperature to provide a corresponding compound of formula 3 where $R_6$ or $R_7$ is an amino group, followed by treatment with an acetylating agent such as acetic anhydride in the present of an organic base such as pyridine.

A compound of formula 3 where $R_6$ and\or $R_7$ is a hydroxy can be converted to a compound of formula 4 where $R_6$ and\or $R_7$ is a sulfonamido group (i.e., $-NHSO_2R_{15}$ where $R_{15}$ is as defined in the Summary of the Invention) by first converting the hydroxy group into amino group, followed by treatment with a sulfonylating agent. A detailed description of this transformation is provided in Example 34 below.

A compound of formula 3 where $R_6$ and\or $R_7$ is a suitably protected carboxyl group can be converted to a compound of formula 4 where $R_6$ and\or $R_7$ is an aminocarbonyl group (i.e., $-CONHR_{14}$ or $-CONR_{14}R_{15}$ where $R_{14}$ and $R_{15}$ is as defined in the Summary of the Invention) by first deprotecting the carboxy group and then treating with an amine of formula $-NHR_{14}$ or $-NR_{14}R_{15}$ (where $R_{14}$ and $R_{15}$ is as defined in the Summary of the Invention). Briefly, the reaction conditions for deprotecting of the carboxy group will depend on the nature of the protecting group. For example, if it is a benzyl ester, then treatment with hydrogen gas and an appropriate catalyst (e.g., 10% palladium on carbon) will liberate the free carboxylic acid. The amination reaction is typically carried out in the presence of an inert, polar aprotic solvent (e.g. DMF, dioxane, etc.) with a non-nucleophilic base (e.g. triethylamine, diisopropylethylamine, etc.) and a coupling reagent (e.g. EDCI, PyBOP, DIC, etc.). The reaction is initially started at low temperature, such as 0° C., and then allowed to warm to room temperature, and then stirred for several hours. Many amines of formulae $NHR_{14}$ and $NHR_{14}R_{15}$ are available commercially, or can be readily prepared by methods well known in the art. For example, methylamine, aniline, 2-aminothiazole, etc., are commercially available. Others can be prepared, for example, via reductive amination of an aldehyde, or Fukuyama alkylation of a suitable nitroaryl sulfonamide followed by cleavage of the sulfonamide to liberate the desired amine.

Compound 3 or 4 is then converted to a hydroxamate compound of Formula (I) by treating it at 0° C. with aqueous 50% hydroxylamine in a polar organic solvent such as dioxane and the like. After the reaction is complete the mixture is then purified by preparative reverse-phase (C18) HPLC to afford compound of Formula (I). If desirable, suitable O-protected hydroxylamine such as O-benzylhydroxylamine can also be used to give an O-protectedhydroxamate compound. Removal of the protecting group will provide a compound of Formula (I).

A compound of Formula (I) can be converted to other compounds of Formula (I) by methods well known in the art. Some such methods are described below. Compounds of Formula (I) containing a hydroxy group may be prepared by dealkylation/benzylation of an alkyloxy/benzyloxy substituent; and those containing an acid group, by hydrolysis of an ester group. Similarly, a compound of Formula (I) having an alkenyl or alkynyl group can be prepared by reacting a corresponding compound of Formula (I) containing a bromine or iodine atom with trimethylsilylacetylene under the Castro-Stephens reaction conditions. Furthermore, a compound of Formula (I) containing an alkoxy group may be prepared by alkylation of hydroxy substituent. A compound of Formula (I) containing a carboxy group can be prepared by hydrolyzing an ester group in a corresponding compound of Formula (I) under acid hydrolysis reaction conditions. The resulting carboxy group can optionally be converted to an amido group, if desired, by first converting the carboxy group to an activated ester derivative e.g., treating the carboxy compound with dicyclohexyl carbodiimide, DEAD and the like, followed by treatment with an amine. It will be recognized by a person skilled in the art that some of these transformations can be carried out prior to converting the compound of formula 5 to a compound of Formula (I).

A compound of Formula (I) where $R_1$ is hydroxy, $R_2$, and $R_4$ are hydrogen, and $R_3$, $R_6$, $R_7$, Y, and n are as defined in the Summary of the Invention can be prepared as described in Scheme B below.

Scheme B

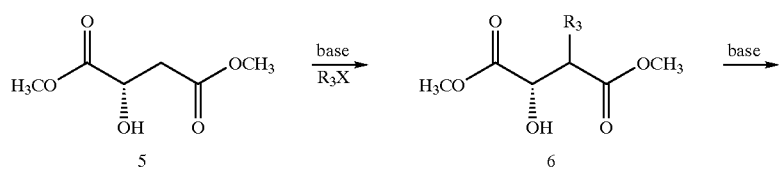

-continued

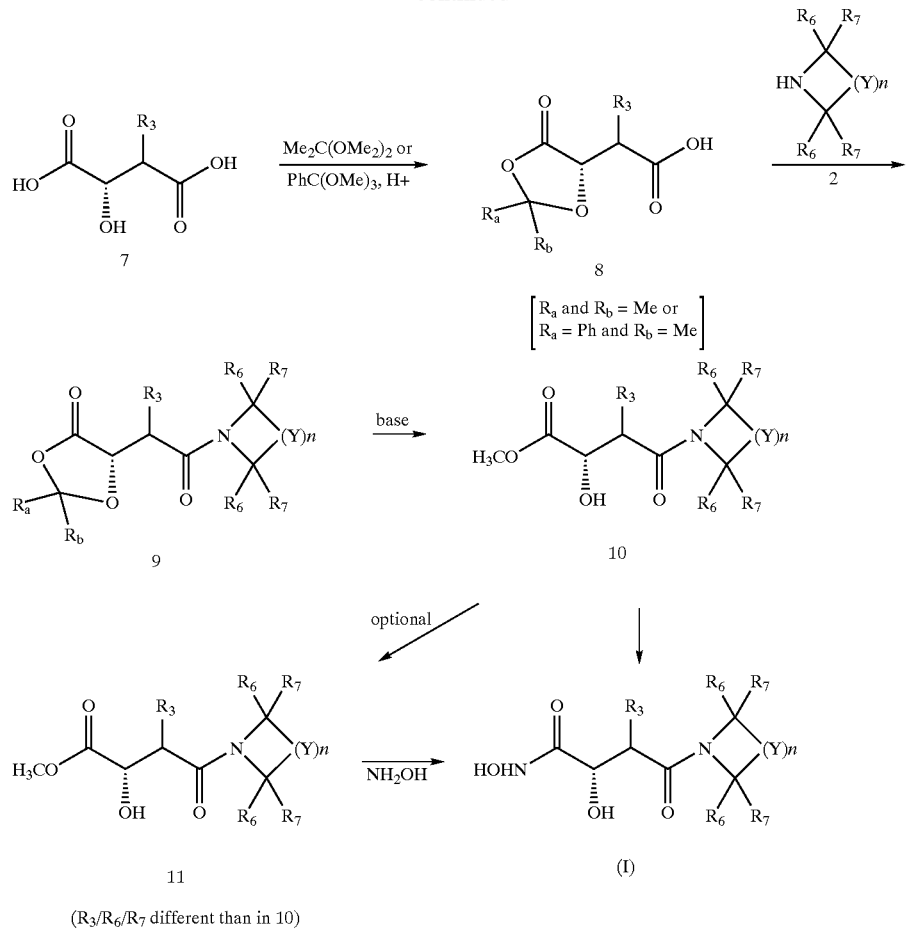

(R3/R6/R7 different than in 10)

Treatment of dimethyl malate 5 under strongly basic conditions with an appropriate alkylhalide $R_3X$ (where $R_3$ is alkyl, alkenyl, alkynyl, substituted, heteroalkyl and X is halo such as chloro, bromo, or iodo) provides 2-substituted dimethyl malate 6. The reaction is typically carried out in a polar aprotic solvent such as THF, and the base is typically lithium diisopropylamide (LDA). The reaction is initially carried out at a low temperature, preferably at about −78° C., and then allowed to slowly warm to room temperature. The reaction is then stirred for several hours. The reaction is typically higher yielding when $R_3X$ is an allylic halide. After the alkylation is complete the resulting olefin can be reduced, if desired, to provide a compound of formula 6 where $R_3$ is alkyl. The typically reduction procedure involves a suspension of 6 and a catalyst (e.g., 10% palladium on carbon) in a solvent such as ethylacetate and would be stirred under a hydrogen atmosphere for several hours to afford the corresponding compound of formula 6 where $R_3$ is alkyl. Many compounds of formula $R_3X$ are commercially available or they can be prepared by methods well known in the art. For example, iodomethane, benzylbromide, crotylbromide, allylbromide, vinylbromide are commercially available. Others can be prepared from the corresponding alcohol by first activating the hydroxy group as a p-toluenesulfonate ester (tosyl ester), followed by tosylate displaced with a halide ion in a modified Finkelstein procedure to afford an alkylhalide as described in working examples below.

Treatment of 6 with a base affords a malic acid derivative of formula 7. The base can be an inorganic base such as lithium hydroxide or potassium hydroxide, and is most preferably sodium hydroxide. This reaction is usually performed in a polar, protic solvent such as methanol. Treatment of 7 with an orthoacetate, such as trimethylorthobenzoate, in the presence of an acidic catalyst affords an orthoester 8 ($R_a$ is —Ph and $R_b$ is —OMe). This reaction is ideally performed with a co-solvent, preferably in a mixture of toluene. The reaction is ideally performed at a higher temperature, most preferably at 110° C. The catalyst is typically a sulfonic acid, such as p-toluenesulfonic acid, or most preferably camphorsulfonic acid.

Alternatively, treatment of 7 with 2,2-dimethoxypropane in the presence of p-toluenesulfonic acid provides an acetonide of formula 8 where $R_a$ and $R_b$ are methyl.

Treatment of the orthoester or acetonide 8 with a dialkylamine of formula 2 under the reaction conditions described in Scheme A provides a compound of formula 9 which upon treatment with a base, preferably the salt of an alcohol, and more preferably sodium methoxide in an alcoholic solvent then provides a 2-hydroxy-3-aminocarbonyl-propionate derivative of formula 10.

Compound 10 is then optionally converted to a compound of formula 11 for reasons discussed in Scheme A such as derivatizing the $R_3$, $R_6$ and/or $R_7$ groups prior to converting it to a compound of Formula (I). Alternatively, compound 10 it can be directly converted to a compound of Formula (I) as described in Scheme A above.

It will be recognized by a person skilled in the art that the hydroxy group in compound 10 can be replaced by various other $R_1$ groups as defined in the Summary of the Invention prior to converting it to a compound of Formula (I). Some representative examples are discussed below:

(i) the hydroxy group in compound 10 can be replaced by a fluoro group prior to converting it to a compound of Formula (I) as shown below.

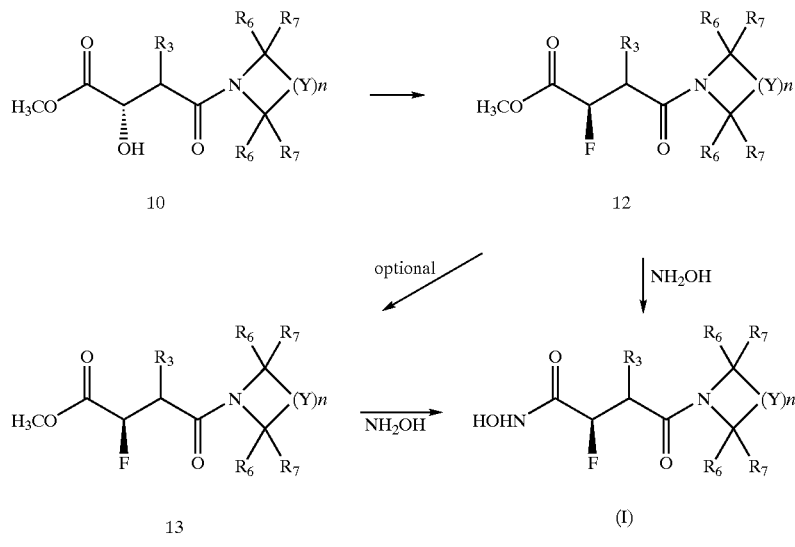

The hydroxyl group at the C2 carbon in compound 10 can be replaced by a fluoro group by first converting the hydroxyl group into an active ester followed by displaced with fluorine to afford compound 12. The reaction is performed in a halogenated solvent, such as dichloromethane (DCM), in the presence of an organic base, such as pyridine. The alcohol is typically activated as a sulfonate ester, preferably the trifluoromethane-sulfonate. This esterification reaction is typically carried out at a low temperature, preferably about −20° C. The active ester is then reacted with a fluoride ion, typically derived from tris(dimethylamino)sulfur-(trimethylsilyl)difluoride (TAS-F). This reaction is also carried out at a low temperature, preferably at about −50° C., and then slowly allowed to warm to ambient temperature. Compound 12 is then converted to a compound of Formula (I) either directly or through compound 13 as described above. A detailed description of this procedure is provided in Example 6 below. It will be noted that the stereochemistry at the C2 carbon atom is inverted during this transformation.

(ii) the hydroxy group in compound 10 can be converted to an alkoxy under alkylation reaction conditions such as treatment of 10 with an alkyl halide such as methyl iodide, ethyl iodide, benzyl bromide, and the like, in the presence of a strong base such as sodium hydride and in a polar solvent such as dimethylformamide. Detailed description of this procedure is provided in Example 45 below.

(iii) the hydroxy group in compound 10 can be converted to benzoyloxy group by first converting it into an activated ester such as a sulfonate ester, preferably the trifluoromethanesulfonate, followed by treatment with tetrabutyl ammonium benzoate. Detailed description of this procedure is provided in Example 47 below.

(iii) the hydroxy group in compound 10 can be converted to thiol group by first converting it into an activated ester such as a sulfonate ester, preferably the trifluoromethanesulfonate, followed by treatment potassium thioacetate. Detailed description of this procedure is provided in Example 48 below.

(iv) the hydroxy group in compound 10 can be converted to an azido or amino group or it's derivatives by first converting it into an activated ester such as a sulfonate ester, preferably the trifluoromethanesulfonate, followed by treatment with sodium azide. The azide group can optionally reduced under catalytic hydrogenation reaction conditions to give an amino group which can be further derivatized by methods well known in the art. Detailed description of this procedure is provided in Example 49 and 34 below.

(vi) the maintainence of the stereochemistry at the carbon atom carrying the hydroxy group in compound 10, the C2 carbon, can be achieved by carrying out double inversion as illustrated and described below.

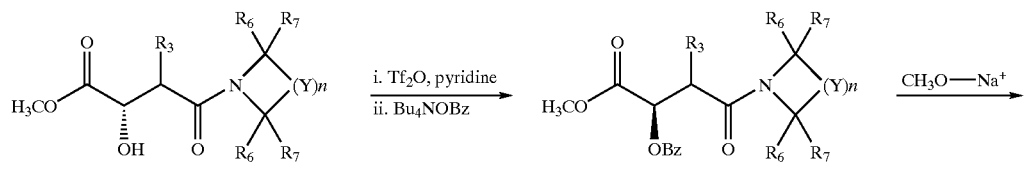

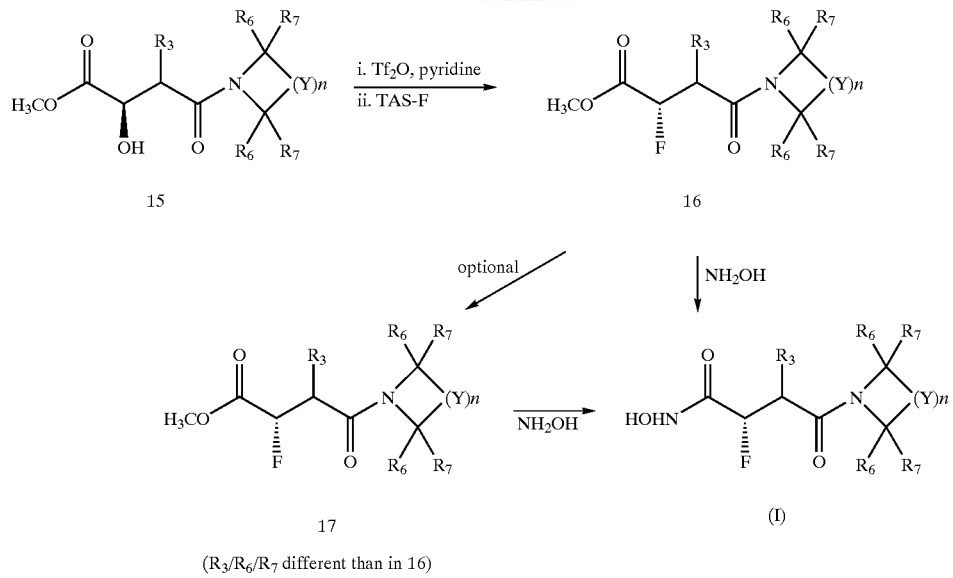

15 → 16 i. Tf$_2$O, pyridine
ii. TAS-F optional ↙   ↓ NH$_2$OH 17 (R$_3$/R$_6$/R$_7$ different than in 16) — NH$_2$OH → (I)

The hydroxyl at the C-2 carbon of intermediate 10 is converted to an active ester as described above in (i) above. Nucleophilic substitution with a variety of nucleophiles such as acetate anion, or more preferably, tetrabutylammonium benzoate, provides intermediate 14. This reaction proceeds in a hydrocarbon solvent, preferably in toluene. One skilled in the art will understand that the above nucleophilic displacement reaction results in an inversion of stereochemistry at the C-2 position.

Compound 14 is treated with a base to afford hydroxy derivative 15. This base is preferably the salt of an alcohol such as sodium methoxide, sodium ethoxide and the like, and more preferably sodium methoxide. The reaction proceeds in an alcoholic solvent such as methanol, ethanol and the like, most preferably in methanol.

Compound 15 is re-activated as a sulfonate ester, preferably a trifluoromethane sulfonate as described above and then treated with a fluorination reagent, preferably TAS-F, to afford the corresponding fluoro intermediate 16 which has the same stereochemistry at the C-2 carbon as in intermediate 10.

Compound 16 or 17 is then converted to a compound of Formula (I) as discussed above.

A compound of Formula (I) can also be prepared as illustrated in Scheme C below.

Scheme C

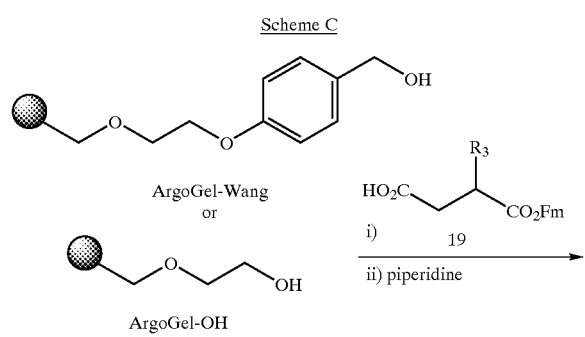

ArgoGel-Wang or ArgoGel-OH

HO$_2$C—CH(R$_3$)—CO$_2$Fm
19 i) 
ii) piperidine

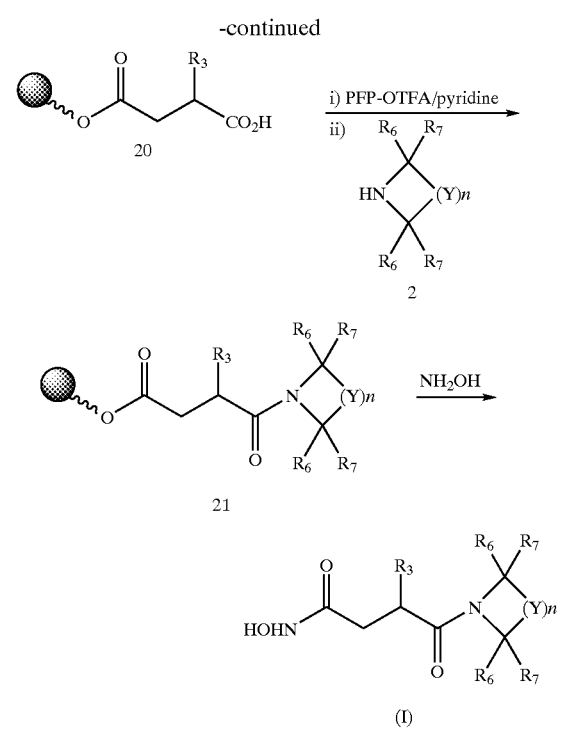

20 
i) PFP-OTFA/pyridine
ii) R$_6$, R$_7$ ... HN azetidine 2

21 → NH$_2$OH → (I)

Treatment of a suspension of ArgoGel-Wang or ArgoGel-OH resin with an Fm-protected succinic acid of formula 19 (wherein R$_3$ is as defined in the Summary of the Invention) in the presence of a coupling agent such as di-isopropylazodi-carboxylate and triphenylphosphine, followed by treatment with piperidine provides a resin bound Fm-protected succinic acid 20. The coupling reaction is carried out in a polar solvent such as dichloromethane in the presence of a base such as dimethylaminopyridine. The reaction is typically carried out at ambient temperature. Treatment of 20 with PFP-OTFA and pyridine, followed by treatment with an amine 2 then provides resin bound 3-aminocarbonylpropionate 21. The reaction is carried out in the presence of a non-nucleophilic base such as pyridine, diethylisopropylamine, 2,4,6-collidine, and the like. The reaction is typically carried out at ambient temperature. Treatment of 21 with hydroxylamine then provides a compound of Formula (I).

A compound of Formula (I) where $R_1$ & $R_2$ are fluoro and $R_2$, $R_3$, $R_6$, $R_7$, Y and n are as defined in summary of the invention can be prepared as illustrated in Scheme D below.

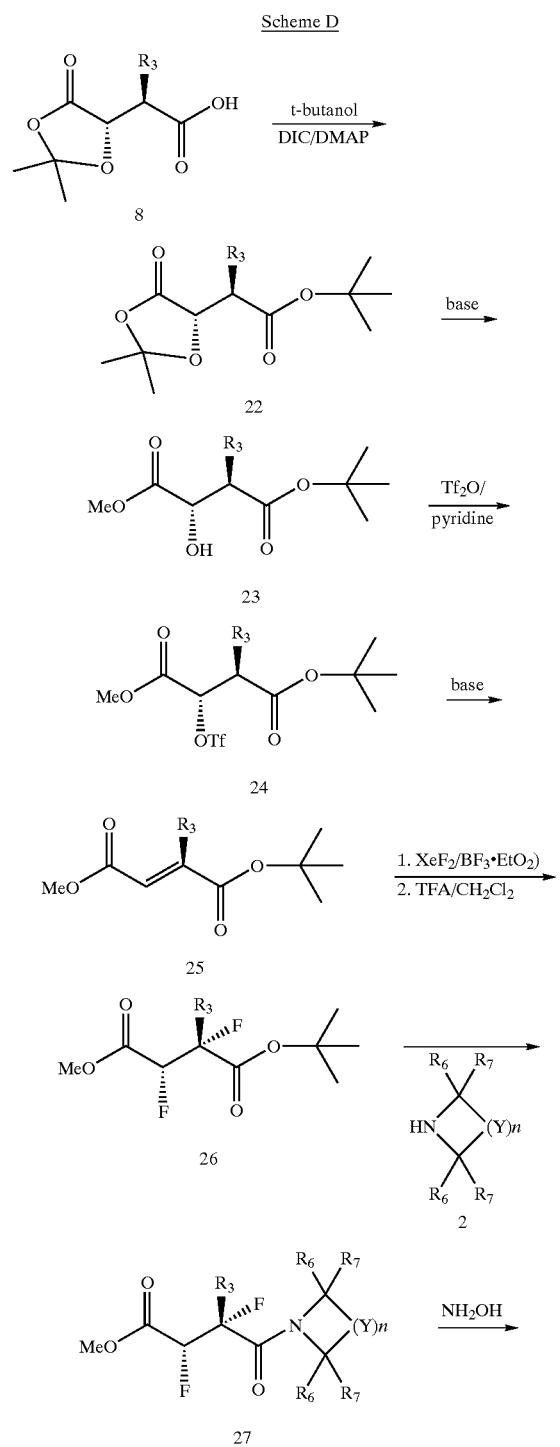

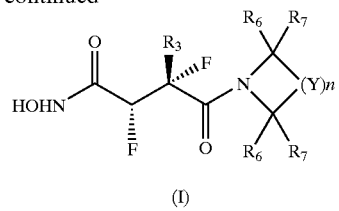

Treatment of a compound of formula 8 with an alcohol such as tert-butanol in the presence of a suitable coupling agent such as DIC and a base such as DMAP provides the corresponding tert-butyl ester of formula 22. Treatment of 22 with a base such as sodium methoxide in methanol provides 2-hydroxysuccinate derivative of formula 23. Compound 23 is then converted to a trifluoromethanesulfonate ester derivative 24 using triflic anhydride in the presence of a base such as triethyamine, pyridine and the like. Treatment of 24 with a base such as triethylamine provides a maleic acid derivative of formula 25 which upon reaction with xenon difluoride in the presence of boron trifluoride etherate provides a 2,3-difluorosuccinate derivative. Removal of the tert-butyl group with trifluoroacetic acid provides the corresponding succinic acid derivative 26 which is then converted to a compound of Formula (I) as described above.

Administration, Utility and Testing

Administration and Pharmaceutical Composition

The present invention also provides pharmaceutical compositions which comprise a bioactive hydroxamic acid compound or derivative, or a pharmaceutically acceptable salt thereof, and a pharmaceutically acceptable carrier. The compositions of the invention include those in a form adapted for oral, topical or parenteral use and can be used for the treatment of bacterial infection in animals, preferably mammals, more preferably humans.

The antibiotic compounds, also referred to herein as antimicrobial compounds, according to the invention can be formulated for administration in any convenient way for use in human or veterinary medicine, by analogy with other antibiotics. Such methods are known in the art (see, e.g., Remington's Pharmaceutical Sciences, Easton, Pa.: Mack Publishing Co.) and are not described in detail herein.

The composition can be formulated for administration by any route known in the art, such as subdermal, inhalation, oral, topical or parenteral. The compositions can be in any form known in the art, including but not limited to tablets, capsules, powders, granules, lozenges, creams or liquid preparations, such as oral or sterile parenteral solutions or suspensions. The compounds can also be administered in liposome formulations. The compounds can also be administered as prodrugs, where the prodrug administered undergoes biotransformation in the treated mammal to a form which is biologically active.

The topical formulations of the present invention can be presented as, for instance, ointments, creams or lotions, solutions, salves, emulsions, plasters, eye ointments and eye or ear drops, impregnated dressings and aerosols, and can contain appropriate conventional additives such as preservatives, solvents to assist drug penetration and emollients in ointments and creams.

The formulations can also contain compatible conventional carriers, such as cream or ointment bases and ethanol or oleyl alcohol for lotions. Such carriers can be present, for example, from about 1% up to about 99% of the formulation. For example, they can form up to about 80% of the formulation.

Tablets and capsules for oral administration can be in unit dose presentation form, and can contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets can be coated according to methods well known in standard pharmaceutical practice.

Oral liquid preparations can be in the form of, for example, aqueous or oily suspensions, solutions, emulsions, syrups or elixirs, or can be presented as a dry product for reconstitution with water or another suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate, or acacia; non-aqueous vehicles (which can include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being preferred. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection can be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions can contain, for example, from about 0.1% by weight to about 99% by weight, e.g., from about 10–60% by weight, of the active material, depending on the method of administration. Where the compositions comprise dosage units, each unit will contain, for example, from about 1–500 mg of the active ingredient. The dosage as employed for adult human treatment will range, for example, from about 1 to 3000 mg per day, for instance 1500 mg per day depending on the route and frequency of administration. Such a dosage corresponds to about 0.015 to 50 mg/kg per day. Suitably the dosage is, for example, from about 5 to 20 mg/kg per day.

Utility

The hydroxamate compounds of the present invention can be used for the treatment or prevention of infectious disorders caused by a variety of bacterial or prokaryotic organisms. Examples include Gram positive and Gram negative aerobic and anaerobic bacteria, including Staphylococci, for example *S. aureus* and *S. epidermidis*; Enterococci, for example *E. faecalis* and *E. faecium*; Streptococci, for example *S. pneumoniae*; Haemophilus, for example *H. influenza*; Moraxella, for example *M. catarrhalis*; and Escherichia, for example *E. coli*. Other examples include Mycobacteria, for example *M. tuberculosis*; intercellular microbes, for example Chlamydia and Rickettsiae; and Mycoplasma, for example *M. pneumoniae*.

In one embodiment, compositions, for treating or preventing infectious disorders are provided, comprising a hydroxamic acid compound or derivative as disclosed herein in combination with a pharmaceutically acceptable carrier.

In another embodiment, there is provided a dosage amount of a hydroxamic acid compound or derivative as disclosed herein in an effective amount for the treatment, prevention or alleviation of a disorder, such as an infectious disorder.

Hydroxamic acid compounds or derivatives can be screened for activity against different microbial agents and appropriate dosages can be determined using methods available in the art. The compounds can be used to treat a subject to treat, prevent, or reduce the severity of an infection. Subjects include animals, plants, blood products, cultures and surfaces such as those of medical or research equipment, such as glass, needles, surgical equipment and tubing, and objects intended for temporary or permanent implantation into an organism. Treating a subject includes, but is not limited to, preventing, reducing, or eliminating the clinical symptoms caused by an infection of a subject by a microorganism; preventing, reducing, or eliminating an infection of a subject by a microorganism; or preventing, reducing, or eliminating contamination of a subject by a microorganism. The microorganism involved is preferably a prokaryote, more preferably a bacterium.

In one embodiment, methods of treating or preventing an infectious disorder in a subject, such as a human or other animal subject, are provided, by administering an effective amount of a hydroxamic acid compound or derivative as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as the presence of bacteria. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, nasal, vaginal, rectal, and oral administration. The specific dosage of antimicrobial to be administered, as well as the duration of treatment, can be adjusted as needed.

Additionally, the compounds of this invention can also be used to prepare a composition in an inert diluent which is useful in inhibiting bacterial growth. An "inert diluent" means an excipient that is useful in preparing a composition that is generally safe, non-toxic and neither biologically nor otherwise undesirable.

Representative pharmaceutical formulations containing a compound of Formula (I) are described below.

Testing

The ability of the compounds of this invention to inhibit peptide deformylase was measured by in vitro assay described in detail in Biological Example below. The antimicrobial activity of the compounds of this invention was tested as described in detail in Biological Example 2 below. The selective inhibition of PDF compared to MMP-7 (Matrilysin) by the compounds of this invention was tested as described in detail in Biological Example 3 below.

EXAMPLES

The following preparations and examples are given to enable those skilled in the art to more clearly understand and to practice the present invention. They should not be considered as limiting the scope of the invention, but merely as being illustrative and representative thereof.

Abbreviations

The following abbreviations are used:
AcOH, HOAc=acetic acid
Ac$_2$O=acetic anhydride
BOC, Boc=t-butyloxycarbonyl
DCC=dicyclohexylcarbodiimide
DCM=dichloromethane
DIC=diisopropylcarbodiimide
DIAD=diisopropylazodicarboxylate
DIEA=diisopropylethylamine
DMF=dimethylformamide
EDC=N-(3-Dimethylaminopropyl)-N'-ethylcarbodiimide
Et=ethyl
EtOAc=ethyl acetate
Fmoc, FMOC=9-fluorenylmethyloxycarbonyl
HATU=O-(7-aza-benzotriazol-1-yl)-N,N,N',N'-tetramethyluronium hexafluorophosphate
HBTU=O-(benzotriazol-1-yl)-N,N,N',N'-tetramethyluronium hexafluorophosphate
HHMPA=(4-hydroxymethyl-3-methoxyphenoxy)-alkanoic acid
HMP resin=hydroxymethylphenoxy resin
HOAt=1-hydroxy-7-azabenzotriazole
HOBt=1-hydroxybenzotriazole
Me=methyl
Mem=methoxy ethoxy methyl ether
MeOH=methanol
MMP=matrix metalloproteinase
Mom=methoxy methyl ether
NMM=N-methyl morpholine
NPEOC=4-nitrophenethyloxycarbonyl
NPEOM=4-nitrophenethylmethyloxycarbonyl
NVOC=6-nitroveratryloxycarbonyl
NVOM=nitroveratryloxymethyl ether
PEG-PS resins or PS-PEG resin=polyethylene glycol-polystyrene graft copolymer resins
PFP-OTFA=pentafluorophenyl trifluoroacetate
PyBOP=benzotriazole-1-yl-oxy-tris-pyrrolidinophosphonium hexafluorophosphate
PyBROP=bromotripyrrolidinophosphonium hexafluorophosphate
RT=room temperature
TBP=tributylphosphate
TBS, TBDIMS=t-butyldimethylsilyl
tBu=t-butyl
TES=triethylsilane
TFA=trifluoroacetic acid
TGS resin=TENTAGEL S resin
TGS NH$_2$ resin=TENTAGEL S NH$_2$ resin
THF=tetrahydrofuran
THP=2-tetrahydropyranyl
TMAD=N,N,N',N'-tetramethylazodicarboxamide (1,1'-Azobis(N,N-dimethylformamide))
TMOF=trimethylorthoformate
TPP=triphenyl phosphine
TsCl=tosyl chloride
TsOH=toluenesulfonic acid
Trt=trityl Synthetic Examples General Procedure A Synthesis of N-hydroxy-3-aminocarbonylpropionamide Following Scheme A

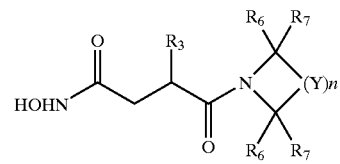

Step 1

To a solution of mono-protected succinate e.g., mono-4-methyl 2-(R)-butylsuccinic acid 1 (1 mmol) in DMF was added dialkylamine 2 (1 mmol), DIEA (0.4 mL, 2.3 mmol), and an activating reagent (e.g. EDC, PyBOP, DIC, DCC, etc.; 1 mmol). The mixture was stirred overnight, then diluted with ethyl acetate and washed with aqueous HCl (1 N), water, saturated sodium bicarbonate, brine, and then dried (Na$_2$SO$_4$). The filtrate was concentrated and then purified on silica gel (Merck 60; ethyl acetate/hexane) to afford 3-aminocarbonylpropionate 3.

Step 2

3-Aminocarbonylpropionate 3 (0.1 mmol) was treated with dioxane (1 mL) and hydroxylamine (50% in water, 2 mL) for 1 to 3 days, and then can be purified by preparative reverse-phase (C18) HPLC to afford the desired N-hydroxy-3-aminocarbonylpropionamide.

General Procedure B

Synthesis of N-hydroxy-3-(R)-n-butyl-3-aminocarbonylpropionamide

Alternate Method

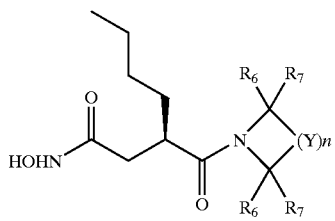

To mono-4-methyl 2-(R)-butylsuccinic acid (0.2 mmol) in dioxane (1 mL) was added amine 2 (0.2 mmol), DIEA (0.4 mmol) and an activating reagent (e.g. EDC, PyBOP, DIC, DCC, etc.; 0.2 mmol); and the mixture was stirred for 2 h. Aqueous 50% hydroxylamine was added (1.5 mL) and the mixture was stirred an additional 1–2 days. The reaction mixture can then be purified by preparative reverse-phase (C18) HPLC to afford N-hydroxy-3-(R)-n-butyl-3-aminocarbonylpropionamide.

General Procedure C

Synthesis of N-hydroxy-3-(R)-n-butyl-3-[2-(S)-aminocarbonylpyrrolidin-1-ylcarbonyl)-2-(S)-hydroxypropionamide

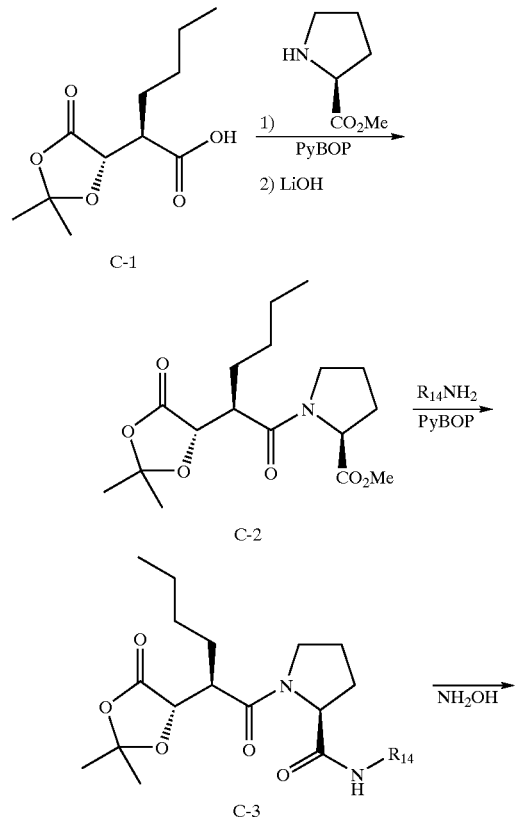

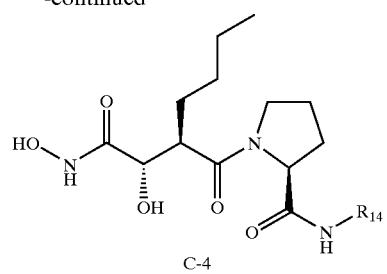

Step 1

To 2-(2,2-dimethyl-4-oxo-1,3-dioxolan-5-yl)hexanoic acid C-1 (prepared in four steps from dimethyl malate; see Example 21 for details) in DMF was added proline O-methyl ester, DIEA and HATU and the solution stirred 4 hours. Standard aqueous workup afforded the desired amide, which was dissolved in methanol and treated with lithium hydroxide to yield 1-(2,2-dimethyl-4-oxo-1,3-dioxolan-5-yl)-1-(2-(S)-carboxypyrrolidin-1-ylcarbonyl)pentane C-2.

Step 2

To 1-(2,2-dimethyl-4-oxo-1,3-dioxolan-5-yl)-1-(2-(S)-carboxypyrrolidin-1-ylcarbonyl)pentane C-2 in DMF was added an amine $R_{14}NH_2$, DIEA and HATU and the solution stirred for 2 h. Aqueous workup followed by silica gel chromatography afforded 1-(2,2-dimethyl-4-oxo-1,3-dioxolan-5-yl)-1-(2-(S)-aminocarbonylpyrrolidin-1-ylcarbonyl)pentane C-3.

Step 3

To 1-(2,2-dimethyl-4-oxo-1,3-dioxolan-5-yl)-1-(2-(S)-aminocarbonylpyrrolidin-1-ylcarbonyl)pentane C-3 in dioxane was treated with 50% aqueous hydroxylamine for 4 h. The reaction mixture was then purified by preparative reverse-phase (C18) HPLC to afford N-hydroxy-3-(R)-n-butyl-3-[2-(S)-aminocarbonylpyrrolidin-1-ylcarbonyl)-2-(S)-hydroxypropionamide C-4.

General Procedure D

Synthesis of N-hydroxy-3-(R)-n-butyl-3-[2-(S)-aminocarbonylpyrrolidin-1-yl-carbonyl)propionamide

Following Scheme C

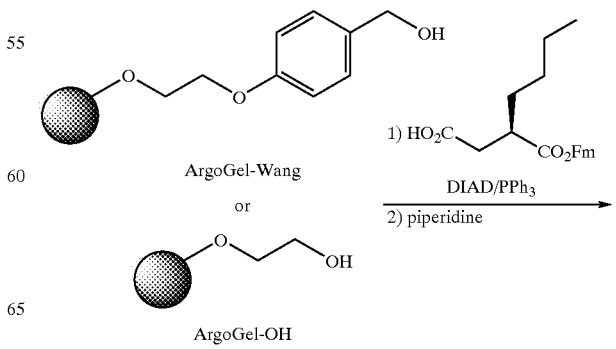

General Procedure E

Synthesis of N-hydroxy-3-(R)-n-butyl-3-[2-(S)-aminocarbonylpyrrolidin-1-ylcarbonyl)propionamide

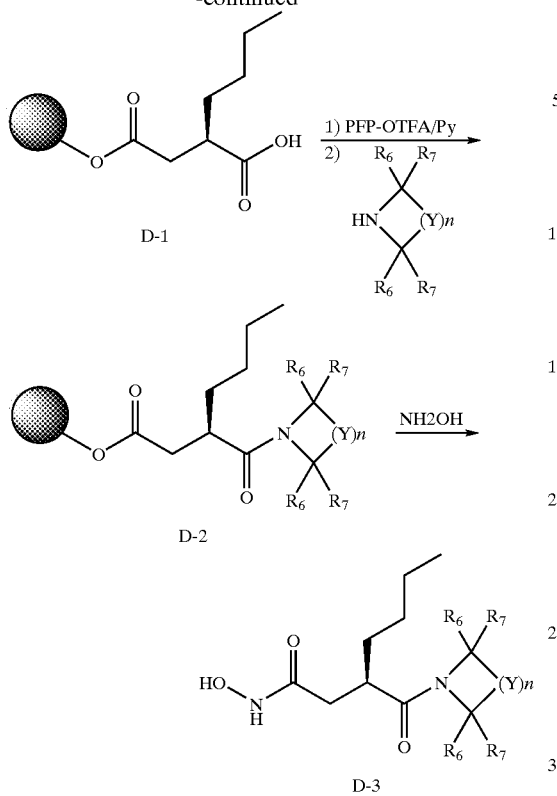

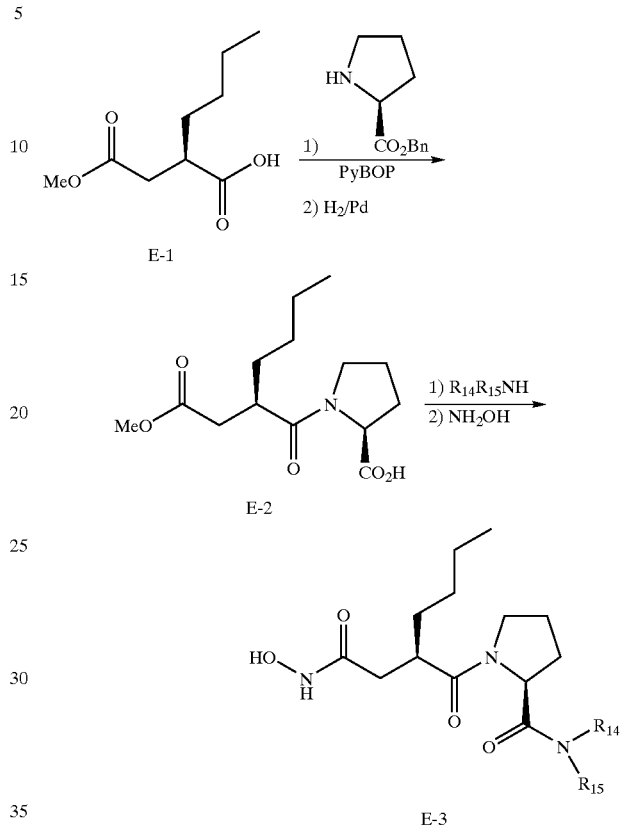

Step 1

To ArgoGel resin (20 g) solvated in DCM was added 2-(R)-n-butylsuccinate 1-(9-fluorenyl) ester (10.0 g, 23.2 mmol), diisopropylazodicarboxylate (DIAD; 4.8 mL, 24.3 mmol) and triphenylphosphine (PPh$_3$, 6.38 g, 24.3 mmol); the reaction mixture was shaken for 6 h. The resin is filtered and was washed with DCM (3×), MeOH (3×) and DMF (3×). A solution of piperidine (40 mL, 10% in DMF) was added and the resin mixture is shaken for 3 h. The resin was filtered and then washed sequentially with DMF (3×), DCM (2×), MeOH (2×) and DMF (3×) to afford intermediate D-1.

Step 2

To resin D-1 in DMF was added PFP-OTFA and pyridine and the mixture was shaken for 4 h. The resin was filtered and washed with DMF (3×), MeOH (2×), DCM (2×), and ether (2×) and dried under vacuum. To a portion of the resin was added a solution of an amine (1 mmol) and DIEA (1.5 mmol) in DMF (1 mL). The resin was shaken overnight, filtered and washed with DMF, MeOH, and DCM to afford D-2.

Step 3

To D-2 was added dioxane (0.5 mL) and aqueous 50% hydroxylamine (1 mL). After 18 h, the cleavage products were drained and then purified by preparative reverse-phase (C18) HPLC to afford the desired hydroxamate D-3.

Step 1

To a solution of mono-4-methyl 2-(R)-butylsuccinic acid, (prepared in three steps from hexanoylchloride and t-butyl bromoacetate as described below; 1 mmol) in DMF was added proline O-benzyl ester (1 mmol), DIEA (0.4 mL, 2.3 mmol), and a coupling reagent (e.g. EDCI, PyBOP, DIC, etc.; 1 mmol). The mixture was stirred overnight, then diluted with ethyl acetate and washed with aqueous HCl (1 N), water, saturated sodium bicarbonate, brine, and then dried (Na$_2$SO$_4$). The filtrate was concentrated and then purified on silica gel (Merck 60; ethyl acetate/hexane) to afford methyl-3-(R)-butyl-3-(2-(S)-benzyloxycarbonyl-pyrrolidin-1-ylcarbonyl)propionate. To this amide (0.1 mmol) in ethylacetate (10 mL) was added 10% Pd/C (100 mg) and the solution stirred under a hydrogen atmosphere for 8 h. The suspension was filtered through a Celite plug and then concentrated to afford methyl-3-(R)-butyl-3-(2-(S)-carboxypyrrolidin-1-ylcarbonyl)propionate E-2.

Step 2

To methyl-3-(R)-butyl-3-(2-(S)-carboxycarbonyl-pyrrolidin-1-ylcarbonyl)-propionate E-2 (100 mg) in DMF (1 mL) was added an amine (1 equivalent), DIEA (2.5 equivalents) and HATU (1 equivalent) and the reaction stirred for 4 h. The solution was then cooled to 0° C., 50% aqueous hydroxylamine was added (400 µL), and the reaction stirred at 4° C. for 4 hours to 3 days, depending upon the succinate. The crude reaction mixture was then purified by preparative reverse-phase (C18) HPLC to afford the desired compound methyl-3-(R)-butyl-3-(2-(S)-aminocarbonylpyrrolidin-1-ylcarbonyl)propionate E-3.

General Procedure F

Synthesis of N-hydroxy-3-(R)-n-butyl-3-[2-(S)-aminocarbonylpyrrolidin-1-ylcarbonyl)-2-(S)-hydroxypropionamide

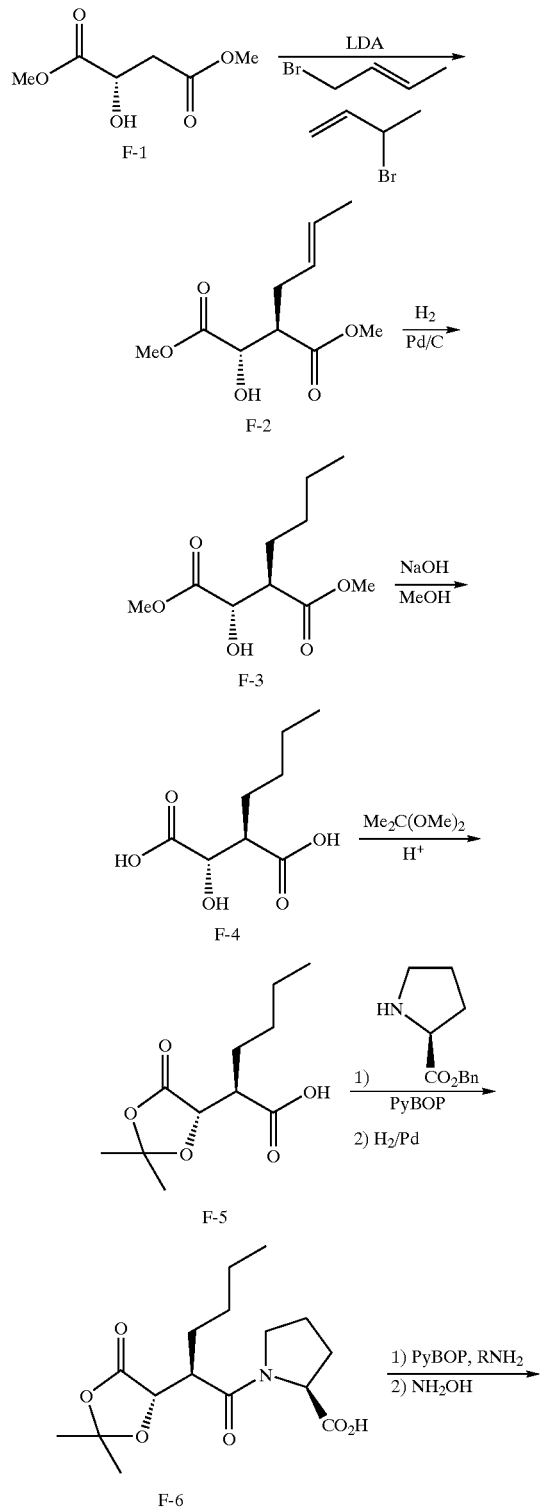

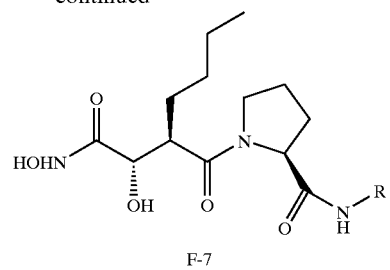

Step 1

To a solution of diisopropylamine (14 mL, 100 mmol) in THF at 0° C. was added n-butyllithium (2.5 M in hexane, 40 mL, 100 mmol) over 10 min. The mixture was stirred at RT for 30 min., and then added via cannula to a −78° C. solution of dimethyl malate F-1 (7.71 g, 47.6 mmol) in THF (130 mL). The mixture was warmed to −20° C. over 2 h, and then cooled to −78° C. Crotyl bromide (8.1 g, 60 mmol) was added, then the mixture was allowed to warm to room temperature and then stirred overnight. The solution was then cooled to −10° C. and quenched with NH$_4$Cl (10%, 100 mL). The THF was removed and the residue extracted with ethyl acetate (2×200 mL). The combined organic layers were washed with HCl (1N, 3×50 mL), saturated aqueous sodium bicarbonate (3×50 mL), and brine, then dried over Na$_2$SO$_4$. The solution was filtered and concentrated to give a residue, which was purified on silica gel (ethyl acetate/hexane 1:4) to afford (2S,3R)-3-(2-butenyl)-2-hydroxysuccinic dimethyl ester F-2 (2.5 g, 24%).

Step 2

To (2S,3R)-3-(2-butenyl)-2-hydroxysuccinic dimethyl ester F-2 (2.5 g) in ethyl acetate (50 mL) was added 10% Pd/C (0.25 g) and the reaction stirred under a hydrogen atmosphere for 20 h. The suspension was filtered through a pad of Celite, washed with EtOAc (3×) and then concentrated in vacuo to afford (2S,3R)-3-(n-butyl)-2-hydroxysuccinic dimethyl ester F-3.

Step 3

To (2S,3R)-3-(n-butyl)-2-hydroxysuccinic dimethyl ester F-3 in methanol (28 mL) was added a solution of NaOH (2.2 g, 55 mmol) in water (28 mL). After 24 h the MeOH was removed, the crude reaction was acidified with HCl (6N, 12 mL) to pH=1, and then extracted with ethyl acetate (3×50 mL). The combined organic layers were dried (Na$_2$SO$_4$) and concentrated to give (2S,3R)-3-(n-butyl)-2-hydroxysuccinic acid F-4 (1.96 g, 90%).

Step 4

To a solution of (2S, 3R)-3-(n-butyl)-2-hydroxysuccinic acid F-4 (300 mg, 1.58 mmol) in 2,2-dimethoxypropane (10 mL) was added p-toluenesulfonic acid (20 mg) and the reaction was stirred at room temperature for 16 h. The solution was diluted with dichloromethane and washed with brine, dried (Na$_2$SO$_4$) and then purified by silica gel chromatography to afford 1.2 mmol 2-(2,2-dimethyl-4-oxo-1,3-dioxolan-5-yl)hexanoic acid F-5 (78%).

Step 5

To a solution of 2-(2,2-dimethyl-4-oxo-1,3-dioxolan-5-yl) hexanoic acid F-5 (1.2 mmol) in DCM (10 mL) was added L-Pro-OBn (1.2 mmol), PyBOP (1.2 mmol), and DIEA (2.5 mmol). The mixture was stirred overnight, then concentrated, and purified on silica gel (ethylacetate/hexane 1:4) to afford 275 mg of the desired amide (45%). To the product in ethylacetate (25 mL) was added 10% Pd/C (50 mg) and the reaction stirred under a hydrogen atmosphere for 8 h. The suspension was filtered through a pad of Celite, washed with EtOAc (3×) and then concentrated in vacuo to afford 1-(2,2-dimethyl-4-oxo-1,3-dioxolan-5-yl)-1-(2-(S)-carboxy-pyrrolidin-1-ylcarbonyl)pentane F-6 (quant.).

Step 6

To 1-(2,2-dimethyl-4-oxo-1,3-dioxolan-5-yl)-1-(2-(S)-carboxy-pyrrolidin-1-ylcarbonyl)pentane F-6 (50 mg) in dioxane (1 mL) was added an amine $RNH_2$ (1 equivalent), DIEA (2.5 equivalents) and HATU or PyBOP (1 equivalent) and the solution stirred for 4 h. The reaction was then cooled to 0° C., 50% aqueous hydroxylamine was added (400 μL), and the solution stirred at 4° C. for 8 hours. The crude reaction mixture was then purified by preparative reverse-phase (C18) HPLC to afford N-hydroxy-3-(R)-n-butyl-3-[2-(S)-aminocarbonylpyrrolidin-1-yl-carbonyl)-2-(S)-hydroxypropionamide F-7.

General Procedure G

Synthesis of N-hydroxy-3-(S)-n-butyl-3-[2-(S)-aminocarbonylpyrrolidin-1-ylcarbonyl)-2-(R)-fluoropropionamide

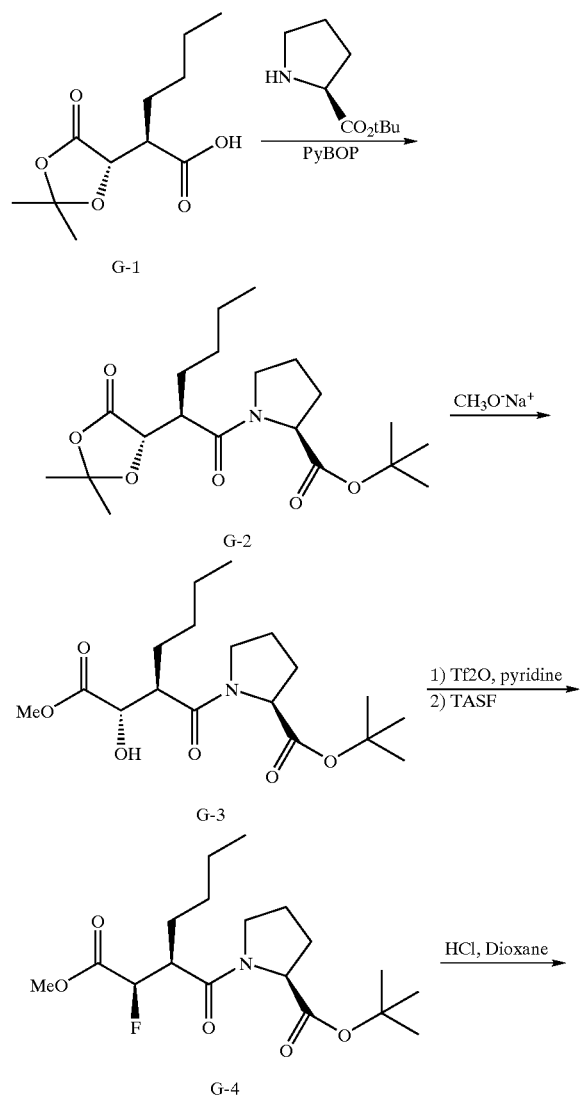

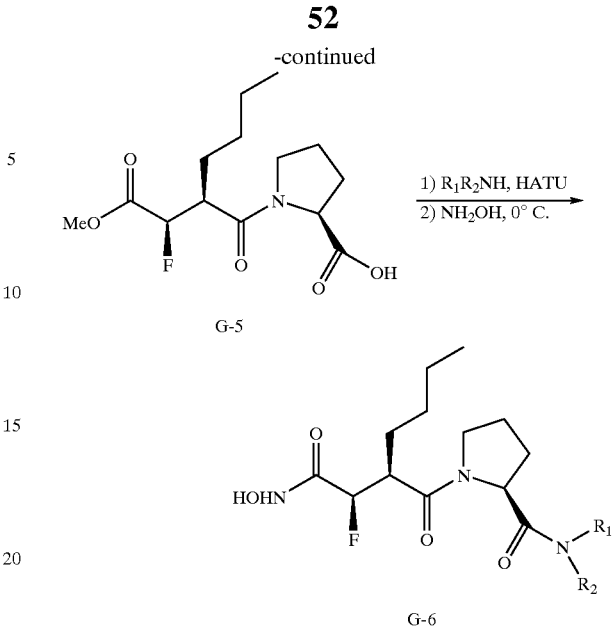

Step 1

To 2-(2,2-dimethyl-4-oxo-1,3-dioxolan-5-yl)hexanoic acid G-1 (10 mmol; prepared as described in Method F, above) in DMF (50 mL) was added proline O-t-butyl ester (10 mmol), DIEA (25 mmol) and PyBOP (10 mmol) and the solution stirred for 8 h. The reaction was diluted with ethyl acetate and washed with water, sodium bicarbonate, brine, and then dried ($Na_2SO_4$). The filtrate was concentrated and then purified on silica gel (Merck 60; ethyl acetate/hexane) to afford 1-(2,2-dimethyl-4-oxo-1,3-dioxolan-5-yl)-1-(2-(S)-tert-butoxycarbonylpyrrolidin-1-ylcarbonyl)pentane G-2 (5 mmol, 50%).

Step 2

To 1-(2,2-dimethyl-4-oxo-1,3-dioxolan-5-yl)-1-(2-(S)-tert-butoxycarbonylpyrrolidin-1-ylcarbonyl)pentane G-2 (5 mmol, 50%) (5 mmol) in methanol (20 mL) was added sodium methoxide (catalytic; pH adjusted to 10) and the solution stirred for 1 hour. Amberlite IR-120 resin ($H^+$ form) was added, then the solution was filtered and concentrated to afford methyl 3-(R)-n-butyl-3-[2-(S)-tert-butoxycarbonylpyrrolidin-1-yl-carbonyl)-2-(S)-hydroxypropionate G-3 (quant.).

Step 3

To methyl 3-(R)-n-butyl-3-[2-(S)-tert-butoxycarbonylpyrrolidin-1-ylcarbonyl)-2-(S)-hydroxypropionate G-3 (5 mmol) in DCM (5 mL) was added pyridine (15 mmol), the reaction was cooled to −20° C., then triflic anhydride was added (7.5 mmol). The solution was stirred for 1 hour, then washed with aqueous citric acid, sodium bicarbonate and brine, then dried ($Na_2SO_4$) and concentrated. The intermediate triflate was then resuspended in DCM and cooled to −50° C. Tris(dimethylamino)sulfur (trimethylsilyl)difluoride (TAS-F) was added (5 mmol) and the solution allowed to warm to rt. The reaction mixture was washed with aqueous sodium bicarbonate and brine, dried ($Na_2SO_4$) and concentrated then purified on silica gel (ethylacetate/hexanes) to afford 2.3 mmol (45%) of methyl 3-(S)-n-butyl-3-[2-(S)-tert-butoxycarbonylpyrrolidin-1-yl-carbonyl)-2-(R)-fluoropropionate G-4.

Step 4

To methyl 3-(S)-n-butyl-3-[2-(S)-tert-butoxycarbonylpyrrolidin-1-ylcarbonyl)-2-(R)-fluoropropionate G-4 (2.3 mmol) was added 4 N HCl in dioxane (10 mL), the solution stirred for 2 h, then evaporated to dryness to afford 2.3 mmol of methyl 3-(S)-n-butyl-3-[2-(S)-carboxypyrrolidin-1-yl-carbonyl)-2-(R)-fluoropropionate G-5 (quant.). To intermediate G-5 (0.15 mmol) in dioxane (1 mL) was added an amine (0.15 mmol), DIEA (0.38 mmol), and HATU or other coupling reagent (0.15 mmol) and the solution stirred for 8 h. The reaction was cooled to 0° C., aqueous 50% hydroxylamine was added (0.5 mL) and the reaction stirred for 4 h. The crude reaction mixture was then purified by preparative reverse-phase (C18) HPLC to afford N-hydroxy-3-(S)-n-butyl-3-[2-(S)-aminocarbonylpyrrolidin-1-ylcarbonyl)-2-(R)-fluoropropionamide G-6.

General Procedure H

Synthesis of N-hydroxy-3-(S)-n-butyl-3-[2-(S)-aminocarbonylpyrrolidin-1-ylcarbonyl)-2-(S)-fluoropropionamide

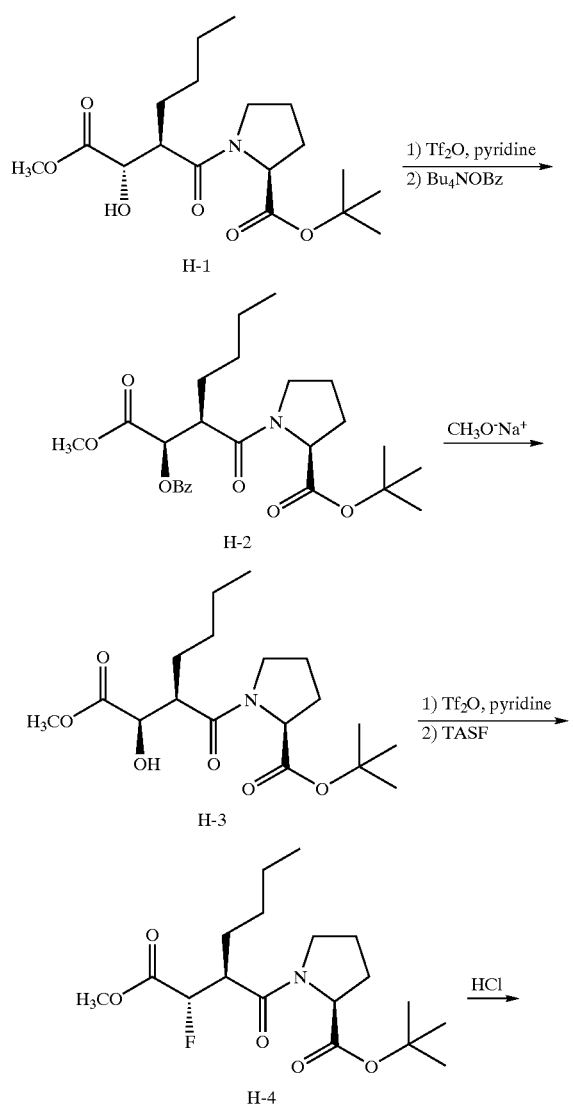

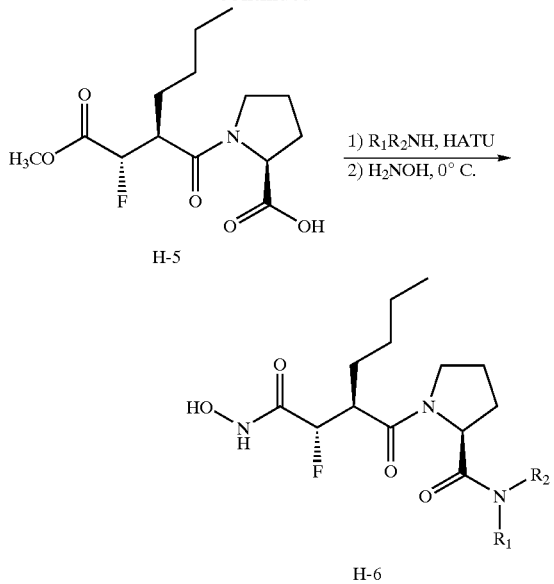

Step 1

To methyl 3-(R)-n-butyl-3-[2-(S)-tert-butoxycarbonylpyrrolidin-1-ylcarbonyl)-2-(S)-hydroxypropionate H-1 (10 mmol; prepared as described in Method G, above) in DCM (10 mL) was added pyridine (30 mmol), the reaction was cooled to −20° C. then triflic anhydride (15 mmol) was added. The solution was stirred for 1 hour, then washed with aqueous citric acid, sodium bicarbonate and brine, then dried ($Na_2SO_4$) and concentrated. The resulting oil was dissolved in toluene (30 mL), cooled to 0° C., then treated with tetrabutylammonium benzoate. After 1.5 h, the reaction was concentrated and then purified on silica gel (ethylacetate/hexanes) to afford 8.7 mmol of methyl 3-(R)-n-butyl-3-[2-(S)-tert-butoxycarbonylpyrrolidin-1-ylcarbonyl)-2-(R)-benzoyloxypropionate H-2 (87%).

Step 2

To methyl 3-(R)-n-butyl-3-[2-(S)-tert-butoxycarbonylpyrrolidin-1-ylcarbonyl)-2-(R)-benzoyloxypropionate H-2 (8.7 mmol) in methanol (25 mL) at 0° C. was added sodium methoxide (catalytic; pH adjusted to 10) and the solution stirred for 2 h. Amberlite IR-120 resin ($H^+$ form) was added, then the solution was filtered and concentrated to afford methyl 3-(R)-n-butyl-3-[2-(S)-tert-butoxycarbonylpyrrolidin-1-yl-carbonyl)-2-(R)-hydroxypropionate H-3 (quant.).

Step 3

To methyl 3-(R)-n-butyl-3-[2-(S)-tert-butoxycarbonylpyrrolidin-1-ylcarbonyl)-2-(R)-hydroxypropionate H-3 (8.7 mmol) in DCM (10 mL) was added pyridine (25 mmol), the reaction was cooled to −20° C., then triflic anhydride (12.5 mmol) was added. The solution was stirred for 1 hour, then worked up as described above. The intermediate triflate was resuspended in DCM and cooled to −50° C. Tris(dimethylamino)sulfur (trimethylsilyl)difluoride (TAS-F) was added (8.7 mmol) and the solution allowed to warm to rt. The reaction mixture was washed with aqueous sodium bicarbonate and brine, dried ($Na_2SO_4$) and concentrated, then purified on silica gel (ethylacetate/hexanes) to afford 4.3 mmol (50%) of methyl 3-(S)-n-butyl-3-[2-(S)-tert-butoxycarbonylpyrrolidin-1-yl-carbonyl)-2-(S)-fluoropropionate H-4.

Step 4

To methyl 3-(S)-n-butyl-3-[2-(S)-tert-butoxycarbonylpyrrolidin-1-ylcarbonyl)-2-(S)-fluoropropionate H-4 (4.3 mmol) was added 4 N HCl in dioxane (15 mL), the solution stirred for 2 h, then evaporated to dryness to afford 4.3 mmol of methyl 3-(S)-n-butyl-3-[2-(S)-carboxypyrrolidin-1-yl-carbonyl)-2-(S)-fluoropropionate H-5 (quant.). To H-5 (0.15 mmol) in dioxane (1 mL) was added an amine (0.15 mmol), DIEA (0.38 mmol), and HATU or similar coupling reagent (0.15 mmol) and the solution stirred for 8 h. The reaction was cooled to 0° C., aqueous 50% hydroxylamine was added (0.5 mL) and the reaction stirred for 4 h. The crude reaction mixture was then purified by preparative reverse-phase (C18) HPLC to afford N-hydroxy-3-(S)-n-butyl-3-[2-(S)-aminocarbonylpyrrolidin-1-yl-carbonyl)-2-(S)-fluoropropionamide H-6.

General Procedure I

Synthesis of N-hydroxy-3-(R)-n-butyl-3-[2-(S)-(tert-butoxycarbonyl)-pyrrolidin-1-ylcarbonyl)-2-(S)-hydroxypropionamide

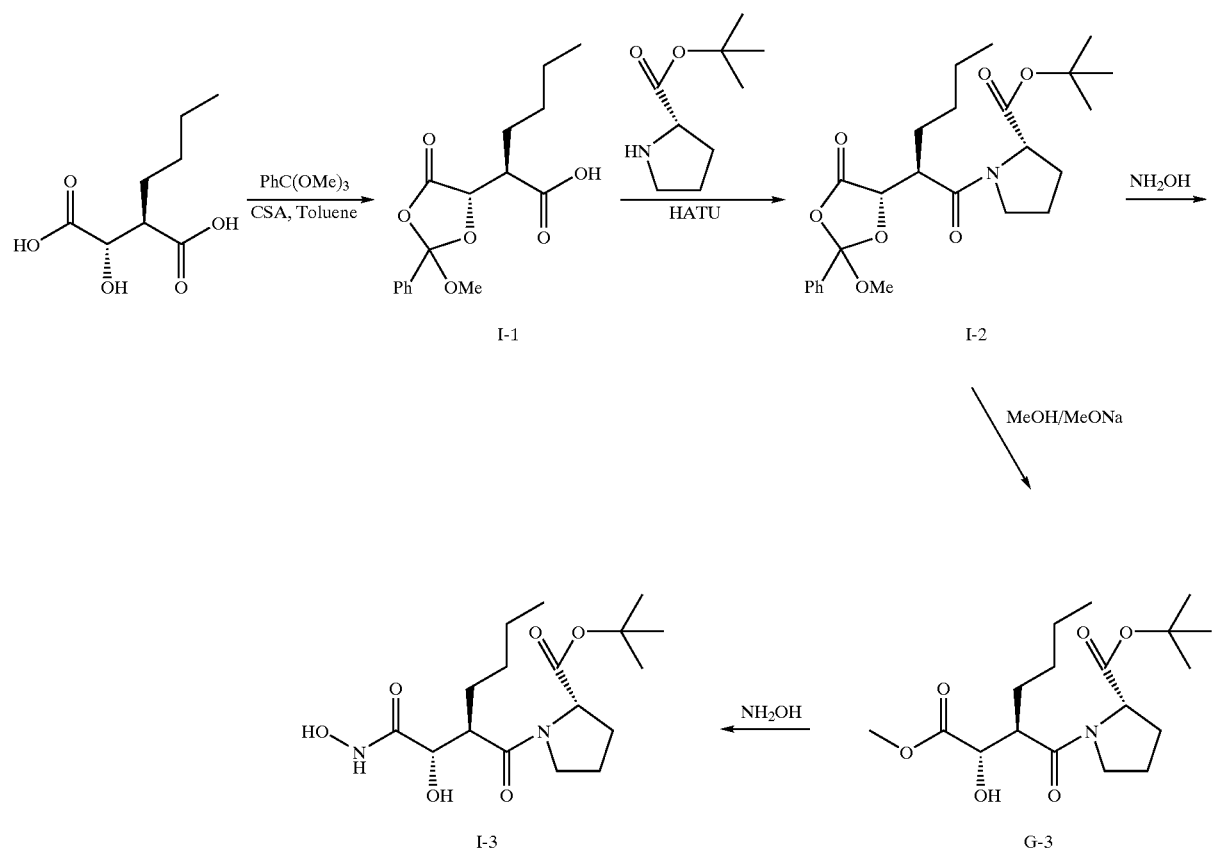

Step 1

To a solution of (2S,3R)-3-(n-butyl)-2-hydroxysuccinic acid F-4 (300 mg, 1.58 mmol) and powdered molecular sieves (1 g) in trimethyl orthobenzoate (5 mL) and toluene (5 ml) was added 10-Camphorsulfonic acid (20 mg) and the reaction was heated at 110° C. under vacuum (20 torr) for 5 h. The solution was diluted with ethyl acetate, filtered through Celite and washed with brine, dried (Na$_2$SO$_4$) and then purified by silica gel chromatography to afford 1.2 mmol 2-(2-methoxy-2-phenyl-4-oxo-1,3-dioxolan-5-yl) hexanoic acid I-1 (40%).

Step 2

To 2-(2-methoxy-2-phenyl-4-oxo-1,3-dioxolan-5-yl) hexanoic acid I-1 (10 mmol; prepared as described in Method I, above) in DMF (50 mL) was added proline O-t-butyl ester (10 mmol), DIEA (25 mmol) and PyBOP (10 mmol) and the solution stirred for 8 h. The reaction was diluted with ethyl acetate and washed with water, sodium bicarbonate, brine, and then dried (Na$_2$SO$_4$). The filtrate was concentrated and then purified on silica gel (Merck 60; ethyl acetate/hexane) to afford 1-(2-methoxy-2-phenyl-4-oxo-1,3-dioxolan-5-yl)-1-(2-(S)-tert-butoxycarbonylpyrrolidin-1-yl-carbonyl)pentane 1–2 (5 mmol, 50%).

Step 3

To 1-(2-methoxy-2-phenyl-4-oxo-1,3-dioxolan-5-yl)-1-(2-(S)-tert-butoxycarbonylpyrrolidin-1-ylcarbonyl)pentane 1–2 (5 mmol, 50%) (5 mmol) in methanol (20 mL) was added sodium methoxide (catalytic; pH adjusted to 10) and the solution stirred for 1 hour. Amberlite IR-120 resin (H$^+$ form) was added, then the solution was filtered and concentrated to afford methyl 3-(R)-n-butyl-3-[2-(S)-tert-butoxycarbonylpyrrolidin-1-yl-carbonyl)-2-(S)-hydroxypropionate G-3 (quant.).

Step 4

To G-3 and I-2 (50 mg) in dioxane (1 mL) was added aqueous 50% hydroxylamine (0.5 mL) and the reaction stirred for 16 h. The crude reaction mixture was then purified by preparative reverse-phase (C18) HPLC to afford N-hydroxy-3-(R)-n-butyl-3-[2-(S)-(tert-butoxycarbonyl)-pyrrolidin-1-yl-carbonyl)-2-(S)-hydroxypropionamide.

General Procedure J

Synthesis of N-hydroxy-3-(S)-n-butyl-3-[2-(S)-aminocarbonylpyrrolidin-1-ylcarbonyl)-2-(RS)-fluoropropionamide

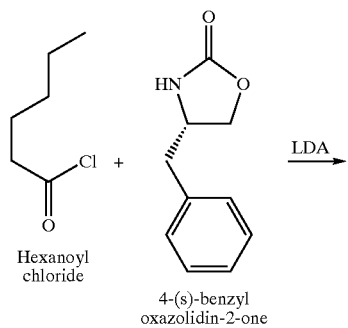

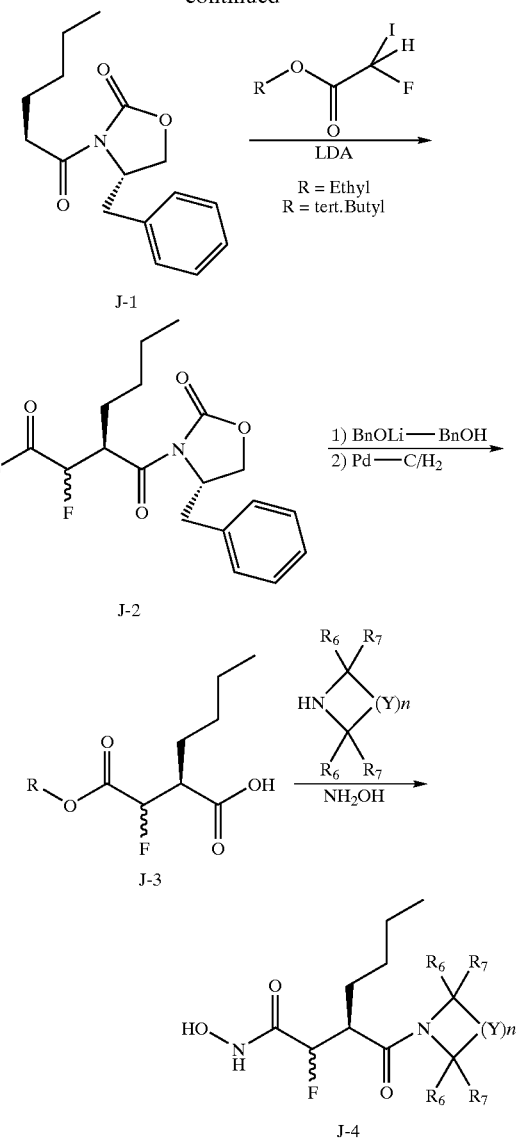

Step 1

To a solution of 4-(S)-benzyloxazolidin-2-one (56 mmol) (Aldrich, Milwaukee, Wis.) in THF at −78° C. was added 2.5 M n-BuLi in hexane (22.4 mL, 56 mmol) and the reaction stirred at −78° C. for 2 hr. To this was added via cannula a −78° C. solution of hexanoyl chloride (65 mmol) in THF and the mixture stirred at −78° C. for 2 hr, then allowed to warm to room temperature and stirred overnight. The reaction was then quenched with aqueous saturated NH$_4$Cl, extracted with ethyl acetate, dried, and purified by silica gel chromatography (hexanes/ethyl acetate) to afford N-hexanoyl-4-(S)-benzyloxazolidin-2-one J-1.

Step 2

To a solution of N-hexanoyl-4-(S)-benzyloxazolidin-2-one (7.3 mmol) in THF at −78° C. was added 1.0 M sodium hexamethyldisilazide (NaHMDS, 8.8 mmol) and the reaction stirred at −78° C. for 1 hr. A solution of alkyl iodofluorooacetate (8.8 mmol) in THF was then added dropwise, and the resulting mixture was stirred at −78° C. for 1 hr and then at room temperature overnight. The reaction was quenched with NH$_4$Cl, concentrated, then suspended in ethyl acetate and washed with 0.5 N HCl and brine, dried, and purified by silica gel chromatography (ethyl acetate/hexanes) to afford the alkyl 3-(S)-(n-butyl)-3-[4-(S)-benzyloxazolidin-2-one-3-ylcarbonyl)-2-(RS)-(fluoro)propionate J-2.

Step 3

To alkyl 3-(S)-(n-butyl)-3-[4-(S)-benzyloxazolidin-2-one-3-ylcarbonyl)-2-(RS)-(fluoro)propionate (1.44 mmol) in THF at 0° C. was added LiOBn (5.76 mmol) in benzyl alcohol and the reaction stirred at 0° C. for 3 hr. The reaction was then quenched with 5% $KHSO_4$, concentrated, suspended in ethyl acetate and subjected to standard aqueous workup. The crude product was purified by silica gel chromatography (methanol/dichloromethane) to afford alkyl 3-(R)-(n-butyl)-2-(RS)-(fluoro)propionate J-3.

Step 4

To J-3 (0.15 mmol) in dioxane (1 mL) was added an amine (0.15 mmol), DIEA (0.38 mmol), and HATU or similar coupling reagent (0.15 mmol) and the solution stirred for 8 h. The reaction was cooled to 0° C., aqueous 50% hydroxylamine was added (0.5 mL) and the reaction stirred for 4 h. The crude reaction mixture was then purified by preparative reverse-phase (C18) HPLC to afford N-hydroxy-3-(S)-n-butyl-3-[2-(S)-aminocarbonylpyrrlidin-1-yl-carbonyl)-2-(RS)-fluoropropionamide J-4.

Example 1

Synthesis of N-hydroxy-3-(R)-(n-butyl)-3-[(2-(S)-(tert-butoxycarbonyl)-pyrrolidin-1-ylcarbonyl]propionamide

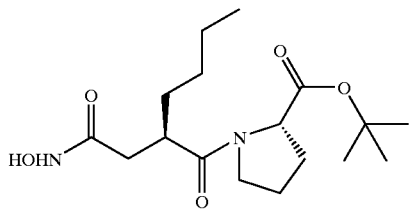

The title compound was prepared according to General Procedure A from mono-methyl 2-(R)-butylsuccinic acid and L-proline tert-butyl ester. This compound has also been prepared according to General Procedure D using L-proline tert-butyl ester as the amine. $^1$H NMR (300 MHz, $CDCl_3$) δ 0.89 (t, J=7.2 Hz, 3H), 1.43 (s, 9H), 1.24–1.71 (m, 6H), 1.86–2.43 (m, 5H), 2.53 (dd, J=10.5 and 13.2 Hz, 1H), 3.06 (m, 1H), 3.45–3.80 (m, 2H), 4.28–4.40 (m, 1H).

Example 2

Synthesis of N-hydroxy-3-(R)-(n-butyl)-3-[(2-(S)-(tert-butylaminocarbonyl)-pyrrolidin-1-ylcarbonyl]propionamide

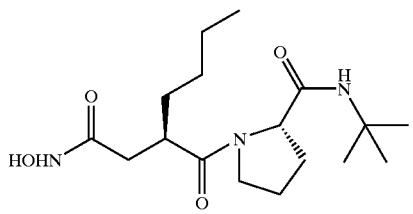

The title compound was prepared according to General Procedure A from mono-methyl 2-(R)-butylsuccinic acid and L-proline t-butylamide hydrochloride. $^1$H NMR (300 MHz, $CDCl_3$): δ 0.77 (t, J=7.2 Hz, 3H), 1.19 (s, 9H), 1.28–2.00 (m, 10H), 2.08 (dd, J=4.1 and 9.6 Hz, 1H), 2.26 (dd, J=9.6 and 15 Hz, 1H), 2.99 (m, 1H), 3.47 (m, 1H), 3.63 (dd, J=9.0 and 16.8 Hz, 1H), 4.28 (dd, J=1.9 and 7.8 Hz, 1H).

Example 3

Synthesis of N-hydroxy-3-(R)-(n-butyl)-3-[(2-(S)-(methylaminocarbonyl)-pyrrolidin-1-ylcarbonyl]propionamide

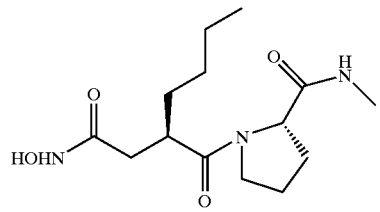

Small-scale Synthesis

The title compound was prepared according to General Procedure A from mono-methyl 2-(R)-butylsuccinic acid and L-proline methylamide hydrochloride. $^1$H NMR (300 MHz, $CDCl_3$): δ 0.80 (t, J=7.2 Hz, 3H), 1.28–2.50 (m, 12H), 2.98 (m, 1H), 3.47 s, 3H), 3.58 (m, 2H), 4.27 (m, 1H).

Large-scale Synthesis

Step 1

To a solution of Boc-Pro-OH (5 g, 23.2 mmol), methylamine (2M in THF, 15 mL, 30 mmol), EDC (4.79 g, 25 mmol), and HOBt (3.38 g, 25 mmol) in THF (150 mL) was added DIEA (4.35 mL, 25 mmol) and the mixture stirred overnight. THF was removed, the residue was dissolved in ethyl acetate and then washed with aqueous HCl (1 N, 2×), 5% KHSO4 (2×), saturated sodium bicarbonate, brine, dried ($Na_2SO_4$), concentrated, and purified on silica gel (Merck 60, ethyl acetate/hexanes) to give N-Boc-(2-methylaminocarbonyl)pyrrolidine (3.3 g, 63%).

Step 2

N-Boc-(2-methylaminocarbonyl)pyrrolidine (3.3 g, 14.5 mmol) was treated with HCl (4 N in dioxane, 10 mL) for 1 h. The solvent was removed and the white solid treated with mono-methyl 2-(R)-butylsuccinic acid (2.82 g, 15 mmol), HOBt (2.02 g, 15 mmol), EDC (2.88 g, 15 mmol) and DIEA (6.96 mL, 40 mmol) in THF for 16 h. Similar work-up and purification gave the methyl ester (2.2 g). A solution of methyl ester and lithium hydroxide (400 mg, 10 mmol) in methanol (15 mL) and water (10 mL) was stirred for 16 h. Methanol was removed and the aqueous layer was acidified to pH=1 and extracted with ethyl acetate (4×). The organic layers were dried ($Na_2SO_4$) and concentrated to afford 3-(R)-(n-butyl)-3-[(2-(S)-(methylaminocarbonyl)pyrrolidin-1-ylcarbonyl]propionic acid as a white solid (1.5 g).

Step 3

To a solution of 3-(R)-(n-butyl)-3-[(2-(S)-(methylaminocarbonyl)-pyrrolidin-1-ylcarbonyl]propionic acid (1.5 g, 5.28 mmol), O-benzylhydroxylamine (932 mg, 5.84 mmol), HOBt (784 mg, 5.84 mmol), and DIEA (2.3 mL, 13.2 mmol) in THF (100 mL) was added EDC (1.12 g, 5.84 mmol) and the reaction stirred for 16 h. Conventional work-up and purification gave N-benzyloxy-3-(R)-(n-butyl)-3-[(2-(S)-(methylaminocarbonyl)pyrrolidin-1-ylcarbonyl]propionamide (1.56 g).

A solution of N-benzyloxy-3-(R)-(n-butyl)-3-[(2-(S)-(methylaminocarbonyl)-pyrrolidin-1-ylcarbonyl]

propionamide (1.5 g) in ethyl acetate (50 mL) was hydrogenated over Pd/C for 14 h. The mixture was filtered through a pad of Celite, washed with ethyl acetate, and concentrated to give N-hydroxy-3-(R)-(n-butyl)-3-[(2-(S)-(methylaminocarbonyl)pyrrolidin-1-ylcarbonyl] propionamide (1.1 g).

Example 4

Synthesis of N-hydroxy-3-(R)-(n-butyl)-3-[(2-(S)-(methoxymethyl)-pyrrolidin-1-ylcarbonyl] propionamide

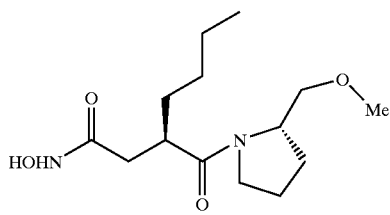

The title compound was prepared according to General Procedure A from (S)-(+)-2-(methoxymethyl)pyrrolidine and mono-methyl 2-(R)-butylsuccinic acid. $^1$H NMR (300 MHz, CDCl$_3$): δ 0.90 (t, J=7.5 Hz, 3H), 1.22–1.64 (m, 6H), 1.84–2.05 (m, 2H), 1.84–2.05 (m, 2H), 2.25–2.42 (m, 1H), 2.51–2.66 (m, 1H), 2.99–3.16 (m, 1H), 3.33 (s, 3H), 3.38 (dd, J=1.9 and 6.9 Hz, 1H), 3.44 (bd, J=6.9 Hz, 1H), 3.47–3.54 (m, 1H), 3.61–3.69 (m, 1H), 4.24 (m, 1H).

Example 5

Synthesis of N-hydroxy-3-(R)-(n-butyl)-3-[(2-(S)-(N-methoxy-N-methylaminocarbonyl)pyrrolidin-1-ylcarbonyl]propionamide

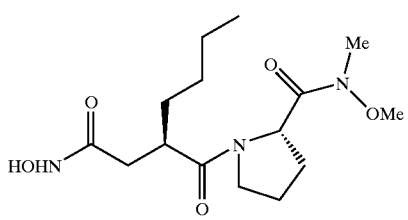

The title compound was prepared according to General Procedure A from L-proline N-methoxyl N-methylamide hydrochloride and mono-methyl 2-(R)-butylsuccinic acid. $^1$H NMR (300 MHz, CDCl$_3$): δ 0.80 (t, J=7.2 Hz, 3H), 1.27–2.60 (m, 12H), 3.05 (m, 1H), 3.19 (s, 3H), 3.72 (m, 2H), 3.78 (s, 3H), 4.85 (m, 1H).

Example 6

Synthesis of N-hydroxy-3-(R)-(n-butyl)-3-[(2-(S)-(methoxycarbonyl)-pyrrolidin-1-ylcarbonyl] propionamide

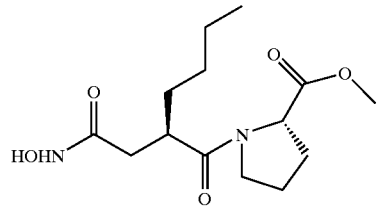

The title compound was prepared according to General Procedure A from L-proline methyl ester hydrochloride and mono-methyl 2-(R)-butylsuccinic acid. $^1$H NMR (300 MHz, CDCl$_3$): δ 0.90 (m, 3H), 1.23–1.70 (m, 6H), 1.86–2.09 (m, 3H), 2.15–2.62 (m, 3H), 3.01–3.17 (m, 1H), 3.59–3.86 (m, 2H), 3.71 (s, 3H), 4.42–4.53(m, 1H).

Example 7

Synthesis of N-hydroxy-3-(R)-(3-methylpropyl)-3-[(2-(S)-(tert-butoxycarbonyl) pyrroldin-1-ylcarbonyl]propionamide

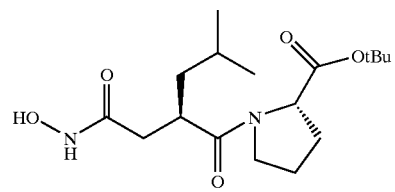

The title compound was prepared according to General Procedure A from L-proline t-butyl ester hydrochloride and mono-methyl 2-(R)-isobutylsuccinic acid. 1H NMR (300 MHz, CDCl$_3$): δ 0.90–0.99 (m, 6H), 1.27–2.58 (m, 18H), 2.78–2.91 (m, 1H), 3.08–3.18 (m, 1H), 3.43–3.81 (m, 3H), 4.26–4.40 (m, 2H).

Example 8

Synthesis of N-hydroxy-3-(R)-(n-butyl)-3-(pyrrolidin-1-ylcarbonyl)propionamide

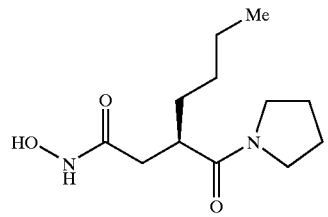

The title compound was prepared according to General Procedure A using pyrrolidine as the amine and mono methyl-2-(R)-butylsuccinic acid. MS (APCI) m/z=243 [M+H].

Example 9

Synthesis of N-hydroxy-3-(R)-(n-butyl)-3-[(2-(S)-(pyrrolidin-1-ylmethyl)pyrrolidin-1-ylcarbonyl]propionamide

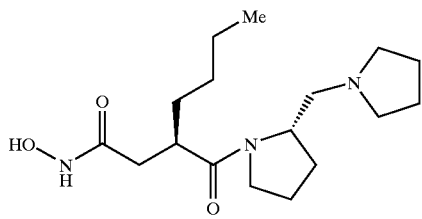

The title compound was prepared according to General Procedure A from 2-(S)-(pyrrolidin-1-ylmethyl)pyrrolidine and mono-methyl 2-(R)-butylsuccinic acid. MS (APCI) m/z=326 [M+H].

Example 10

Synthesis of N-hydroxy-3-(R)-(n-butyl)-3-[(2-(S)-(morpholin-4-ylcarbonyl)pyrrolidin-1-ylcarbonyl]propionamide

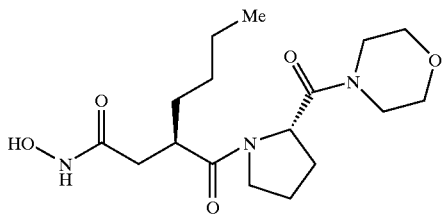

The title compound was prepared according to General Procedure D using L-proline N-morpholinylamide as the amine. MS (APCI) m/z=356 [M+H].

Example 11

Synthesis of N-hydroxy-3-(R)-(n-butyl)-3-[(2-(S)-(dimethylaminocarbonyl)pyrrolidin-1-ylcarbonyl]propionamide

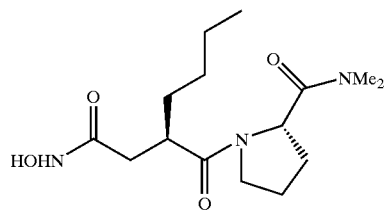

The title compound was prepared according to General Procedure A from L-proline N,N-dimethylamide hydrochloride and mono-methyl 2-(R)-butylsuccinic acid. MS (APCI) m/z=314 [M+H].

Example 12

Synthesis of N-hydroxy-3-(R)-(n-butyl)-3-[4-(R)-(tert-butoxy-2-(S)-tert-butoxycarbonyl)pyrrolidin-1-ylcarbonyl]propionamide

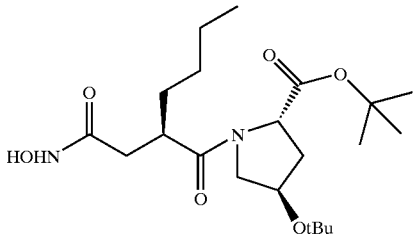

The title compound was prepared according to General Procedure A from 3-(R)-O-tert-butyloxy-L-proline t-butyl ester and mono-methyl 2-(R)-butylsuccinic acid. MS (APCI) m/z=415 [M+H].

Example 13

Synthesis of N-hydroxy-3-(R)-(n-butyl)-3-[2-(S)-(methoxycarbonyl)piperidin-1-ylcarbonyl]propionamide

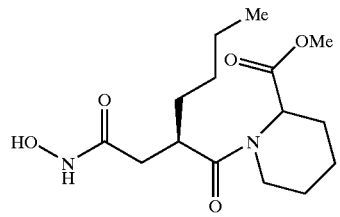

The title compound was prepared according to General Procedure A from homoproline methyl ester and mono-methyl 2-(R)-butylsuccinic acid. MS (APCI) m/z=315 [M+H].

Example 14

Synthesis of N-hydroxy-3-(R)-(n-butyl)-3-[2-(S)-(tert-butoxycarbonyl)piperidin-1-ylcarbonyl]propionamide

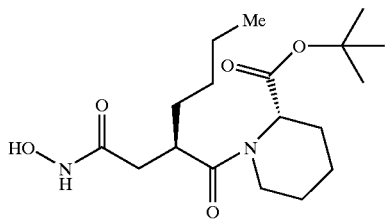

The title compound was prepared according to General Procedure D using L-homoproline t-butyl ester as the amine. MS (APCJ) m/z=357 [M+H].

Example 15

Synthesis of N-hydroxy-3-(R)-(n-butyl)-3-[2-(S)-(tert-butoxycarbonyl)-tetrahydroisoquinolin-1-ylcarbonyl]propionamide

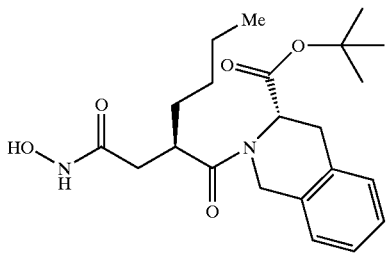

The title compound was prepared according to General Procedure A from L-tetrahydroisoquinoline t-butyl ester and mono-methyl 2-(R)-butylsuccinic acid. MS (APCI) m/z= 405 [M+H].

Example 16

Synthesis of N-hydroxy-3-(R)-(n-butyl)-3-[2-(S)-(acetamidomethyl)pyrrolidin-1-ylcarbonyl]propionamide

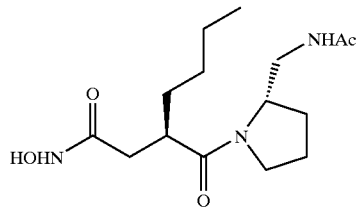

Step 1

To a solution of 4-(S)-benzyloxazolidin-2-one (56 mmol) (Aldrich, Milwaukee, Wis.) in THF at −78° C. was added 2.5 M n-BuLi in hexane (22.4 mL, 56 mmol) and the reaction stirred at −78° C. for 2 hr. To this was added via cannula a −78° C. solution of hexanoyl chloride (65 mmol) in THF and the mixture stirred at −78° C. for 2 hr, then allowed to warm to room temperature and stirred overnight. The reaction was then quenched with aqueous saturated $NH_4Cl$, extracted with ethyl acetate, dried, and purified by silica gel chromatography (hexanes/ethyl acetate) to afford N-hexanoyl-4-(S)-benzyloxazolidin-2-one.

Step 2

To a solution of N-hexanoyl-4-(S)-benzyloxazolidin-2-one (7.3 mmol) in THF at −78° C. was added 1.0 M sodium hexamethyldisilazide (NaHMDS, 8.8 mmol) and the reaction stirred at −78° C. for 1 hr. A solution of methyl bromoacetate (8.8 mmol) in THF was then added dropwise, and the resulting mixture was stirred at −78° C. for 1 hr and then at room temperature overnight. The reaction was quenched with $NH_4Cl$, concentrated, then suspended in ethyl acetate and washed with 0.5 N HCl and brine, dried, and purified by silica gel chromatography (ethyl acetate/hexanes) to afford the methyl 3-(R)-(n-butyl)-3-[4-(S)-benzyloxazolidin-2-one-3-ylcarbonyl)propionate.

Step 3

To methyl 3-(R)-(n-butyl)-3-[4-(S)-benzyloxazolidin-2-one-3-ylcarbonyl)-propionate (1.44 mmol) in THF/water at 0° C. was added 30% $H_2O_2$ (5.76 mmol) and solid lithium hydroxide (1.44 mmol) and the reaction stirred at 0° C. for 3 hr. The reaction was then quenched with 2.0 M $Na_2SO_3$, concentrated, suspended in ethyl acetate and subjected to standard aqueous workup. The crude product was purified by silica gel chromatography (methanol/dichloromethane) to afford methyl 3-(R)-(n-butyl)-propionate.

Step 4

To Boc-L-prolinol (1 mmol) (Advanced Chemtech, Louisville, Ky.) in THF at 0° C. was added mesitylenesulfonylchloride (MsCl, 1.2 mmol) and DIEA (1.5 mmol) and the solution allowed to warm to rt, then stirred an additional hour. Solid sodium azide was added (1.5 mmol) and the reaction was allowed to stir overnight. Conventional aqueous workup followed by silica gel chromatography afforded the N-Boc-(S)-(2-azidomethyl)pyrrolidine.

Step 5

A solution of the N-Boc-(S)-(2-azidomethyl)pyrrolidine in ethylacetate was added to 10% Pd/C and the reaction evacuated and flushed with hydrogen gas three times. The reaction was then stirred under a hydrogen atmosphere overnight, then filtered through a pad of celite and concentrated to dryness. The resulting amine was dissolved in DMF and then acylated with acetic anhydride to afford the N-Boc-(S)-(2-acetamidomethyl)pyrrolidine. The Boc group was deprotected with 1N HCl in dioxane to afford the desired (S)-(2-acetamidomethyl)pyrrolidine.

Step 6

The title compound was prepared from (S)-(2-acetamidomethyl)pyrrolidine and methyl 3-(R)-(n-butyl) propionate according to General Procedure A. MS (APCI) m/z=314 [M+H].

Example 17

Synthesis of N-hydroxy-3-(R)-(n-butyl)-3-[(4-(R)-hydroxy-2-(S)-tert-butoxycarbonyl)pyrrolidin-1-ylcarbonyl]propionamide

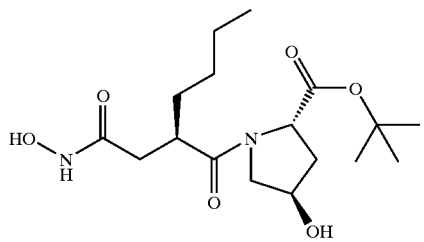

Small-scale Synthesis

Step 1

Cbz-protected trans-3-hydroxy-L-proline (20 g, 75 mmol) in DCM was treated with 60 ml of acetic anhydride and 10 mL of pyridine. The solution was stirred at rt for 18 hours, then the reaction was quenched with icewater, extracted with EtOAc (3×200 mL), and the organic layer washed with water, brine, and dried over $MgSO_4$. Concentration in vacuo gave Cbz-protected trans-3-acetoxy-L-proline as a colorless oil.

Step 2

To a solution of Cbz-protected trans-3-acetoxy-L-proline (75 mmol) in dry dioxane was added tert-butyl alcohol (14.2 mL, 150 mmol), diisopropylcarbodiimide (23 mL, 147 mmol), and DMAP (2.3 g) and the mixture was stirred at rt for two days. The reaction was concentrated to an oil and purified via silica gel chromatography (hexanes/ethyl acetate) to afford the desired Cbz-protected trans-3-acetoxy-L-proline t-butyl ester. ESMS (negative): 362 (M−1).

Step 3

To Cbz-protected trans-3-acetoxy-L-proline t butyl ester (1 mmol) in ethyl acetate (10 mL) was added 10% Pd/C and the reaction evacuated and flushed with hydrogen gas three times. The reaction was then stirred under a hydrogen atmosphere overnight, then filtered through a pad of celite and concentrated to dryness to afford the desired trans-3-acetoxy-L-proline t-butyl ester. MS (APCI negative) m/z 357 [M−H]. $^1$H NMR (300 MHz, CD$_3$OD) Λ 4.0 (m, 2H), 3.75 (m, 2H), 3.10 (m, 1H), 2.85 (m, 1H), 2.40 (m, 2H), 2.2 (m, 2H), 2.0 (m, 2H), 1.65 to 1.0 (m, 15H), 0.90 (m, 3H).

Step 4

The title compound was prepared according to General Procedure A using trans-3-acetoxy-L-proline O-t-butyl ester and methyl 3-(R)-(n-butyl)propionate. The final treatment with hydroxylamine removed the acetyl group from the 3-hydroxy group of the proline.

Large-scale Synthesis

Step 1

To trans-3-acetyloxy-L-proline t-butyl ester (11.8 mmol) in DCM (60 mL) was added mono-methyl 2-(R)-butylsuccinic acid (11.2 mmol), DIEA (23.6 mmol) and PyBOP (11.8 mmol) and the solution stirred for 16 h. The reaction was concentrated to an oil and purified on silica gel (Merck 60; hexanes/ethylacetate) to afford 2.2 g of methyl 3-(R)-(n-butyl)-3-[(4-(R)-acetoxy-2-(S)-tert-butoxycarbonyl)pyrrolidin-1-ylcarbonyl]propionate as a clear oil 5 (50%).

Step 2

To methyl 3-(R)-(n-butyl)-3-[(4-(R)-acetoxy-2-(S)-tert-butoxycarbonyl)-pyrrolidin-1-ylcarbonyl]propionate (5.5 mmol) in methanol (25 mL) was added water (1 mL) and LiOH-H$_2$O (12.1 mmol) and the solution stirred 20 h. Standard aqueous work-up afforded 3-(R)-(n-butyl)-3-[(4-(R)-hydroxy-2-(S)-tert-butoxycarbonyl)-pyrrolidin-1-ylcarbonyl]propionic acid 2 g of a colorless oil which solidified upon standing (quant.).

Step 3

To a solution of 3-(R)-(n-butyl)-3-[(4-(R)-hydroxy-2-(S)-tert-butoxycarbonyl)-pyrrolidin-1-ylcarbonyl]propionic (5.51 mmol) in DCM (30 mL) was added O-benzylhydroxylamine-HCL (6.06 mmol), DIEA (13.3 mmol) and PyBOP and the solution stirred for 18 h. Standard aqueous work-up followed by silica gel chromatography (Merck 60; ethylacetate) afforded 1.14 g of the protected N-benzyloxy-3-(R)-(n-butyl)-3-[(4-(R)-hydroxy-2-(S)-tert-butoxycarbonyl)pyrrolidin-1-ylcarbonyl]propionamide as a white gum (45%). This was dissolved in ethylacetate (50 mL), 5% Pd/C was added (110 mg), and a hydrogen atmosphere introduced. After 16 h the reaction was filtered through celite and concentrated to afford 810 mg of the title compound as a white foam (89%).

Example 18

Synthesis of N-hydroxy-3-(R)-(n-butyl)-3-[(4-(S)-hydroxy-2-(S)-tert-butoxycarbonyl)pyrrolidin-1-ylcarbonyl]propionamide

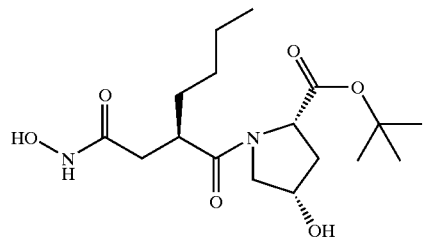

To methyl 3-(R)-(n-butyl)-3-[(4-(R)-hydroxy-2-(S)-tert-butoxycarbonyl)-pyrrolidin-1-ylcarbonyl]propionate (prepared by General Procedure A, omitting the final treatment with NH$_2$O H) in THF was added chloroacetic acid, TPP and DIAD and the reaction stirred 18 h. The chloroacetate ester was purified on silica gel (Merck 60; hexanes/ethylacetate), dissolved in dioxane and then treated with aqueous 50% hydroxylamine. The reaction mixture was purified by preparative reverse-phase (C18) HPLC to afford the title compound. MS (APCI negative) m/z 357 [M−H].

Example 19

Synthesis of N-hydroxy-3-(R)-(n-butyl)-3-[(4-(R)-methoxy-2-(S)-tert-butoxycarbonyl)pyrrolidin-1-ylcarbonyl]propionamide

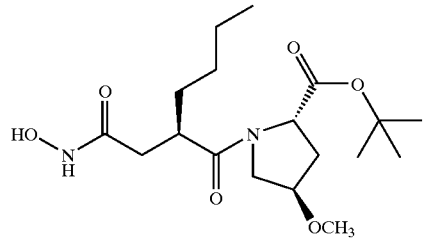

To methyl 3-(R)-(n-butyl)-3-[(4-(R)-hydroxy-2-(S)-tert-butoxycarbonyl)-pyrrolidin-1-ylcarbonyl]propionate in THF at 0° C. was added sodium hydride (60% dispersion in mineral oil) and the mixture stirred for 1 h. Iodomethane was added, and the reaction allowed to wam to rt and then stirred an additional 2 h. Standard aqueous work-up followed by purification on silica gel afforded the penultimate methyl ester. This was dissolved in dioxane and then treated with aqueous 50% hydroxylamine for 48 h. The reaction mixture was purified by preparative reverse-phase (C18) HPLC to afford the title compound. MS (APCI negative) m/z 371 [M−H].

Example 20

Synthesis of N-hydroxy-3-(R)-(n-butyl)-3-[3-(RS)-(tert-butoxycarbonylamino)pyrrolidin-1-ylcarbonyl]propionamide

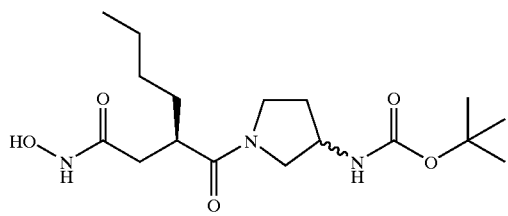

The title compound was prepared according to General Procedure B from (±)-3-(N-Boc-amino)pyrrolidine (obtained from TCI America, Portland, Oreg.) and mono-4-methyl 2-(R)-butylsuccinic acid. MS (APCI) m/z 358[M+H].

Example 21

Synthesis of N-hydroxy-3-(R)-(n-butyl)-3-[2-(S)-(tert-butoxycarbonyl)pyrrolidin-1-ylcarbonyl]-2-(S)-hydroxypropionamide

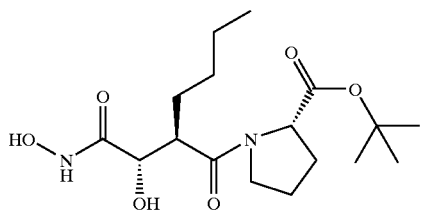

The title compound was prepared according to General Procedure F or I. $^1$H NMR (300 MHz, CDCl$_3$): δ 0.93 (t, J=7.5 Hz, 3H), 1.31–1.49 (m, 4H), 1.44 (s, 9H), 1.76–2.23 (m, 6H), 3.23 (dt, J=2.5 and 7.5 Hz, 1H), 3.67–3.77 (m, 1H), 3.55–3.64 (m, 1H), 4.26 (d, J=2.5 Hz, 1H), 4.32 (dd, J=4.2 and 8.7 Hz, 1H). ES-MS: calcd. For C$_{17}$H$_{30}$N$_2$O$_6$(358.43); found: 359 [M+1].

Example 22

Synthesis of N-hydroxy-3-(R)-(n-butyl)-3-[2-(S)-(methylaminocarbonyl)pyrrolidin-1-ylcarbonyl]-2-(S)-hydroxypropionamide

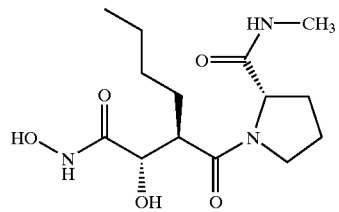

The title compound was prepared according to General Procedure C from methylamine. MS (APCI negative) m/z 314 [M–H].

Example 23

Synthesis of N-hydroxy-3-(R)-(n-butyl)-3-[2-(S)-(dimethylaminocarbonyl)pyrrolidin-1-ylcarbonyl]-2-(S)-hydroxypropionamide

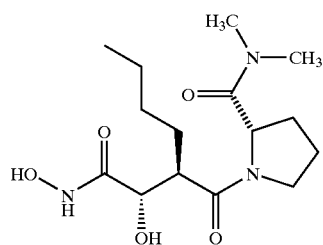

The title compound was prepared according to General Procedure C from N,N-dimethylamine. MS (APCJ negative) m/z 328 [M–H].

Example 24

Synthesis of N-hydroxy-3-(R)-(n-butyl)-3-[2-(S)-(tert-butylaminocarbonyl)pyrrolidin-1-ylcarbonyl]-2-(S)-hydroxypropionamide

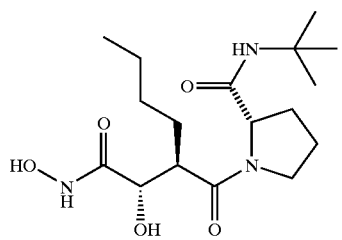

The title compound was prepared according to General Procedure C from t-butylamine. MS (APCI negative) m/z 356 [M–H].

Example 25

Synthesis of N-hydroxy-3-(R)-(n-butyl)-3-[2-(S)-(morpholin-4-ylcarbonyl)pyrrolidin-1-ylcarbonyl]-2-(S)-hydroxypropionamide

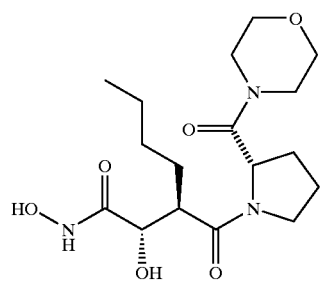

The title compound was prepared according to General Procedure C from morpholine. MS (APCI negative) m/z 370 [M–H].

Example 26

Synthesis of N-hydroxy-3-(R)-(n-butyl)-3-[3-(RS)-(acetylamino)pyrrolidin-1-ylcarbonyl]propionamide

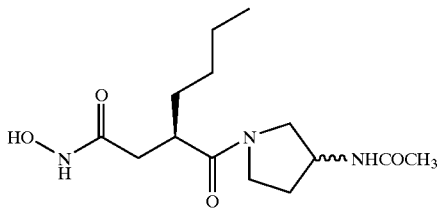

To methyl 3-(R)-(n-butyl)-3-[3-(RS)-(tert-butoxycarbonylamino)pyrrolidin-1-ylcarbonyl]propionate, prepared from (±)-3-(N-Boc-amino)pyrrolidine (TCI America, Portland, Oreg.) and mono-4-methyl 2-(R)-butylsuccinic acid, was added 4 N HCl in dioxane and the solution stirred for 4 h. The solution was evaporated to dryness, dissolved in dioxane, and then treated with acetic anhydride and pyridine and stirred for 2 h. Aqueous 50% hydroxylamine was added and the solution stirred for 2 d. The crude reaction mixture was purified by preparative reverse-phase (C18) HPLC to afford the title compound. MS (APCI negative) m/z 298 [M–H].

Example 27

Synthesis of N-hydroxy-3-(R)-(n-butyl)-3-[3-(RS)-(2-phenylethylcarbonylamino)-pyrrolidin-1-ylcarbonyl]propionamide

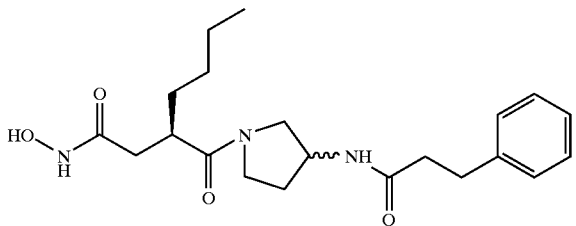

To methyl 3-(R)-(n-butyl)-3-[3-(RS)-(tert-butoxycarbonylamino)pyrrolidin-1-ylcarbonyl]propionate, prepared from (±)-3-(N-Boc-amino)pyrrolidine and mono-4-methyl 2-(R)-butylsuccinic acid, was added 4 N HCl in dioxane and the solution stirred for 4 h. The solution was evaporated to dryness, dissolved in dioxane, and then treated with 3-phenylpropionic acid, DIEA, and HATU and stirred for 2 h. Aqueous 50% hydroxylamine was added and the solution stirred for 2 d. The crude reaction mixture was purified by preparative reverse-phase (C18) HPLC to afford the title compound.

Example 28

Synthesis of N-hydroxy-3-(R)-(n-butyl)-3-[2-(S)-(methoxycarbonyl)pyrrolidin-1-ylcarbonyl]-2-(S)-methylpropionamide

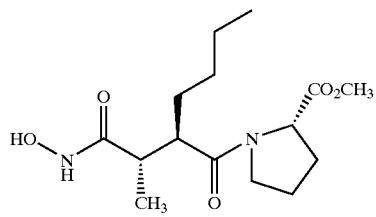

Step 1

To mono t-butyl 2-(R)-(n-butyl)succinic acid (2.0 g, 8.70 mmol; prepared in three steps from hexanoylchloride using the procedure of Example 16, Step A for the synthesis of monomethyl-2-R-butylsuccinic acid, with substitution of t-butyl bromoacetate for methyl bromoacetate) in anhydrous THF (40 mL) at −78° C. was added LDA (2.2 eq., 19.1 mmol, 9.56 ml of a 2.0 M solution in THF/hexane/ethylbenzene) and the reaction stirred for 1 h. Iodomethane (11.3 mmol, 1.6 g) was then added and the reaction allowed to warm to room temperature over 2 h. The solution was quenched with methanol (ca. 5 mL), evaporated to dryness, and the residue dissolved in ethylacetate (50 mL). This solution was extracted with saturated sodium bicarbonate (3×30 mL), the combined aqueous layers acidified to pH 3 with 1 N HCl, and these were extracted with ethylacetate (3×50 mL). The combined organic layers were dried ($Na_2SO_4$), concentrated, and purified by silica gel chromatography (Merck 60; 95:5 DCM/methanol) to afford mono t-butyl 2-(R)-(n-butyl)-3-(RS)-methylsuccinic acid as a light orange oil (1.25 g). The ratio of R/S diastereomers was >6:1.

Step 2

An aliquot of mono t-butyl 2-(R)-(n-butyl)-3-(RS)-methylsuccinic acid (1.0 g, 4.10 mmol) was epimerized by first dissolving it in THF (22 mL), cooling to −78° C. and then adding LDA (9.02 mmol, 4.52 mL of a 2.0 M solution). The solution was allowed to warm to rt over 2 hours, then cooled back down to −78° C. and quenched with methanol (1.7 mL). This epimerization procedure was repeated once more, then an aqueous work-up was performed as described above to afford 700 mg of mono t-butyl 2-(R)-(n-butyl)-3-(RS)-methylsuccinic acid. $^1$H NMR analysis of this product suggested approximately 2:1 ratio of R/S diastereomers.

Step 3

To mono t-butyl 2-(R)-(n-butyl)-3-(RS)-methylsuccinic acid (680 mg, 1.39 mmol, prepared in step 2 above) in DCM (15 mL) was added L-proline methyl ester hydrochloride (3.34 mmol, 554 mg), DIEA (1.28 mL, 7.34 mmol) and then PyBOP (1.74 g, 3.34 mmol). The reaction was stirred for 16 h, concentrated to dryness, and then purified via silica gel chromatography (1:1 hexanes/ethylacetate) to afford mono t-butyl 3-(R)-(n-butyl)-3-[2-(S)-methoxycarbonyl)pyrrolidin-1-ylcarbonyl]-2-(S)-methylpropionate (260 mg).

Step 4

The t-butyl group was removed from mono t-butyl 3-(R)-(n-butyl)-3-[2-(S)-methoxycarbonyl)pyrrolidin-1-ylcarbonyl]-2-(S)-methylpropionate (260 mg, 732 µmol) using 1:2 TFA/DCM, followed by evaporation of the TFA and solvent. To the resulting product in DCM (5 mL) at 0° C. was added O-benzylhydroxylamine hydrochloride (129 mg, 805 µmol), HOBt (112 mg, 732 µmol), DIEA (708 µL, 1.61 mmol) and then solid EDC (154 mg, 805 µmol) and the reaction allowed to warm to rt and then stirred overnight. The reaction was evaporated to dryness, and purified on a silica gel column (1:1 hexanes/ethylacetate) to afford N-benzyloxy-3-(R)-(n-butyl)-3-[2-(S)-methoxycarbonyl) pyrrolidin-1-ylcarbonyl]-2-(S)-methylpropionamide as a colorless glass (212 mg).

Step 5

To N-benzyloxy-3-(R)-(n-butyl)-3-[2-(S)-methoxycarbonyl)pyrrolidin-1-ylcarbonyl]-2-(S)-methylpropionamide (40 mg) in methanol (3 mL) was added 10% Pd/C (10 mg). The reaction was evacuated briefly under high-vacuum, and the atmosphere replaced with 1 atm hydrogen gas (balloon). This procedure was repeated twice more, then the suspension was stirred under $H_2$ gas for 3 h. The reaction was then filtered through a plug of celite to afford the title compound as a clear, colorless gum (31 mg). MS (APCI) m/z 315 [M+H].

Example 29

Synthesis of N-hydroxy-3-(R)-(n-butyl)-3-[2-(S)-(3-trifluoromethylbenzylaminocarbonyl)pyrrolidin-1-ylcarbonyl]propionamide

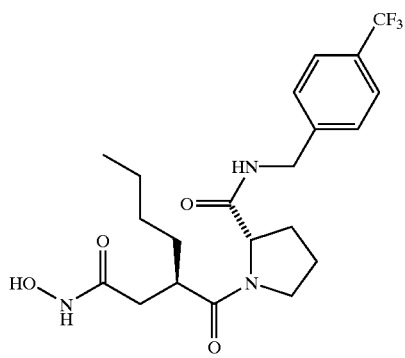

The title compound was prepared according to General Procedure D from L-proline-(4-trifluoromethyl) benzylamide. MS (APCI) m/z 444 [M+H].

Example 30

Synthesis of N-hydroxy-3-(R)-(n-butyl)-3-[2-(S)-(cyclohexylmethylaminocarbonyl)-pyrrolidin-1-ylcarbonyl]propionamide

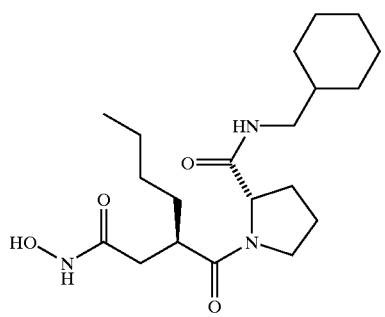

The title compound was prepared according to General Procedure A from mono-methyl 2-(R)-butylsuccinic acid and L-proline-(cyclohexyl)methylamide. MS (APCI) m/z 382 [M+H].

Example 31

Synthesis of N-hydroxy-3-(R)-(n-butyl)-3-[3-(RS)-((4-trifluoromethylbenzyl)-aminocarbonyl)piperidin-1-ylcarbonyl]propionamide

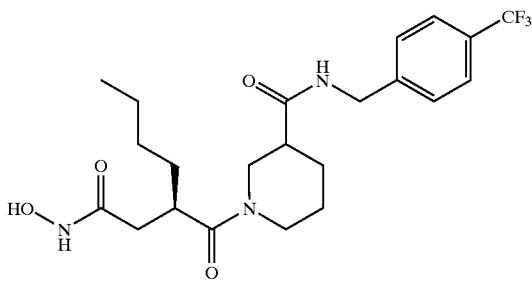

The title compound was prepared according to General Procedure A from mono-methyl 2-(R)-butylsuccinic acid and (±)-3-carboxypiperidine-(4-trifluoromethylbenzyl) amide. MS (APCI) m/z 458 [M+H].

Example 32

Synthesis of N-hydroxy-3-(R)-(n-butyl)-3-[(2-(S)-(hydroxymethyl)-pyrrolidin-1-ylcarbonyl] propionamide

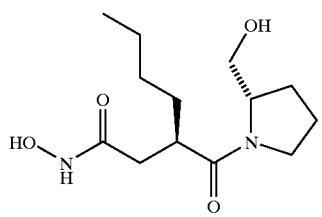

The title compound was prepared according to General Procedure A from mono-methyl 2-(R)-butylsuccinic acid and L-prolinol. MS (APCI) m/z 273[M+H].

Example 33

Synthesis of N-hydroxy-3-(R)-(n-butyl)-3-[(2-(S)-(pyrrolidin-1-ylmethyl)-pyrrolidin-1-ylcarbonyl] propionamide

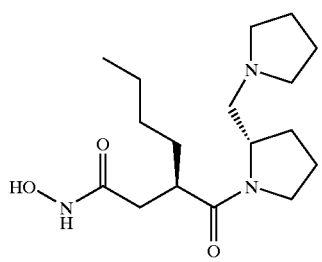

The title compound was prepared according to General Procedure A from mono-methyl 2-(R)-butylsuccinic acid and (S)-2-(N-pyrrolidinylmethyl)-pyrrolidine. MS (APCI) m/z 326 [M+H].

Example 34

Synthesis of N-hydroxy-3-(R)-(n-butyl)-3-[4-(S)-(phenylsulfonamido)-2-(S)-(tert-butyloxycarbonyl)pyrrolidin-1-ylcarbonyl]propionamide

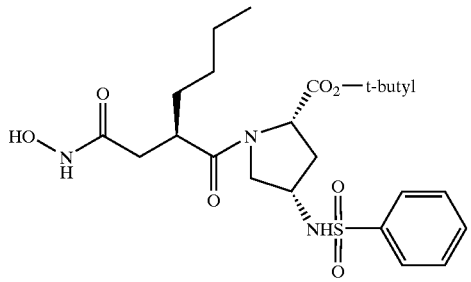

Step 1

To mono methyl 3-(R)-(n-butyl)-3-[2-(S)-tert-butoxycarbonyl)-4-(R)-hydroxypyrrolidin-1-ylcarbonyl] propionate (1.4 g, 3.92 mmol; prepared according to General Procedure A from methyl 2-(R)-butylsuccinic acid and trans-L-hydroxy-proline tert-butyl ester) in DCM at −20° C. was slowly added methanesulfonyl chloride (MeSO$_2$Cl) (0.62 mL, 7.84 mmol) and the reaction stirred 4 h. DCM was removed in vacuo, and the residue was dissolved in EtOAc (100 mL), washed with saturated NaHCO$_3$, dilute HCl (5%) and brine and then dried (MgSO$_4$). Concentration in vacuo afforded methyl 3-(R)-(n-butyl)-3-[2-(S)-tert-butoxycarbonyl)-4-(R)-mesyloxy-pyrrolidin-1-ylcarbonyl] propionate which was used directly without further purification.

Step 2

To methyl 3-(R)-(n-butyl)-3-[2-(S)-tert-butoxycarbonyl)-4-(R)-mesyloxy-pyrrolidin-1-ylcarbonyl]propionate in DMF (30 mL) was added NaN$_3$ (2.6 g) and the resulting solution heated at 65° C. for 48. The DMF was removed in vacuo and the residue was purified by silica gel column chromatography to afford 1.3 gram of the desired methyl 3-(R)-(n-butyl)-3-[2-(S)-tert-butoxycarbonyl)-4-(S)-azido-pyrrolidin-1-ylcarbonyl]propionate.

Step 3

Methyl 3-(R)-(n-butyl)-3-[2-(S)-tert-butoxycarbonyl)-4-(S)-azido-pyrrolidin-1-ylcarbonyl]propionate (1.3 g, 3.4 mmol) was hydrogenated at rt with Pd-C (10%) for 18 h. The reaction was filtered through a pad of celite, and washed with EtOAc. Concentration of the filtrate yielded 1.2 g of methyl 3-(R)-(n-butyl)-3-[2-(S)-tert-butoxycarbonyl)-4-(S)-aminopyrrolidin-1-ylcarbonyl]propionate.

Step 4

Phenylsulfonyl chloride (2 eq.) was added slowly to a solution of methyl 3-(R)-(n-butyl)-3-[2-(S)-tert-butoxycarbonyl)-4-(S)-azido-pyrrolidin-1-ylcarbonyl]-propionate (ca. 0.1 g) in DCM (1 mL) and pyridine (0.1 mL) at 0° C. The solution was allowed to warm to rt and then stirred an additional 2 h. The solvent was removed in vacuo, the residue dissolved in EtOAc (5 mL) and washed with HCl solution (5%), NaHCO$_3$ (sat.) and brine. Concentration in vacuo gave the crude methyl 3-(R)-(n-butyl)-3-[2-(S)-tert-butoxycarbonyl)-4-(S)-phenylsulfonamidopyrrolidin-1-ylcarbonyl]propionate which was directly converted to the corresponding hydroxamate by treatment with aqueous 50% NH$_2$OH (1 mL) and dioxane (2 mL) at rt for 3 days. The final product N-hydroxy-3-(R)-(n-butyl)-3-[4-(S)-(phenylsulfonamido)-2-(S)-(tert-butyloxycarbonyl)pyrrolidin-1-ylcarbonyl]-propionamide was purified by preparative HPLC. $^1$H NMR (CD$_3$OD): δ 7.90 (m, 2H), 7.60 (m, 3H), 4.15(t, J=7.9 Hz, 1H), 4.0 (m, 1H), 3.90 (m, 1H), 3.25(m, 1H), 2.90 (m, 1H), 2.35 (m, 2H), 2.15 (m, 3H), 1.75(m, 1H), 1.60 to 1.20 (m, 13H), 0.90 ppm (s, 3H); MS (APCI negative) m/z 496 [M−1].

Example 35

Synthesis of N-hydroxy-3-(R)-(n-pentyl)-3-[(2-(S)-(tert-butoxycarbonyl)-pyrrolidin-1-ylcarbonyl]propionamide

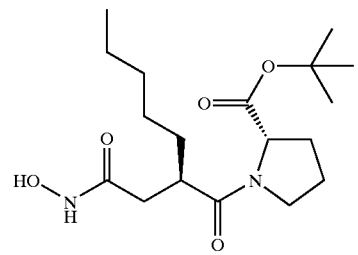

The title compound was prepared according to General Procedure A from mono-methyl 2-(R)-pentylsuccinic acid and L-proline t-butyl ester. MS (APCI) m/z 357 [M+H].

Example 36

Synthesis of N-hydroxy-3-(R)-(n-butyl)-3-[(2-(S)-(tert-butoxycarbonyl)-pyrrolidin-1-ylcarbonyl]-2-(S)-methoxypropionamide

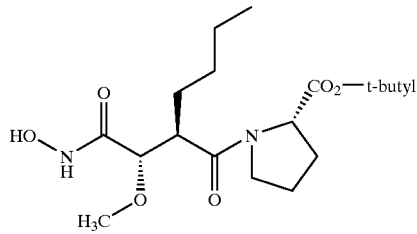

Step 1

To 1-(2,2-dimethyl-4-oxo-1,3-dioxolan-5-yl)-1-(2-(S)-tert-butoxycarbonylpyrrolidin-1-ylcarbonyl)pentane (4 mmol; prepared as described previously using, tert-butyl ester of compound F-6, General Procedure F) in methanol (20 mL) was added 1 m MeONa (1 ml) and stirred for 1 h. The reaction was neutralized with H$^+$ resin, filtered, and the filtrate was concentrated to dryness. The residue purified on silica gel to afford methyl 3-(R)-(n-butyl)-3-[(2-(S)-(tert-butoxycarbonyl)-pyrrolidin-1-ylcarbonyl]-2-(S)-hydroxypropionate.

Step 2

To a solution of methyl 3-(R)-(n-butyl)-3-[(2-(S)-(tert-butoxycarbonyl)-pyrrolidin-1-ylcarbonyl]-2-(S)-hydroxypropionate (1 mmol) in DMF (10 ml) was added NaH. After 30 minutes, methyl iodide (3 mmol) was added and the solution stirred an additional hour. The reaction was then diluted with ethyl acetate, washed with water, dried with Na$_2$SO$_4$, filtered and concentrated. The crude methyl ether was dissolved in dioxane, treated with aqueous 50% hydroxylamine, and stirred for two days. The crude reaction mixture was purified by preparative reverse-phase (C18) HPLC to afford the title compound. MS (APCI negative) m/z 371 [M−H].

Example 37

Synthesis of N-hydroxy-3-(R)-(n-butyl)-3-[(2-(S)-(tert-butoxycarbonyl)-pyrrolidin-1-ylcarbonyl]-2-(R)-hydroxypropionamide

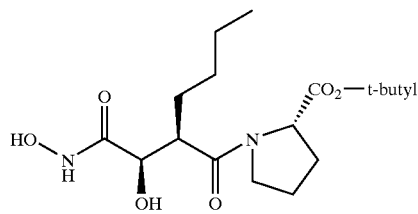

To a solution of triflic anhydride (1.2 mmol) in CH$_2$Cl$_2$ (5 ml) at −15° C. was added pyridine (2.5 mmol) followed by the addition of a solution of methyl 3-(R)-(n-butyl)-3-[(2-(S)-(tert-butoxycarbonyl)pyrrolidin-1-ylcarbonyl]-2-(S)-hydroxypropionate (1 mmol, see Example 36 for preparation) in dichloromethane. The reaction was allowed to warm to −5° C. over 1 hour, then the solution was washed with aqueous 10% citric acid, water and sodium bicarbonate solutions, then dried (Na$_2$SO$_4$) and concentrated. This residue was dissolved in toluene (10 ml) and treated with tetrabutylammonium benzoate (TBAB, 2 mmol) for 1 hour. After removal of solvent, the residue was purified on silica gel (hexanes/ethylacetate) to afford methyl 3-(R)-(n-butyl)-3-[(2-(S)-(tert-butoxycarbonyl)pyrrolidin-1-ylcarbonyl]-2-(R)-benzoyloxypropionate. Treatment of this intermediate with aqueous hydroxylamine/dioxane solution for 2 days, followed by purification via semi-preparative HPLC provided title compound. MS (APCI) m/z 359 [M+H].

Example 38

Synthesis of N-hydroxy-3-(S)-(n-butyl)-3-[(2-(S)-(tert-butoxycarbonyl)-pyrrolidin-1-ylcarbonyl]-2-(R)-thiolpropionamide

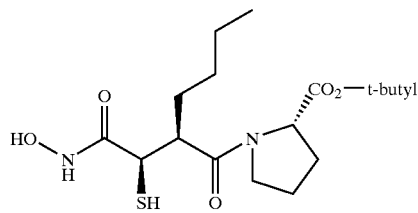

To methyl 3-(R)-(n-butyl)-3-[(2-(S)-(tert-butoxycarbonyl)pyrrolidin-1-ylcarbonyl]-2-(S)-hydroxypropionate (see Example 36 for preparation) in THF is added triphenylphosphine (TPP), diisopropylazodicarboxylate (DIAD) and thioacetic acid and the solution stirred overnight. Aqueous work-up and purification on silica gel affords methyl 3-(S)-(n-butyl)-3-[(2-(S)-(tert-butoxycarbonyl)pyrrolidin-1-ylcarbonyl]-2-(R)-acetylthiopropionate. This compound was dissolved in degassed dioxane and aqueous 50% hydroxylamine, then stirred for 2 d. The crude reaction mixture was purified by preparative reverse-phase (C18) HPLC to afford the title compound.

Example 39

Synthesis of N-hydroxy-3-(S)-(n-butyl)-3-[(2-(S)-(tert-butoxycarbonyl)-pyrrolidin-1-ylcarbonyl]-2-(S)-thiolpropionamide

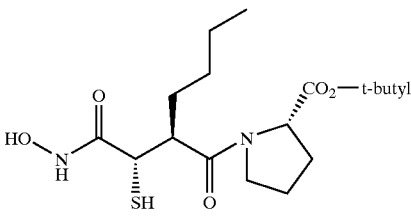

To a solution of triflic anhydride (Tf$_2$O, 1.2 mmol) in CH$_2$Cl$_2$ (5 ml) at −15° C. was added pyridine (2.5 mmol) followed by the addition of a solution of methyl 3-(R)-(n-butyl)-3-[(2-(S)-(tert-butoxycarbonyl)pyrrolidin-1-yl-carbonyl]-2-(R)-hydroxypropionate (1 mmol, prepared as described in Example 40, below) in DCM. The reaction was allowed to warm to −5° C. over 1 hr, then the solution was washed with aqueous 10% citric acid, water, and sodium bicarbonate solution, then dried (Na$_2$SO$_4$) and concentrated. This residue was dissolved in THF (5 ml) and treated with potassium thioacetate (2 mmol) for 1 h. After removal of solvent, the residue was purified on silica gel (hexanes/ethyl acetate) to afford methyl 3-(R)-(n-butyl)-3-[(2-(S)-(tert-butoxycarbonyl)pyrrolidin-1-yl-carbonyl]-2-(S)-acetylthiopropionate. Treatment of this compound with aqueous hydroxylamine/dioxane solution for 2 days, followed by purification via semi-preparative HPLC, provided the title compound. MS(APCI) m/z 375 [M+H].

Example 40

Synthesis of N-hydroxy-3-(R)-(n-butyl)-3-[(2-(S)-(tert-butoxycarbonyl)-pyrrolidin-1-ylcarbonyl]-2-(R)-methoxypropionamide

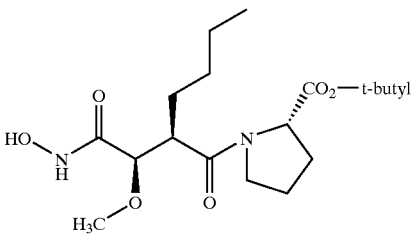

Methyl 3-(R)-(n-butyl)-3-[(2-(S)-(tert-butoxycarbonyl)pyrrolidin-1-ylcarbonyl]-2-(R)-benzoyloxypropionate (prepared as described in Example 37) was de-O-benzoylated by treatment with methanolic sodium methoxide at 0° C. for 2 hours. The solution was neutralized with IR-120 (H$^+$) resin, filtered, concentrated and purified on silica gel (hexanes/ethyl acetate) to afford methyl 3-(R)-(n-butyl)-3-[(2-(S)-(tert-butoxycarbonyl)pyrrolidin-1-ylcarbonyl]-2-(R)-hydroxypropionate. To a solution of methyl 3-(R)-(n-butyl)-3-[(2-(S)-(tert-butoxycarbonyl)pyrrolidin-1-ylcarbonyl]-2-(R)-hydroxypropionate in DMF at 0° C. was added sodium hydride and the reaction stirred for 1 hour. Methyl iodide was added and the reaction stirred for 1 hour at 0° C., then allowed to warm to rt and stirred an additional 2 h. Conventional aqueous workup afforded the intermediate ether, which was treated with dioxane/aqueous

Example 41

Synthesis of N-hydroxy-3-(S)-(n-butyl)-3-[(2-(S)-(tert-butoxycarbonyl)-pyrrolidin-1-ylcarbonyl]-2-(R)-methylthiopropionamide

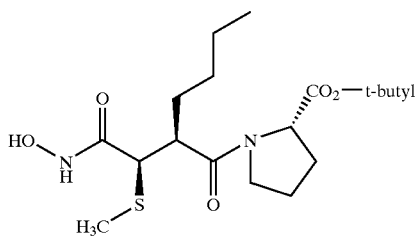

To a solution of triflic anhydride (1.2 mmol) in CH$_2$Cl$_2$ (5 ml) at −15° C. is added pyridine (2.5 mmol) followed by the addition of a solution of methyl 3-(R)-(n-butyl)-3-[(2-(S)-(tert-butoxycarbonyl)pyrrolidin-1-yl-carbonyl]-2-(S)-hydroxypropionate (prepared as described in Example 36 above; 1 mmol) in dichloromethane. The solution is concentrated to dryness, dissolved in DMF and then treated with sodium thiomethoxide. Aqueous work-up followed by purification on silica gel affords methyl 3-(S)-(n-butyl)-3-[(2-(S)-(tert-butoxycarbonyl)pyrrolidin-1-ylcarbonyl]-2-(R)-methylthiopropionate which is dissolved in dioxane, treated with aqueous 50% hydroxylamine, and then stirred for 2 d. The crude reaction mixture is purified by preparative reverse-phase (C18) HPLC to afford title compound.

Example 42

Synthesis of N-hydroxy-3-(S)-(n-butyl)-3-[(2-(S)-(tert-butoxycarbonyl)-pyrrolidin-1-ylcarbonyl]-2-(S)-methylthiopropionamide

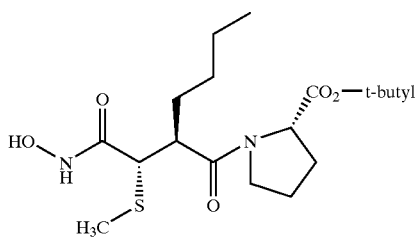

To a solution of triflic anhydride (1.2 mmol) in CH$_2$Cl$_2$ (5 ml) at −15° C. is added pyridine (2.5 mmol) followed by the addition of a solution of methyl 3-(R)-(n-butyl)-3-[(2-(S)-(tert-butoxycarbonyl)pyrrolidin-1-yl-carbonyl]-2-(R)-hydroxypropionate (prepared as described in Example 40; 1 mmol) in dichloromethane. The solution is concentrated to dryness, dissolved in DMF and then treated with sodium thiomethoxide. Aqueous work-up followed by purification on silica gel affords methyl 3-(S)-(n-butyl)-3-[(2-(S)-(tert-butoxycarbonyl)pyrrolidin-1-yl-carbonyl]-2-(S)-methylthiopropionate which is dissolved in dioxane, treated with aqueous 50% hydroxylamine, and then stirred for 2 d. The crude reaction mixture is purified by preparative reverse-phase (C18) HPLC to afford the title compound.

Example 43

Synthesis of N-hydroxy-3-(R)-(n-butyl)-3-[(2-(S)-(2-cyclohex-1-enylethylaminocarbonyl)pyrrolidin-1-ylcarbonyl]propionamide

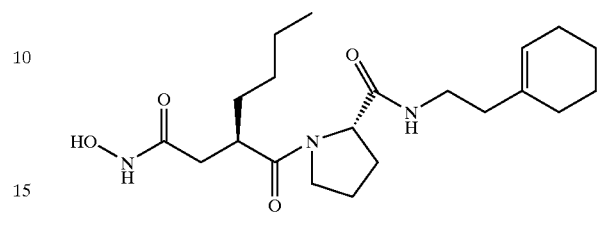

Step 1

To methyl 3-(R)-(n-butyl)-3-[(2-(S)-(tert-butoxycarbonyl)pyrrolidin-1-ylcarbonyl]propionate (1 mmol; prepared in one step from mono-4-methyl 2-(R)-butylsuccinic acid and L-proline t-butyl ester) was added 1 M HCl in dioxane (5 mL) and the solution stirred 4 h. Conventional aqueous workup afforded methyl 3-(R)-(n-butyl)-3-[(2-(S)-(carboxy)pyrrolidin-1-yl-carbonyl]propionate.

Step 2

To methyl 3-(R)-(n-butyl)-3-[(2-(S)-(carboxy)pyrrolidin-1-ylcarbonyl]propionate (0.2 mmol) in dioxane (1 mL) was added 2-(1-cyclohexenyl)-ethyl amine (0.22 mmol), DIEA (0.22 mmol) and HATU (0.22 mmol) and the reaction stirred for 2 h. Aqueous 50% hydroxylamine was then added (1 mL), and the reaction stirred an additional 24 h. The reaction mixture was purified by preparative reverse-phase (C18) HPLC to afford the title compound. MS (APCI) m/z 394 [M+H].

Example 44

Synthesis of N-hydroxy-3-(R)-(n-butyl)-3-[(2-(S)-(phenylaminocarbonyl)-pyrrolidin-1-ylcarbonyl]propionamide

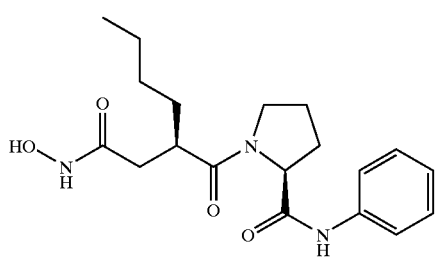

The title compound was prepared as described in Example 43, above, using aniline in place of 2-(1-cyclohexenyl)ethylamine. MS (APCI) m/z 362 [M+H].

Example 45

Synthesis of N-hydroxy-3-(R)-(n-butyl)-3-[2-(S)-(tert-butoxycarbonyl)-pyrrolidin-1-carbonyl]-2-(R)-azidopropionamide

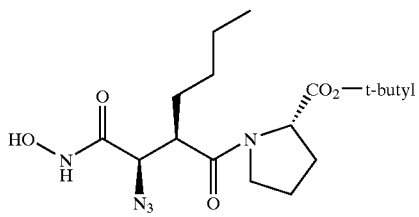

To a solution of methyl 3-(R)-(n-butyl)-3-[(2-(S)-(tert-butoxycarbonyl)-pyrrolidin-1-ylcarbonyl]-2-(S)-hydroxypropionate (intermediate G-3 from General Procedure G, 2 mmol) in DCM (10 mL) was added pyridine (6 mmol), the reaction was cooled to −20° C., then triflic anhydride (4 mmol) was added. The solution was stirred for 1 hour and after the usual work-up was concentrated, resuspended in DMF (10 mL), and treated with sodium azide (2.5 mmol). The reaction was stirred for 16 h, then diluted with ethylacetate, washed with water, saturated aqueous sodium bicarbonate, and brine, then dried ($Na_2SO_4$) and purified on silica gel (ethylacetate/hexanes) to afford methyl 3-(R)-(n-butyl)-3-[(2-(S)-(tert-butoxycarbonyl)-pyrrolidin-1-ylcarbonyl]-2-(R)-azidopropionate. To a solution of the azido compound (0.5 mmol) in dioxane (2 mL) was added aqueous 50% hydroxylamine (1 mL) and the reaction stirred for 48 h. The crude reaction mixture was then purified by preparative reverse-phase (C18) HPLC to afford the title compound. $^1$H NMR(CDCl3): δ 4.28–4.24 (dd, J=5.1 & 4.6 Hz, 1H), 3.92 (d, J=9.8 Hz, 1H), 3.80–3.74 (m, 1H), 3.64–3.57 (m, 1H), 3.16–3.09 (m, 1H), 2.22–1.91 (m, 4H), 1.89–1.76 (m, 2H), 1.43 (s, 9H), 1.40–1.35 (m, 4H), 0.92 (t, J=6.7 Hz). ES-MS: calcd. For $C_{17}H_{29}N_5O_5$ (383.3); found: 384 [M+1].

Example 46

Synthesis of N-hydroxy-3-(S)-(n-butyl)-3-[2-(S)-(tert-butoxycarbonyl)-pyrrolidin-1-carbonyl]-2-(S)-sulfonyloxypropionamide

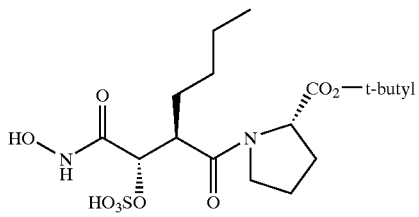

To a solution of methyl 3-(R)-(n-butyl)-3-[(2-(S)-(tert-butoxycarbonyl)-pyrrolidin-1-ylcarbonyl]-2-(S)-hydroxypropionate (intermediate G-3 from General Procedure G, 2 mmol) in DMF (10 mL) was added pyridinium sulfurtrioxide (2.2 mmol) and the solution stirred for 1 h. The reaction was diluted with ethylacetate and washed with saline, dried ($Na_2SO_4$) and concentrated to afford methyl 3-(S)-(n-butyl)-3-[(2-(S)-(tert-butoxycarbonyl)-pyrrolidin-1-ylcarbonyl]-2-(S)-sulfonyloxypropionate. This sulfonyloxy compound was dissolved in dioxane, treated with aqueous 50% hydroxylamine (1 mL) and the reaction stirred for 48 h. The crude reaction mixture was then purified by preparative reverse-phase (C18) HPLC to afford the title compound. $^1$H NMR (CDCl3): δ 4.63 (m, 2H), 4.19–3.82 (m, 2H), 3.79–3.67 (m, 1H), 2.36–1.83 (m, 4H), 1.81–1.59 (2H), 1.45 (s, 9H), 1.34–1.26 (m, 2H), 0.89 (t, J=6.3 Hz). ES-MS: calcd. For $C_{17}H_{30}N_2O_9S$ (438.49); found: 439.2 [M+1].

Example 47

Synthesis of N-hydroxy-3-(S)-(n-butyl)-3-[2-(S)-(tert-butoxycarbonyl)-pyrrolidin-1-carbonyl]-2-(S)-fluoropropionamide

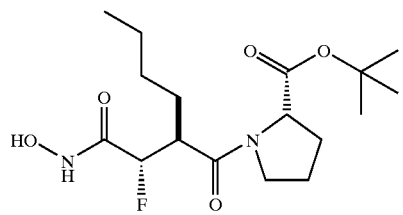

The title compound was prepared by treatment of methyl 3-(S)-(n-butyl)-3-[(2-(S)-(tert-butoxycarbonyl)pyrrolidin-1-ylcarbonyl]-2-(S)-fluoropropionate (intermediate H-4, General Procedure H), with aqueous 50% hydroxylamine followed by purification on preparative reverse-phase (C18) HPLC. $^1$H NMR (CDCl3) δ 5.16–4.98 (dd, $J_{H2,3}$=6.8 Hz & $J_{H,F}$=47 Hz, 1H), 4.39–4.35 (dd, J=4.4 & 3.8 Hz, 1H), 3.78 (m, 1H), 3.66–3.61 (m, 1H), 3.31–3.22 (m, 1H), 2.24–1.91 (m, 4H), 1.77–1.70 (m, 2H), 1.44 (s, 9H), 1.40–1.23 (m, 4H), 0.89 (t, J=6.9 & 7.2 Hz). ES-MS: calcd. For $C_{17}H_{29}FN_2O_5$ (360.42); found: 361 [M+1].

Example 48

Synthesis of N-hydroxy-3-(S)-(n-butyl)-3-[2-(S)-(tert-butoxycarbonyl)-pyrrolidin-1-carbonyl]-2-(R)-fluoropropionamide

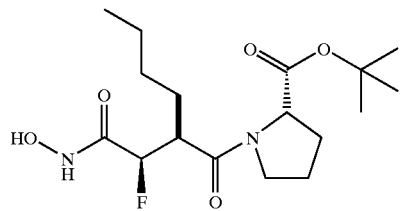

The title compound was prepared by treatment of methyl 3-(S)-(n-butyl)-3-[(2-(S)-(tert-butoxycarbonyl)pyrrolidin-1-ylcarbonyl]-2-(R)-fluoropropionate (intermediate G-4, General Procedure G), with aqueous 50% hydroxylamine followed by purification on preparative reverse-phase (C18) HPLC. $^1$H NMR (CDCl3): δ 5.32–5.13 (dd, $J_{H2,3}$=8.3 Hz & $J_{H,F}$=48 Hz, 1H), 4.54–4.51 (t, J=4.1 Hz, 1H), 3.93–3.87 (m, 1H), 3.84–3.77 (m, 1H), 3.45–3.40 (m, 1H), 2.43–2.11 (m, 4H), 2.10–1.95 (m, 2H), 1.63 (s, 9H), 1.58–1.52 (m, 4H), 1.10 (t, J=6.6 & 7.1 Hz, 3H). ES-MS: calcd. For $C_{17}H_{29}FN_2O_5$ (360.42); found: 361 [M+1].

Example 49

Synthesis of N-hydroxy-3-(R)-(n-butyl)-3-[2-(S)-(tert-butoxycarbonyl)-pyrrolidin-1-carbonyl]-2-oxopropionamide

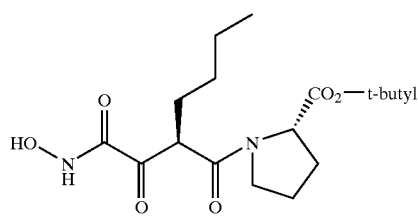

To a solution of methyl 3-(R)-(n-butyl)-3-[(2-(S)-(tert-butoxycarbonyl)-pyrrolidin-1-ylcarbonyl]-2-(S)-hydroxypropionate (intermediate G-3 from General Procedure G, 2 mmol) in DCM (10 mL) at 0° C. was added pyridinium dichromate (2.2 mmol) and the solution stirred for 2 h. The reaction was quenched with methanol, then diluted with ethylacetate and washed with water, aqueous bicarbonate, and brine, then dried (Na$_2$SO$_4$) and purified on silica gel (ethylacetate/hexanes) to afford methyl 3-(R)-(n-butyl)-3-[(2-(S)-(tert-butoxycarbonyl)-pyrrolidin-1-ylcarbonyl]-2-oxo-propionate. To a solution of the 2-oxo intermediate (0.5 mmol) in dioxane (2 mL) was added aqueous 50% hydroxylamine (1 mL) and the reaction stirred for 48 h. The crude reaction mixture was then purified by preparative reverse-phase (C18) HPLC to afford the title compound. $^1$H NMR (CDCl$_3$): δ 4.41–4.39 (dd, J=4.4 Hz), 4.29–4.24 (m, 1H), 3.99–3.96 (m, 1H), 3.70–3.67 (m, 1H), 2.29–1.97 (m, 4H), 1.79–1.77 (m, 2H), 1.43 (s, 9H), 1.37–1.35 (m, 4H), 0.91 (t, J=6.7 & 7.1 Hz, 3H). ES-MS: calcd. For C$_{17}$H$_{28}$N$_2$O$_6$(356.41); found: 357.4 [M+1].

Example 50

Synthesis of N-hydroxy-3-(S)-(n-butyl)-3-[2-(S)-(n-butylaminocarbonyl)-pyrrolidin-1-carbonyl]-2-(R)-fluoropropionamide

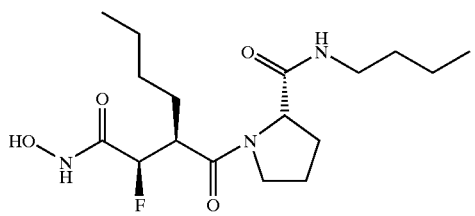

The title compound was prepared according to General Procedure G from n-butylamine. $^1$H NMR (CDCl$_3$): δ 7.07 (t, J=5.2 & 5.5 Hz, 1H), 5.13 (dd, J$_{H2,3}$=8.5 Hz & J$_{H,F}$=47 Hz, 1H), 4.48–4.46 (dd, J=4.9 Hz, 1H), 3.68–3.55 (m, 2H), 3.25–3.16 (m, 3H), 2.23–2.18 (m, 2H), 2.15–2.09 (m, 4H), 2.06–1.80(m, 4H), 1.52–1.43(m, 4H), 1.32(t, J=7.5 Hz, 3H), 0.90(t, J=6.6&7.2 Hz). ES-MS: cfalcd. For C$_{17}$H$_{30}$FN$_3$O$_4$ (359.44); found: 360.3 [M+1], 382.4 [M+Na].

Example 51

Synthesis of N-hydroxy-3-(S)-(n-butyl)-3-[2-(S)-(benzylaminocarbonyl)-pyrrolidin-1-carbonyl]-2-(R)-fluoropropionamide

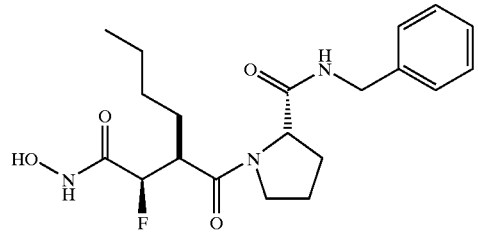

The title compound was prepared according to General Procedure G from benzylamine. $^1$H NMR (CDCl$_3$): δ 7.47–7.40 (m, 5H), 4.66–4.60 (dd, J=5.1 Hz & 47 Hz, 1H), 4.58–4.45 (m, 1H), 3.97–3.76 (m, 4H), 3.35–3.28 (m, 1H), 2.31–1.94 (m, 6H), 1.61–1.45 (m, 4H), 1.07 (t, J=6.6 Hz, 3H). ES-MS: calcd. For C$_{17}$H$_{28}$FN$_3$O$_4$ (393.45); found: 394.3 [M+1], 416.2 [M+Na].

Example 52

Synthesis of N-hydroxy-3-(S)-(n-butyl)-3-[2-(S)-(1,1-dimethylpropylaminocarbonyl)pyrrolidin-1-carbonyl]-2-(R)-fluoropropionamide

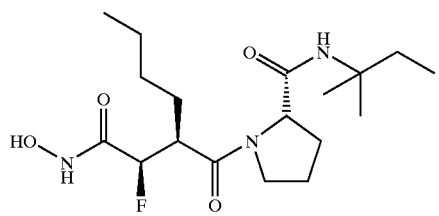

The title compound was prepared according to General Procedure G from 1,1-dimethylpropylamine. $^1$H NMR (CDCl$_3$): δ 5.34–5.16 (dd, J=7.9 & 8.3 Hz, J$_{H,F}$=47 Hz), 4.61 (d, J=4.6 Hz), 3.80–3.78 (m, 2H), 3.40–3.35 (m, 1H), 2.39–1.84 (m, 8H), 1.53–1.44 (m, 10H), 1.09 (t, J=6.8 Hz, 3H), 1.01 (t, J=7.7 Hz, 3H). ES-MS: calcd. For C$_{18}$H$_{32}$FN$_3$O$_4$(373.46); found: 374.4 [M+1], 396.2 [M+Na].

Example 53

Synthesis of N-hydroxy-3-(S)-(n-butyl)-3-[2-(S)-(2-cyclohex-1-enylethylaminocarbonyl)pyrrolidin-1-carbonyl]-2-(R)-fluoropropionamide

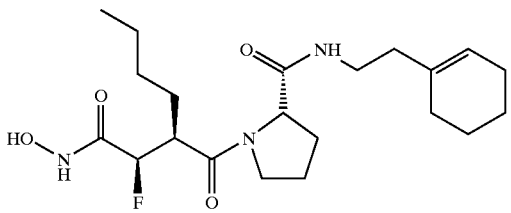

The title compound was prepared according to General Procedure G from 2-(1-cyclohexenyl)ethylamine. $^1$H NMR (CDCl$_3$): δ 7.11 (t, J=4.6 & 5.2 Hz, 1H), 5.62 (bs, 1H), 5.32–5.13 (dd, J=9.3 & 9.6 Hz, $J_{H,F}$=47 Hz, 1H), 4.64–4.63 (m, 1H), 3.81–3.73 (m, 2H), 3.59–3.52 (m, 1H), 3.50–3.37 (m, 3H), 2.31–2.16 (m, 9H), 2.10–1.99 (m, 2H), 1.79–1.52 (m, 9H), 1.09 (t, J=6.5 & 5.5 Hz). ES-MS: calcd. For $C_{21}H_{34}FN_3O_4$(411.51); found: 412.4[M+1], 434.5 [M+Na].

Example 54

Synthesis of N-hydroxy-3-(S)-(n-butyl)-3-[2-(S)-(indan-5-ylaminocarbonyl)pyrrolidin-1-carbonyl]-2-(R)-fluoropropionamide

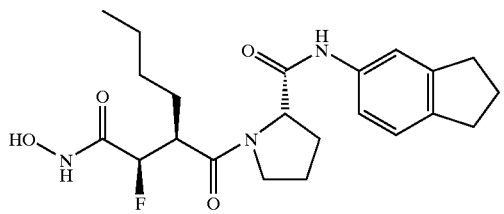

The title compound was prepared according to General Procedure G from 5-aminoindan. $^1$H NMR (CDCl$_3$): δ 7.52 (s, 1H), 7.35 (d, J=8 Hz, 1H), 7.21 (d, J=8 Hz, 1H), 5.34–5.15 (dd, J=8.2 & 8.5 Hz, $J_{H,F}$=47 Hz, 1H), 4.86–4.84 (m, 1H), 3.80–3.78 (m, 2H), 3.36–3.31 (m, 1H), 3.06–2.96 (m, 4H), 2.41–1.97 (m, 8H), 1.58–1.48 (m, 4H), 1.04 (t, J=6.6 & 7.2 Hz, 3H). ES-MS: calcd. For $C_{22}H_{30}FN_3O_4$ (419.49); found: 420.3 [M+1].

Example 55

Synthesis of N-hydroxy-3-(S)-(n-butyl)-3-[2-(S)-(4,5-dimethylthiazol-2-ylaminocarbonyl)pyrrolidin-1-carbonyl]-2-(R)-fluoropropionamide

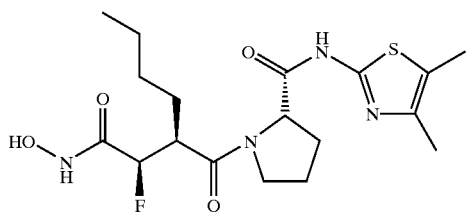

The title compound was prepared according to General Procedure G from 2-amino-4,5-dimethylthiazole. $^1$H NMR (CDCl$_3$): δ 5.32–5.13 (dd, J=8.3 & 7.9 Hz, $J_{H,F}$=47 Hz, 1H), 4.83–4.80 (m, 1H), 3.97–3.85 (m, 2H), 3.40–3.38 (m, 1H), 2.51 (s, 3H), 2.50 (s, 3H), 2.33–2.21 (m, 4H), 2.18–1.95 (m, 2H), 1.59–1.49 (m, 4H), 1.07 (t, J=6.6 & 7.2 Hz, 3H). ES-MS: calcd. For $C_{18}H_{27}FN_4O_4S$ (414.50); found: 415.4 [M+1], 437.3 [M+Na].

Example 56

Synthesis of N-hydroxy-3-(S)-(n-butyl)-3-[2-(S)-(4-phenoxyphenyl)aminocarbonyl)pyrrolidin-1-carbonyl]-2-(R)-fluoropropionamide

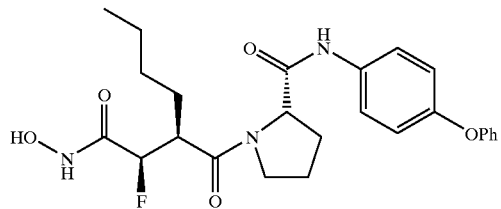

The title compound was prepared according to General Procedure G from 4-phenoxyaniline. $^1$H NMR (CDCl$_3$): δ 7.69–7.16 (m, 2H), 7.53–7.46 (m, 2H), 7.29–7.24 (m, 1H), 7.18–7.06 (m, 4H), 5.37–5.20 (dd, J=7.8 Hz, $J_{H,F}$=47 Hz, 1H), 4.90–4.85 (m, 1H), 3.92–3.82 (m, 2H), 3.33–3.37 (m, 1H), 2.47–2.36 (m, 2H), 2.30–2.00 (m, 4H), 1.50–1.13 (m, 4H), 1.02 (t, J=6.6 & 6.9 Hz, 3H). ES-MS: calcd. For $C_{25}H_{30}FN_3O_5$ (471.52); found: 472.4 [M+1].

Example 57

Synthesis of N-hydroxy-3-(S)-(n-butyl)-3-[2-(S)-(cyclopropylmethylaminocarbonyl)pyrrolidin-1-carbonyl]-2-(R)-fluoropropionamide

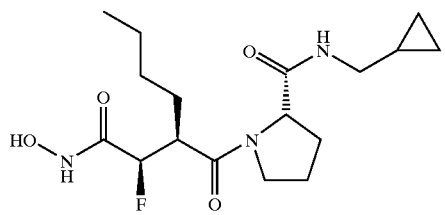

The title compound was prepared according to General Procedure G from (aminomethyl)cyclopropane. $^1$H NMR (CDCl$_3$): δ 6.90 (t, J=5.2 Hz, 1H), 4.99–4.82 (dd, J=6.4 & 8 Hz, $J_{H,F}$=49.8 & 48.6 Hz, 1H), 4.34–4.32 (m, 1H), 3.56–3.47 (m, 2H), 3.09–2.85 (m, 3H), 2.09–1.83 (m, 4H), 1.67–1.64 (m, 2H), 1.30–1.11 (m, 5H), 0.72 (t, J=6.9 & 7.1 Hz, 3H), 0.33–0.29 (dd, J=5.3 Hz, 2H), 0.05–0.00 (dd, J=4.6 Hz, 2H). ES-MS: calcd. For $C_{17}H_{28}FN_3O_4$(357.42); found: 358.4 [M+1].

Example 58

Synthesis of N-hydroxy-3-(S)-(n-butyl)-3-[2-(S)-(pyridin-3-yl)aminocarbonyl)pyrrolidin-1-carbonyl]-2-(R)-fluoropropionamide

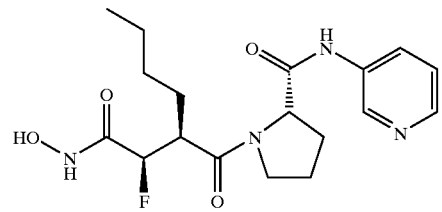

The title compound was prepared according to General Procedure G from 3-aminopyridine. $^1$H NMR (DMSO-D6):

δ 9.15 (s, 1H), 8.62 (d, J=4.2 Hz, 1H), 8.42 (d, J=8.2 Hz, 1H), 7.88–7.83 (dd, J=5.3 & 4.9 Hz, 1H), 5.09–4.91 (dd, J=8 Hz, $J_{H,F}$=48.6 Hz, 1H), 4.60–4.56 (dd, J=4.8 Hz, 1H), 3.92–3.89 (m, 1H), 3.87–3.79 (m, 1H), 3.42–3.35 (m, 1H), 2.37–2.04 (m, 4H), 1.81–1.51 (m, 2H), 1.50–1.39 (m, 4H), 1.04 (t, J=6.9 & 7.2 Hz, 3H). ES-MS: calcd. For $C_{18}H_{25}FN_4O_4$ (380.41); found: 381.3 [M+1].

Example 59

Synthesis of N-hydroxy-3-(S)-(n-butyl)-3-[2-(S)-((pyridin-4-ylmethyl)aminocarbonyl)pyrrolidin-1-carbonyl]-2-(R)-fluoropropionamide

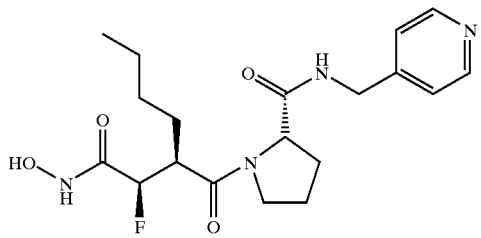

The title compound was prepared according to General Procedure G from 4-(aminomethyl)pyridine. $^1$H NMR (DMSO-D6): δ 8.94–8.86 (m, 3H), 7.94–7.93 (m, 1H), 5.14–4.95 (dd, J=7.7 Hz, $J_{H,F}$=48.4 Hz, 1H), 4.68–4.67 (m, 1H), 4.51–4.47 (m, 1H), 3.95–3.75 (m, 3H), 3.38–3.35 (m, 1H), 2.33–2.01 (m, 4H), 1.99–1.79 (m, 2H), 1.41–1.38 (m, 4H), 0.92 (t, J=6.6 & 7.1 Hz, 3H). ES-MS: calcd. For $C_{19}H_{27}FN_4O_4$ (394.44); found: 395.4 [M+1].

Example 60

Synthesis of N-hydroxy-3-(S)-(n-butyl)-3-[2-(S)-(morpholin-4-ylcarbonyl)pyrrolidin-1-carbonyl]-2-(R)-fluoropropionamide

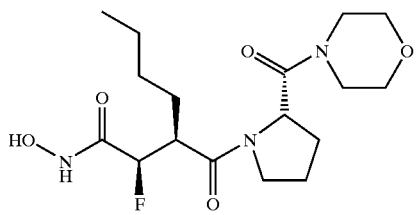

The title compound was prepared according to General Procedure G from morpholine. $^1$H NMR (CDCl$_3$): δ 5.30–5.11 (dd, J=8.2 Hz, $J_{H,F}$=47.6 Hz, 1H), 5.06–5.04 (t, J=3.6 & 4.4 Hz, 1H), 3.92–3.67 (m, 10H), 3.44–3.42 (m, 1H), 2.40–1.98 (m, 6H), 1.74–1.52 (m, 4H), 1.10 (t, J=6.8 & 7.4 Hz, 3H). ES-MS: calcd. For $C_{17}H_{28}FN_3O_5$ (373.42); found: 374.3 [M+1].

Example 61

Synthesis of N-hydroxy-3-(S)-(n-butyl)-3-[2-(S)-(3,4-methylenedioxyphenylaminocarbonyl)pyrrolidin-1-carbonyl]-2-(R)-fluoropropionamide

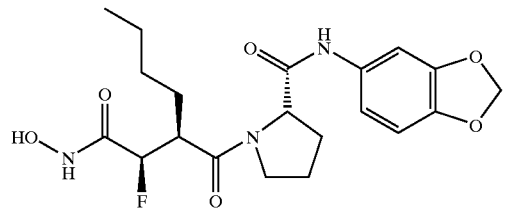

The title compound was prepared according to General Procedure G from 3,4-(methylenedioxy)aniline. $^1$H NMR (CDCl$_3$): δ 7.47 (s, 1H), 7.34 (d, J=2 Hz, 1H), 6.99–6.95 (dd, J=2 Hz, 1H), 6.80 (d, J=8.5 Hz, 1H), 6.08 (s, 2H), 5.36–5.17 (dd, J=8.5 & 8.8 Hz, $J_{H,F}$=47 Hz, 1H), 4.82–4.81 (dd, J=4.4 Hz, 1H), 3.84–3.80 (m, 2H), 3.38–3.33 (m, 1H), 2.40–1.97 (m, 6H), 1.57–1.52 (m, 4H), 1.059 (t, J=6.9 & 7.1 Hz, 3H). ES-MS: calcd. For $C_{20}H_{26}FN_3O_6$ (423.44); found: 424.3 [M+1].

Example 62

Synthesis of N-hydroxy-3-(S)-(n-butyl)-3-[2-(S)-(quinolin-3-ylaminocarbonyl)pyrrolidin-1-carbonyl]-2-(R)-fluoropropionamide

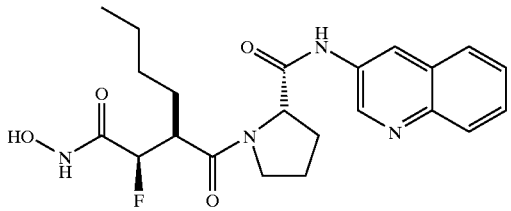

The title compound was prepared according to General Procedure G from 3-aminoquinoline. $^1$H NMR (CDCl$_3$): δ 9.32 (s, 1H), 8.31 (d, J=8.8 Hz, 1H), 8.03–7.81 (m, 3H), 7.48–7.46 (m, 2H), 5.35–5.17 (dd, J=7.7 & 8 Hz, $J_{H,F}$=47 Hz, 1H), 4.89–4.85 (m, 1H), 3.90–3.85 (m, 2H), 3.45–3.37 (m, 1H), 2.41–2.02(m, 5H), 1.67–1.52 (m, 5H), 1.10 (t, J=6.9 & 5.7 Hz, 3H). ES-MS: calcd. For $C_{22}H_{27}FN_4O_4$ (430.47); found: 431.3 [M+1].

Example 63

Synthesis of N-hydroxy-3-(S)-(n-butyl)-3-[2-(S)-(methylaminocarbonyl)-pyrrolidin-1-carbonyl]-2-(R)-fluoropropionamide

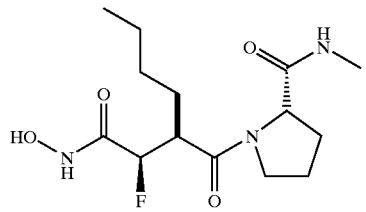

The title compound was prepared according to General Procedure G from methylamine. $^1$H NMR (CDCl$_3$): δ 7.30

(d, J=5.6 Hz, 1H), 5.30–5.12 (dd, J=7.9 & 8.8 Hz, $J_{H,F}$=47 Hz, 1H), 3.84–3.82 (m, 2H), 3.41–3.39 (m, 1H), 2.95 (s, 3H), 2.32–1.99 (m, 6H), 1.63–1.51 (m, 4H), 1.09 (t, J=6.4 & 4.9 Hz, 3H). ES-MS: calcd. For $C_{14}H_{24}FN_3O_4$ (317.36); found 318.3 [M+1].

Example 64

Synthesis of N-hydroxy-3-(S)-(n-butyl)-3-[2-(S)-((4-biphenyl)aminocarbonyl)-pyrrolidin-1-carbonyl]-2-(R)-fluoropropionamide

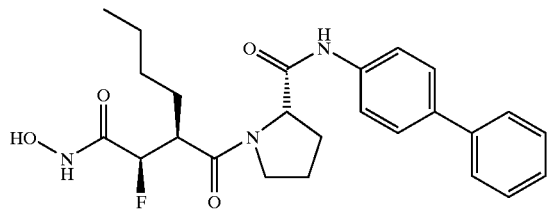

The title compound was prepared according to General Procedure G from 4-phenylaniline. $^1$H NMR (CDCl$_3$): δ 7.75–7.46 (m, 10H), 5.39–5.21 (dd, J=8.8 Hz, $J_{H,F}$=47 Hz, 1H), 4.91–4.89 (m, 1H), 3.85–3.83 (m, 2H), 3.41–3.36 (m, 1H), 2.45–2.02 (m, 6H), 1.63–1.50 (m, 4H), 1.06 (t, J=6.6 & 7.4 Hz, 3H). ES-MS: calcd. For $C_{25}H_{30}FN_3O_4$(455.52); found 456.3 [M+1].

Example 65

Synthesis of N-hydroxy-3-(S)-(n-butyl)-3-[(2-(S)-((3-phenoxyphenyl)aminocarbonyl)-pyrrolidin-1-carbonyl]-2-(R)-fluoropropionamide

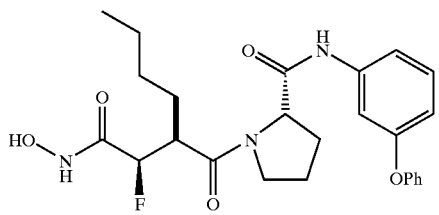

The title compound was prepared according to General Procedure G from 3-phenoxyaniline. $^1$H NMR (CDCl3): δ 7.53–7.46 (m, 4H), 7.35–7.25 (m, 3H), 7.18–7.14 (m, 2H), 6.85–6.18 (m, 1H), 5.35–5.16 (dd, J=8.8 Hz, $J_{H,F}$=47 Hz, 1H), 4.84–4.82 (m, 1H), 3.81–3.78 (m, 2H), 3.36–3.31 (m, 1H), 2.41–1.97 (m, 6H), 1.53–1.46 (m, 4H), 1.02 (t, J=6.6 & 7.1 Hz, 3H). ES-MS: calcd. For $C_{25}H_{30}FN_3O_5$ (471.52); found 472.4 [M+1].

Example 66

Synthesis of N-hydroxy-3-(S)-(n-butyl)-3-[2-(S)-((3,4-dichlorophenyl)aminocarbonyl)pyrrolidin-1-carbonyl]-2-(R)-fluoropropionamide

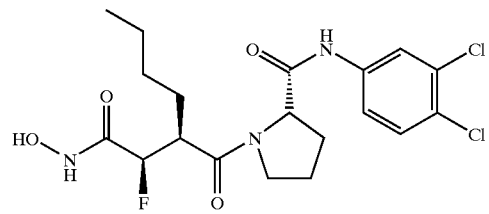

The title compound was prepared according to General Procedure G from 3,4-dichloroaniline. $^1$H NMR (CDCl$_3$): δ 7.78 (s, 1H), 7.47–7.32 (m, 2H), 5.35–5.16 (dd, J=8.8 Hz, $J_{H,F}$=47 Hz, 1H) 4.82–4.80 (m, 1H), 3.85–3.79 (m, 2H), 3.36–3.31 (m, 11H), 2.35–2.03 (m, 6H), 1.67–1.54 (m, 4H), 1.10 (t, J=6.6 & 6.8 Hz, 3H). ES-MS: calcd. For $C_{19}H_{24}Cl_2FN_3O_4$(444.11); found: 448.2 [M+1].

Example 67

Synthesis of N-hydroxy-3-(S)-(n-butyl)-3-[2-(S)-((4-tert-butylphenyl)aminocarbonyl)pyrrolidin-1-carbonyl]-2-(R)-fluoropropionamide

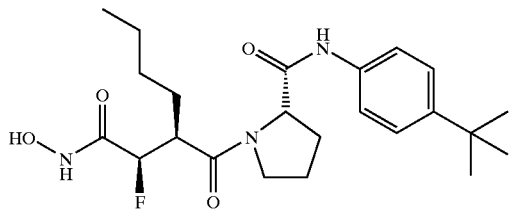

The title compound was prepared according to General Procedure G from 4-tert-butylaniline. $^1$H NMR (CDCl$_3$): δ 7.67(m, 2H), 7.57–7.45 (m, 3H), 5.35–5.16 (dd, J=8.2 & 8.5 Hz, $J_{H,F}$=47 Hz, 1H), 4.85 (d, J=4.4 Hz, 1H), 3.83–3.80 (m, 2H), 3.39–3.34 (m, 1H), 2.43–2.00 (m, 6H), 1.57–1.45 (m, 13H), 1.023 (t, J=6.6 & 7.1 Hz, 3H). ES-MS: calcd. For $C_{23}H_{34}FN_3O_4$(435.53); found: 436.4 [M+1].

Example 68

Synthesis of N-hydroxy-3-(S)-(n-butyl)-3-[2-(S)-(tert-butylaminocarbonyl)-pyrrolidin-1-carbonyl]-2-(R)-fluoropropionamide The title compound was prepared according to General Procedure G from tert-butylamine. $^1$H NMR (CDCl$_3$): δ 5.33–5.14 (dd, J=8 Hz, $J_{H,F}$=48 Hz, 1H), 4.58 (d, J=4.7 Hz, 1H), 3.81–3.79 (m, 2H), 3.42–3.39 (m, 1H), 2.40–1.98 (m, 10H), 1.55–1.49 (m, 13H), 1.11 (t, J=5.8 & 6.6 Hz, 3H). ES-MS: calcd. For $C_{17}H_{30}FN_3O_4$ (359.44); found: 360.3 [M+1].

Example 69

Synthesis of N-hydroxy-3-(S)-(n-butyl)-3-[2-(S)-((indan-2-yl)aminocarbonyl)pyrrolidin-1-carbonyl]-2-(R)-fluoropropionamide

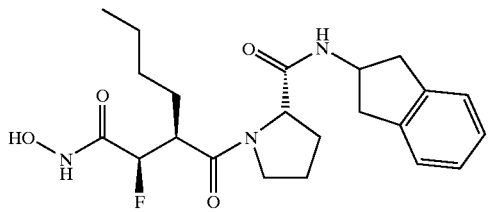

The title compound was prepared according to General Procedure G from 2-aminoindan. $^1$H NMR (CDCl$_3$): δ 7.48–7.33 (m, 4H), 5.25–5.07 (dd, J=8.5 Hz, $J_{H,F}$=47.5 Hz, 1H), 4.86–4.80 (m, 1H), 4.57–4.55 (m, 1H), 3.78–3.76 (m, 2H), 3.51–3.42 (m, 2H), 3.35–3.30 (m, 1H), 3.01–2.92 (m, 2H), 2.37–2.27 (m, 2H), 2.17–1.92 (m, 2H), 1.52–1.42 (m, 4H), 1.08 (t, J=6.8 Hz, 3H). ES-MS: calcd. For $C_{22}H_{30}FN_3O_4$ (419.49); found: 420.6 [M+1].

Example 70

Synthesis of N-hydroxy-3-(S)-(n-butyl)-3-[2-(S)-((2,2-dimethylpropyl)aminocarbonyl)pyrrolidin-1-carbonyl]-2-(R)-fluoropropionamide

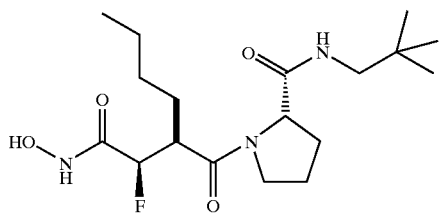

The title compound was prepared according to General Procedure G from 2,2-dimethylpropylamine. $^1$H NMR (CDCl$_3$): δ 7.28 (t, J=6 Hz, 1H), 5.36–5.18 (dd, J=8.4 Hz, $J_{H,F}$=47.5 Hz, 1H), 4.75 (d, J=5.2 Hz, 1H), 3.85–3.77 (m, 2H), 3.40–3.35 (m, 1H), 3.29–3.19 (m, 2H), 2.50–2.27 (m, 2H), 2.17–2.13 (m, 2H), 2.09–1.98 (m, 2H), 1.53–1.51 (m, 4H), 1.08 (bs, 3H). $C_{18}H_{32}FN_3O_4$ (373.24); found: 374.4 [M+1].

Example 71

Synthesis of N-hydroxy-3-(S)-(n-butyl)-3-[2-(S)-((4-phenylthiazol-2-yl)aminocarbonyl)pyrrolidin-1-carbonyl]-2-(R)-fluoropropionamide

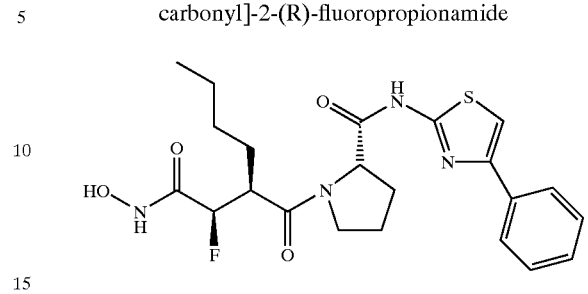

The title compound was prepared according to General Procedure G from 2-amino-4-phenylthiazole. $^1$H NMR (CDCl$_3$): δ 7.92–7.90 (m, 2H), 7.71 (m, 3H), 7.46 (s, 1H), 7.28 (s, 1H), 5.37–5.18 (dd, J=8.5 & 8.2 Hz, $J_{H,F}$=47 Hz, 1H), 4.95–4.93 (m, 1H), 3.99–3.95 (m, 2H), 3.43–3.38 (m, 1H), 2.54–2.26 (m, 4H), 2.21–1.96 (m, 2H), 1.62–1.50 (m, 4H), 1.08 (t, J=6.9 & 7.1 Hz, 3H). ES-MS: calcd. For $C_{22}H_{27}FN_4O_4S$ (462.54); found: 463.4 [M+1].

Example 72

Synthesis of N-hydroxy-3-(S)-(n-butyl)-3-[2-(S)-((5-phenylthiadiazol-2-yl)aminocarbonyl)pyrrolidin-1-carbonyl]-2-(R)-fluoropropionamide

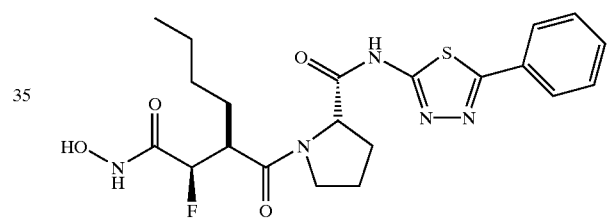

The title compound was prepared according to General Procedure G from 2-amino-5-phenylthiadiazole. $^1$H NMR (CDCl$_3$): δ 8.08–8.05 (m, 2H), 7.68–7.48 (m, 3H), 5.45–5.26 (dd, J=9.2 Hz, $J_{H,F}$=47 Hz, 1H), 4.99–4.97 (m, 1H), 3.96–3.94 (m, 2H), 3.38–3.36 (m, 1H), 2.50–1.98 (m, 6H), 1.61–1.51 (m, 4H), 1.09 (t, J=6.9 Hz, 3H). ES-MS: calcd. For $C_{21}H_{26}FN_5O_4S$ (463.53); found: 464.2 [M+1].

Example 73

Synthesis of N-hydroxy-3-(S)-(n-butyl)-3-[2-(S)-((5-ethylthiadiazol-2-yl)aminocarbonyl)pyrrolidin-1-carbonyl]-2-(R)-fluoropropionamide

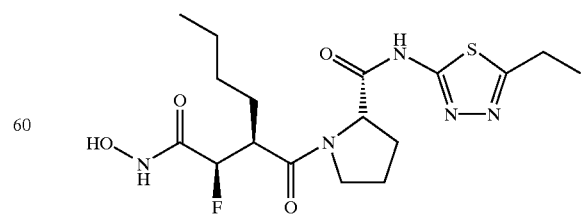

The title compound was prepared according to General Procedure G from 2-amino-5-ethylthiadiazole. $^1$H NMR (CDCl$_3$): δ 5.43–5.24 (dd, J=9.6 Hz, J$_{H,F}$=47.5 Hz, 1H), 5.00–4.98 (m, 1H), 3.97–3.88 (m, 1H), 3.38–3.36 (m, 2H), 3.27–3.20 (m, 2H), 2.47–2.21 (m, 4H), 2.19–1.97 (m, 2H), 1.58 (t, J=7.7 Hz, 3H), 1.58–1.49 (m, 4H), 1.09 (t, J=6.8 & 7.2 Hz, 3H). ES-MS: calcd. For C$_{17}$H$_{26}$FN$_5$O$_4$S (415.48); found: 416.2 [M+1].

Example 74

Synthesis of N-hydroxy-3-(S)-(n-butyl)-3-[2-(S)-((3-trifluoromethoxyphenyl)aminocarbonyl)pyrrolidin-1-carbonyl]-2-(R)-fluoropropionamide

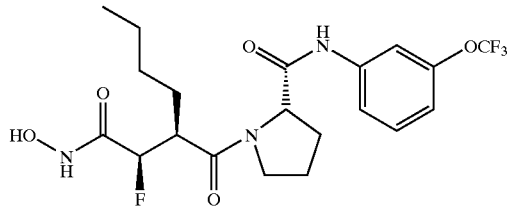

The title compound was prepared according to General Procedure G from 3-(trifluoromethoxy)aniline. $^1$H NMR (CDCl$_3$): δ 7.71 (s, 1H), 7.48–7.41 (m, 2H), 7.29 (t, J=8.2 Hz, 1H), 6.98 (d, J=7.9 Hz, 1H), 5.39–5.21 (dd, J=9.3 & 8.8 Hz, 1H), 4.88–4.86 (m, 1H), 3.85–3.82 (m, 2H), 3.39–3.37 (m, 1H), 2.41–2.04 (m, 6H), 1.61–1.53 (m, 4H), 1.06 (t, J=6.9 Hz, 3H). ES-MS: calcd. For C$_{20}$H$_{25}$F$_4$N$_3$O$_5$ (463.42); found: 454.2 [M +1].

Example 75

Synthesis of N-hydroxy-3-(S)-(n-butyl)-3-[2-(S)-((benzthiazol-2-yl)aminocarbonyl)pyrrolidin-1-carbonyl]-2-(R)-fluoropropionamide

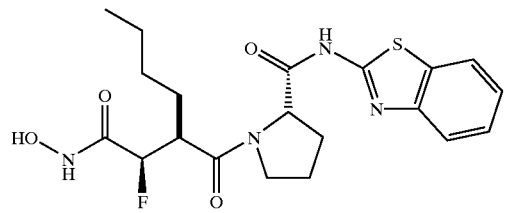

The title compound was prepared according to General Procedure G from 2-aminobenzothiazole. $^1$H NMR (CDCl$_3$): δ 7.99–7.92 (dd, J=7.5 & 8.2 Hz, 2H), 7.70–7.64 (dd, J=8 & 7.6 Hz, 1H), 7.56 (t, J=7.9 & 8.5 Hz, 1H), 5.43–5.24 (dd, J=8.2 & 8.5 Hz, J$_{H,F}$=47 Hz, 1H), 5.04–5.01 (m, 1H), 4.00–3.97 (m, 2H), 3.47–3.42 (m, 1H), 2.57–2.21 (m, 4H), 2.00–1.97 (m, 2H), 1.64–1.52 (m, 4H), 1.09 (t, J=6.8 & 7.2 Hz, 3H). ES-MS: calcd. For C$_{20}$H$_{25}$FN$_4$O$_4$S (436.50); found: 437.3 [M+1].

Example 76

Synthesis of N-hydroxy-3-(S)-(n-butyl)-3-[2-(S)-((2,5-dimethylphenyl)aminocarbonyl)pyrrolidin-1-carbonyl]-2-(R)-fluoropropionamide

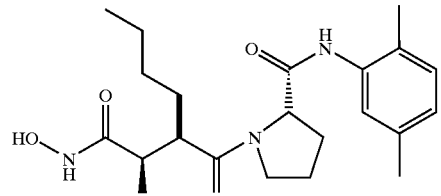

The title compound was prepared according to General Procedure G from 2,5-dimethylamline. $^1$H NMR (CDCl$_3$): δ 7.81 (s, 1H), 7.22 (d, J=7.7 Hz, 1H), 7.05 (d, J=7.9 Hz, 1H), 5.42–5.23 (dd, J=8.5 Hz, J$_{H,F}$=47 Hz, 1H), 4.99–4.97 (m, 1H), 3.83–3.79 (m, 2H), 3.40–3.35 (m, 1H), 2.66–2.63 (m, 2H), 2.47 (s, 3H), 2.38 (s, 3H), 2.24–2.19 (m, 2H), 2.18–1.99 (m, 2H), 1.64–1.46 (m, 4H), 0.99 (t, J=6.6 & 6.9 Hz, 3H). ES-MS: calcd. For C$_{21}$H$_{30}$FN$_3$O$_4$ (407.48); found: 408.3 [M+1].

Example 77

Synthesis of N-hydroxy-3-(S)-(n-butyl)-3-[2-(S)-((2,5-dimethoxyphenyl)aminocarbonyl)pyrrolidin-1-carbonyl]-2-(R)-fluoropropionamide

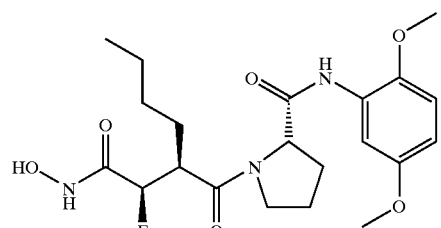

The title compound was prepared according to General Procedure G from 2,5-dimethoxyaniline. $^1$H NMR (CDCl$_3$): δ 8.22 (d, J=3 Hz, 1H), 6.96 (d, J=8.8 Hz. 1H), 6.79–6.75 (dd, J=3 Hz, 1H), 5.41–5.22 (dd, J=8 Hz; J$_{H,F}$=47 Hz, 1H), 4.92–4.90 (m, 1H), 4.00 (s, 3H), 3.96 (s, 3H), 3.95–3.85 (m, 2H), 3.45–3.39 (m, 1H), 2.56–2.23 (m, 4H), 2.02–1.99 (m, 2H), 1.64–1.49 (m, 4H), 1.00 (t, J=6.3 & 7.1 Hz, 3H). ES-MS: calcd. For C$_{21}$H$_{30}$FN$_3$O$_6$ (439.48); found: 440.4 [M +1].

Example 78

Synthesis of N-hydroxy-3-(S)-(n-butyl)-3-[2-(S)-((4,5-dimethylthiazol-2-yl)aminocarbonyl)pyrrolidin-1-carbonyl]-2-(S)-fluoropropionamide

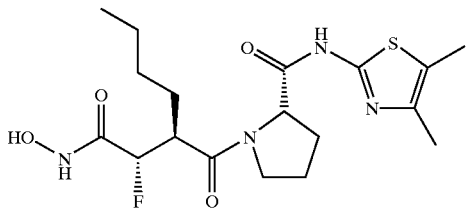

The title compound was prepared according to General Procedure H from 2-amino-4,5-dimethylthiazole. $^1$H NMR (CDCl$_3$): δ 5.32–5.14 (dd, J=5.7 Hz, J$_{H,F}$=47 Hz, 1H), 4.85–4.81 (dd, J=6 & 5.3 Hz, 1H), 4.03–3.99 (m, 2H), 3.53–3.43 (m, 1H), 2.52 (s, 3H), 2.50 (s, 3H), 2.36–2.22 (m, 4H), 2.19–1.79 (m, 2H), 1.60–1.50 (m, 4H), 1.08 (t, J=6.6 & 6.9 Hz, 3H). ES-MS: calcd. For C]$_8$H$_{27}$FN$_4$O$_4$S (414.50); found: 415.4 [M+1].

Example 79

Synthesis of N-hydroxy-3-(S)-(n-butyl)-3-[2-(S)-((3,4-dichlorophenyl)aminocarbonyl)pyrrolidin-1-carbonyl]-2-(S)-fluoropropionamide

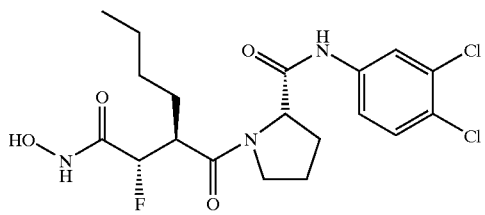

The title compound was prepared according to General Procedure H from 3,4-dichloroaniline. $^1$H NMR (CDCl$_3$): δ 7.94 (s, 1H), 7.48–7.46 (m, 2H), 5.38–5.21 (dd, J=4.4 Hz, J$_{H,F}$=47 Hz, 1H), 4.73–4.71 (m, 1H), 3.92–3.91 (m, 2H), 3.53–3.52 (m, 1H), 2.53–1.97 (m, 6H), 1.59–1.58 (m, 4H), 1.09 (t, J=6.9 Hz, 3H). ES-MS: calcd. For C$_{19}$H$_{24}$Cl$_2$FN$_3$O$_4$S (447.11); found: 448.2 [M+1].

Example 80

Synthesis of N-hydroxy-3-(S)-(n-butyl)-3-[2-(S)-((benzthiazol-2-yl)aminocarbonyl)pyrrolidin-1-carbonyl]-2-(S)-fluoropropionamide

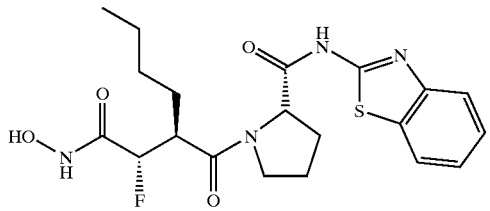

The title compound was prepared according to General Procedure H from 2-aminobenzothiazole. $^1$H NMR (CDCl$_3$): δ 7.66 (t, J=7.7 Hz, 2H), 7.34 (t, J=6.9 & 7.9 Hz, 1H), 7.26 (t, J=7.7 & 7.4 Hz, 1H), 5.10–5.92 (dd, J=5.8 Hz; J$_{H,F}$=47 Hz, 1H), 4.75–4.73 (m, 1H), 3.75–3.70 (m, 2H), 3.30–3.21 (m, 1H), 2.24–1.97 (m, 4H), 1.70–1.56 (m, 2H), 1.33–1.25 (m, 4H), 0.78 (t, J=6.8 Hz, 3H). ES-MS: calcd. For C$_{20}$H$_{25}$FN$_4$O$_4$S (436.50); found: 437.3 [M +1].

Example 81

Synthesis of N-hydroxy-3-(S)-(n-butyl)-3-[2-(S)-((3-phenoxyphenyl)aminocarbonyl)pyrrolidin-1-carbonyl]-2-(S)-fluoropropionamide

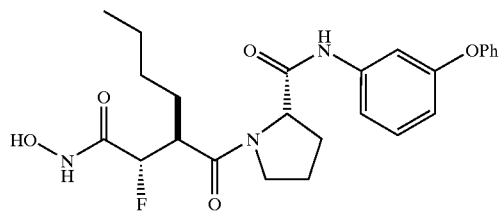

The title compound was prepared according to General Procedure H from 3-phenoxyaniline. $^1$H NMR (CDCl$_3$): δ 7.62–7.51 (m, 5H), 7.50–7.43 (m, 1H), 7.42–7.30 (m, 1H), 7.28–7.16 (m, 2H), 6.90–6.86 (m, 1H), 5.32–5.14 (dd, J=5.3 Hz, J$_{H,F}$=47 Hz, 1H), 4.76–4.74 (m, 1H), 3.89–3.87 (m, 2H), 3.51–3.41 (m, 1H), 2.47–1.92 (m, 6H), 1.53–1.51 (m, 4H), 1.05 (t, J=6.9 & 7.1 Hz, 3H). ES-MS: calcd. For C$_{25}$H$_{30}$FN$_3$O$_5$ (471.52); found: 472.4 [M+1].

Example 82

Synthesis of N-hydroxy-3-(S)-(n-butyl)-3-[2-(S)-((2-(RS)-hydroxybutyl)aminocarbonyl)pyrrolidin-1-carbonyl]-2-(S)-fluoropropionamide

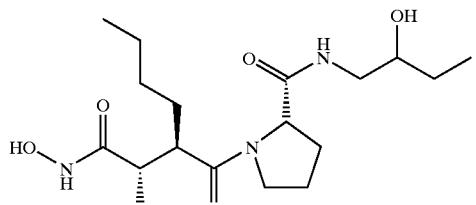

The title compound was prepared according to General Procedure H from (I) 2-hydroxy-n-butylamine. $^1$H NMR (CD$_3$OD): δ 5.09–4.92 (dd, J=8.8 Hz, J$_{H,F}$=47 Hz, 1H), 4.63–4.59 (m, 1H), 4.03–3.90 (m, 1H), 3.88–3.79 (m, 1H), 3.76–3.73 (m, 1H), 3.51 (s, 2H), 3.46–3.23 (m, 1H), 2.41–2.14 (m, 4H), 1.79–1.52 (m, 8H), 1.17 (t, J=7.3 Hz, 3H), 1.11 (t, J=6 & 7.4 Hz, 3H). ES-MS: calcd. For C$_{17}$H$_{30}$FN$_3$O$_5$ (375.44); found: 376.4 [M+1].

Example 83

Synthesis of N-hydroxy-3-(S)-(n-butyl)-3-[2-(S)-((4-hydroxybutyl)aminocarbonyl)pyrrolidin-1-carbonyl]-2-(S)-fluoropropionamide

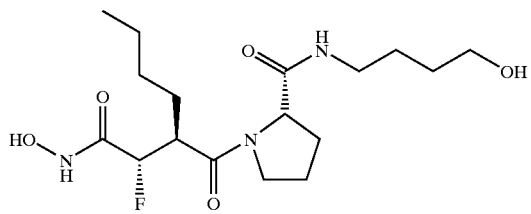

The title compound was prepared according to General Procedure H from 4-aminobutanol. $^1$H NMR (CD$_3$OD): δ 5.07–4.90 (dd, J=8.8 Hz, J$_{H,F}$=47 Hz, 1H), 4.60–4.55 (dd, J=4.5 & 4.9 Hz, 1H), 4.05–3.92 (m, 1H), 3.90–3.81 (m, 1H), 3.76 (s, 2H), 3.51 (s, 2H), 3.44–3.38 (m, 1H), 2.44–2.10 (m, 6H), 1.86–1.63 (m, 4H), 1.60–1.52 (m, 2H), 1.14 (t, J=6.8 Hz, 3H). ES-MS: calcd. For C$_{17}$H$_{30}$FN$_3$O$_5$ (375.44); found: 376.4 [M+1].

Example 84

Synthesis of N-hydroxy-3-(S)-(n-butyl)-3-[2-(S)-((3,4-methylenedioxyphenyl)aminocarbonyl)pyrrolidin-1-carbonyl]-2-(S)-fluoropropionamide

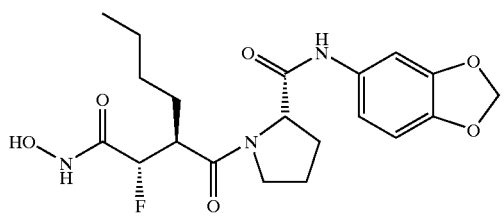

The title compound was prepared according to General Procedure H from 3,4-(methylenedioxy)aniline. $^1$H NMR (CDCl$_3$): 7.19 (s, 1H), 6.86 (d, J=8 Hz, 1H), 6.67 (d, J=8 Hz, 1H), 5.89 (s, 2H), 5.13–4.96 (dd, J=4.4 Hz, J$_{H,F}$=47 Hz, 1H), 4.55–4.53 (m, 1H), 3.76–3.72 (m, 2H), 3.30–3.21 (dd, J=4.1 Hz, 1H), 2.26–2.24 (m, 2H), 2.01–1.95 (m, 2H), 1.73 (bs, 2H), 1.32 (bs, 4H), 0.86 (t, J=6.3 Hz, 3H). ES-MS: calcd. For C$_{20}$H$_{26}$FN$_3$O$_6$ (423.44); found: 424.3 [M+1].

Example 85

Synthesis of N-hydroxy-3-(S)-(n-butyl)-3-[2-(S)-((1,4-benzodioxan-6-yl)aminocarbonyl)pyrrolidin-1-carbonyl]-2-(S)-fluoropropionamide

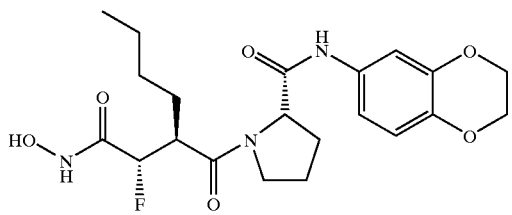

The title compound was prepared according to General Procedure H from 1,4-benzodioxan-6-amine. $^1$H NMR (CDCl$_3$): δ 7.14 (s, 1H), 6.93 (d, J=8.5 Hz, 1H), 6.74, (d, J=8.5 Hz, 1H), 5.14–4.97 (dd, J=4.5 Hz, J$_{H,F}$=47 Hz, 1H), 4.58–4.56 (m, 1H), 4.20 (s, 4H), 3.73–3.64 (m2H), 3.49–3.21 (m, 1H), 2.30–2.27 (m, 2H), 2.01–1.94 (m, 2H), 1.74 (bs, 2H), 1.32 (bs, 4H), 0.85 (t, J=6.6 & 7.1 Hz, 3H). ES-MS: calcd. For C$_{21}$H$_{28}$FN$_3$O$_6$ (437.46); found: 438.3 [M+1].

Example 86

Synthesis of N-hydroxy-3-(S)-(n-butyl)-3-[2-(S)-((isoquinolin-3-yl)aminocarbonyl)pyrrolidin-1-carbonyl]-2-(S)-fluoropropionamide

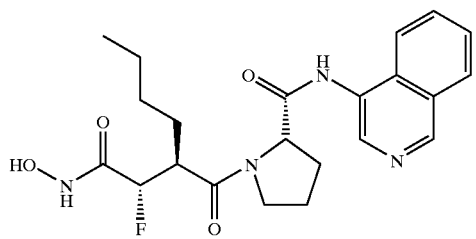

The title compound was prepared according to General Procedure H from 6-aminoisoquinoline. $^1$H NMR (CDCl$_3$): δ 9.89 (s, 1H), 9.63 (s, 1H), 7.85 (d, J=8.5 Hz, 1H), 7.71 (m, 2H), 7.61 (d, J=8.5 Hz, 1H), 5.16–4.99 (dd, J=5.8 Hz, J$_{H,F}$=47 Hz, 1H), 4.76–4.73 (m, 1H), 3.85 (m, 2H), 3.41–3.25 (m, 1H), 2.35–1.99 (m, 4H), 1.33–1.25 (m, 6H), 0.85 (t, J=6.8 & 7.1 Hz, 3H). ES-MS: calcd. For C$_{22}$H$_{27}$FN$_4$O$_4$ (430.47); found: 431.3 [M+1].

Example 87

Synthesis of N-hydroxy-3-(S)-(n-butyl)-3-[2-(S)-(methylaminocarbonyl)pyrrolidin-1-carbonyl]-2-(S)-fluoropropionamide

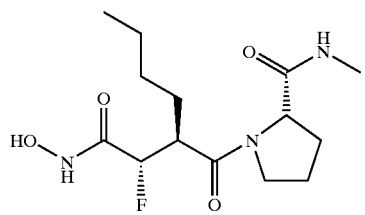

The title compound was prepared according to General Procedure H from methylamine. $^1$H NMR (CD$_3$OD): δ 5.064.90 (dd, J=8.7 Hz, J$_{H,F}$=47 Hz, 1H), 4.58–4.54 (dd, J=5 Hz, 1H), 4.05–4.00 (m, 1H), 3.99–3.82 (m, 1H), 3.50–3.49 (m, 1H), 2.93 (s, 3H), 2.40–2.08 (m, 4H), 1.79–1.51 (m, 6H), 1.21 (t, J=6.8 Hz, 3H). ES-MS: calcd. For C$_{14}$H$_{24}$FN$_3$O4 (317.36); found: 318.3 [M+1].

Example 88

Synthesis of N-hydroxy-3-(S)-(n-butyl)-3-[2-(S)-((5-phenylthiadiazol-2-yl)aminocarbonyl)pyrrolidin-1-carbonyl]-2-(S)-fluoropropionamide

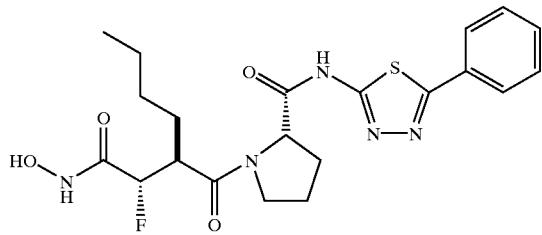

The title compound was prepared according to General Procedure H from 2-amino-5-phenylthiadiazole. $^1$H NMR (CDCl$_3$+DMSO-D6): δ 7.47–7.34 (m, 5H), 5.06–5.03 (dd, J=7.7HZ, J$_{H,F}$=47 Hz, 1H), 5.02–4.87 (m, 1H), 3.80–3.71 (m, 2H), 3.31–3.28 (m, 1H), 2.18–2.12 (m, 4H), 1.73–1.33 (m, 6H), 0.87 (t, J=6.7 Hz, 3H). ES-MS: calcd. For C$_{21}$H$_{26}$FN$_5$O$_4$S (463.53); found: 464.2 [M+1].

Example 89

Synthesis of N-hydroxy-3-(S)-(n-butyl)-3-[2-(S)-(n-butylaminocarbonyl)pyrrolidin-1-carbonyl]-2-(S)-fluoropropionamide

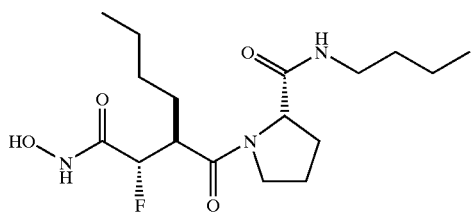

The title compound was prepared according to General Procedure H from n-butylamine. $^1$H NMR (CDCl$_3$): δ 7.21 (t, J=6.5 & 5.5 Hz, 1H), 5.14–4.97 (dd, J=5.8 Hz, J$_{H,F}$=47 Hz, 1H), 3.65–3.57 (m, 2H), 3.30–3.16 (m, 3H), 2.23–2.17 (m, 2H), 1.97–1.72 (m, 2H), 1.69–1.50 (m, 2H), 1.48–1.25 (m, 8H), 0.92–0.87 (m, 6H). ES-MS: calcd. For C$_{17}$H$_{30}$FN$_3$O$_4$ (359.44); found: 360.3 [M+1].

Example 90

Synthesis of N-hydroxy-3-(S)-(n-butyl)-3-[2-(S)-((thiazol-2-yl)aminocarbonyl)pyrrolidin-1-carbonyl]-2-(S)-fluoropropionamide

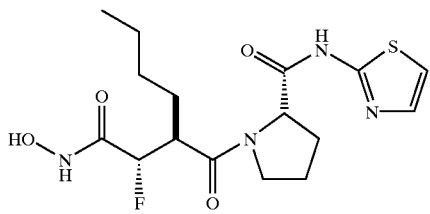

The title compound was prepared according to General Procedure H from 2-aminothiazole. $^1$H NMR (CDCl$_3$+DMSO-D6): δ 7.40 (d, J=3.6 Hz, 1H), 6.95 (d, J=3.6 Hz, 1H), 5.05–4.88 (dd, J=7.4 Hz, J$_{H,F}$=47 Hz, 1H), 4.86–4.84 (m, 1H), 3.84–3.71 (m, 2H), 3.33–3.23 (m, 1H), 2.16–1.99 (m, 4H), 1.72–1.30 (m, 6H), 0.84 9 (t, J=6.8 & 7.1 Hz, 3H). ES-MS: calcd. For C$_{16}$H$_{23}$FN$_4$O$_4$S (386.44); found: 387.4 [M+1].

Example 91

Synthesis of N-hydroxy-3-(S)-(n-butyl)-3-[2-(S)-((4-methylthiazol-2-yl)aminocarbonyl)pyrrolidin-1-carbonyl]-2-(S)-fluoropropionamide

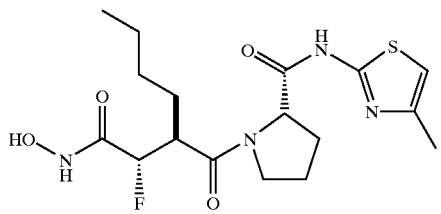

The title compound was prepared according to General Procedure H from 2-amino-4-methylthiazole. $^1$H NMR (CDCl$_3$+DMSO-D6): δ 6.49 (s, 1H), 5.10–4.92 (dd, J=6.6 Hz, J$_{H,F}$=47 Hz, 1H), 4.85–4.83 (m, 1H), 3.79–3.68 (m, 2H), 3.37–3.23 (m, 1H), 2.31 (s, 3H), 2.22–1.99 (m, 4H), 1.74–1.52 (m, 2H), 1.29–1.27 (m, 4H), 0.83 (t, J=6.6 & 7.1 Hz, 3H). ES-MS: calcd. For C$_{17}$H$_{25}$FN$_4$O$_4$S (400.47); found: 401.6 [M+1].

Example 92

Synthesis of N-hydroxy-3-(S)-(n-butyl)-3-[2-(S)-((4-phenylthiazol-2-yl)aminocarbonyl)pyrrolidin-1-carbonyl]-2-(S)-fluoropropionamide

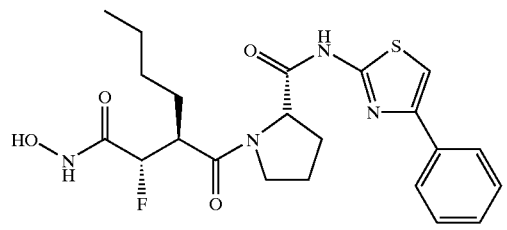

The title compound was prepared according to General Procedure H from 2-amino-4-phenylthiazole. $^1$H NMR (CDCl$_3$): δ 7.38–7.26 (m, 5H), 6.95 (s, 1H), 5.15–5.01 (dd, J=4.2 Hz, J$_{H,F}$=47 Hz, 1H), 4.99–4.83 (m, 1H), 3.76–3.70 (m, 2H), 3.31–3.27 (m, 1H), 2.15–1.99 (m, 4H), 1.72–1.50 (m, 2H), 1.44–1.25 (m, 4H), 0.81 (t, J=6.6 & 7.1 Hz, 3H). ES-MS: calcd. For C$_{22}$H$_{27}$FN$_4$O$_4$S (462.54); found: 463.5 [M+1].

Example 93

Synthesis of N-hydroxy-3-(S)-(n-butyl)-3-[2-(S)-((2,2-dimethylpropyl)aminocarbonyl)pyrrolidin-1-carbonyl]-2-(S)-fluoropropionamide

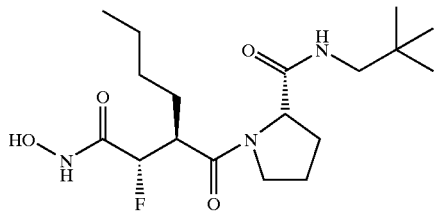

The title compound was prepared according to General Procedure H from 2,2-dimethylpropylamine. $^1$H NMR (CDCl$_3$): δ 7.16 (t, J=6 Hz, 1H), 5.14–4.96 (dd, J=6.1 Hz, $J_{H,F}$=47 Hz, 1H), 4.55–4.48 (m, 1H), 3.69–3.61 (m, 2H), 3.31–3.22 (m, 1H), 3.14–3.07 (m, 1H), 2.98–2.91 (m, 1H), 2.24–1.96 (m, 4H), 1.72–1.63 (m, 2H), 1.33–1.30 (m, 4H), 0.88 (m, 12H). ES-MS: calcd. For C$_{18}$H$_{32}$FN$_3$O$_4$ (373.46); found: 374.7 [M+1].

Example 94

Synthesis of N-hydroxy-3-(S)-(n-butyl)-3-[2-(S)-((3-methylbutyl)aminocarbonyl)pyrrolidin-1-carbonyl]-2-(S)-fluoropropionamide

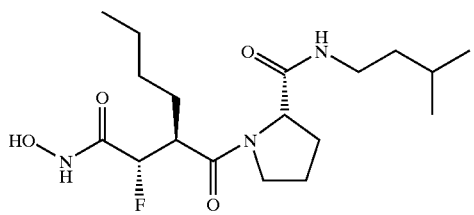

The title compound was prepared according to General Procedure H from 3-methylbutylamine. $^1$H NMR (CDCl$_3$): δ 7.17 (t, J=5.2 Hz, 1H), 5.13–4.95 (dd, J=6.1 Hz, $J_{H,F}$=47 Hz, 1H), 4.47–4.44 (m, 1H), 3.66–3.57 (m, 2H), 3.31–3.17 (m, 3H), 2.23–2.17 (m, 2H), 1.96–1.91 (m, 2H), 1.74–1.54 (m, 3H), 1.42–1.32 (m, 6H), 0.91–0.87 (m, 9H). ES-MS: calcd. For C$_{18}$H$_{32}$FN$_3$O$_4$ (373.46); found: 374.7 [M+1].

Example 95

Synthesis of N-hydroxy-3-(S)(n-butyl)-3-[2-(S)-((n-pentyl)aminocarbonyl)pyrrolidin-1-carbonyl]-2-(S)-fluoropropionamide

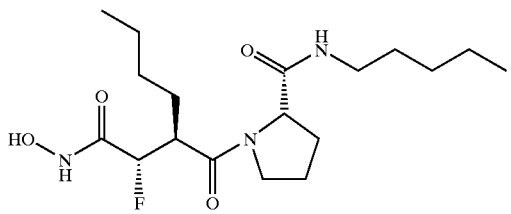

The title compound was prepared according to General Procedure H from amylamine. $^1$H NMR (CDCl$_3$): δ 7.18 (t, J=5.2 Hz, 1H), 5.13–4.95 (dd, J=6 Hz, $J_{H,F}$=47 Hz, 1H), 4.47–4.45 (m, 1H), 3.66–3.64 (m, 2H), 3.31–3.14 (m, 3H), 2.23–2.17 (m, 2H), 1.96–1.93 (m, 2H), 1.76–1.63 (m, 2H), 1.52–1.42 (m, 3H), 1.34–1.26 (m, 8H), 0.91–0.85 (m, 6H). ES-MS: calcd. For C$_{18}$H$_{32}$FN$_3$O$_4$ (373.46); found: 374.7 [M+1].

Example 96

Synthesis of N-hydroxy-3-(S)-(n-butyl)-3-[2-(S)-((cyclohexyl)aminocarbonyl)pyrrolidin-1-carbonyl]-2-(S)-fluoropropionamide

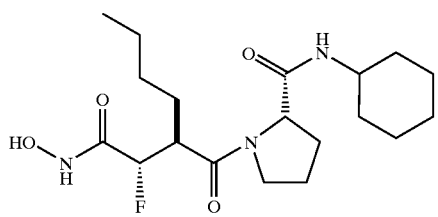

The title compound was prepared according to General Procedure H from cyclohexylamine. $^1$H NMR (CDCl$_3$): δ 7.00 (d, J=8.2 Hz, 1H), 5.14–4.96 (dd, J=6.2 Hz, $J_{H,F}$=47 Hz, 1H), 4.46–4.44 (m, 1H), 3.73–3.59 (m, 3H), 3.31–3.22 (m, 1H), 2.19–2.10 (m, 4H), 1.96–1.64 (m, 6H), 1.33–1.27 (m, 6H), 1.20 1.12 (m, 4H), 0.89 (t, J=6.6 Hz, 3H). ES-MS: calcd. For C$_{19}$H$_{32}$FN$_3$O$_4$ (385.47); found: 386.7 [M+1].

Example 97

Synthesis of N-hydroxy-3-(S)-(n-butyl)-3-[2-(S)-((n-propyl)aminocarbonyl)pyrrolidin-1-carbonyl]-2-(S)-fluoropropionamide

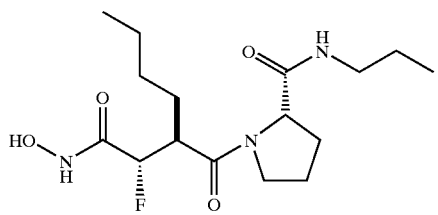

The title compound was prepared according to General Procedure H from propylamine. $^1$H NMR (CDCl$_3$+DMSO-D6): δ 7.24 (t, J=5.2 Hz, 1H), 4.99–4.80 (dd, J=8.8 Hz, $J_{H,F}$=47 Hz, 1H), 4.59–4.57 (m, 1H), 3.72–3.56 (m, 2H), 3.37–3.12 (m, 3H), 2.31–2.26 (m, 2H), 2.09–1.84 (m, 4H), 1.66–1.43 (m, 2H), 1.28–1.03 (m, 4H), 0.91–0.87 (m, 6H). ES-MS: calcd. For C$_{16}$H$_{28}$FN$_3$O$_4$ (345.41); found: 346.6 [M+1].

Example 98

Synthesis of N-hydroxy-3-(S)-(n-butyl)-3-[2-(S)-((5-methylthiazol-2-yl)aminocarbonyl)pyrrolidin-1-carbonyl]-2-(S)-fluoropropionamide

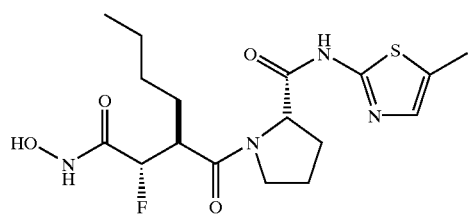

The title compound was prepared according to General Procedure H from 2-amino-5-methylthiazole. $^1$H NMR (CDCl$_3$): δ 7.31 (s, 1H), 5.32–5.14 (dd, J=6.1 Hz, J$_{H,F}$=47 Hz, 1H), 4.84.83 (m, 1H), 4.03–3.94 (m, 2H), 3.53–3.44 (m, 1H), 2.62 (s, 3H), 2.58–2.21 (m, 4H), 1.99–1.78 (m, 2H), 1.54–1.45 (m, 4H), 1.08 (t, J=6.6 & 7.4 Hz, 3H). ES-MS: calcd. For C$_{17}$H$_{25}$FN$_4$O$_4$S (400.47); found: 401.6 [M+1].

Example 99

Synthesis of N-hydroxy-3-(S)-(n-butyl)-3-[2-(S)-((3,4-dimethoxybenzyl)aminocarbonyl)pyrrolidin-1-carbonyl]-2-(S)-fluoropropionamide

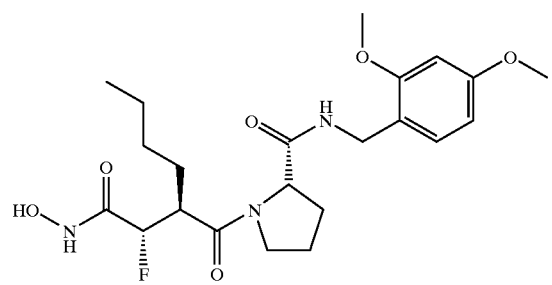

The title compound was prepared according to General Procedure H from 2,4-dimethoxybenzylamine. $^1$H NMR (CDCl$_3$): δ 7.31 (d, J=8 Hz, 1H), 6.67–6.58 (m, 2H), 5.30–5.14 (dd, J=2 Hz, J$_{H,F}$=47 Hz, 1H), 4.67–4.45 (m, 3H), 4.00 (s, 3H), 3.98 (s, 3H), 3.86–3.78 (m, 2H), 3.45–3.39 (m, 1H), 2.37–2.13 (m, 4H), 1.89–1.84 (m, 2H), 1.47–1.45 (m, 4H), 1.04 (t, J=6.3 & 7.1 Hz, 3H). ES-MS: calcd. For C$_{22}$H$_{32}$FN$_3$O$_6$ (453.51); found: 454.8 [M+1].

Example 100

Synthesis of N-hydroxy-3-(S)-(n-butyl)-3-[2-(S)-(piperidin-1-ylcarbonyl)pyrrolidin-1-carbonyl]-2-(S)-fluoropropionamide

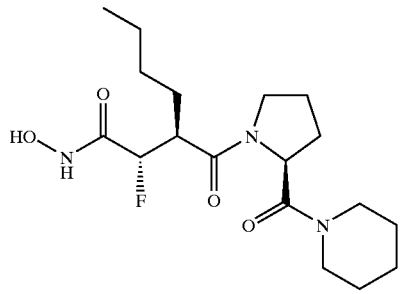

The title compound was prepared according to General Procedure H from piperidine. $^1$H NMR (CDCl3): δ 5.14–4.97 (dd, J=6.5 Hz, J$_{H,F}$=47 Hz, 1H), 4.91–4.87 (m, 1H), 3.80–3.47 (m, 6H), 3.39–3.21 (m, 1H), 2.22–1.83 (m, 3H), 1.65–1.27 (m, 13H), 0.90 (t, J=7 Hz, 3H). ES-MS: calcd. For C$_{18}$H$_{30}$FN$_3$O$_4$ (371.45); found: 372.4 [M+1].

Example 101

Synthesis of N-hydroxy-3-(S)-(n-butyl)-3-[2-(S)-(azetidin-1-ylcarbonyl)pyrrolidin-1-carbonyl]-2-(S)-fluoropropionamide

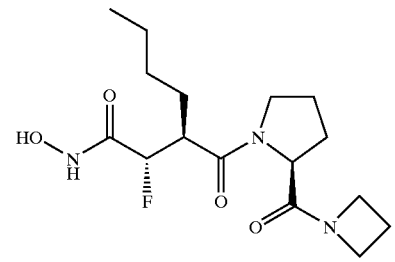

The title compound was prepared according to General Procedure H from azetidine. $^1$H NMR (CD$_3$OD): δ 5.10–4.92 (dd, J=8.7 Hz, J$_{H,F}$=47 Hz, 1H), 4.73–4.65 (m, 1H), 4.60–4.57 (m, 1H), 4.49–4.41 (m, 1H), 4.32–4.21 (m, 1H), 4.18–4.12 (m, 1H), 4.06–3.99 (m, 1H), 3.89–3.81 (m, 1H), 2.59–2.41 (m, 2H), 2.41–2.30 (m, 2H), 2.28–2.05 (m, 2H), 1.84–1.49 (m, 6H), 1.11 (t, J=7 Hz, 3H). ES-MS: calcd. For C$_{16}$H$_{26}$FN$_3$O$_4$ (343.39); found: 344.4 [M+1].

Example 102

Synthesis of N-hydroxy-3-(R)-(n-butyl)-3-[2-(S)-((N-pyridin-2-yl)methylaminocarbonyl)-pyrrolidin-1-carbonyl]-2-(S)-hydroxypropionamide

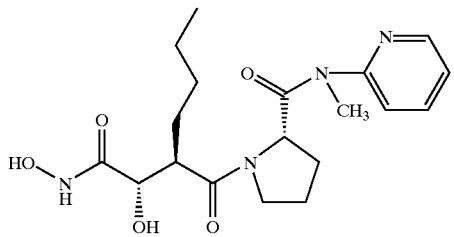

The title compound was prepared according to General Procedure F from N-methyl-2-amino pyridine. $^1$H NMR (CDCl$_3$): δ 8.75–8.04 (m, 2H), 7.71–7.46 (m, 2H), 4.76 bs, 1H), 4.46 (bs, 1H), 3.93–3.63 (m, 2H), 3.56 (s, 3H), 3.42–3.39 (m, 1H), 2.28–2.00 (m, 6H), 1.66–1.62 (m, 4H), 1.13 (t, J=7 Hz, 3H). ES-MS: calcd. For 9C$_{19}$H$_{28}$N$_4$O$_5$ (392.45); found: 393.6 [M+1].

Example 103

Synthesis of N-hydroxy-3-(S)-(n-butyl)-3-[2-(S)-((3,4-methylenedioxybenzyl)-aminocarbonyl)pyrrolidin-1-carbonyl]-2-(S)-fluoropropionamide

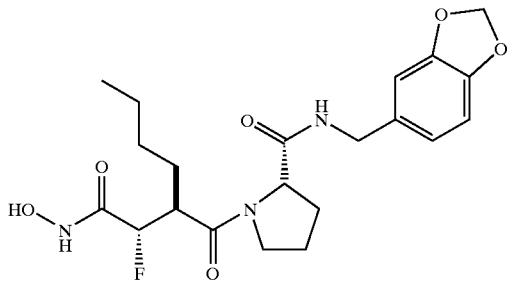

The title compound was prepared according to General Procedure H from piperonylamine. $^1$H NMR (CDCl$_3$): 7.63 (s, 1H), 6.93 (d, J=9.9 Hz, 2H), 6.11 (s, 2H), 5.30–5.13 (dd, J=5.5 Hz, J$_{H,F}$=47 Hz, 1H), 4.62–4.39 (m,3H), 3.97–3.71 (m, 2H), 3.48–3.39 (m, 1H), 2.38–2.13 (m, 4H), 1.87–1.85 (m, 2H), 1.49–1.48 (m, 4H), 1.05 (t, J=6.3 Hz, 3H). ES-MS: calcd. For C$_{21}$H$_{28}$FN$_3$O$_6$ (437.46); found: 438.7 [M+1]

Example 104

Synthesis of N-hydroxy-3-(S)-(n-butyl)-3-[2-(S)-((allyl)aminocarbonyl)pyrrolidin-1-carbonyl]-2-(S)-fluoropropionamide

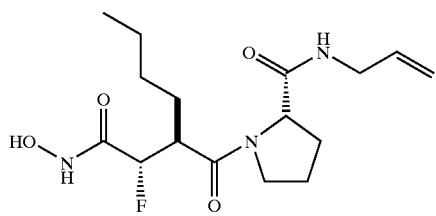

The title compound was prepared according to General Procedure H from allylamine. $^1$H NMR (CDCl$_3$): δ 6.06–5.95 (m, 1H), 5.39–5.17 (m, 3H), 4.69–4.67 (m, 1H), 4.05–3.85 (m, 4H), 3.51–3.44 (m, 1H), 2.40–2.17 (m, 4H), 1.91–1.89 (m, 2H), 1.62–1.53 (m, 4H), 1.09 (t, J=6.3 Hz, 3H). ES-MS: calcd. For C$_{16}$H$_{26}$FN$_3$O$_4$ (343.39); found: 344.7 [M+1].

Example 105

Synthesis of N-hydroxy-3-(S)-(n-butyl)-3-[2-(S)-((2-methylallyl)aminocarbonyl)-pyrrolidin-1-carbonyl]-2-(S)-fluoropropionamide

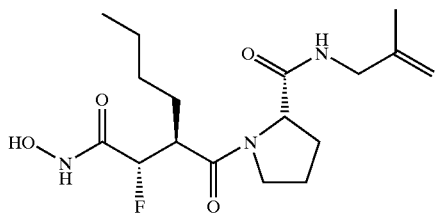

The title compound was prepared according to General Procedure H from 2-methylallylamine. $^1$H NMR (CDCl$_3$): δ 5.34–5.16 (dd, J=5.8 Hz, J$_{H,F}$=47 Hz, 1H), 5.00 (s, 2H) 4.73–4.66 (m, 1H), 4.05–3.87 (m, 4H), 3.51–3.43 (m, 1H), 2.43–2.17 (m, 4H), 1.90 (s, 3H), 1.86–1.84 (m, 2H), 1.66–1.53 (m, 4H), 1.08 (t, J=6.6 Hz, 3H). ES-MS: calcd. For C$_{17}$H$_{28}$FN$_3$O$_4$ (357.42); found: 358.6 [M+1].

Example 106

Synthesis of N-hydroxy-3-(S)-(n-butyl)-3-[2-(S)-(morpholin-4-ylcarbonyl)pyrrolidin-1-carbonyl]-2-(S)-fluoropropionamide

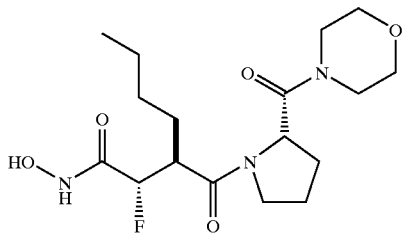

The title compound was prepared according to General Procedure H from morpholine. $^1$H NMR (CDCl$_3$): δ 5.34–5.16 (dd, J=6.2 Hz, J$_{H,F}$=47 Hz, 1H), 5.08–5.05 (m, 1H), 4.00–3.71 (m, 10H), 3.68–3.43 (m, 1H), 2.42–1.83 (m, 6H), 1.78–1.50 (m, 4H), 1.10 (t, J=6.6 & 7.1 Hz, 3H). ES-MS: calcd. For C$_{17}$H$_{28}$FN$_3$O$_5$ (373.42); found: 374.5 [M+1].

Example 107

Synthesis of N-hydroxy-3-(S)-(n-butyl)-3-[2-(S)-(pyrrolidin-1-carbonyl)pyrrolidin-1-carbonyl]-2-(S)-fluoropropionamide

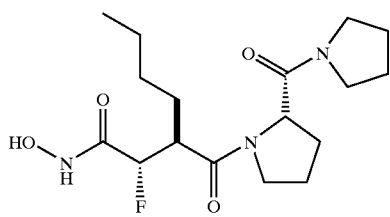

The title compound was prepared according to General Procedure H from pyrrolidine. $^1$H NMR (CDCl$_3$): δ 5.34–5.17 (dd, J=6.5 Hz, $J_{H,F}$=47 Hz, 1H), 4.86–4.82 (m, 1H), 3.94–3.89 (m, 4H), 3.77–3.71 (m, 1H), 3.64–3.42 (m, 2H), 2.38–2.20 (m, 2H), 2.18–1.74 (m, 8H), 1.65–1.48 (m, 4H), 1.10 (t, J=6.9 & 7.2 Hz, 3H). ES-MS: calcd. For C$_{17}$H$_{28}$FN$_3$O$_4$ (357.42); found: 358.5 [M+1].

Example 108

Synthesis of N-hydroxy-3-(S)-(n-butyl)-3-[2-(S)-((ethyl)aminocarbonyl)pyrrolidin-1-carbonyl]-2-(S)-fluoropropionamide

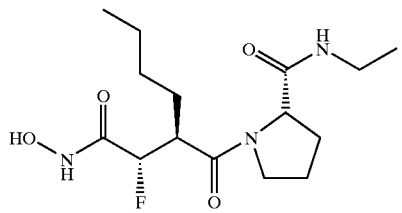

The title compound was prepared according to General Procedure H from ethylamine. $^1$H NMR (CDCl$_3$): δ 5.35–5.19 (d, $J_{H,F}$=47 Hz, 1H), 4.64–4.60 (m, 1H), 3.85–3.78 (m, 2H), 3.45–3.19 (m, 3H), 2.44–2.13 (m, 4H), 1.93–1.84 (m, 2H), 1.55–1.38 (m, 4H), 1.30 (t, J=7.2 Hz & 6.9 Hz, 3H), 1.10 (bs, 3H). ES-MS: calcd. For C$_{15}$H$_{26}$FN$_3$O$_4$ (331.38); found: 332.5 [M+1].

Example 109

Synthesis of N-hydroxy-3-(R)-(n-butyl)-3-[2-(S)-((4-phenoxyphenyl)aminocarbonyl)pyrrolidin-1-carbonyl]-2-(S)-hydroxypropionamide

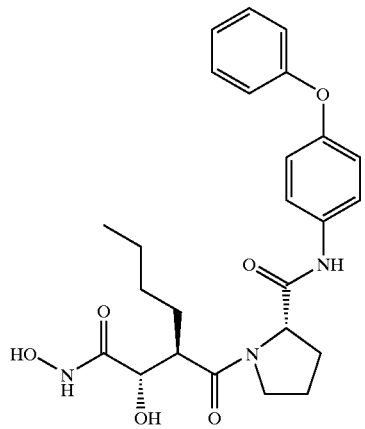

The title compound was prepared according to General Procedure F from 4-phenoxyaniline. $^1$H NMR (CDCl$_3$): δ 7.48–6.92 (m, 9H), 4.55–4.53 (d, J=6.0 Hz, 1H), 4.29–4.29 (d, J=2.2 Hz, 1H), 3.73 (bs, 2H), 3.27 (bs, 1H), 2.29–1.78 (m, 6H), 1.41–1.36 (m, 4H), 0.89 (t, J=6.6 & 7.14 Hz, 3H). ES-MS: calcd. For C$_{25}$H$_{31}$N$_3$O$_6$ (469.54); found: 470.4 [M+1].

Example 110

Synthesis of N-hydroxy-3-(R)-(n-butyl)-3-[2-(S)-((phenyl)aminocarbonyl)-pyrrolidin-1-carbonyl]-2-(S)-hydroxypropionamide

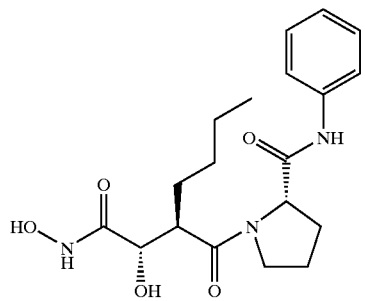

The title compound was prepared according to General Procedure F from aniline. $^1$H NMR (CDCl$_3$): δ 7.52–7.03 (m, 6H), 4.58–4.55 (d, J=8.0 Hz, 1H), 4.28–4.27 (d, J=2.4 Hz, 1H), 3.71 (bs, 2H), 3.262 (bs, 1H), 2.31–1.77 (m, 6H), 1.41–1.33 (m, 4H), 0.89 (t, J=6.6 & 7.4 Hz, 3H). ES-MS: calcd. For C$_{19}$H$_{27}$N$_3$O$_5$ (377.44); found: 378.3 [M+1].

Example 111

Synthesis of N-hydroxy-3-(R)-(n-butyl)-3-[2-(S)-((indan-1-yl)aminocarbonyl)pyrrolidin-1-carbonyl]-2-(S)-hydroxypropionamide

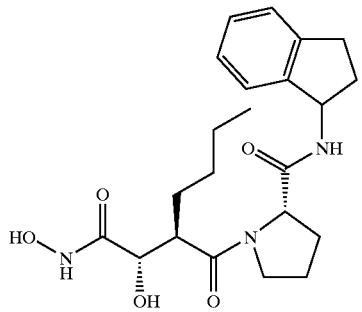

The title compound was prepared according to General Procedure F from 1-aminoindan. 1H NMR (CDCl$_3$): δ 7.27–7.15 (m, 4H), 5.38 (t, J=8.2 & 7.7 Hz, 1H), 4.45 (bs, 1H), 4.18 (bs, 1H), 3.64 (m, 2H), 3.20–3.18 (m, 1H), 2.98–2.49 (m, 4H), 2.24–1.73 (m, 6H), 1.95–1.326 (m, 4H), 0.88 (t, J=6.0 & 5.5 Hz, 3H). ES-MS: calcd. For C$_{22}$H$_{31}$N$_3$O$_5$ (417.51); found: 418.4 [M+1]

Example 112

Synthesis of N-hydroxy-3-(R)-(n-butyl)-3-[2-(S)-((2-methoxyethyl)aminocarbonyl)pyrrolidin-1-carbonyl]-2-(S)-hydroxypropionamide

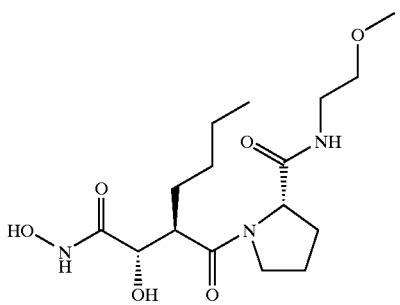

The title compound was prepared according to General Procedure F from 2-methoxyethylamine. $^1$H NMR (CDCl$_3$): δ 4.45–4.27 (d, J=6.87 Hz, 1H), 4.255 (bs, 1H), 3.69–3.29 (m, 9H), 2.15–1.77 (m, 6H), 1.43–1.3 (m, 4H), 0.92 (t, J=6.593 & 6.867 Hz, 3H). ES-MS: calcd. For C$_{16}$H$_{29}$N$_3$O$_6$ (359.42); found: 360.3 [M+1].

Example 113

Synthesis of N-hydroxy-3-(R)-(n-butyl)-3-[2-(S)-((indan-5-yl)aminocarbonyl)-pyrrolidin-1-carbonyl]-2-(S)-hydroxypropionamide

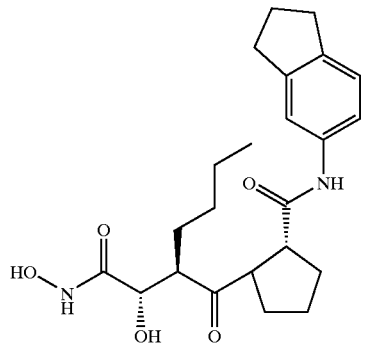

The title compound was prepared according to General Procedure F from 5-aminoindan. $^1$H NMR (CDCl$_3$): δ 7.46–7.08 (m, 3H), 4.57–4.55 (d, J=67.14 Hz, 1H), 4.28 (bs, 1H), 3.71 (bs, 2H), 3.26 (bs, 1H), 2.87–2.79 (dd, J=6.87 & 7.14 Hz, 4H), 2.3–1.77 (m, 8H), 1.35 (bs, 4H), 0.89 (t, J=6.32 & 6.87 Hz, 3H). ES-MS: calcd. For C$_{22}$H$_{31}$N$_3$O$_5$ (417.51); found: 418.4 [M+1].

Example 114

Synthesis of N-hydroxy-3-(R)-(n-butyl)-3-[2-(S)-((4,5-dimethylthiazol-2-yl)aminocarbonyl)-pyrrolidin-1-carbonyl]-2-(S)-hydroxypropionamide

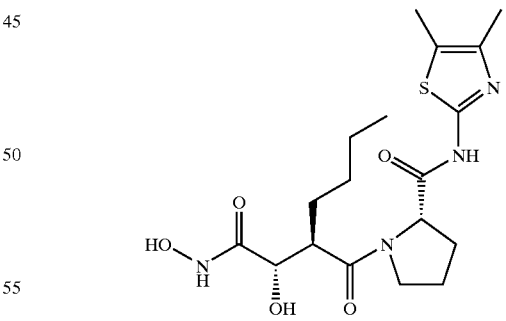

The title compound was prepared according to General Procedure F from 2-amino-4,5-dimethylthiazole. $^1$H NMR (CDCl$_3$): δ 4.60 (bs, 1H), 4.25 (bs, 1H), 3.79 (t, J=5.77 & 4.67 Hz, 2H), 3.26 (bs, 11H), 2.30–2.24 (m, 8H), 1.74–2.12 (m, 4H), 1.36 (m, 4H), 0.901 (t, J=6.77 & 6.87 Hz, 3H). ES-MS: calcd. For C$_{18}$H$_{28}$N$_4$O$_5$S (412.51); found: 413.3 [M+1].

Example 115

Synthesis of N-hydroxy-3-(R)-(n-butyl)-3-[2-(S)-((quinolin-3-yl)aminocarbonyl)-pyrrolidin-1-carbonyl]-2-(S)-hydroxypropionamide

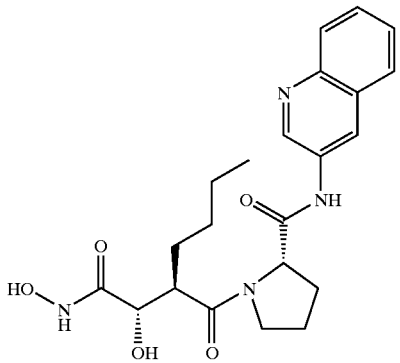

The title compound was prepared according to General Procedure F from 3-aminoquinoline. $^1$H NMR (CDCl$_3$): δ 8.17–7.26 (m, 6H), 4.68 (m, 1H), 4.32 (m, 1H), 3.77–3.67 (d, J=30.217 Hz, 2H), 3.22 (bs, 1H), 2.17–1.69 (m, 6H), 1.30 (bs, 4H), 0.89–0.82 (m, 3H). ES-MS: calcd. For C$_{22}$H$_{28}$N$_4$O$_5$ (428.49); found: 429.3 [M+1].

Example 116

Synthesis of N-hydroxy-3-(R)-(n-butyl)-3-[2-(S)-((benzthiazol-2-yl)amino-carbonyl)-pyrrolidin-1-carbonyl]-2-(S)-hydroxypropionamide

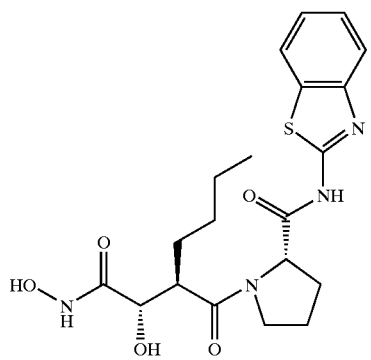

The title compound was prepared according to General Procedure F from 2-aminobenzothiazole. $^1$H NMR (DMSO-d6): δ 8.18–7.49 (m, 4H), 4.802 (bs, 1H), 3.98–3.94 (d, J=9.066 Hz, 1H), 3.59 (bs, 2H), 3.11 (bs, 1H), 2.11–1.38 (m, 10H), 1.06–1.04 (m, 3H). ES-MS: calcd. For C$_{20}$H$_{26}$N$_4$O$_5$S (434.52); found: 435.3 [M+1].

Example 117

Synthesis of N-hydroxy-3-(R)-(n-butyl)-3-[2-(S)-((3,4-difluorophenyl)aminocarbonyl)-pyrrolidin-1-carbonyl]-2-(S)-hydroxypropionamide

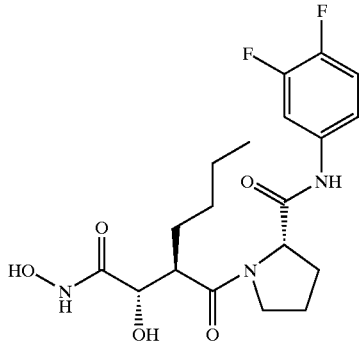

The title compound was prepared according to General Procedure F from 3,4-difluoroaniline. $^1$H NMR (CDCl$_3$): δ 7.60–6.97 (m, 3H), 4.49–4.61 (d, J=7.97 Hz, 1H), 4.29–4.28 (d, J=2.2 Hz, 1H), 3.79–3.69 (m, 2H), 3.26 (bs, 1H), 2.36–1.76 (m, 6H), 1.49–1.35 (m, 4H), 0.918 (t, J=6.867 & 7.143 Hz, 3H). ES-MS: calcd. For C$_{19}$H$_{25}$F$_2$N$_3$O$_5$ (413.42); found: 414.3 [M+1].

Example 118

Synthesis of N-hydroxy-3-(R)-(n-butyl)-3-[2-(S)-((3,4-dichlorophenyl)aminocarbonyl)-pyrrolidin-1-carbonyl]-2-(S)-hydroxypropionamide

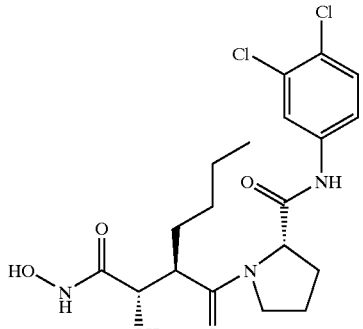

The title compound was prepared according to General Procedure F from 3,4-dichloroaniline. $^1$H NMR (CDCl$_3$): δ 7.94–7.44 (m, 3H), 4.73–4.71 (d, J=8.24 Hz, 1H), 4.52–4.51 (d, J=2.8 Hz, 1H), 3.95–3.94 (m, 2H), 3.49 (t, J=5.8 & 6.0 Hz, 1H), 2.52–1.99 (m, 6H), 1.70–1.57 (m, 4H), 1.122 (t, J=6.9 & 7.1 Hz, 3H). ES-MS: calcd. For C$_{19}$H$_{25}$Cl$_2$N$_3$O$_5$ (445.1); found: 446.3 [M+1].

Example 119

Synthesis of N-hydroxy-3-(R)-(n-butyl)-3-[2-(S)-((5-methylisoxazol-3-yl)aminocarbonyl)pyrrolidin-1-carbonyl]-2-(S)-hydroxypropionamide

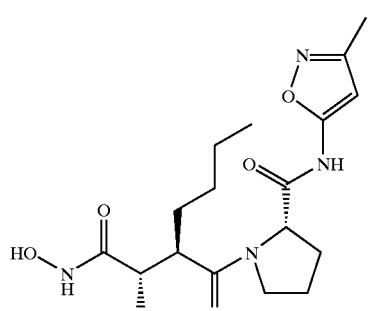

The title compound was prepared according to General Procedure F from 3-amino-5-methylisoxazole. $^1$H NMR (DMSO-d6): δ 6.64–5.95 (m, 1H), 4.66–4.62 (dd, J=4.9 & 4.7 Hz, 1H), 4.01–3.93 (m, 1H), 3.76–3.70 (m, 1H), 3.56 (bs, 31H), 3.11–3.05 (t, J=8.8, 1H), 2.70–2.00 (m, 6H), 1.59–1.37 (m, 4H), 1.02 (t, J=5.8 & 7.1 Hz, 3H). ES-MS: calcd. For $C_{17}H_{26}N_4O_6$ (382.42); found: 383.3 [M+1].

Example 120

Synthesis of N-hydroxy-3-(R)-(n-butyl)-3-[2-(S)-((3-phenoxyphenyl)aminocarbonyl)-pyrrolidin-1-carbonyl]-2-(S)-hydroxypropionamide

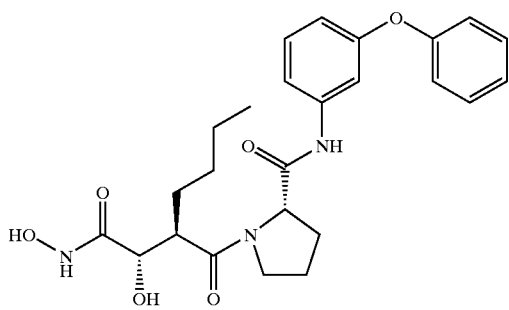

The title compound was prepared according to General Procedure F from 3-phenyoxyaniline. $^1$H NMR (CDCl$_3$): δ 7.55–6.88 (m, 9H), 4.75–4.72 (d, J=7.7 Hz, 1H), 4.47 (bs, 1H), 3.90–3.88 (m, 2H), 3.46–3.44 (m, 1H), 2.51–1.96 (m, 6H), 1.65–1.53 (m, 4H), 1.09 (t, J=6.7 & 7.1 Hz, 3H). ES-MS: calcd. For $C_{25}H_{31}N_3O_6$ (469.54); found: 470.4 [M+1].

Example 121

Synthesis of N-hydroxy-3-(R)-(n-butyl)-3-[2-(S)-((4-phenylthiazol-2-yl)aminocarbonyl)-pyrrolidin-1-carbonyl]-2-(S)-hydroxypropionamide

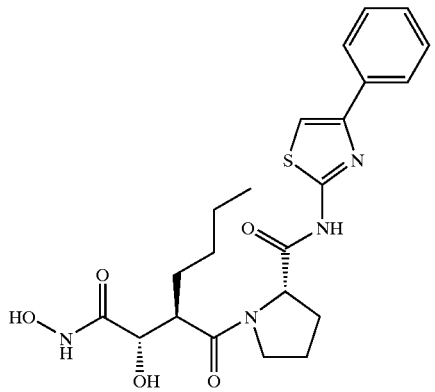

The title compound was prepared according to General Procedure F from 2-amino-5-phenylthiazole. $^1$H NMR (CDCl$_3$): δ 7.94–7.28 (m, 6H), 4.89–4.88 (d, J=4.4 Hz, 1H), 4.47–4.47 (d, J=2.5 Hz, 1H), 3.92–4.05 (m, 2H), 3.48–3.44 (m, 1H), 2.54–1.95 (m, 6H), 1.57–1.48 (m, 4H), 1.10 (t, J=6.6 & 7.7 Hz, 3H). ES-MS: calcd. For $C_{22}H_{28}N_4O_5S$ (460.55); found: 461.2 [M+1].

Example 122

Synthesis of N-hydroxy-3-(R)-(n-butyl)-3-[2-(S)-((2-fluorophenyl)aminocarbonyl)-pyrrolidin-1-carbonyl]-2-(S)-hydroxypropionamide

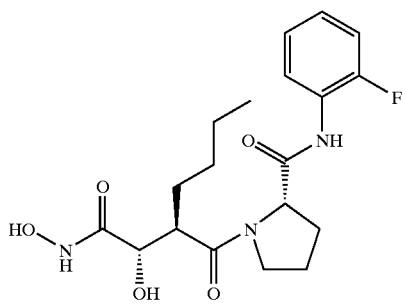

The title compound was prepared according to General Procedure F from 2-fluoroaniline. $^1$H NMR (CDCl$_3$): δ 8.42–7.23 (m, 4H), 4.97–4.95 (d, J=6.9 Hz, 1H), 4.49 (bs, 1H), 3.96–3.83 (m, 2H), 3.49 (t, J=5.5 & 7.4 Hz, 1H), 2.61–2.01 (m, 6H), 1.64–1.46 (m, 4H), 1.06 (t, J=6.6 & 7.1 Hz, 3H). ES-MS: calcd. For $C_{19}H_{26}FN_3O_5$ (395.43); found: 396.4 [M+1].

Example 123

Synthesis of N-hydroxy-3-(R)-(n-butyl)-3-[2-(S)-((3-fluorophenyl)aminocarbonyl)-pyrrolidin-1-carbonyl]-2-(S)-hydroxypropionamide

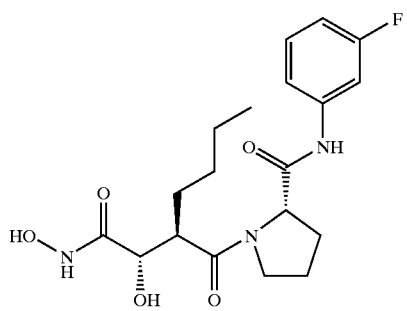

The title compound was prepared according to General Procedure F from 3-fluoroaniline. ¹H NMR (CDCl₃): δ 7.66–6.92 (m, 4H), 4.75–4.73 (d, J=8.0 Hz, 1H), 4.52 (bs, 1H), 3.94 (t, J=8.5 & 8.81 Hz, 2H), 3.49 (bs, 1H), 2.57–1.99 (m, 6H), 1.70–1.56 (m, 4H), 1.12 (t, J=6.6 & 6.9 Hz, 3H). ES-MS: calcd. For $C_{19}H_{26}FN_3O_5$ (395.43); found: 396.3 [M+1].

Example 124

Synthesis of N-hydroxy-3-(R)-(n-butyl)-3-[2-(S)-((4-fluorophenyl)aminocarbonyl)-pyrrolidin-1-carbonyl]-2-(S)-hydroxypropionamide

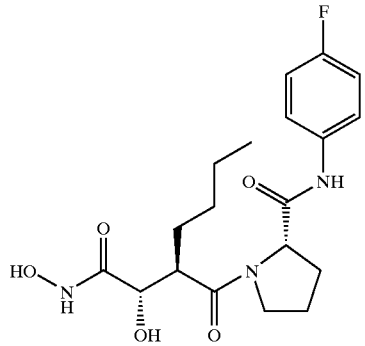

The title compound was prepared according to General Procedure F from 4-fluoroaniline. ¹H NMR (CDCl₃): δ 7.71–7.13 (m, 4H), 4.74–4.71 (d, J=8.2 Hz, 1H), 4.51–4.49 (d, J=2.8 Hz, 1H), 3.96–3.90 (m, 2H), 3.52–3.46 (m, 1H), 2.58–1.96 (m, 6H), 1.69–1.54 (m, 4H), 1.11 (t, J=6.9 Hz, 3H). ES-MS: calcd. For $C_{19}H_{26}FN_3O_5$ (395.43); found: 396.3 [M+1].

Example 125

Synthesis of N-hydroxy-3-(R)-(n-butyl)-3-[2-(S)-((N-phenyl-N-methylamino)-carbonyl)pyrrolidin-1-carbonyl]-2-(S)-hydroxypropionamide

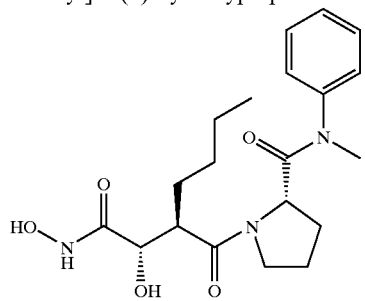

The title compound was prepared according to General Procedure F from N-methylaniline. ¹H NMR (CDCl₃): δ 7.26–7.5 (m, 5H), 4.38 (d, J=7.1 Hz, 1H), 4.24 (bs, 1H), 3.69–3.65 (m, 5H), 3.33–3.20 (m, 1H), 2.08–1.82 (m, 6H), 1.49–1.36 (m, 4H), 0.94 (t, J=7.1 Hz, 3H). ES-MS: calcd. For $C_{20}H_{29}N_3O_5$ (391.47); found: 392.4 [M+1].

Example 126

Synthesis of N-hydroxy-3-(R)-(n-butyl)-3-[2-(S)-((ethyl)aminocarbonyl)-pyrrolidin-1-carbonyl]-2-(S)-hydroxypropionamide

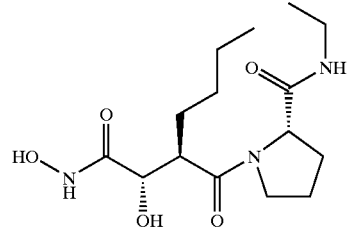

The title compound was prepared according to General Procedure F from ethylamine. ¹H NMR (CDCl₃): δ 4.39–4.37 (d, J=6.0 Hz, 1H), 4.25–4.24 (d, J=2.5 Hz, 1H), 3.69–3.52 (m, 4H), 3.20–3.32 (m, 1H), 2.25–1.76 (m, 6H), 1.44–1.25 (m, 4H), 1.183–1.11 (m, 3H), 0.94–0.85 (m, 3H). ES-MS: calcd. For $C_{15}H_{27}N_3O_5$ (329.4); found: 330.4 [M+1].

Example 127

Synthesis of N-hydroxy-3-(R)-(n-butyl)-3-[2-(S)-((2-propyl)aminocarbonyl)-pyrrolidin-1-carbonyl]-2-(S)-hydroxypropionamide

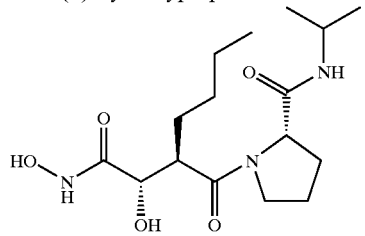

The title compound was prepared according to General Procedure F from 2-aminopropane. ¹H NMR (CDCl₃): δ 4.41–4.38 (d, J=8.0 Hz, 1H), 4.26–4.25 (d, J=2.2 Hz, 1H), 4.01–3.94 (dd, J=6.6 Hz, 1H), 3.66 (t, J=7.4 Hz, 2H), 3.25–3.22 (m, 1H), 2.21–1.77 (m, 6H), 1.44–1.22 (m, 4H), 1.19–1.11 (m, 6H). 0.893 (t, J=6.6 Hz, 3H). ES-MS: calcd. For $C_{16}H_{29}N_3O_5$ (343.42); found: 344.4 [M+1].

Example 128

Synthesis of N-hydroxy-3-(R)-(n-butyl)-3-[2-(S)-((2,2-dimethylpropyl)-aminocarbonyl)pyrrolidin-1-carbonyl]-2-(S)-hydroxypropionamide

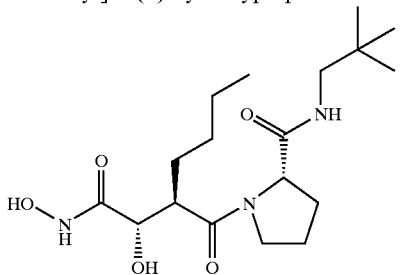

The title compound was prepared according to General Procedure F from 2,2-dimethylpropylamine. $^1$H NMR (CDCl$_3$): δ 4.52–4.5 (d, J=6.0 Hz, 1H), 4.26–4.25 (d, J=2.5 Hz, 1H), 3.7–3.59 (m, 2H), 3.28–3.22 (m, 1H), 3.12–2.94 (m. 2H), 2.29–1.73 (m, 6H), 1.44–1.33 (m, 4H), 0.93–0.88 (m, 12H). ES-MS: calcd. For $C_{18}H_{33}N_3O_5$ (371.48); found: 372.4 [M+1].

Example 129

Synthesis of N-hydroxy-3-(R)-(n-butyl)-3-[2-(S)-((1,1-dimethylpropyl)-aminocarbonyl)-pyrrolidin-1-carbonyl]-2-(S)-hydroxypropionamide

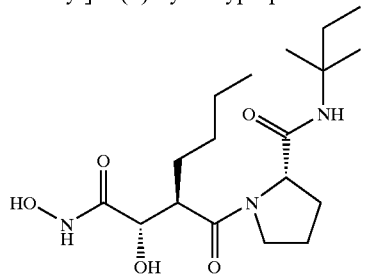

The title compound was prepared according to General Procedure F from 1,1-dimethyipropylamine. $^1$H NMR (CDCl$_3$): δ 4.42–4.40 (d, J=7.7 Hz, 1H), 4.26 (bs, 1H), 3.67–3.61 (m, 2H), 3.26–3.22 (t, J=5.0 & 7.1 Hz, 1H), 2.22–1.65 (m,6H), 1.44–1.24 (m, 6H), 0.94–0.79 (m, 6H). ES-MS: calcd. For $C_{18}H_{33}N_3O_5$ (371.48); found: 372.4 [M+1].

Example 130

Synthesis of N-hydroxy-3-(R)-(n-butyl)-3-[2-(S)-((cyclohexyl)aminocarbonyl)-pyrrolidin-1-carbonyl]-2-(S)-hydroxypropionamide

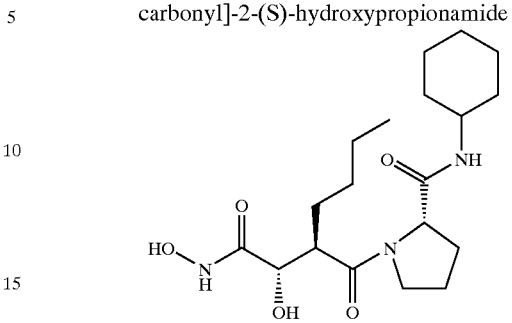

The title compound was prepared according to General Procedure F from cyclohexylamine. $^1$H NMR (CDCl$_3$): δ 4.43–4.40 (d, J=8.0 Hz, 1H), 4.26–4.25 (d, J=2.5 Hz, 1H), 3.66–3.63 (d, J=7.4 Hz, 3H), 3.27–3.21 (m, 1H), 2.21–1.10 (m, 20H), 0.94–0.89 (m, 3H). ES-MS: calcd. For $C_{19}H_{33}N_3O_5$ (383.49); found: 384.3 [M+1].

Example 131

Synthesis of N-hydroxy-3-(R)-(n-butyl)-3-[2-(S)-((thiazol-2-yl)aminocarbonyl)-pyrrolidin-1-carbonyl]-2-(S)-hydroxypropionamide

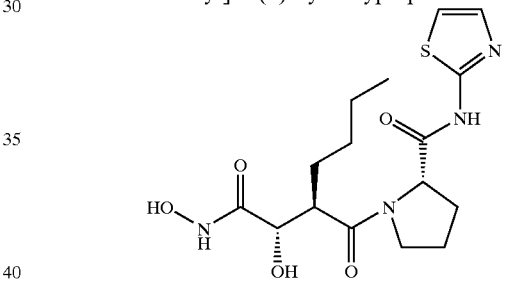

The title compound was prepared according to General Procedure F from 2-aminothiazole. $^1$H NMR (CDCl$_3$): δ 7.5–7.04 (m, 2H), 4.66 (t, J=5.0 Hz, 1H), 4.27–4.26 (d, J=2.5 Hz, 1H), 3.86–3.76 (m, 2H), 3.3–3.25 (m, 1H), 2.34–1.74 (m, 6H), 1.36–1.28 (m, 4H), 0.93–0.86 (m, 3H). ES-MS: calcd. For $C_{16}H_{24}N_4O_5S$ (384.46); found: 385.2 [M+1].

Example 132

Synthesis of N-hydroxy-3-(R)-(n-butyl)-3-[2-(S)-((4-methylthiazol-2-yl)aminocarbonyl)pyrrolidin-1-carbonyl]-2-(S)-hydroxypropionamide

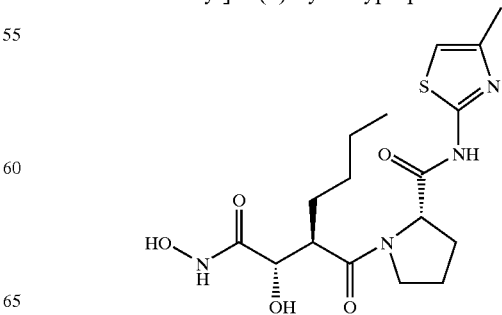

The title compound was prepared according to General Procedure F from 2-amino-4-methylthiazole. $^1$H NMR (CDCl$_3$): δ 6.62–6.61(d, J=1.1 Hz, 1H), 4.65–4.63 (dd, J=4.7 & 5.2 Hz, 1H), 4.26–4.25 (d, J=2.5 Hz, 1H), 3.85–3.78 (dd, J=6.0 & 7.4 Hz, 2H), 3.29–3.25 (dd, J=5.2 & 5.0 Hz, 1H), 2.46–1.69 (m, 9H), 1.38–1.27 (m, 4H), 0.893–0.85 (m, 3H). ES-MS: calcd. For C$_{17}$H$_{26}$N$_4$O$_5$S (398.48); found: 399.3 [M+1].

Example 133

Synthesis of N-hydroxy-3-(R)-(n-butyl)-3-[2-(S)-((2-phenylpropyl)aminocarbonyl)-pyrrolidin-1-carbonyl]-2-(S)-hydroxypropionamide

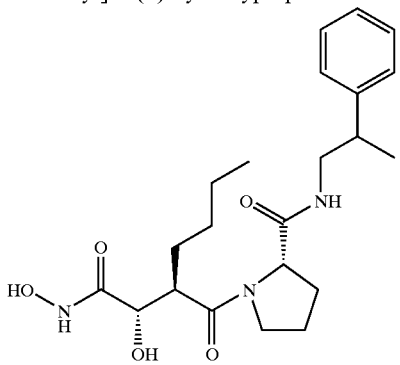

The title compound was prepared according to General Procedure F from 1-amino-2-phenylpropane. $^1$H NMR (CDCl$_3$): δ 7.3–6.78 (m, 5H), 5.17 (bs, 1H), 4.34 (bs, 1H), 4.21 (bs, 1H), 3.61–3.16 (m, 4H), 3.25–3.22 (m, 1H), 2.92 (bs, 1H), 2.09–1.09 (m, 13H), 0.94–0.83 (m, 3H). ES-MS: calcd. For C$_{22}$H$_{33}$N$_3$O$_5$ (419.52); found: 420.3 [M+1].

Example 134

Synthesis of N-hydroxy-3-(R)-(n-butyl)-3-[2-(S)-((n-propyl)aminocarbonyl)-pyrrolidin-1-carbonyl]-2-(S)-hydroxypropionamide

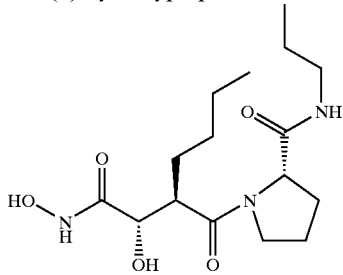

The title compound was prepared according to General Procedure F from propylamine. $^1$H NMR (CDCl$_3$): δ 4.44–4.41 (d, J=7.4 Hz, 1H), 4.25 (bs, 1H), 3.67–3.65 (d, J=5.5 Hz, 2H), 3.24–3.14 (m, 3H), 2.23–1.79 (m, 6H), 1.54–1.35 (m, 6H), 0.94–0.85 (m, 6H). ES-MS: calcd. For C$_{16}$H$_{29}$N$_3$O$_5$ (343.42); found: 344.4 [M+1].

Example 135

Synthesis of N-hydroxy-3-(R)-(n-butyl)-3-[2-(S)-((N-butyl-N-methylamino)carbonyl)-pyrrolidin-1-carbonyl]-2-(S)-hydroxypropionamide

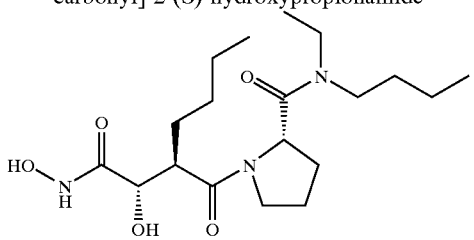

The title compound was prepared according to General Procedure F from N-ethyl-n-butylamine. $^1$H NMR (CDCl$_3$): δ 4.74 (t, J=3.9 Hz, 1H), 4.25 (bs, 1H), 3.73–3.02 (m, 7H), 2.16–1.74 (m, 6H), 1.53–1.23 (m, 8H), 1.08 (t, J=6.9 & 7.1 Hz, 2H), 0.98–0.88 (m, 9H). ES-MS: calcd. For C$_{19}$H$_{35}$N$_3$O$_5$ (358.50); found: 386.4 [M+1].

Example 136

Synthesis of N-hydroxy-3-(R)-(n-butyl)-3-[2-(S)-((tert-butyl)aminocarbonyl)-pyrrolidin-1-carbonyl]-2-(S)-hydroxypropionamide

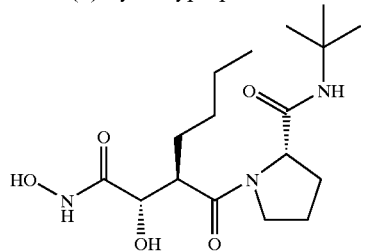

The title compound was prepared according to General Procedure F from t-butylamine. $^1$H NMR (CDCl$_3$): δ 4.36–4.34 (d, J=6.7 Hz, 1H), 4.31–4.25 (d, J=6.5 Hz, 1H), 3.65–3.55 (m, 2H), 3.26–3.22 (m, 1H), 2.2–1.8 (m, 6H), 1.5–1.3 (m, 13H), 0.94–0.85 (m, 3H). ES-MS: calcd. For C$_{17}$H$_{31}$N$_3$O$_5$ (357.45); found: 358.4 [M+1].

Example 137

Synthesis of N-hydroxy-3-(R)-(n-butyl)-3-[2-(S)-((n-pentyl)aminocarbonyl)-pyrrolidin-1-carbonyl]-2-(S)-hydroxypropionamide

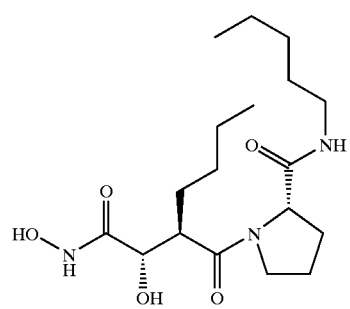

The title compound was prepared according to General Procedure F from n-pentylamine. $^1$H NMR (CDCl$_3$): δ 4.44–4.41 (d, J=7.4 Hz, 1H), 4.24 (d, J=2.2 Hz, 1H), 3.71–3.62 (m, 2H), 3.27–3.15 (m, 3H), 2.26–1.74 (m, 6H), 1.52–1.24 (m, 10H), 0.94–0.86 (m, 6H). ES-MS: calcd. For C$_{18}$H$_{33}$N$_3$O$_5$ (371.48); found: 372.4 [M+1].

Example 138

Synthesis of N-hydroxy-3-(R)-(n-butyl)-3-[2-(S)-((3-methylbutyl)aminocarbonyl)-pyrrolidin-1-carbonyl]-2-(S)-hydroxypropionamide

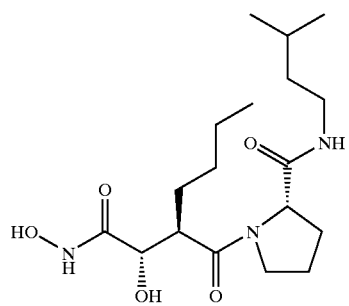

The title compound was prepared according to General Procedure F from 3-methyl-1-butylamine. $^1$H NMR (CDCl$_3$): δ 4.44–4.41 (d, J=7.4 Hz, 1H), 4.25–4.24 (d, J=2.5 Hz, 1H), 3.71–3.61 (m, 2H), 3.27–3.17 (m, 3H), 2.64–1.77 (m, 6H), 1.63–1.33 (m, 7H), 0.94–0.88 (m, 9H). ES-MS: calcd. For C$_{18}$H$_3$N$_3$O$_5$ (271.48); found: 372.5 [M+1].

Example 139

Synthesis of N-hydroxy-3-(R)-(n-butyl)-3-[2-(S)-((benzyl)aminocarbonyl)pyrrolidin-1-carbonyl]-2-(S)-hydroxypropionamide

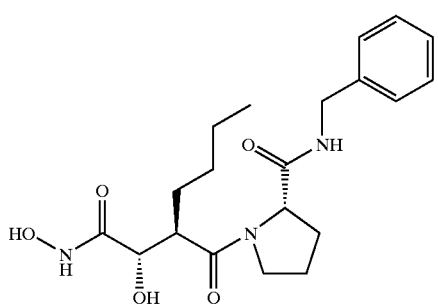

The title compound was prepared according to General Procedure F from benzylamine. $^1$H NMR (CDCl$_3$): δ 7.37–7.21 (m, 5H), 4.49–4.29 (m, 3H), 4.20–4.19 (d, J=2.5 Hz 1H), 3.71–3.62 (m, 2H), 3.19 (t, J=7.4 & 5.5 Hz, 1H), 2.22–1.73 (m, 6H), 1.32–1.29 (m, 4H), 0.88 (t, J=6.6 & 6.9 Hz, 3H). ES-MS: calcd. For C$_{20}$H$_{29}$N$_3$O$_5$ (391.47); found: 392.4 [M+1].

Example 140

Synthesis of N-hydroxy-3-(R)-(n-butyl)-3-[2-(S)-((pyridin-2-yl)aminocarbonyl)-pyrrolidin-1-carbonyl]-2-(S)-hydroxypropionamide

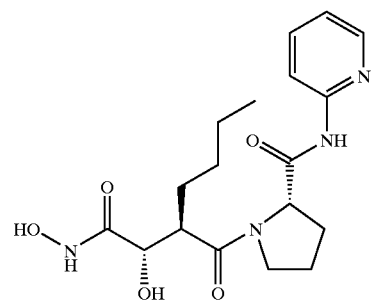

The title compound was prepared according to General Procedure F from 2-aminopyridine. $^1$H NMR (CDCl$_3$): δ 8.4–7.47 (m, 4H), 4.87–4.83 (m, 1H), 4.47–4.46 (d, J=2.8 Hz, 1H), 4.04–3.87 (in, 2H), 3.5–3.48 (t, J=2.8 & 4.9 Hz, 1H), 2.52–1.95 (m, 6H), 1.63–1.56 (m, 4H), 1.11 (t, J=7.1 Hz, 3H). ES-MS: calcd. For C$_{18}$H$_{26}$N$_4$O$_5$ (378.43); found: 377.2 [M-1].

Example 141

Synthesis of N-hydroxy-3-(R)-(n-butyl)-3-[2-(S)-((thiazolidin-1-yl)aminocarbonyl)-pyrrolidin-1-carbonyl]-2-(S)-hydroxypropionamide

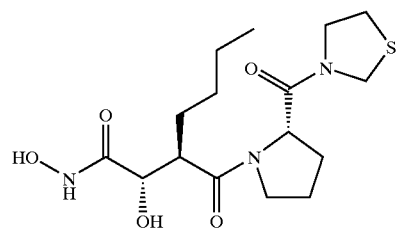

The title compound was prepared according to General Procedure F from thiazolidine. $^1$H NMR (CDCl$_3$): δ 4.94–4.66 (m, 3H), 4.46–4.45 (d, J=2.2 Hz, 1H), 4.24–3.84 (m, 4H), 3.46–3.18 (m, 3H), 2.37–2.01 (m, 6H), 1.68–1.53 (m, 4H), 1.12 (t, J=7.417 & 6.767 Hz, 3H). ES-MS: calcd. For C$_{16}$H$_{27}$N$_3$O$_5$S (373.47); found: 374.6 [M+1].

Example 142

Synthesis of N-hydroxy-3-(R)-(n-butyl)-3-[2-(S)-((thiadiazolidin-5-yl)aminocarbonyl)pyrrolidin-1-carbonyl]-2-(S)-hydroxypropionamide

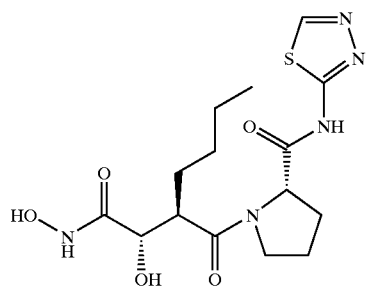

The title compound was prepared according to General Procedure F from 2-aminothiadiazole. $^1$H NMR (CDCl$_3$): δ 7.47–7.46 (d, J=5.5 Hz, 1H), 5.03–5.02 (d, J=5.5 Hz, 1H), 4.49–4.47 (d, J=3.4 Hz, 1H), 4–3.89 (m, 2H), 3.45–3.44 (d, J=3.6 Hz, 1H), 2.4–1.9 (m, 6H), 1.53 (bs, 4H), 1.08 (t, J=6.6 & 6.9 Hz, 3H). ES-MS: calcd. For C$_{15}$H$_{23}$N$_5$O$_5$S (385.44); found: 386.5 [M+1].

Example 143

Synthesis of N-hydroxy-3-(R)-(n-butyl)-3-[2-(S)-((5-phenylthiadiazolidin-2-yl)-aminocarbonyl)-pyrrolidin-1-carbonyl]-2-(S)-hydroxypropionamide

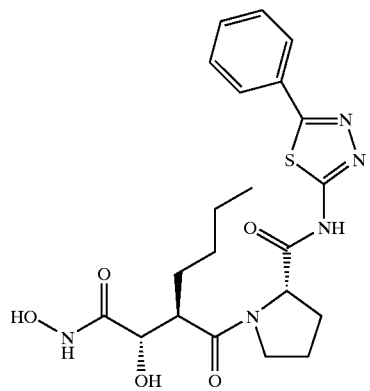

The title compound was prepared according to General Procedure F from 2-amino-5-phenylthiadiazole. $^1$H NMR (CDCl$_3$): δ 7.82–7.21 (m, 5H), 4.82–4.79 (d, J=7.4 Hz, 1H), 4.24–4.23 (d, J=3.6 Hz, 1H), 3.76–3.62 (m, 2H), 3.20–3.19 (d, J=3.6 Hz, 1H), 2.18–1.95 (m, 6H), 1.68–1.66 (m, 4H), 0.807 (t, J=6.6 & 7.2 Hz, 3H). ES-MS: calcd. For C$_{21}$H$_{27}$N$_5$O$_5$S (461.54); found: 462.7 [M+1].

Example 144

Synthesis of N-hydroxy-3-(R)-(n-3-methylbutyl)-3-[2-(S)-(tert-butoxycarbonyl)-pyrrolidin-1-carbonyl]-2-(S)-hydroxypropionamide

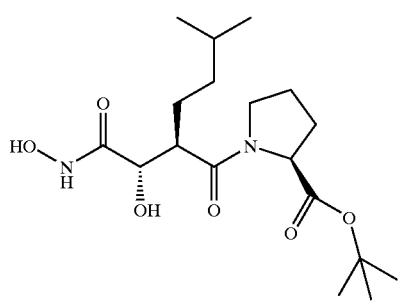

The title compound was prepared according to General Procedure F from 3-methyl-1-bromo-2-butene and proline -O-t-butyl ester. $^1$H NMR (CDCl$_3$): δ 4.52 (t, J=4.4 Hz, 1H), 4.46 (t, J=1.3 & 2.2 Hz, 1H), 3.93–3.76 (m, 1H), 3.4–3.34 (m, 2H), 2.41–1.95 (m, 6H), 1.81–1.49 (m, 12H), 1.10 (t, J=6.6 & 6.9 Hz, 6H). ES-MS: calcd. For C$_{18}$H$_{32}$N$_2$O$_6$ (372.46); found: 373.5 [M+1].

Example 145

Synthesis of N-hydroxy-3-(R)-(n-butyl)-3-[2-(S)-((4-methylthiazol-2-yl)aminocarbonyl)pyrrolidin-1-carbonyl]propionamide

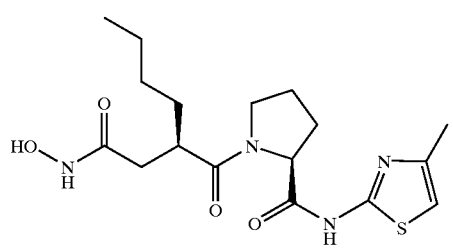

The title compound was prepared according to General Procedure E from 2-amino-4-methylthiazole. $^1$H NMR (DMSO-d6): δ 6.74 (s, 1H), 4.48 (dd, 8.5 & 4.7 Hz, 1H), 3.75–3.63 (m, 1H), 3.61–3.55 (m, 1H), 2.95 (bs, 1H), 2.25 (s, 3H), 2.23–1.80 (m, 6H), 1.45–1.25 (m, 6H), 0.85 (t, 6.6 Hz, 3H). ES-MS: cald. For C$_{17}$H$_{26}$N$_4$O$_4$S (382.17); found 383.6 [M+1].

Example 146

Synthesis of N-hydroxy-3-(R)-(n-butyl)-3-[2-(S)-((5-phenylthiadiazol-2-yl)aminocarbonyl)pyrrolidin-1-carbonyl]propionamide

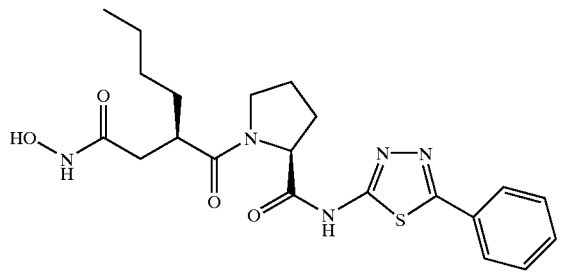

The title compound was prepared according to General Procedure E from 2-amino-5-phenylthiadiazole. $^1$H NMR (DMSO-d6): δ 10.3 (s, 1H), 7.94 (m, 2H), 7.53 (m, 3H), 4.56 (dd, 8.5 & 4.8 Hz, 1H), 3.8–3.59 (m, 2H), 2.96 (bs, 1H), 2.29–1.86 (m, 6H), 1.45–1.27 (m, 6H), 0.87 (t, 6.6 Hz, 3H). ES-MS: cald. For $C_{21}H_{27}N_5O_4S$ (445.18); found 446.5 [M+1].

Example 147

Synthesis of N-hydroxy-3-(R)-(n-butyl)-3-[2-(S)-((4,5-dimethylthiazol-2-yl)aminocarbonyl)pyrrolidin-1-carbonyl]propionamide

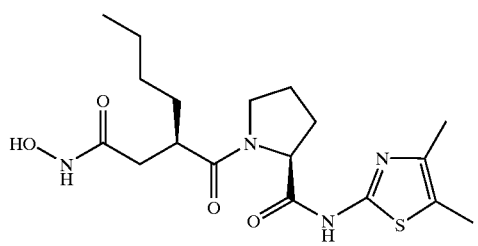

The title compound was prepared according to General Procedure E from 2-amino-4,5-dimethylthiazole. $^1$H NMR (DMSO-d6): δ 4.45 (dd, 8.2 & 4.8 Hz, 1H), 3.74–3.62 (m, 1H), 3.60–3.55 (m, 1H), 2.93 (bs, 1H), 2.22 (s, 3H), 2.15 (s, 3H), 2.11–1.78 (m, 6H), 1.46–1.25 (m, 6H), 0.85 (t, 6.3 Hz, 3H). ES-MS: cald. For $C_{18}H_{28}N_4O_4S$ (396.18); found 397.5 [M+1].

Example 148

Synthesis of N-hydroxy-3-(R)-(n-butyl)-3-[2-(S)-((3-phenoxyphenyl)aminocarbonyl)pyrrolidin-1-carbonyl]propionamide

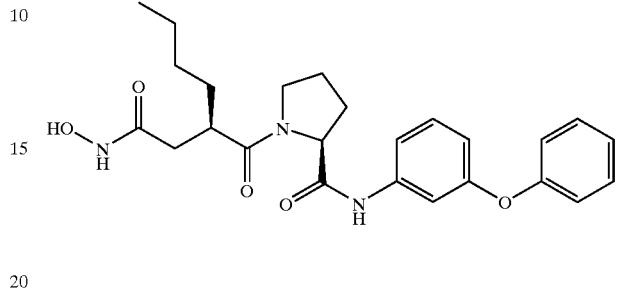

The title compound was prepared according to General Procedure E from 3-phenoxyaniline. $^1$H NMR (DMSO-d6): δ 7.42 (m, 2H), 7.37 (m, 3H), 7.15 (m, 1H), 7.02 (m, 2H), 6.69 (m, 1H), 4.35 (dd, 8.0 & 4.5 Hz, 1H), 3.71–3.45 (m, 2H), 2.93 (bs, 1H), 2.28–1.82 (m, 6H), 1.42–1.22 (m, 6H), 0.82 (t, 6.3 Hz, 3H). ES-MS: cald. For $C_{25}H_{31}N_3O_5$ (453.23); found 454.5 [M+1].

Example 149

Synthesis of N-hydroxy-3-(R)-(n-butyl)-3-[2-(S)-((3,4-methylenedioxybenzyl)aminocarbonyl)pyrrolidin-1-carbonyl]propionamide

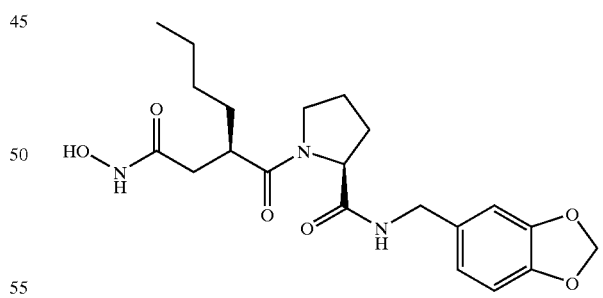

The title compound was prepared according to General Procedure E from piperonylamine. $^1$H NMR (DMSO-d6): δ 10.4 (bs, 1H), 8.18 (m, 1H), 6.87–6.69 (m, 3H), 6.00–5.96 (m, 2H), 4.29–4.11 (m, 2H), 3.71–3.53 (m, 2H), 2.92 (bs, 1H), 2.29–1.76 (m, 6H), 1.49–1.21 (m, 6H), 0.84 (m, 3H). ES-MS: cald. For $C_{21}H_{29}N_3O_6$ (419.21); found 420.5 [M+1].

Example 150

Synthesis of N-hydroxy-3-(S)-(n-butyl)-3-[2-(S)-((benzthiazol-2-yl)aminocarbonyl)pyrrolidin-1-carbonyl]propionamide

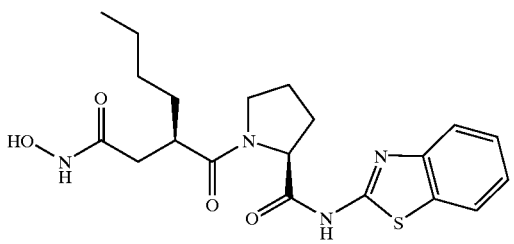

The title compound was prepared according to General Procedure E from 2-aminobenzothiazole. ES-MS: cald. For $C_{20}H_{26}N_4O_4S$ (418.17); found 419.4 [M+1].

Example 151

Synthesis of N-hydroxy-3-(R)-(n-butyl)-3-[2-(S)-((4-phenylthiazol-2-yl)aminocarbonyl)pyrrolidin-1-carbonyl]propionamide

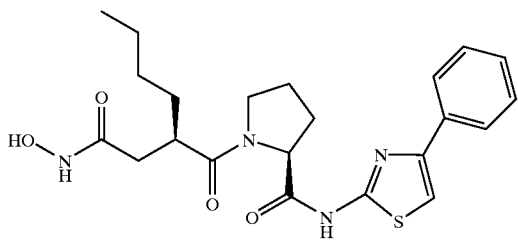

The title compound was prepared according to General Procedure E from 2-amino-4-phenylthiazole. ES-MS: cald. For $C_{22}H_{28}N_4O_4S$ (444.18); found 445.5 [M+1].

Example 152

Synthesis of N-hydroxy-3-(R)-(n-butyl)-3-[2-(S)-(piperazin-1-ylcarbonyl)pyrrolidin-1-carbonyl]-2-(S)-hydroxypropionamide

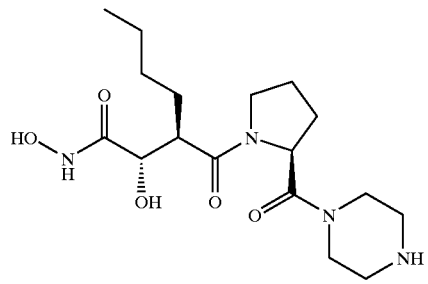

The title compound was prepared according to General Procedure F from piperazine. $^1$H NMR (CD$_3$OD): δ 4.25–4.15 (m, 2H), 4.14–3.82 (m, 4H), 3.72–3.45 (m, 6H), 3.36–3.29 (m, 1H), 2.46–2.04 (m, 4H), 1.83–1.49 (m, 6H), 1.12 (t, J=7 Hz). ES-MS: calcd. For $C_{17}H_{30}N_4O_5$ (370.44); found: 371.4 [M+1].

Example 153

Synthesis of N-hydroxy-3-(R)-(n-butyl)-3-[2-(S)-(piperidin-1-ylcarbonyl)pyrrolidin-1-carbonyl]-2-(S)-hydroxypropionamide

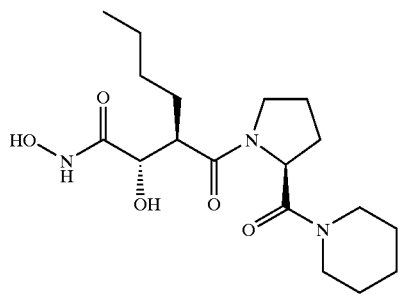

The title compound was prepared according to General Procedure F from piperidine. $^1$H NMR (CDCl$_3$): δ 5.07–5.03 (m, 1H), 4.45 (d, J=2.6 Hz, 1H), 3.97–3.82 (m, 4H), 3.71–3.56 (m, 2H), 3.47–3.40 (m, 1H), 2.37–2.14 (m, 4H), 2.09–1.98 (m, 4H), 1.96–1.61 (m, 4H), 1.59–1.52 (m, 4H), 1.12 (t, J=7 Hz, 3H). ES-MS: calcd. For $C_{18}H_{31}N_3O_5$ (369.46); found: 370.3 [M+1].

Example 154

Synthesis of N-hydroxy-3-(R)-(n-butyl)-3-[2-(S)-(azetidin-1-ylcarbonyl)pyrrolidin-1-carbonyl]-2-(S)-hydroxypropionamide

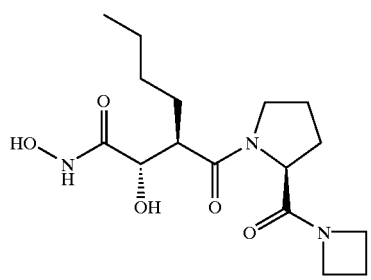

The title compound was prepared according to General Procedure F from azetidine. $^1$H NMR (CDCl$_3$): δ 4.67–4.55 (m, 2H), 4.53–4.31 (m, 3H), 4.28–4.16 (m, 1H), 3.94–3.83 (m, 1H), 3.81–3.77 (m, 1H), 3.43–3.38 (m, 1H), 2.55–2.45 (m, 2H), 2.37–2.22 (m, 2H), 2.20–2.07 (m, 2H), 2.05–1.91 (m, 2H), 1.66–1.47 (m, 4H), 1.01 (t, J=7 Hz, 3H). ES-MS: calcd. For $C_{16}H_{27}N_3O_5$ (341.40); found: 342.3 [M+1].

Example 155

Synthesis of N-hydroxy-3-(R)-(n-butyl)-3-[2-(S)-(homopiperazin-1-ylcarbonyl)-pyrrolidin-1-carbonyl]-2-(S)-hydroxypropionamide

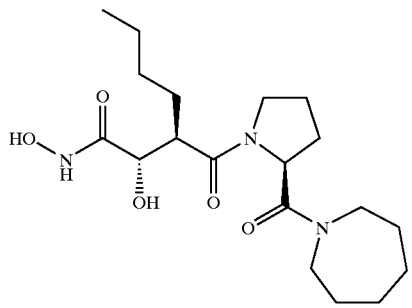

The title compound was prepared according to General Procedure F from hexamethyleneimine. $^1$H NMR (CDCl$_3$): δ 5.00–4.96 (m, 1H), 4.44 (d, J=2.7 Hz, 1H), 3.97–3.82 (m, 2H), 3.79–3.59 (m, 4H), 3.44–3.38 (m, 1H), 2.41–2.30 (m, 2H), 2.19–1.83 (m, 8H), 1.82–1.69 (m, 4H), 1.67–1.50 (m, 4H), 1.10 (t, J=7 Hz, 3H). ES-MS: calcd. For C$_{19}$H$_{33}$N$_3$O$_5$ (383.48); found: 384.4 [M+1].

Example 156

Synthesis of N-hydroxy-3-(R)-(n-butyl)-3-[2-(S)-((pyrimidin-2-yl)aminocarbonyl)pyrrolidin-1-carbonyl]-2-(S)-hydroxypropionamide

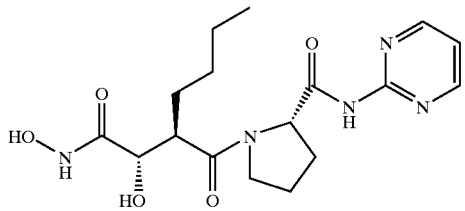

Step 1

To Cbz-protected-L-proline (20 mmol) in DCM (100 mL) was added thionylchloride (200 mmol) and the solution heated to reflux for 20 min. The reaction was concentrated to dryness and the residue coevaporated two times with DCM. An aliquot (6.7 mmol) in DCM (3 mL) was added to a 0° C. solution of 2-aminopyrimidine in pyridine (3 mL) and the reaction stirred overnight. The reaction was concentrated, the residue dissolved in ethylacetate and then washed with water, 10% citric acid, saturated NaHCO$_3$ and brine, then dried (Na$_2$SO$_4$) to afford N-Cbz-(2-(S)-pyrimidin-2-ylaminocarbonyl)pyrrolidine, which was used without further purification.

Step 2

To afford N-Cbz-(2-(S)-pyrimidin-2-ylaminocarbonyl) pyrrolidine (5.0 mmol) in HOAc (10 mL) was added 30% HBr in acetic acid and the solution stirred for 40 min. The reaction was quenched by addition of 100 mL ethylether, and the resulting precipitate collected and recrystalized from MeOH/Et2O to afford 3.5 mmol afford of 2-(S)-(pyrimidin-2-ylaminocarbonyl)pyrrolidine hydrobromide salt (70%).

Step 3

To 2-(S)-(pyrimidin-2-ylaminocarbonyl)pyrrolidine hydrobromide (200 µmol) in DMF (2 mL) was added DIEA (500 µmol), compound G-1, (General Procedure G, 200 µmol) and solid HATU (200 µmol) and the reaction stirred 4 h. The reaction was cooled to 0° C., diluted with aqueous 50% hydroxylamine (600 µL), stirred for 4 h, and then purified via preparative reverse-phase (C18) HPLC to afford the title compound. $^1$H NMR (DMSO-d6): δ 10.85 (bs, 1H), 8.84 (d, J=5.0 Hz, 2H), 7.37 (t, J=5.0 Hz, 1H), 4.98–4.83 (bs, 1H), 4.04–3.95 (m, 2H), 3.78–3.65 (m, 1H), 3.18–3.05 (m, 1H), 2.39–2.25 (m, 4H), 1.57–1.38 (m, 6H), 1.00 (t, J=6.6 Hz, 3H). ES-MS: calcd. For C$_{17}$H$_{25}$N$_5$O$_5$ (379.4162); found: 380.3 [M+1].

Example 157

Synthesis of N-hydroxy-3-(R)-(n-butyl)-3-[2-(S)-(4-methylpiperazin-1-ylcarbonyl)-pyrrolidin-1-carbonyl]-2-(S)-hydroxypropionamide

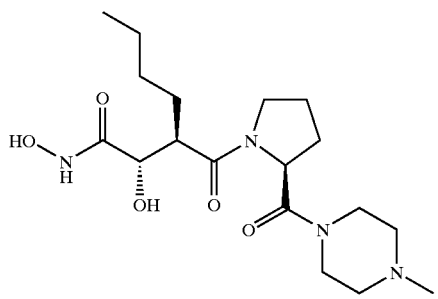

The title compound was prepared according to General Procedure F from N-methylpiperazine. $^1$H NMR (CD$_3$OD): δ 4.24–4.12 (m, 2H), 3.89–3.86 (m, 2H), 3.64–3.51 (m, 4H), 3.35–3.19 (m, 1H), 3.14 (s, 3H), 2.46–2.08 (m, 4H), 1.85–1.53 (m, 6H), 1.11 (t, J=7 Hz). ES-MS: calcd. For C$_{18}$H$_{32}$N$_4$O$_5$ (384.47); found: 385.3 [M+1].

Example 158

Synthesis of N-hydroxy-3-(R)-(n-butyl)-3-[2-(S)-((4-methylpyrimidin-2-yl)aminocarbonyl)pyrrolidin-1-carbonyl]-2-(S)-hydroxypropionamide

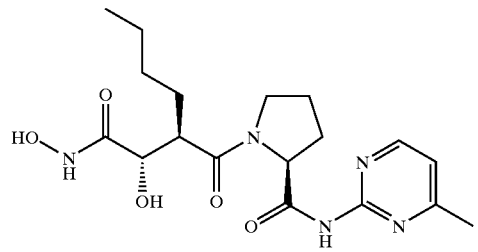

The title compound was prepared as described in General Procedure F from 4-methyl-2-aminopyrimidine. $^1$H NMR (DMSO-d6): δ 8.57 (d, J=5.2 Hz, 1H), 7.16 (d, J=5.2 Hz, 1H), 4.9 (bs, 1H), 3.93–3.85 (m, 2H), 3.67–3.60 (m, 1H), 3.02–2.90 (m, 1H), 2.50 (s, 3H), 2.3–2.15 (m, 1H), 2.10–1.98 (m, 3H), 1.55–1.28 (m, 6H), 0.904 (t, J=6.2 Hz, 3H). ES-MS: calcd. For $C_{18}H_{27}N_5O_5$ (393.4431); found: 394.3 [M+1].

Example 159

Synthesis of N-hydroxy-3-(R)-(n-butyl)-3-[2-(S)-((pyrimidin-4-yl)aminocarbonyl)pyrrolidin-1-carbonyl]-2-(S)-hydroxypropionamide

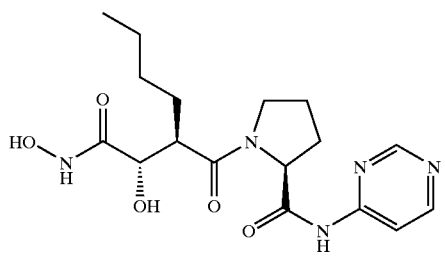

The title compound was prepared as described in General Procedure F from 4-aminopyrimidine. $^1$H NMR (DMSO-d6): δ 8.91 (d, J=0.55 Hz, 1H), 8.66 (d, J=6.1 Hz, 1H), 8.04 (dd, J=6.1 & 1.1 Hz, 1H), 4.64–4.60 (m, 1H), 3.87–3.75 (m, 1H), 3.61–3.51 (m, 1H), 2.93–2.88 (m, 1H), 2.17–2.05 (m, 1H), 1.98–1.83 (m, 3H), 1.45–1.18 (m, 6H), 0.83 (t, J=6.3 Hz, 3H). ES-MS: calcd. For $C_{17}H_{25}N_5O_5$ (379.4162); found: 380.1 [M+1].

Example 160

Synthesis of N-hydroxy-3-(R)-(n-butyl)-3-[2-(S)-((pyrazin-2-yl)aminocarbonyl)pyrrolidin-1-carbonyl]-2-(S)-hydroxypropionamide

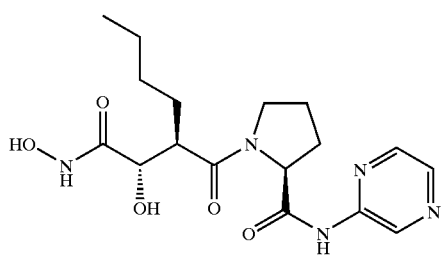

The title compound was prepared as described in General Procedure F from aminopyrazine. $^1$H NMR (DMSO-d6): δ 9.30 (d, J=1.4 Hz, 1H), 8.41–8.35 (m, 2H), 4.66–4.62 (m, 1H), 3.88–3.76 (m, 2H), 3.60–3.53 (m, 1H), 2.94–2.89 (m, 1H), 2.17–2.11 (m, 1H), 2.00–1.84 (m, 3H), 1.42–1.18 (m, 6H), 0.82 (t, J=6.6 Hz, 3H). ES-MS: calcd. For $C_{17}H_{25}N_5O_5$ (379.4162); found: 380.4 [M+1].

Example 161

Synthesis of N-hydroxy-3-(R)-(n-butyl)-3-[2-(S)-(pyrrolidin-1-ylcarbonyl)pyrrolidin-1-ylcarbonyl]-2-(S)-hydroxypropionamide

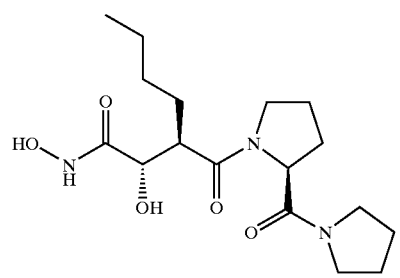

The title compound was prepared according to General Procedure F from pyrrolidine. $^1$H NMR (CDCl$_3$): δ 4.83–4.79 (m, 1H), 4.44 (d, J=2.4 Hz, 1H), 3.96–3.85 (m, 2H), 3.77–3.73 (m, 2H), 3.64–3.56 (m, 2H), 3.42–3.16 (m, 1H), 2.39–2.22 (m, 2H), 2.19–1.96 (m, 8H), 1.66–1.50 (m, 4H), 1.11 (t, J=7 Hz, 3H). ES-MS: calcd. For $C_{17}H_{29}N_3O_5$ (355.43); found: 356.4 [M+1].

Example 162

Synthesis of N-hydroxy-3-(R)-(n-butyl)-3-[2-(S)-((imidazol-2-yl)aminocarbonyl)pyrrolidin-1-carbonyl]-2-(S)-hydroxypropionamide

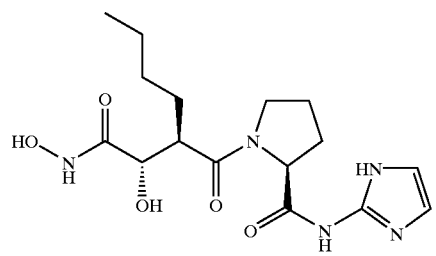

The title compound was prepared as described in General Procedure F from 2-amino-imidazole. $^1$H NMR (DMSO-d6): δ 7.24 (s, 2H), 4.50–4.46 (m, 1H), 3.83–3.61 (m, 3H), 2.94–2.88 (m, 1H), 2.21–2.11 (m, 1H), 2.05–1.94 (m, 3H), 1.41–1.18 (m, 6H), 0.81 (t, J=6.0 Hz, 3H). ES-MS: calcd. For $C_{16}H_{25}N_5O_5$ (367.4052); found: 368.4 [M+1].

Formulation Examples

The following are representative pharmaceutical formulations containing a compound of Formula (I).

Example 1

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Example 4

Injectable Formulation

The following ingredients are mixed to form an injectable formulation.

| Ingredient | Amount |
| --- | --- |
| compound of this invention | 0.2 mg–20 mg |
| sodium acetate buffer solution, 0.4M | 2.0 ml |
| HCl (1N) or NaOH (1N) | q.s. to suitable pH |
| water (distilled, sterile) | q.s. to 20 ml |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
| --- | --- |
| compound of the invention | 500 mg |
| Witepsol ® H-15 | balance |

Biological Examples

Example 1

Inhibition of Peptide Deformylase Activity

The PDF/FDH coupled assay (Lazennec, C. & Meinnel, T., Anal. Biochem. 224:180–182 (1997)) was used. In this coupled assay, the formate released by PDF from its substrate fMAS is oxidized by the coupling enzyme FDH, reducing one molecule of $NAD^+$ to NADH, which causes an increase in absorption at 340 nm. All assays were carried out at room temperature in a buffer of 50 mM HEPES, pH 7.2, 10 mM NaCl, 0.2 mg/mL BSA, in half-area 96-well microtiter plates (Corning). The reaction was initiated by adding a mixture of 0.5 Unit/mL FDH, 1 mM $NAD^+$, and fMAS at the desired concentration. To determine $IC_{50}$ (the concentration needed to inhibit 50% of enzyme activity) values, PDF was pre-incubated for 10 min with varying concentrations of actinonin, and the deformylation reaction was initiated by the addition of reaction mixture containing 4 mM FMAS. The initial reaction velocity, y, was measured as the initial rate of absorption increase at 340 nm using a SpectraMax plate reader (Molecular Devices, Sunnyvale, Calif.). The inhibitor concentration [In] at which 50% of the enzyme activity is inhibited, $IC_{50}$, was calculated using the following formula:

$$y = y_o/(1+[In]/IC_{50})$$

where $y_o$ is the reaction velocity in the absence of inhibitor. Solving this equation for $IC_{50}$ at the [In] when $y=y_o/2$ yields $IC_{50}$. The $IC_{50}$ was calculated based on a nonlinear least-square regression fit using a commercial software package (DeltaGraph 4.0).

Using this assay, the $IC_{50}$ of various compounds were determined. The $IC_{50}$ for the various compounds was determined against deformylase enzyme containing nickel or zinc as the metal ion. The compound tested had an IC50 of less than 2 $\mu$M against deformylase enzyme containing nickel as the metal ion and less than 9 $\mu$M against deformylase enzyme containing zinc as the metal ion Example 2

Assay For Testing Antimicrobial Activity

Minimum inhibitory concentrations (MICs) were determined using the microdilution method in 96-well format plates. Compounds were suspended in DMSO at 5 or 10 mg/ml and stored at 4° C. until used. They were diluted in Mueller-Hinton Broth (MHB) or Trypticase Soy Broth (TSB) and used for MIC determination. The range of concentrations tested was 64–0.0625 Tg/ml final concentration using a two-fold dilution system.

The inoculum was prepared from cells grown on Trypticase Soy Agar (TSA) and incubated overnight at 35° C., 5 to 10 colonies were used to inoculate MHB or TSB broths, and the culture was incubated overnight at 35° C. The overnight culture was diluted 1:10, incubated for one hour at 35° C., diluted to the appropriate inoculum size and applied to the wells containing broth and test compound. Inoculum sizes were 2×10$^4$ CFU/ml.

Plates were incubated at 35° C. for 48 hours and MIC were recorded after 18 hours of incubation for bacteria. MIC was defined as the lowest concentration of compound that does not produce visible growth after incubation.

Minimum inhibitory concentrations for various compounds against *H. influenza* and *S. aureus* was approximately 64 $\mu$g/mL or less. Minimum inhibitory concentrations for certain compounds of the Invention against *S. aureus, S. epidermidis, E. faecium, S. pneumoniae, H. Influenzae, H. influenzae* acr, *M. catarrhalis, E. coli* and *E. coli* acr was approximately 64 $\mu$g/mL or less.

Example 3

Demonstration of Selective Inhibition of PDF Compared to MMP-7 (Matrilysin)

As noted previously, inhibitors which are selective for peptidyl deformylase over matrix metalloproteinases are desirable in order to avoid side effects.

In order to test the compounds of the invention for possible inhibitory effects on matrix metalloproteinases, the following assay for MMP-7 (matrilysin) was used. MMP-7 (Matrilysin) Assay:

Matrilysin activity is assayed using a thio-peptide (Pro-Leu-Gly-S-Leu-Leu-Gly) as substrate. Upon enzyme hydrolysis, the thiolate is released as a product. The thiolate thus generated reacts with DTNB (dithionitrobenzene), giving rise to a yellow color which is monitored at 405 nm. The assay is carried out at room temperature; the assay buffer contains 50 mM Tricine, pH 7.5, 0.2 M NaCl, 10 mM CaCl$_2$, and 0.05% Brij, in a half-area 96-well microtiter plate. The reaction is initiated by adding a mixture of 200 TM DTNB and 100 TM thiopeptide in buffer. To determine IC$_{50}$ (the concentration needed to inhibit 50% of enzyme activity) values, MMP-7 was preincubated for 10 minutes with varying concentrations of compounds, and the hydrolysis initiated by the addition of reaction mixture containing thiopeptide and DTNB. The reaction rate was recorded as the absorbance increase in OD$_{405}$ over 30 minutes using a SpectraMax plate reader (Molecular Devices, Sunnyvale, Calif.). The inhibitor concentration [In] at which 50% of the enzyme activity is inhibited, IC$_{50}$, was calculated using the following formula:

$$y=y_o/(1+[In]/IC_{50})$$

where y$_o$ is the reaction velocity in the absence of inhibitor. Solving this equation for IC$_{50}$ at the [In] when y=y$_o$/2 yields IC$_{50}$.

Using this assay, the IC$_{50}$ of various compounds were determined. The compounds of the Invention tested were at least approximately 800 times more select for PDF than MMP-7. Similar selectivity of the compounds for peptidyl deformylase over MMP-1, MMP-2, MMP-3, MMP-9, MMP-13, MT-MMP-1, and tissue necrosis factor converting enzyme was observed. Similar selectivity was also observed over other metalloproteinases such as angiotensin converting enzyme.

Example 4

Discontinuous PDF Assay

The gene for PDF was cloned from *S. aureus* and *E. coli* by PCR amplification. The PDF proteins were overexpressed in *E. coli*. The native Fe$^{2+}$-containing PDF or its more stable surrogate Ni$^{2+}$-containing PDF were prepared according to Wagner et al. (1998) *Biochemical & Biophysical Research Communications* 246:342–6. Both enzymes have similar activity as reported in the literature. Discontinuous assay is carried out in a buffer of 10 mM NaCl and 50 mM HEPES, pH 7.2. Typically, 2 nM of PDF was incubated with inhibitor for 30 minutes prior to the addition of 4 mM fMAS substrate. The deformylation proceeded at room temperature for 30 minute. The enzyme activity is directly proportional to the amount of formate released, which can be quantified by monitoring the absorbance increase at 340 nm after the addition of 1 mM of NAD$^+$ and 0.5 U/ml of formate dehydrogenase.

Example 5

Mouse Septicemia Model For Determining in vivo Efficacy

CD1 female out-bred mice (Charles River Laboratories) weighing 18–22 grams each were injected intraperitoneally with 0.5 ml of a suspension containing 5×10$^7$ cfu of *S. aureus* (Smith strain) in 7% hog gastric mucosa (mucin). The mice were treated, either subcutaneously (SC), intravenously (IV) or orally (PO), 1 hr and 5 hr after infection. Six groups of six mice each were given different dosage levels representing two-fold dilutions of each compound (range of 100 mg/kg–0.1 mg/kg). Vancomycin was used as the control antibiotic and was administered SC. Compounds were formulated in PBS and untreated controls were dosed with vehicle alone.

Deaths in each group were monitored daily for 6 days and cumulative mortality was used to determine the 50% protective doses (PD$_{50}$), which were calculated using the method of Reed and Muench.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula (I):

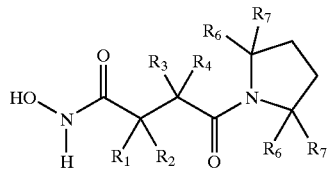

wherein:

$R_1$ is hydrogen, halo, —OH, —$R_8OR_9$, —$R_9$, —$OR_9$, —SH, —$SR_9$, —$NH_2$, —$NHR_9$, —$NR_9R_{10}$, —NHC(=O)H, —$NR_9C(=O)H$, —NHC(=O)$R_9$, —$NR_9C$(=O)$R_{10}$, —NHC(=O)$NH_2$, —$NR_9C$(=O)$NH_2$, —NHC(=O)$NHR_9$, —NHC(=O)$NR_9R_{10}$, —$NR_9C$(=O)$NR_{9a}R_{10}$, —NHC(=O)$OR_9$, —$NR_9C$(=O)$OR_{10}$, —NHS(=O)$_2R_9$, —$NR_9S$(=O)$_2R_{10}$, —NHS(=O)$_2OR_9$, or —$NR_9S$(=O)$_2OR_{10}$ where $R_8$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n1}$—($C_3$–$C_{12}$ arylene or heteroarylene)-($C_1$–$C_8$ alkyl or substituted alkyl)$_{n2}$ where n1 and n2 are independently 0 or 1; and $R_9$, $R_{9a}$ and $R_{10}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n3}$—($C_3$–$C_{12}$ arylene or heteroarylene)-($C_1$–$C_8$ alkyl or substituted alkyl)$_{n4}$ where n3 and n4 are independently 0 or 1;

$R_2$ is independently hydrogen or —$R_9$ wherein $R_9$ is as defined above;

$R_3$ is hydrogen, halo, —$R_{11}$, —OH, —$OR_{11}$, —$R_{12}OR_{11}$, —SH, —$SR_{11}$, —$NH_2$, —$NHR_{11}$, —$NR_{11}R_{13}$, —NHC(=O)H, —$NR_{11}C$(=O)H, —NHC(=O)$R_{11}$, —$NR_{11}C$(=O)$R_{13}$, —NHC(=O)$NH_2$, —$NR_{11}C$(=O)$NH_2$, —NHC(=O)$NHR_{11}$, —NHC(=O)$NR_{11}R_{13}$, —$NR_{11}C$(=O)$NR_{11a}R_{13}$, —NHC(=O)$OR_{11}$, —$NR_{11}C$(=O)$OR_{13}$, —NHS(=O)$_2R_{13}$, —$NR_{11}S$(=O)$_2R_{13}$, —NHS(=O)$_2OR_{11}$, or —$NR_{11}S$(=O)$_2OR_{13}$, where $R_{12}$ is selected from the group consisting of —$C_1$–$C_{12}$ alkylene, substituted alkylene, or heteroalkylene, —$C_1$–$C_{12}$ alkenylene, substituted alkenylene, or heteroalkenylene, —$C_1$–$C_{12}$ alkynylene, substituted alkynylene, or heteroalkynylene, and —($C_1$–$C_8$ alkylene or substituted alkylene)$_{n5}$—($C_3$–$C_{12}$ arylene or heteroarylene)-($C_1$–$C_8$ alkyl or substituted alkyl)$_{n6}$ where n5 and n6 are independently 0 or 1; and $R_{11}$, $R_{11a}$ and $R_{13}$ are independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, and —($C_1$–$C_8$ alkyl or substituted alkyl)$_{n7}$—($C_3$–$C_{12}$ arylene or heteroaxylene)-($C_1$–$C_8$ alkyl or substituted alkyl)$_{n8}$ where n7 and n8 are independently 0 or 1;

$R_4$ is hydrogen or —$R_{11}$ where —$R_{11}$ is as defined above;

$R_6$ and $R_7$ are each independently selected from the group consisting of hydrogen, —$R_{14}$, —OH, —$OR_{14}$, —SH, —$SR_{14}$, —$NH_2$, —$NHR_{14}$, —$NR_{14}R_{15}$, —C(=O)H, —C(=O)$R_{14}$, —C(=O)$NH_2$, —C(=O)$NHR_{14}$, —C(=O)$NR_{14}R_{15}$, —C(=O)OH, —C(=O)$OR_{14}$, —C(=O)SH, —C(=O)$SR_{14}$, —C(=O)$CH_3$, —C(=O)$CH_2R_{14}$, —C(=O)$CHR_{14}R_{15}$, —C(=O)$CR_{14}R_{15}R_{16}$, —C(=O)$OCH_3$, —C(=O)$OCH_2R_{14}$, —C(=O)$OCHR_{14}R_{15}$, —C(=O)$OCR_{14}R_{15}R_{16}$, —S(=O)$_2NH_2$, —S(=O)$_2NHR_{14}$, —S(=O)$_2NR_{14}R_{15}$, —NHC(=O)H, —N($R_{14}$)C(=O)H, —NHC(=O)$R_{15}$, —N($R_{14}$)C(=O)$R_{15}$, —NHC(=O)$OR_{14}$, —NHS(=O)$_2H$, —N($R_{14}$)S(=O)$_2H$, —NHS(=O)$_2OR_{15}$, —N($R_{14}$)S(=O)$_2OR_{15}$, —N(H)S(=O)$_2R_{15}$, —N($R_{14}$)S(=O)$_2R_{15}$ and where two vicinal $R_6$ or $R_7$ groups combine to form a substituted or unsubstituted —$C_4$–$C_{10}$ cyclic alkyl, cyclic heteroalkyl, aryl or heteroaryl group where $R_{14}$, $R_{15}$ and $R_{26}$ are each independently selected from the group consisting of —$C_1$–$C_{12}$ alkyl, substituted alkyl, or heteroalkyl, —$C_1$–$C_{12}$ alkenyl, substituted alkenyl, or heteroalkenyl, —$C_1$–$C_{12}$ alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)-($C_1$–$C_8$ alkyl or substituted alkyl)$_{n10}$ where n9 and n10 are independently 0 or 1;

or when $R_{14}$ and $R_{15}$ are attached to a nitrogen atom they can combine to form a substituted or unsubstituted —$C_4$–$C_{10}$ cyclic alkyl, cyclic heteroalkyl, aryl or heteroaryl group; or a pharmaceutically acceptable salt thereof.

2. The compound of claim 1 wherein $R_1$ is halo.

3. The compound of claim 2 wherein $R_1$ is fluoro.

4. The compound of claim 3 wherein $R_2$ and $R_4$ are hydrogen.

5. The compound of claim 4 wherein $R_3$ is alkyl.

6. The compound of claim 5 wherein $R_7$ is —C(=O)$NR_{14}R_{15}$ where $R_{14}$ and $R_{15}$ are independently selected from the group consisting of hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)-($C_1$–$C_8$ alkyl or substituted alkyl)$_{n10}$ where n9 and n10 are independently 0 or 1; or $R_{14}$ and $R_{15}$ combine to form a substituted or unsubstituted —($C_4$–$C_{10}$)cyclic alkyl, cyclic heteroalkyl, aryl or heteroaryl group.

7. The compound of claim 5 wherein $R_7$ is —C(=O)$NR_{14}R_{15}$ where $R_{14}$ and $R_{15}$ are each independently hydrogen or —($C_1$–$C_{12}$) alkyl, alkoxy, aryl, heteroaryl or $R_{14}$ and $R_{15}$, when attached to the same carbon, combine to form a cyclic heteroalkyl, aryl or heteroaryl group.

8. The compound of claim 5 wherein $R_7$ is —C(=O)$NHR_{15}$ where $R_{15}$ is H or —($C_1$–$C_{12}$) alkyl, aryl, or heteroaryl or —C(=O)$NR_{14}R_{15}$ where $R_{14}$ and $R_{15}$ form a substituted or unsubstituted —($C_4$–$C_{10}$)cyclic heteroalkyl.

9. The compound of claim 5 wherein $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenylaminocarbonyl, cyclopropylmethyl-amrnocarbonyl, pyridin-2-ylaminocarbonyl, pyridin-3-ylaminocarbonyl, pyridin-4-ylmethylaminocarbonyl, morpholin-4-ylcarbonyl, 3,4-methylenedioxy-pbenylaminocarbonyl, quinolin-3-ylaminocarbonyl, methylaminocarbonyl, 4-biphenylaminocarbanyl, 3-phenoxyphenylaminocarbonyl, 3,4-dichlorophenyl-aminocarbonyl, 4-tert-butylphenylaminocarbonyl, 4-tert-butylaminocarbonyl, indan-2-ylaminocarbonyl, 2,2-dimethylpropylaminocarbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenyl-aminocarbonyl, 2,5-dimethylphenylaminocarbonyl, 2,5-dimethoxyphenylamino-carbonyl, 3,4-dichlorophenyl-aminocarbonyl, benzthiazol-2-ylaminocarbonyl, 3-phenoxyphenylaminocarbonyl, 2-hydroxybutylamino-carbonyl, 4-hydroxybutyl-aminocarbonyl, 1,4-benzodioxan-6-ylaminocarbonyl, isoquinolin-6-ylaminocarbonyl, methylaminocarbonyl, thiazol-2-ylaminocarbonyl, 4-methylthiazol-2-yl-aminocarbonyl, 3-methylbutyl-aminocarbonyl, n-pentylaminocarbonyl, cyclohexylaminocarbonyl, 5-methylthiazol-2-ylaminocarbonyl, 4-niethylthiazol-2-yl-aminocarbonyl, 2,4-dimethoxyphenyl-aminocarbonyl, 3,4-methylene-dioxyphen-5-yl-methylaminocarbonyl, allylaminocarbonyl, 2-methylallylaminocarbonyl, pyrrolidin-1-ylcarbonyl, ethylaminocarbonyl, phenylaminocarbonyl, indan-1-ylaminocarbonyl, 2-methoxyethylaminocarbonyl, indan-5-ylaminocarbonyl, 3,4-difluorophenyl-aminocarbonyl, 5-methylisoxazol-5-ylaminocarbonyl, 3-fluorophenyl-aminocarbonyl, 4-fluorophenylaminocarbonyl, N-methyl-N-phenylaminocarbonyl, 2-propylamino-carbonyl, 2-phenylpropylaminocarbonyl, n-propylaminocarbonyl, N-ethyl-N-(n-butyl)aminocarbonyl, benzylaminocarbonyl, thiazolidin-1-ylcarbonyl, piperazin-1-yl-carbonyl, piperidin-1-ylcarbonyl, azetidin-1-ylcarbonyl, homopiperdin-1-ylcarbonyl, pyrimidin-2-ylaminocarbonyl, 4-methylpiperazin-1-ylcarbonyl, 4-methylpyrimidin-2-ylaminocarbonyl, pyrimidin-4-ylaminocarbonyl, pyrazin-2-ylaminocarbonyl, imidazol-2-ylaminocarbonyl.

10. The compound of claim 5 wherein $R_7$ is piperidin-1-ylcarbonyl, azetidin-1-ylcarbonyl, ethylaminocarbonyl, phenylaminocarbonyl, pyrimidin-2-ylaminocarbonyl, or thiazol-2-ylaminocarbonyl, the stereochemistry at the C2 carbon atom of the pyrrolidine ring is (S), and $R_3$ is n-butyl.

11. The compound of claim 5 wherein $R_7$ is —C(=O)$OR_{14}$ where $R_{14}$ is hydrogen or —$(C_1–C_{12})$ alkyl, alkoxy, aryl, or heteroaryl.

12. The compound of claim 5 wherein $R_7$ is —C(=O)$OR_{14}$ where $R_{14}$ is alkyl and the stereochemistry at the $C_2$ carbon atom of the pyrrolidine ring is (S).

13. The compound of claim 1 wherein $R_7$ is —C(=O)$NR_{14}R_{15}$ where $R_{14}$ and $R_{15}$ are independently selected from the group consisting of hydrogen, —$(C_1–C_{12})$ alkyl, substituted alkyl, or heteroalkyl, —$(C_1–C_{12})$ alkenyl, substituted alkenyl, or heteroalkenyl, —$(C_1–C_{12})$ alkynyl, substituted alkynyl, or heteroalkynyl, alkoxy, and —$(C_1–C_8$ alkyl or substituted alkyl$)_{n9}$—$(C_3–C_{12}$ arylene or heteroarylene)-$(C_1–C_8$ alkyl or substituted alkyl$)_{n10}$ where n9 and n10 are independently 0 or 1; or $R_{14}$ and $R_{15}$ combine to form a substituted or unsubstituted —$(C_4–C_{10})$cyclic alkyl, cyclic heteroalkyl, aryl or heteroaryl group.

14. The compound of claim 1 wherein $R_7$ is —C(=O)$NR_{14}R_{15}$ where $R_{14}$ and $R_{15}$ are each independently hydrogen or —$(C_1–C_{12})$ alkyl, alkoxy, aryl, heteroaryl or $R_{14}$ and $R_{15}$, when attached to the same carbon, combine to form a cyclic heteroalkyl, aryl or heteroaryl group.

15. The compound of claim 1 wherein $R_7$ is —C(=O)$NHR_{15}$ where $R_{15}$ is H or —$(C_1–C_{12})$ alkyl, aryl, or heteroaryl or —C(=O)$NR_{14}R_{15}$ where $R_{14}$ and $R_{15}$ form a substituted or unsubstituted —$(C_4–C_{10})$cyclic heteroalkyl.

16. The compound of claim 1 wherein $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenyl-aminocarbonyl, cyclopropylmethyl-aminocarbonyl, pyridin-2-ylaminocarbonyl, pyridin-3-ylaminocarbonyl, pyridin-4-ylmethylaminocarbonyl, morpholin-4-ylcarbonyl, 3,4-methylenedioxy-phenylaminocarbonyl quinolin-3-ylaminocarbonyl, methylaminocarbonyl, 4-biphenylaminocarbonyl, 3-phenoxyphenylaminocarbonyl, 3,4-dichlorophenyl-aminocarbonyl, 4-tert-butylphenylaminocarbonyl, 4-tert-butylaminocarbonyl, indan-2-ylaminocarbonyl, 2,2-dimethylpropylaminocarbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenyl-aminocarbonyl, 2,5-dimethylphenylaminocarbonyl, 2,5-dimethoxyphenylamino-carbonyl, 3,4-dichlorophenyl-aminocarbonyl, benzthiazol-2-ylaminocarbonyl, 3-phenoxyphenylaminocarbonyl, 2-hydroxybutylamino-carbonyl, 4-hydroxybutyl-aminocarbonyl, 1,4-benzodioxan-6-ylaminocarbonyl, isoquinolin-6-ylaminocarbonyl, methylaminocarbonyl, thiazol-2-ylaminocarbonyl, 4-methylthiazol-2-yl-aminocarbonyl, 3-methylbutyl-aminocarbonyl, n-pentylaminocarbonyl, cyclohexylaminocarbonyl, 5-methylthiazol-2-ylaminocarbonyl, 4-methylthiazol-2-yl-aminocarbonyl, 2,4-dimethoxyphenyl-aminocarbonyl, 3,4-methylene-dioxyphen-5-yl-methylaminocarbonyl, allylaminocarbonyl, 2-methylallylaminocarbonyl, pyrrolidin-1-ylcarbonyl, ethylaminocarbonyl, phenylaminocarbonyl, indan-1-ylaminocarbonyl, 2-methoxyethylaminocarbonyl, indan-5-ylaminocarbonyl, 3,4-difluorophenyl-aminocarbonyl, 5-methylisoxazol-5-ylaminocarbonyl, 3-fluorophenyl-aminocarbonyl, 4-fluorophenylaminocarbonyl, N-methyl-N-phenylaminocarbonyl, 2-propylamino-carbonyl, 2-phenylpropylaminocarbonyl, n-propylaminocarbonyl, N-ethyl-N-(n-butyl)aminocarbonyl, benzylaminocarbonyl, thiazolidin-1-ylcarbonyl, piperazin-1-yl-carbonyl, piperidin-1-ylcarbonyl, azetidin-1-ylcarbonyl, homopiperdin-1-ylcarbonyl, pyrimidin-2-ylaminocarbonyl, 4-methylpiperazin-1-ylcarbonyl, 4-methylpyrimidin-2-ylaminocarbonyl, pyrimidin-4-ylaminocarbonyl, pyrazin-2-ylaminocarbonyl, imidazol-2-ylaminocarbonyl.

17. The compound of claim 1 wherein $R_7$ is piperidin-1-ylcarbonyl, azetidin-1-ylcarbonyl, ethylaminocarbonyl, phenylaminocarbonyl, pyrimidin-2-ylaminocarbonyl, or thiazol-2-ylaminocarbonyl and the stereochemistry at the C2 carbon atom of the pyrrolidine ring is (S).

18. The compound of claim 1 wherein $R_7$ is —C(=O)$OR_{14}$ where $R_{14}$ is hydrogen or —$(C_1–C_{12})$ alkyl, alkoxy, aryl, or heteroaryl.

19. The compound of claim 1 wherein $R_7$ is —C(=O)$OR_{14}$ where $R_{14}$ is alkyl and the stereochemistry at the $C_2$ carbon atom of the pyrrolidine ring is (S).

20. The compound of any one of claims 13–19 wherein $R_2$ and $R_4$ are hydrogen.

21. The compound of claim 20 wherein $R_1$ is halo.

22. The compound of claim 21 wherein $R_3$ is alkyl.

23. The compound of claim 22 wherein $R_1$ is fluoro.

24. The compound of claim 22 wherein $R_3$ is n-butyl.

25. The compound of any one of claims 13–19 wherein $R_1$ is halo.

26. The compound of claim 25 wherein $R_1$ is fluoro and $R_2$ and $R_4$ are hydrogen.

27. The compound of claim 26 wherein $R_3$ is alkyl.

28. The compound of claim 19 wherein $R_1$ is hydroxy.

29. The compound of claim 28 wherein $R_3$ is alkyl.

30. The compound of claim 29 wherein $R_3$ is n-butyl.

31. The compound of claim 1 wherein $R_1$ is hydroxy.

32. The compound of claim 31 wherein $R_2$ and $R_4$ are hydrogen and $R_3$ is alkyl.

33. The compound of claim 31 wherein $R_7$ is —C(=O)NR$_{14}$R$_{15}$ where $R_{14}$ and $R_{15}$ are independently selected from the group consisting of hydrogen, —($C_1$–$C_{12}$) alkyl, substituted alkyl, or heteroalkyl, —($C_1$–$C_{12}$) alkenyl, substituted alkenyl, or heteroalkenyl, —($C_1$–$C_{12}$) alkynyl, substituted alkynyl, or heteroalkynyl, alkoxy, and —($C_1$–$C_8$ alkyl or substituted alkyl)$_{n9}$—($C_3$–$C_{12}$ arylene or heteroarylene)-($C_1$–$C_8$ alkyl or substituted alkyl)$_{n10}$ where n9 and n10 are independently 0 or 1; or $R_{14}$ and $R_{15}$ combine to form a substituted or unsubstituted —($C_4$–$C_{10}$)cyclic alkyl, cyclic heteroalkyl, aryl or heteroaryl group.

34. The compound of claim 31 wherein $R_7$ is —C(=O)NR$_{14}$R$_{15}$ where $R_{14}$ and $R_{15}$ are each independently hydrogen or —($C_1$–$C_{12}$) alkyl, alkoxy, aryl, heteroaryl or $R_{14}$ and $R_{15}$, when attached to the same carbon, combine to form a cyclic heteroalkyl, aryl or heteroaryl group.

35. The compound of claim 31 wherein $R_7$ is —C(=O)NHR$_{15}$ where $R_{15}$ is H or —($C_1$–$C_{12}$) alkyl, aryl, or heteroaryl or —C(=O)NR$_{14}$R$_{15}$ where $R_{14}$ and $R_{15}$ form a substituted or unsubstituted —($C_4$–$C_{10}$)cyclic heteroalkyl.

36. The compound of claim 31 wherein $R_7$ is n-butylaminocarbonyl, tert-butylaminocarbonyl, benzylaminocarbonyl, 1,1-dimethylpropylaminocarbonyl, 2-(cyclohexen-1-yl)-ethylaminocarbonyl, indan-5-ylaminocarbonyl, 4,5-dimethylthiazol-2-ylaminocarbonyl, 4-phenoxyphenylaminocarbonyl, cyclopropylmethyl-aminocarbonyl, pyridin-2-ylaminocarbonyl, pyridin-3-ylaminocarbonyl, pyridin-4-ylmethylaminocarbonyl, morpholin-4-ylcarbonyl, 3,4-methylenedioxy-phenylaminocarbonyl, quinolin-3-ylaminocarbonyl, methylaminocarbonyl, 4-biphenylaminocarbonyl, 3-phenoxyphenylaminocarbonyl, 3,4-dichlorophenyl-aminocarbonyl, 4-tert-butylphenylaminocarbonyl, 4-tert-butylaminocarbonyl, indan-2-ylaminocarbonyl, 2,2-dimethylpropylaminocarbonyl, 4-phenylthiazol-2-ylaminocarbonyl, 5-phenylthiadiazol-2-ylaminocarbonyl, 5-ethylthiadiazol-3-ylaminocarbonyl, thiadiazol-2-ylaminocarbonyl, 3-trifluoromethoxyphenyl-aminocarbonyl, 2,5-dimethylphenylaminocarbonyl, 2,5-dimethoxyphenylamino-carbonyl, 3,4-dichlorophenylaminocarbonyl, benzthiazol-2-ylaminocarbonyl, 3-phenoxyphenylaminocarbonyl, 2-hydroxybutylaminocarbonyl, 4-hydroxybutyl-aminocarbonyl, 1,4-benzodioxan-6-ylaminocarbonyl, isoquinolin-6-ylaminocarbonyl, methylaminocarbonyl, thiazol-2-ylaminocarbonyl, 4-methylthiazol-2-yl-aminocarbonyl, 3-methylbutyl-aminocarbonyl, n-pentylaminocarbonyl, cyclohexylaminocarbonyl, 5-methylthiazol-2-ylaminocarbonyl, 4-methylthiazol-2-yl-aminocarbonyl, 2,4-dimethoxyphenyl-aminocarbonyl, 3,4-methylenedioxyphen-5-yl-methylaminocarbonyl, allylaminocarbonyl, 2-methylallylaminocarbonyl, pyrrolidin-1-ylcarbonyl, ethylaminocarbonyl, phenylaminocarbonyl, indan-1-ylaminocarbonyl, 2-methoxyethylaminocarbonyl, indan-5-ylaminocarbonyl, 3,4-difluorophenyl-aminocarbonyl, 5-methylisoxazol-5-ylaminocarbonyl, 3-fluorophenylaminocarbonyl, 4-fluorophenylaminocarbonyl, N-methyl-N-phenylaminocarbonyl, 2-propylamino-carbonyl, 2-phenylpropylaminocarbonyl, n-propylaminocarbonyl, N-ethyl-N-(n-butyl)aminocarbonyl, benzylaminocarbonyl, thiazolidin-1-ylcarbonyl, piperazin-1-yl-carbonyl, piperidin-1-ylcarbonyl, azetidin-1-ylcarbonyl, homopiperdin-1-ylcarbonyl, pyrimidin-2-ylaminocarbonyl, 4-methylpiperazin-1-ylcarbonyl, 4-methylpyrimidin-2-ylaminocarbonyl, pyrimidin-4-ylaminocarbonyl, pyrazin-2-ylaminocarbonyl, imidazol-2-ylaminocarbonyl.

37. The compound of claim 31 wherein $R_7$ is piperidin-1-ylcarbonyl, azetidin-1-ylcarbonyl, ethylaminocarbonyl, phenylaminocarbonyl, pyrimidin-2-ylaminocarbonyl, or thiazol-2-ylaminocarbonyl and the stereochemistry at the C2 carbon atom of the pyrrolidine ring is (S).

38. The compound of claim 31 wherein $R_1$ is —C(=O)OR$_{14}$ where $R_{14}$ is hydrogen or —($C_1$–$C_{12}$) alkyl, alkoxy, aryl, or heteroaryl.

39. The compound of claim 31 wherein $R_7$ is —C(=O)OR$_{14}$ where $R_{14}$ is alkyl and the stereochemistry at the $C_2$ carbon atom of the pyrrolidine ring is (S).

40. The compound of any one of claims 32–38 wherein $R_3$ is n-butyl.

41. The compound of any one of claims 13–19 wherein $R_2$ and $R_4$ are hydrogen.

42. The compound of claim 41 wherein $R_1$ is hydroxy.

43. The compound of claim 42 wherein $R_3$ is alkyl.

44. The compound of claim 41 wherein $R_3$ is n-butyl.

45. The compound of claim 1 selected from the group consisting of:

N-hydroxy-3-[(S)-(n-butyl)-3-(2-(S)-1,1-dimethylethyloxycarbonyl)pyrrolidin-1-carbonyl)]-2-(S)-fluoropropionamide;

N-hydroxy-3-[(S)-(n-butyl)-3-(2-(S)-pyridin-1-ylcarbonyl)pyrrolidin-1-carbonyl)]-2-(S)-fluoropropionamide;

N-hydroxy-3-[(S)-(n-butyl)-3-(2-(S)-azetidin-1-ylcarbonyl)-pyrrolidin-1-carbonyl)]-2-(S)-fluoropropionamide;

N-hydroxy-3-[(S)-(n-butyl)-3-(2-(S)-ethylaminocarbonyl)pyrrolidin-1-carbonyl)]-2-(S)-fluoropropionamide;

N-hydroxy-3-[(S)-(n-butyl)-3-(2-(S)-phenylaminocarbonyl)-pyrrolidin-1-carbonyl)]-2-(S)-hydroxypropionamide;

N-hydroxy-3-[(S)-(n-butyl)-3-(2-(S)-pyrimidin-2-ylaminocarbonyl)pyrrolidin-1-carbonyl)]-2-(S)-hydroxypropionamide; and N-hydroxy-3-[(S)-(n -butyl)-3-(2-(S)-thiazol-2-ylaminocarbonyl)-pyrrolidin-1-carbonyl)]-2-(S)-fluoropropionamide.

46. A pharmaceutical composition comprising a therapeutically effective amount of a compound of any one of claims 1–19, 28–39, and 45 and a pharmaceutically acceptable excipient.

47. A method of treatment of a disease in a mammal treatable by administration of a peptidyl deformylase inhibitor which method comprises administration of a pharmaceutical composition comprising a therapeutically effective amount of a compound of any one of claims 1–19, 28–39, and 45 and a pharmaceutically acceptable excipient.

48. The method of claim 47 wherein the disease is a bacterial disease.

* * * * *